US011034647B2

(12) United States Patent
Feng et al.

(10) Patent No.: US 11,034,647 B2
(45) Date of Patent: Jun. 15, 2021

(54) HISTONE ACETYLTRANSFERASE ACTIVATORS AND USES THEREOF

(71) Applicant: The Trustees of Columbia University in the City of New York, New York, NY (US)

(72) Inventors: Yan Feng, Shanghai (CN); Mauro Fa, New York, NY (US); Ottavio Arancio, New York, NY (US); Shixian Deng, White Plains, NY (US); Donald W. Landry, New York, NY (US); Yitshak Francis, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 16/708,190

(22) Filed: Dec. 9, 2019

(65) Prior Publication Data

US 2020/0115325 A1      Apr. 16, 2020

Related U.S. Application Data

(60) Division of application No. 13/493,490, filed on Jun. 11, 2012, now Pat. No. 10,640,457, which is a continuation-in-part of application No. PCT/US2010/059925, filed on Dec. 10, 2010.

(60) Provisional application No. 61/539,697, filed on Sep. 27, 2011, provisional application No. 61/363,009, filed on Jul. 9, 2010, provisional application No. 61/354,964, filed on Jun. 15, 2010, provisional application No. 61/355,110, filed on Jun. 15, 2010, provisional application No. 61/317,765, filed on Mar. 26, 2010, provisional application No. 61/285,287, filed on Dec. 10, 2009.

(51) Int. Cl.
| | | |
|---|---|---|
| A61K 49/00 | (2006.01) |
| C07C 235/64 | (2006.01) |
| C07C 323/67 | (2006.01) |
| C07C 323/42 | (2006.01) |
| C07D 213/82 | (2006.01) |
| C07D 213/75 | (2006.01) |
| C07C 235/56 | (2006.01) |
| C07C 237/40 | (2006.01) |
| C07D 239/52 | (2006.01) |
| C07D 333/38 | (2006.01) |
| C12Q 1/48 | (2006.01) |
| C07C 323/60 | (2006.01) |
| C07C 323/44 | (2006.01) |

(52) U.S. Cl.
CPC ............ *C07C 235/64* (2013.01); *A61K 49/00* (2013.01); *C07C 235/56* (2013.01); *C07C 237/40* (2013.01); *C07C 323/42* (2013.01); *C07C 323/44* (2013.01); *C07C 323/60* (2013.01); *C07C 323/67* (2013.01); *C07D 213/75* (2013.01); *C07D 213/82* (2013.01); *C07D 239/52* (2013.01); *C07D 333/38* (2013.01); *C12Q 1/48* (2013.01); *C07C 2601/08* (2017.05); *G01N 2500/04* (2013.01); *G01N 2800/2814* (2013.01)

(58) Field of Classification Search
CPC ... C07C 235/64; C07C 323/60; C07C 323/44; C07C 323/42; C07C 235/56; C07C 237/40; C07C 2601/08; C07D 213/82; C07D 213/75; C07D 239/52; C07D 333/38; A61K 49/00; C12Q 1/48; G01N 2500/04
USPC ........................................................ 424/9.2
See application file for complete search history.

(56) References Cited

U.S. PATENT DOCUMENTS

| | | | |
|---|---|---|---|
| 3,254,120 A | 5/1966 | Albin et al. |
| 3,591,684 A | 7/1971 | Chupp et al. |
| 3,671,630 A | 6/1972 | Carroll et al. |
| 3,678,111 A | 7/1972 | Houlihan |
| 4,088,770 A | 5/1978 | Paget, Jr. |
| 4,118,332 A | 10/1978 | Apostolatos et al. |
| 5,304,532 A | 4/1994 | Munro et al. |
| 5,430,062 A | 7/1995 | Cushman et al. |
| 5,565,325 A | 10/1996 | Blake |
| 5,696,138 A | 12/1997 | Olesen et al. |
| 5,712,171 A | 1/1998 | Zambias et al. |
| 5,814,646 A | 9/1998 | Heinz et al. |

(Continued)

FOREIGN PATENT DOCUMENTS

| | | |
|---|---|---|
| CN | 101698651 A | 4/2010 |
| DE | 1303920 B | 11/1974 |

(Continued)

OTHER PUBLICATIONS

"Parkinson's Disease mice models," available from the Jackson Laboratory, Bar Harbor, ME, retrieved from the internet on Jun. 26, 2014 from <http://jaxmice.jax.org/list/ra1594.html> (17 pages).

(Continued)

*Primary Examiner* — Michael G. Hartley
*Assistant Examiner* — Sean R Donohue
(74) *Attorney, Agent, or Firm* — Wilmer Cutler Pickering Hale and Dorr LLP

(57) ABSTRACT

The invention provides for a method for screening compounds that bind to and modulate a histone acetyltransferase protein. The invention further provides methods for treating neurodegenerative disorders, conditions associated with accumulated amyloid-beta peptide deposits, Tau protein levels, and/or accumulations of alpha-synuclein as well as cancer by administering a HAT-activating compound to a subject.

11 Claims, 79 Drawing Sheets

Specification includes a Sequence Listing.

(56) References Cited

U.S. PATENT DOCUMENTS

| | | |
|---|---|---|
| 7,250,514 B1 | 7/2007 | Xiao |
| 7,332,629 B2 | 2/2008 | Kundu et al. |
| 2004/0235888 A1 | 11/2004 | Yamamori et al. |
| 2005/0009163 A1 | 1/2005 | Tong et al. |
| 2005/0227915 A1 | 10/2005 | Steffan et al. |
| 2006/0014811 A1 | 1/2006 | Muto et al. |
| 2006/0019958 A1 | 1/2006 | Muto et al. |
| 2006/0167107 A1 | 7/2006 | Kundu et al. |
| 2007/0042997 A1 | 2/2007 | Itai et al. |
| 2007/0135438 A1* | 6/2007 | Payne .................. C07D 405/12 514/242 |
| 2007/0265296 A1 | 11/2007 | Dalton et al. |
| 2008/0300205 A1 | 12/2008 | Tsai et al. |
| 2009/0076155 A1 | 3/2009 | Kundu et al. |
| 2009/0111863 A1 | 4/2009 | Esposito et al. |
| 2009/0163545 A1 | 6/2009 | Goldfarb |
| 2009/0264414 A1 | 10/2009 | Andersen et al. |
| 2010/0168084 A1 | 7/2010 | Huber et al. |
| 2010/0311616 A1 | 12/2010 | Ozawa et al. |
| 2011/0046154 A1 | 2/2011 | Roux et al. |
| 2011/0081403 A1 | 4/2011 | Templeton |
| 2013/0121919 A1 | 5/2013 | Feng et al. |

FOREIGN PATENT DOCUMENTS

| | | |
|---|---|---|
| DE | 4428380 A1 | 2/1996 |
| EP | 0015110 A2 | 9/1980 |
| EP | 1574504 A1 | 9/2005 |
| EP | 1649852 A1 | 4/2006 |
| GB | 728098 A | 4/1955 |
| GB | 807668 A | 1/1959 |
| GB | 1217868 A | 12/1970 |
| GB | 1436306 A | 5/1976 |
| JP | S52141704 A | 11/1977 |
| JP | S5459325 A | 5/1979 |
| JP | S55-125013 A | 9/1980 |
| JP | 55-129256 A | 10/1980 |
| JP | 56-087501 | 7/1981 |
| JP | 56-087502 | 7/1981 |
| JP | S57139053 A | 8/1982 |
| JP | H9-207445 A | 8/1997 |
| JP | 2001-151742 A | 6/2001 |
| JP | 2002249473 A | 9/2002 |
| JP | 2006-514101 A | 4/2006 |
| JP | 2008-530020 A | 8/2008 |
| JP | 2009108051 A | 5/2009 |
| JP | 2010-535172 A | 11/2010 |
| JP | 55-41202 B2 | 7/2014 |
| JP | 2016-196459 A | 11/2016 |
| JP | 6-504782 B2 | 4/2019 |
| JP | 6616057 B2 | 12/2019 |
| RU | 02/370484 C1 | 10/2009 |
| WO | WO-91/05058 | 4/1991 |
| WO | WO-1992012961 A1 | 8/1992 |
| WO | WO-93/20242 | 10/1993 |
| WO | WO-94/18318 | 8/1994 |
| WO | WO-9509843 A1 | 4/1995 |
| WO | WO-95/18972 | 7/1995 |
| WO | WO-96/22529 | 7/1996 |
| WO | WO-1997045111 A1 | 12/1997 |
| WO | WO-1998037068 A1 | 8/1998 |
| WO | WO-1999/07409 | 2/1999 |
| WO | WO-99/32619 | 7/1999 |
| WO | WO-1999055663 A1 | 11/1999 |
| WO | WO-1999065449 A2 | 12/1999 |
| WO | WO-00/01846 | 1/2000 |
| WO | WO-00/44895 | 8/2000 |
| WO | WO-00/44914 | 8/2000 |
| WO | WO-200062778 A1 | 10/2000 |
| WO | WO-200100566 | 1/2001 |
| WO | WO-200100566 A2 | 1/2001 |
| WO | WO-01/29058 | 4/2001 |
| WO | WO-2001/36646 | 5/2001 |
| WO | WO-2001/092288 | 12/2001 |
| WO | WO-2003103657 | 12/2003 |
| WO | WO-2004006858 A2 | 1/2004 |
| WO | WO-2004006906 A2 | 1/2004 |
| WO | WO-2004041256 A2 | 5/2004 |
| WO | WO-2004/052871 A1 | 6/2004 |
| WO | WO 2004/053140 | 6/2004 |
| WO | WO-2005007151 A1 | 1/2005 |
| WO | WO-2005/080377 A1 | 9/2005 |
| WO | WO-2005/121119 A1 | 12/2005 |
| WO | WO-2006084246 A2 | 8/2006 |
| WO | WO-2006132583 A1 | 12/2006 |
| WO | WO-2007008541 A2 | 1/2007 |
| WO | WO-2007101710 A1 | 9/2007 |
| WO | WO-2008/062436 | 5/2008 |
| WO | WO-2009/010454 A2 | 1/2009 |
| WO | WO-2009/016088 A1 | 2/2009 |
| WO | WO-2009/044410 A1 | 4/2009 |
| WO | WO-2011/072243 | 6/2011 |

OTHER PUBLICATIONS

Abel et al., "Epigenetic targets of HDAC inhibition in neurodegenerative and psychiatric disorders," Current Opinion in Pharmacology, 8, pp. 57-64 (2008).

Alamed et al., "Two-day radial-arm water maze learning and memory task; robust resolution of amyloid-related memory deficits in transgenic mice," Nature Protocols, 1(4), pp. 1671-1679 (2006).

Alarcon et al., "Chromatin acetylation, Memory, and LTP Are Impaired in CBP+/− Mice: A Model for the Cognitive Deficit in Rubinstein-Taybi Syndrome and Its Amelioration," Neuron, 42(6), pp. 947-959 (2004).

Atherton et al., "Solid phase peptide synthesis: A practical approach," Oxford Press, 7 pages (1989).

Bach et al., "Age-related defects in spatial memory are correlated with defects in the late phase of hippocampal long-term potential in vitro and are attenuated by drugs that enhance the cAMP signaling pathway," Proc. Natl. Acad. Sci., 96, pp. 5280-5285 (1999).

Bailey et al., "Morphological basis of long-term habituation and sensitization in aplysia," Science, 220(4592), pp. 91-93 (1983).

Balasubramanyam et al., "Small molecule modulators of histone acetyltransferase p300," J. Biol. Chem., 278(21), pp. 19134-19140 (2003).

Baltrons et al., "Regulation of NO-dependent cyclic GMP formation by inflammatory agents in neural cells," Toxicol. Lett., 139(2-3), pp. 191-198 (2003).

Baratti et al., "Effects of sildenafil on long-term retention of an inhibitory avoidance response in mice," Behav Pharmacol., 10(8), pp. 731-737 (1999).

Bass, "RNA interference: The short answer," Nature, 411, pp. 428-429 (2001).

Berge et al., "Pharmaceutical Salts," Journal of Pharmaceutical Sciences, 66(1), pp. 1-19 (1977).

Biel et al., "Epigenetics—an epicenter of gene regulation: histones and histone-modifying enzymes," Angew Chem. Int. Ed. Engl., 44(21), pp. 3186-3216 (2005).

Bliss et al., "A synaptic model of memory: long-term potentiation in the hippocampus," Nature, 361(6407), pp. 31-39 (1993).

Blondelle et al., "Novel antimicrobial compounds identified using synthetic combinatorial library technology," Tib. Tech., 14, pp. 60-65 (1996).

Bolden et al., "Anticancer activities of histone deacetylase inhibitors," Nature Reviews Drug Discovery, 5, pp. 769-784 (2006).

Bon et al., "On the role of nitric oxide in hippocampal long-term potentiation," J Neurosci, 3(5), pp. 1941-1948 (2003).

Bordoli et al., "Plant orthologs of p300/CMP: conservation of a core domain in metazoan p300/CMP acetyltransferase-related proteins," Nucleic Acids Res., 29, pp. 589-597 (2001).

Bourtchuladze et al., "Deficient Long-Term Memory in Mice with a Targeted Mutation of the cAMP-Responsive Element-Binding Protein," Cell, 79(1), pp. 59-68 (1994).

Bowers et al., "Virtual ligand screening of the p300/CBP histone acetyltransferase: identification of a selective small molecule inhibitor," Chem. Biol., 17(5), pp. 471-482 (2010).

(56) References Cited

OTHER PUBLICATIONS

Brenner et al., "Encoded combinatorial chemistry," Proc. Natl. Acad. Sci. USA, 89, pp. 5381-5383 (1992).
Budillon, A. et al., "Histone Deacetylase Inhibitors in Cancer Therapy", Frontiers in Anti-Cancer Drug Discovery, 1:79-115, 2010 (37 pages).
Bunin et al., "The combinatorial synthesis and chemical and biological evaluation of a 1,4-benzodiazepine library," Proc. Natl. Acad. Sci. USA, 91, pp. 4708-4712 (1994).
Caccia et al., "Disposition and metabolism of minaprine in the rat," Xenobiotica, 15(12), pp. 1111-1119 (1985).
Cao et al., "A transcriptively active complex of APP with Fe65 and histone acetyltransferase Tip60," Science, 293, pp. 115-120 (2001).
Chandregowda, V. et al., "Synthesis of benzamide derivatives of anacardic acid and their cytotoxic activity", European Journal of Medicinal Chemistry, 44, pp. 2711-2719 (2009).
Chapman et al., "Impaired synaptic plasticity and learning in aged amyloid precursor protein transgenic mice," Nat. Neurosci., 2(3), pp. 271-276 (1999).
Chee et al., "An efficient synthesis of (±)-panduratin A and (±)-isopanduratin A, inhibitors of dengue-2 viral activity," Tetrahedron Letters, 51, pp. 495-498 (2010).
Chen et al., "Impairment of hippocampal long-term potentiation by Alzheimer amyloid β-peptides," J. Neurosci. Res., 60, pp. 65-72 (2000).
Christian et al., "Simplified Methods for Construction, Assessment and Rapid Screening of Peptide Libraries in Bacteriophage," J. Mol. Biol., 227, pp. 711-718 (1992).
Chuang, De-Maw et al., "Multiple roles of HDAC inhibition in neurodegenerative conditions", Trends in Neurosciences., 32(11), 11 pages (2009).
Cleary et al., "Natural oligomers of the amyloid-β protein specifically disrupt cognitive function," Nat. Neurosci., 8, pp. 79-84 (2005).
Clements et al., "Crystal structure of the histone acetyltransferase domain of the human PCAF transcriptional regulator bound to coenzyme A," The EMBO Journal, 18(13), pp. 3521-3532 (1999).
Colton et al., "NO synthase 2 (NOS2) deletion promotes multiple pathologies in a mouse model of alzheimer's disease," Proc. Natl. Acad. Sci. USA, 103, pp. 12867-12872 (2006).
Contestabile et al., "Brain Nitric Oxide and Its Dual Role in Neurodegeneration/Neuroprotection: Understanding Molecular Mechanisms to Devise Drug Approaches," Current Medical Chemistry, 10, pp. 2147-2174 (2003).
Coombs et al., "Synthesis and antiinflammatory activity of tert-aminomethylbenzophenones," J. Med. Chem., 14(11), pp. 1072-1074 (1971).
European Search Report for European Patent Application No. 10836767.3, dated Apr. 29, 2013 (14 pages).
Corless et al., "Predictors of Perception of Cognitive Functioning in HIV/AIDS," Journal of the Association of Nurses in AIDS Care, 11(3), pp. 19-26 (2000).
Coutts et al., "Involvement of CYP2D6, CYP3A4, and other cytochrome P-450 isozymes in N-dealkylation reactions," J. Pharmacol. Toxicol. Methods, 31(4), pp. 177-186 (1994).
Cullen et al., "Block of LTP in rat hippocampus in vivo by β-amyloid precursor protein fragments," Neuroreport, 8(15), pp. 3213-3217 (1997).
Czech et al., "Presenilins and alzheimer's disease: biological functions and pathogenic mechanisms," Prog. Neurogiol., 60, pp. 363-384 (2000).
Dahiyat et al., "De novo protein design: fully automated sequence selection," Science, 278, pp. 82-87 (1997).
Dal Paz et al., "The identification of a novel natural activator of p300 histone acetyltransferase provides new insights into the modulation mechanism of this enzyme," ChemBioChem, 11(6), pp. 818-827 (2009).
Dallas et al., "RNAi: a novel antisense technology and its therapeutic potential," Med. Sci. Monit., 12(4), pp. RA67-RA74 (2006).

Damia, G. et al., "Contemporary pre-clinical development of anticancer agents—What are the optimal preclinical models?", European Journal of Cancer, 45:2768-2781, available online Sep. 15, 2009 (14 pages).
Dash et al., "Injection of the cAMP-responsive element into the nucleus of Aplysia sensory neurons blocks long-term facilitation," Nature, 345(6277), pp. 718-721 (1990).
De La Cruz et al., "Do protein motifs read the histone code?" Bioessays, 27(2), pp. 164-175 (2005).
De Ruijter et al., "Histone deacetylases (HDACs): characterization of the classical HDAC family," Biochem. J., 370(pt. 3), pp. 737-749 (2003).
Devlin et al., "Random Peptide Libraries: a Source of Specific Protein Binding Molecules," Science, 249, pp. 404-406 (1990).
Di Rosa et al., "Calpain inhibitors: A Treatment for Alzheimer's Disease," Journal of Molecular Neuroscience, 19, pp. 135-141 (2002).
Dineley et al., "Accelerated plaque accumulation, associative learning deficits, and up-regulation of α7 nicotinic receptor protein in transgenic mice co-expressing mutant human presenilin 1 and amyloid precursor proteins," J. Biol. Chem., 277(25), pp. 22768-22780 (2002).
Dineley et al., "β-Amyloid activates the mitogen-activated protein kinase cascade via hippocampal α7 nicotinic acetylcholine receptors: in vitro and in vivo mechanisms related to alzheimer's disease," J. Neurosci., 21(12), pp. 4125-4133 (2001).
Duff et al., "Increased amyloid-β42(43) in brains of mice expressing mutant presenilin 1," Nature, 383, pp. 710-713 (1996).
Elbashir et al., "Duplexes of 21-nucleotide RNAs mediate RNA interference in cultured mammalian cells," Nature, 411, pp. 494-498 (2001).
Emborg, "Evaluation of animal models of Parkinson's disease for neuroprotective strategies," Journal of Neuroscience Methods, 139, pp. 121-143 (2004).
Erb et al., "Recursive deconvolution of combinatorial chemical libraries," Proc. Natl. Acad. Sci. USA, 91, pp. 11422-11426 (1994).
European Search Report for European Patent Application No. 11850544.5, dated Jul. 29, 2014 (8 pages).
Eyupoglu et al., "Experimental therapy of malignant gliomas using the inhibitor of histone deacetylase MS-275," Mol. Cancer Ther., 5(5), pp. 1248-1255 (2006).
Fischer et al., "Recovery of learning and memory is associated with chromatin remodeling," Nature, 447, pp. 178-182 (2007).
Fitzjohn et al., "Age-related impairment of synaptic transmission but normal long-term potentiation in transgenic mice that overexpress the human APP695SWE mutant form of amyloid precursor protein," J. Neurosci., 21(13), pp. 4691-4698 (2001).
Fleming et al., "Early and progressive sensorimotor anomalies in mice overexpressing wild-type human α-synuclein," J. Neurosci., 24(42), pp. 9434-9440 (2004).
Fodor et al., "Light-directed, spatially addressable parallel chemical synthesis," Science, 251, pp. 767-773 (1991).
Francis et al., "CREB-binding protein activation by presenilin 1 but not by its M146L mutant," Neuroreport, 17, pp. 917-921 (2006).
Francis et al., "Dysregulation of histone acetylation in the APP/PS1 mouse model of alzheimer's disease," J. Alzheimer's Dis., 18(1), pp. 131-139 (2009).
Francis et al., "p300 activation by Presenilin 1 but not by its M146L mutant," Neuroscience Letters, 413, pp. 137-140 (2007).
Freir et al., "Blockade of long-term potentiation by β-amyloid peptides in the CA! region of the rat hippocampus in vivo," J. Neurophysiol., 85(2), pp. 708-713 (2001).
Gallop et al., "Applications of Combinatorial Technologies to Drug Discovery. 1. Background and Peptide Combinatorial Libraries," J. Med. Chem., 37(9), pp. 1233-1251 (1994).
Garcia et al., "Chemical derivatization of histones for facilitated analysis by mass spectrometry," Nat. Protoc., 2(4), pp. 933-938 (2007).
Gong et al., "Persistent improvement in synaptic and cognitive functions in an Alzheimer mouse model after rolipram treatment," J. Clin. Invest., 114, pp. 1624-1634 (2004).

(56) References Cited

OTHER PUBLICATIONS

Gong et al., "Ubiquitin Hydrolase Uch-L1 Rescues β-Amyloid-Induced Decreases in Synaptic Function and Contextual Memory," Cell, 126(4), pp. 775-788 (2006).

Grammaticakis, P. "Remarques sur la préparation et l'absorption dans l'ultraviolet moyen de quelques diméthoxy-2.6 benzoylarylamines", Comptes Rendus de l'Academie des scienes numerises sur le site de la Bibliotheque nationale de France: Série C—Sciences Chimiques, 267:152-155, Jul. 8, 1968 (4 pages).

Green et al., "Nicotinamide restores cognition in alzheimer's disease transgenic mice via a mechanism involving sirtuin inhibition and selective reduction of Thr231-phosphotau," J. Neurosci., 28, pp. 11500-11510 (2008).

Gregoretti et al., "Molecular evolution of the histone deacetylase family: functional implications of phylogenetic analysis," J. Mol. Biol., 338(1), pp. 17-31 (2004).

Guan et al., "HDAC2 negatively regulates memory formation and synaptic plasticity," Nature, 459(7243), pp. 55-60 (2009).

Guo et al., "Epigenetic mechanisms of amyloid-β production in anisomycin-treated SH-SY5Y cells," Neuroscience, 194, pp. 272-281 (Oct. 2011).

Gwack et al., "CREB-Binding Protein and Histone Deacetylase Regulate the Transcriptional Activity of Kaposi's Sarcoma-Associated Herpesvirus Open Reading Frame 50," Journal of Virology, 75(4, pp. 1909-1917 (Feb. 2001).

Haas et al., "Inducible nitric oxide synthase and argininosuccinate synthetase: co-induction in brain tissue of patients with Alzheimer's dementia and following stimulation with β-amyloid 1-42 in vitro," Neuroscience Letters, 322, pp. 121-125 (Apr. 2002).

Hansen, "Towards selective Kir6.2/SUR1 potassium channel openers, medicinal chemistry and therapeutic perspectives," Curr. Med. Chem, 2006, vol. 13(4, pp. 361-376.

He, Huan, et al., "Copper-catalyzed N-arylation of sulfonamides with aryl bromides and iodides using microwave heating", Tetrahedron Letters, 2003, vol. 44, pp. 3385-3386.

Hockly et al., "Suberoylanilide hydroxamic acid, a histone deacetylase inhibitor, ameliorates motor deficits in a mouse model of Huntington's disease," Proc. Natl. Acad. Sci. USA, 100(4), pp. 2041-2046 (Feb. 2003).

Hodgson et al., "A YAC Mouse Model for Huntington's disease with Full-Length Mutant Huntingtin, Cytoplasmic Toxicity, and Selective Striatal Neurodegeneration," Neuron, 23, pp. 181-192 (1999).

Hodgson et al., "ADMET—turning chemicals into drugs: Rapidly resolving the pharmacokinetic and toxicological properties of drug candidates remains a key challenge for drug developers," Nature Biotechnology, 19(8), pp. 722-726 (2001).

Holcomb et al., "Accelerated Alzheimer-type phenotype in transgenic mice carrying both mutant amyloid precursor protein and presenilin 1 transgenes," Nat. Med., 4, pp. 97-100 (1998).

Hoshino, I. et al., "Recent Advances in Histone Deacetylase Targeted Cancer Therapy", Surg Today, 40:809-815, 2010 (7 pages).

Hosseinzadeh, Rahman, et al., "Copper-catalyzed arylation of phenylurea using KF/Al₂O₃", Tetrahedron Letters, 2008, vol. 49, pp. 840-843.

Houghten et al., "Generation and use of synthetic peptide combinatorial libraries for basic research and drug discovery," Nature, 354, pp. 84-86 (1991).

Houghten et al., "The use of synthetic peptide combinatorial libraries for the identification of bioactive peptides," Biotechniques, 13, pp. 412-421 (1992).

Hsia et al., "Plaque-independent disruption of neural circuits in alzheimer's disease mouse models," Proc. Natl. Acad. Sci. USA, 96(6), pp. 3228-3233 (1999).

Hsiao et al., "Correlative Memory Deficits, Aβ Elevation, and Amyloid Plaques in Transgenic Mice," Science, 274, pp. 99-102 (1996).

Hudson, "Recombinant antibody fragments," Curr. Opin. Biotechnol., 9, pp. 395-402 (1998).

Humm, A.W. et al., "Entwicklung potentieller Antiandrogene: N-(4-Niro-3-trifluormethylphenyl)-cyclohexanoylamide und -benzamide, N-(3,4-Dichlorphenyl)- und N-(3,4,5-Trichlorphenyl)-benzamide", Arch. Pharm. (Weinheim), 321:419-422, 1988 (6 pages)—English Abstract.

Hwang et al., "3,4-Dihydroxyphenylalanine reverses the motor deficits in Pitx3-deficient aphakia mice: behavioral characterization of a novel genetic model of Parkinson's disease," J. Neurosci., 25(8), pp. 2132-2137 (2005).

Ienascu. I. et al., "The Antimicrobial Activity and Quantitative Structure—Biological Activity Relationships Evaluation of Some Novel 2-Hydroxbenzamide Derivatives", Revista de Chimie, 59, pp. 247-250 (2008).

International Search Report and Written Opinion as issued by the U.S. Patent and Trademark Office as International Searching Authority in International Application No. PCT/US12/41907 dated Sep. 21, 2012 (8 pages).

International Search Report and Written Opinion as issued by the U.S. Patent and Trademark Office as International Searching Authority, for International Application No. PCT/US11/066851 dated May 1, 2012 (7 pages).

International Search Report and Written Opinion issued by the U.S. Patent and Trademark Office as International Searching Authority in PCT/US2010/059925, dated May 9, 2011 (8 pages).

International Search Report and Written Opinion issued by the U.S.Patent and Trademark Office as Searching Authority in International Application No. PCT/US2010/059925, dated May 9, 2011 (8 pages).

Itoh et al., "Impairments of long-term potentiation in hippocampal slices of β-amyloid-infused rates," European Journal of Pharmacology, 382, pp. 167-175 (1999).

Itoh, K. et al., "Epigenetic Dysregulation in Neurodevelopmental and Neurodegenerative Diseases", J. Kyoto Pref. Univ. Med., 118(8), pp. 523-531 (2009).

Janeway et al., "Immunobiology: the immune system in health and disease," Garland Publishing, New York, 5th Edition, 13 pages (2001).

Japanese Office Action issued in Japanese Patent Application No. 2017-176487, dated Oct. 1, 2018 (11 pages)—English Translation.

Japanese Office Action issued in Japanese Patent Application No. 2017-176487, dated Aug. 8, 2019 (6 pages)—English Translation.

Japanese Office Action dated Sep. 16, 2015 in corresponding Japanese Patent Application No. 2013-546423 (9 pages).

Jayawickreme et al., "Creation and functional screening of a multi-use peptide library," Proc. Natl. Acad. Sci. USA, 91, pp. 1614-1618 (1994).

Johnson, Ji et al., "Relationships between drug activity in NCI preclinical in vitro and in vivo models and early clinical trials", British Journal of Cancer, 84(10):1424-1431, 2001 (8 pages).

Jolas et al., "Long-Term Potentiation Is Increased in the CA1 Area of the Hippocampus of APP swe/ind CRND8 Mice," Neurobiology of Disease, 11(3), pp. 394-409 (2002).

Kalota et al., "Progress in the Development of Nucleic Acid Therapeutics," Handbook Exp. Pharmacol., 173, pp. 173-196 (2006).

Kamal et al., "Kinesin-mediated axonal transport of a membrane compartment containing β-secretase and presenilin-1 requires APP," Nature, 414, pp. 643-648 (2001).

Kandel, "The molecular biology of memory storage: a dialog between genes and synapses," Biosci. Rep., 21(5), pp. 565-611 (2001).

Kang et al., "The precursor of Alzheimer's disease amyloid A4 protein resembles a cell-surface receptor," Nature, 325, pp. 733-736 (1987).

Kay et al., "An M13 phage library displaying random 38-amino-acid peptides as a source of novel sequences with affinity to selected targets," Gene, 128, pp. 59-65 (1993).

Kazantsev et al., "Therapeutic application of histone deacetylase inhibitors for central nervous system disorders," Nat. Rev. Drug Discov., 7, pp. 854-868 (2008).

Kemenes et al., "Critical Time-Window for NO-cGMP-Dependent Long-Term Memory Formation after One-Trial Appetitive Conditioning," J. Neurosci., 22(4), pp. 1414-1425 (2002).

Kim et al., "SIRT1 deacetylase protects against neurodegeneration in models for Alzheimer's disease and amyotrophic lateral sclerosis," The EMBO Journal, 26, pp. 3169-3179 (2007).

(56) References Cited

OTHER PUBLICATIONS

Kim et al., "Use-dependent effects of amyloidogenic fragments of β-amyloid precursor protein on synaptic plasticity in rat hippocampus in vivo," J. Neurosci., 21(4), pp. 1327-1333 (2001).
Kimura et al., "A Decade of Histone Acetylation: Marking Eukaryotic Chromosomes with Specific Codes," Journal of Biochemistry, 138(6), pp. 647-662 (2005).
Kingsbury, et al., "Synthesis of Water-Soluble (Aminoaklyl)camptothecin Analogues: Inhibition of Topoisomerase I and Antitumor Activity", J. Med. Chem., 34:98-107, 1991 (10 pages).
Kornberg et al., "Twenty-Five years of the nucleosome, fundamental particle of the eukaryote chromosome," Cell, 98(3), pp. 285-294 (1999).
Korzus et al., "CBP Histone Acetyltransferase Activity Is a Critical Component of Memory Consolidation," Neuron, 42(6), pp. 961-972 (2004).
Kowalska et al., "Beta-amyloid protein induces platelet aggregation and supports platelet adhesion," Biochem. Biophys. Res. Commun., 205(3), pp. 1829-1835 (1994).
Kuehne et al., "Reduction of amides and lactams to amines by reactions with phosphorus oxychloride and sodium borohydride," J. Org. Chem., 42, pp. 2082-2087 (1977).
Kurt et al., "Neurodegenerative changes associated with β-amyloid deposition in the brains of mice carrying mutant amyloid precursor protein and mutant presenilin-1 transgenes," Exp. Neurol., 171(1), pp. 59-71 (2001).
Lam et al., "A new type of synthetic peptide library for identifying ligand-binding activity," Nature, 354, pp. 82-84 (1991).
Lambert et al., "Diffusible, nonfibrillar ligands derived from Aβ1-42 are potent central nervous system neurotoxins," Proc. Natl. Acad. Sci. USA, 95, pp. 6448-6453 (1998).
Lander et al., "Initial sequencing and analysis of the human genome," Nature, 409(6822), pp. 860-921 (2001).
Lane et al., "Animal models of Parkinson's disease and L-dopa induced dyskinesia: how close are we to the clinic?" Psychopharmacology, 199, pp. 303-312 (2008).
Lane et al., "Histone deacetylase inhibitors in cancer therapy," J. Clin. Oncol., 27(32), pp. 5459-5468 (2009).
Langley et al., "Remodeling Chromatin and Stress Resistance in the Central Nervous System: Histone Deacetylase Inhibitors as Novel and Broadly Effective Neuroprotective Agents," Current Drug Targets: CNS & Neurological Disorders, 4(1), pp. 41-50 (2005).
Larson et al., "Alterations in synaptic transmission and long-term potentiation in hippocampal slices from young and aged PDAPP mice," Brain Research, 840(1), pp. 23-35 (1999).
Lee et al., "Histone acetyltransferase complexes: one size doesn't fit all," Nat. Rev. Mol. Cell Biol., 8(4), pp. 284-295 (2007).
Lenstra et al., "Isolation of sequences from a random-sequence expression library that mimic viral epitopes," J. Immunol. Meth., 152, pp. 149-157 (1992).
Levenson et al., "Epigenetic mechanism in memory formation," Nature Reviews, 6(2), pp. 108-118 (2005).
Levenson et al., "Regulation of histone acetylation during memory formation in the hippocampus," J. Biol. Chem., 279, pp. 40545-40559 (2004).
Levy-Lahad et al., "A Familial Alzheimer's Disease Locus on Chromosome 1," Science, 269, pp. 970-973 (1995).
Lodish et al., "Molecular Cell Biology," 4 ed., New York: W.H. Freeman Company, 2000 (24 pages).
Lu et al., "Chromatin Remodeling of the Kaposi's Sarcoma-Associated Herpesvirus ORF50 Promoter Correlates with Reactivation from Latency," Journal of Virology, 77(21), pp. 11425-11435 (2003).
Lu et al., "Nitric oxide signaling contributes to late-phase LTP and CREB phosphorylation in the hippocampus," J. Neurosci., 19(23), pp. 10250-10261 (1999).
Lutzelberger et al., "Strategies to identify potential therapeutic target sites in RNA," Handbook Exp. Pharmacol., 173, pp. 243-259 (2006).

Mahmoud et al., "Synthesis of novel indeno[1,2-c]isoquinoline derivatives," Synthetic Communications, 40, pp. 666-676 (2010).
Malm et al., "β-Amyloid infusion results in delayed and age-dependent learning deficits without role of inflammation or β-amyloid deposits," Proc. Natl. Acad. Sci. USA, 103, pp. 8852-8857 (2006).
Manh et al., "Amyloid β-peptide induces nitric oxide production in rat hippocampus: association with cholinergic dysfunction and amelioration by inducible nitric oxide synthase inhibitors," FASEB J., 15(8), pp. 1407-1409 (2001).
Mannhold, "Structure-activity relationships of KATP channel openers," Curr. Top. Med. Chem., 6(10), pp. 1031-1047 (2006).
Mantelingu, K., et al., "Activation of p300 Histone Acetyltransferase by Small Molecules Altering Enzyme Structure: Probed by Surface-Enhanced Raman Spectroscopy", J. Phys. Chem. B, 2007, vol. 111, pp. 4527-4534.
Mao et al., "GCN5 is a required cofactor for a ubiquitin ligase that targets NF-κB/RelA," Genes Dev., 23(7), pp. 849-861 (2009).
Marmonstein et al., "Histone acetyltransferases: function, structure, and catalysis," Curr. Opin. Genet. Develop., 11, pp. 155-161 (2001).
Marmorstein, "Structure of histone acetyltransferases," J. Molec. Biol., 311, pp. 433-444 (2001).
Marmorstein, R. et al., "Histone Modifying Enzymes: Structues, Mechanisms, and Specificities", Author Manuscript, Biochim Biophys Acta., 1789(1):58-68, Jan. 2009 (30 pages).
Masliah, "Mechanisms of synaptic dysfunction in Alzheimer's disease," Histology and Histopathology, 10, pp. 509-519 (1995).
Mattheakis et al., "An in vitro polysome display system for identifying ligands from very large peptide libraries," Proc. Natl. Acad. Sci. USA, 91, pp. 9022-9026 (1994).
Mattson et al., "Secreted form of amyloid precursor protein enhances basal glucose and glutamate transport and protects against oxidative impairment of glucose and glutamate transport in synaptosomes by a cyclic GMP-mediated mechanism," J. Neurochem., 73(2), pp. 532-537 (1999).
Maurice et al., "Altered memory capacities and response to stress in p300/CBP-associated factor (PCAF) histone acetylase knockout mice," Neuropsychopharmacology, 33(7), pp. 1584-1602 (2008).
Maynard et al., "Antibody Engineering," Ann. Rev. Biomed. Eng., 2, pp. 339-376 (2008).
McCann, "The nitric oxide hypothesis of brain aging," Exp. Gerontol., 32(4-5), pp. 431-440 (1997).
McCarty, "Vascular nitric oxide may lessen alzheimer's risk," Med. Hypotheses, 51(6), pp. 465-476 (1998).
McConnell et al., "The Cytosensor Microphysiometer: Biological Applications of Silicon Technology," Science, 257, pp. 1906-1912 (1992).
McGowan et al., "Amyloid phenotype characterization of transgenic mice overexpressing both mutant amyloid precursor protein and mutant presenilin 1 transgenes," Neurobiol. Dis., 6(4), pp. 231-244 (1999).
Medynski, "Synthetic peptide combinatorial libraries," BioTechnology, 12, pp. 709-710 (1994).
Melgar-Fernandez et al., "Synthesis of novel derivatives of (1S,4S)-2,5-diazabicyclo[2.2.1]heptane and their evaluation as potential ligands in asymmetric catalysis," Eur. J. Org. Chem., pp. 655-672 (2008).
Meredith et al., "Animal Models of Parkinson's Disease Progression," 21 pages, Author manuscript published in final edited form as: Acta Neuropathology, 115(4), pp. 385-398, (2008).
Middleton et al., "Designing rapid onset selective serotonin re-uptake inhibitors. 2: Structure-activity relationships of substituted (aryl)benzylamines," Bioorg. Med. Chem. Lett., 18, pp. 4018-4021 (2008).
Moechars et al., "Early phenotypic changes in transgenic mice that overexpress different mutants of amyloid precursor protein in brain," J. Biol. Chem., 274(10), pp. 6483-6492 (1999).
Mondal et al., "Facile Synthesis of 1,3,7-Trihydroxyxanthone and Its Regioselective Coupling Reactions with Prenal: Simple and Efficient Access to Osajaxanthone and Nigrolineaxanthone F," The Journal of Organic Chemistry, 71(13), pp. 4992-4995 (2006).
Monsonego et al., "Microglia-Mediated Nitric Oxide Cytotoxicity of T Cells Following Amyloid β-Peptide Presentation to Th1 Cells," Journal of Immunology, 171(5), pp. 2216-2224 (2003).

(56) References Cited

OTHER PUBLICATIONS

Montarolo et al., "A critical period for macromolecular synthesis in long-term heterosynaptic facilitation in Aplysia," Science, 234(4781), pp. 1249-1254 (1986).
Mosbach, "Molecular Imprinting," Trends Biochem. Sci., 19(9), pp. 9-14 (1994).
Movassaghi, Mohammad, et al., "Single-Step Synthesis of Pyrimidine Derivatives", J. Am. Chem. Soc., 2006, vol. 128, pp. 14254-14255.
Nakagami et al., "A novel β-sheet breaker, RS-0406, reverses amyloid β-induced cytotoxicity and impairment of long-term potentiation in vitro," British Journal of Pharmacology, 137, pp. 676-682 (2002).
Nalbantoglu et al., "Impaired learning and LTP in mice expressing the carboxy terminus of the Alzheimer amyloid precursor protein," Nature, 387, pp. 500-505 (1997).
Narayanan et al., "Structure and Function of PA4872 from Pseudomonas aeruginosa, A Novel Class of Oxaloacetate Decarboxylase from the PEP Mutase/Isocitrate Lyase Superfamily," Biochemistry, 47, pp. 167-182 (2008).
Nebbioso, A. et al., "Chapter 3: Histone deacetylase inhibitors: Use and mechanism(s) of anticancer activity", in Histone Deacetylase Inhibitors in Medicine, El-Osta and Karagiannis, Eds., Transworld Research Network, pp. 41-74, 2010 (36 pages).
Neipp, "The effect of propylene glycol and other alcohols on the action of antibacterial substances," Schweizerische Zeitschrift fuer Allgemeine Pathologie und Bakteriologie, 20, pp. 150-160 (1957).
Ng et al., "Histone deacetylases: silencers for hire," Trends Biochem. Sci., 25(3), pp. 121-126 (2000).
Ninan et al., "Presynaptic CaMKII Is Necessary for Synaptic Plasticity in Cultured Hippocampal Neurons," Neuron, 42, pp. 129-141 (2004).
Ocana, A. et al., "Preclinical development of molecular-targeted agents for cancer", Nat. Rev. Clin. Oncol. 8:200-209, Apr. 2011, published online Dec. 7, 2010 (10 pages).
Ohlmeyer et al., "Complex synthetic chemical libraries indexed with molecular tags," Proc. Natl. Acad. Sci. USA, 90, pp. 10922-10926 (1993).
Ostresh et al., ""Libraries from libraries": chemical transformation of combinatorial libraries to extend the range and repertoire of chemical diversity," Proc. Natl. Acad. Sci. USA, 91, pp. 11138-11142 (1994).
Paakkari et al., "Nitric oxide in the central nervous system," Ann. Med., 27(3), pp. 369-377 (1995).
Patani, et al., "Bioisosterism: A Ratioinal Approach in Drug Design", Chem. Rev., 96:3147-3176, 1996 (30 pages).
Paxinos et al., "The mouse brain in stereotaxic coordinates," 2nd ed., New York: Academic Press, 4 pages (2001).
Peleg et al., "Altered histone acetylation is associated with age-dependent memory impairment in mice," Science, 328(5979), pp. 753-756 (2010).
Peterson et al., "Histones and histone modifications," Curr. Biol., 14(14), pp. R546-R551 (2004).
Phillips et al., "Differential Contribution of Amygdala and Hippocampus to Cued and Contextual Fear Conditioning," Behav. Neurosci., 106(2), pp. 274-285 (1992).
Pittenger et al., "In search of general mechanisms for long-lasting plasticity: Aplysia and the hippocampus," Phil. Trans. R. Soc. Lond. B, 358, pp. 757-763 (2003).
Prickaerts et al., "cGMP but not cAMP, in rat hippocampus is involved in early stages of object memory consolidation," Eur. J. Pharmacol., 436(1-2), pp. 83-87 (2003).
Puzzo et al., "Amyloid-β peptide inhibits activation of the nitric oxide/cGMP/cAMP-responsive element-binding protein pathway during hippocampal synaptic plasticity," J. Neurosci., 25(29), pp. 6887-6897 (2005).
Puzzo et al., "Picomolar amyloid-β positively modulates synaptic plasticity and memory in hippocampus," J. Neurosci., 28(53), pp. 14537-14545 (2008).
Puzzo et al., "Sildenafil rescues synaptic and cognitive impairment in a mouse model of alzheimer's disease," Soc. Neurosci. Abstr., Atlanta, 1 page (2006).
Rajan et al., "Loss of the putative catalytic domain of HDAC4 leads to reduced thermal nociception and seizures while allowing normal bone development," PLoS One, 4(8), e6612, 11 pages (2009).
Rakyan et al., "The marks, mechanism and memory of epigenetic states in mammals," Biochem. J., 356, pp. 1-10 (2001).
Renaud et al., "Estrogen Receptor Modulators: Identification and Structure-Activity Relationships of Potent ERα-selective tetrahydroisoquinoline ligands," Journal of Medicinal Chemistry, American Chemical Society, 46, pp. 2945-2957 (2003).
Roelfsema et al., "Rubinstein-Taybi syndrome: clinical and molecular overview," Expert Rev. Mol. Med., 9(23), pp. 1-16 (2007).
Rouaux et al., "Critical loss of CBP/p300 histone acetylase activity by caspase-6 during neurodegeneration," The EMBO Journal, 22(24), pp. 6537-6549 (2003).
Salmon et al., "Discovery of biologically active peptides in random libraries: solution-phase testing after staged orthogonal release from resin beads," Proc. Natl. Acad. Sci. USA, 90, pp. 11708-11712 (1993).
Sant'angelo et al., "Usefulness of behavioral and electrophysiological studies in transgenic models of alzheimer's disease," Neurochem. Res., 28(7), pp. 1009-1015 (2003).
Saura et al., "Loss of presenilin function causes impairments of memory and synaptic plasticity followed by age-dependent neurodegeneration," Neuron, 42, pp. 23-36 (2004).
Sbardella et al., "Identification of long chain alkylidenemalonates as novel small molecule modulators of histone acetyltransferases," Bioorg. Med. Chem. Lett., 18(9), pp. 2788-2792 (2008).
Schenk et al., "Immunization with amyloid-β attenuates Alzheimer-disease-like pathology in the PDAPP mouse," Nature, 400, pp. 173-177 (1999).
Schulteiss et al., "Central effects of sildenafil (Viagra) on auditory selective attention and verbal recognition memory in humans: a study with event-related brain potentials," World J. Urol., 19(1), pp. 46-50 (2001).
Scott et al., "Searching for Peptide Ligands with an Epitope Library," Science, 249, pp. 386-390 (1990).
Selig et al., "Examination of the role of cGMP in long-term potentiation in the CA1 region of the hippocampus," Learn Mem., 3(1), pp. 42-48 (1996).
Selkoe, "Alzheimer's disease is a synaptic failure," Science, 298(5594), pp. 789-791 (2002).
Sharma, S.V. et al., "Cell line-based platforms to evaluate the therapeutic efficacy of candidate anticancer agents", Nature Reviews: Cancer, 10:241-253, Apr. 2010 (13 pages).
Shea, "Molecular imprinting of synthetic network polymers: the de novo synthesis of macromolecular binding and catalytic sites," Trip, 2(5), pp. 166-173 (1994).
Sherrington et al., "Cloning of a gene bearing missense mutations in early-onset familial Alzheimer's disease," Nature, 375, pp. 754-760 (1995).
Simon et al., "Peptoids: A modular approach to drug discovery," Proc. Natl. Acad. Sci. USA, 89, pp. 9367-9371 (1992).
Sipos et al., "β-amyloid pathology in the entorhinal cortex of rats induces memory deficits: implications for Alzheimer's disease," Neuroscience, 147, pp. 28-36 (2007).
Sjolander et al., "Integrated Fluid Handling System for Biomolecular Interaction Analysis," Anal. Chem., 63, pp. 2338-2345 (1991).
Solomons, Organic Chemistry, Sixth Edition, John Wiley & Sons. Inc., New York, pp. 81-82, 1996 (3 pages).
Souto et al., "New Anacardic Acid-Inspired Benzamides: Histone Lysine Acetyltransferase Activators," ChemMedChem, 5, 1530-1540 (2010).
Souto, et al, "Synthesis of Benzamides Related to Anacardic Acid and Their Histone Acetyltransferase (HAT) Inhibitory Activities", Chem Med Cem, 3:1435-1442, 2008 (8 pages).
Sperling et al., "fMRI studies of associative encoding in young and elderly controls and mild alzheimer's disease," J. Neurol. Neurosurg. Psychiatry, 74(1), pp. 44-50 (2003).

(56) References Cited

OTHER PUBLICATIONS

Stephan et al., "Generation of Aggregated β-Amyloid in the Rat Hippocampus Impairs Synaptic Transmission and Plasticity and Causes Memory Deficits," Journal of Neuroscience, 21(15), pp. 5703-5714 (2001).
Stine et al., "In vitro characterization of conditions for amyloid-β peptide oligomerization and fibrillogenesis," J. Biol. Chem., 278, pp. 11612-11622 (2003).
Strahl et al., "The language of covalent histone modifications," Nature, 403(6765), pp. 41-45 (2000).
Suhara et al., "Aβ42 generation is toxic to endothelial cells and inhibits eNOS function through an Akt/GSK-3β signaling-dependent mechanism," Neurobiol. Aging, 24(3), pp. 437-451 (2003).
Sweatt, "Epigenetics and Cognitive Aging," Science, 328, pp. 701-702 (2010).
Takahashi et al., "Impaired proteolytic processing of Presenilin-1 in chromosome 14-linked familial Alzheimer's disease patient lymphocytes," Neuroscience Letters, 260, pp. 121-124 (1999).
Tanzi, "The synaptic Aβ hypothesis of Alzheimer disease," Nature Neuroscience, 8(8), pp. 977-979 (2005).
Thatcher et al., "Nitric oxide mimetic molecules as therapeutic agents in alzheimer's disease," Curr. Alzheimer Res., 2(2), pp. 171-182 (2005).
Thompson, "Optimization of metabolic stability as a goal of modern drug design," Med. Res. Rev., 21(5), pp. 412-449 (2001).
Tran et al., "Amyloid β-peptide induces nitric oxide production in rat hippocampus: association with cholinergic dysfunction and amelioration by inducible nitric oxide synthase inhibitors," The FASEB Journal, 20 pages (2001).
Trinchese et al., "Progressive Age-Related Development of Alzheimer-like Pathology in APP/PS1 Mice," American Neurological Association, 55(6), pp. 801-814 (2004).
Troy et al., "Caspase-2 Mediates Neuronal Cell Death Induced by β-Amyloid," Journal of Neuroscience, 20(4), pp. 1386-1392 (2000).
Tsuritani et al., "Efficient synthesis of 1,4-diaryl-5-methyl-1,2,3-triazole, a potential mGluR1 antagonist, and the risk assessment study of arylazides," Organic Process Research & Development, 13(6), pp. 1407-1412 (2009).
Van Staveren et al., "mRNA expression patterns of the cGMP-hydrolyzing phosphodiesterases types 2, 5, and 9 during development of the rat brain," J. Comp. Neurol., 467(4), pp. 566-580 (2003).
Van Staveren et al., "Species differences in the localization of cGMP-producing and NO-responsive elements in the mouse and rat hippocampus using cGMP immunocytochemistry," Eur. J. Neurosci., 19(8), pp. 2155-2168 (2004).
Vecsey et al., "Histone deacetylase inhibitors enhance memory and synaptic plasticity via CREB:CBP-dependent transcriptional activation," J. Neurosci., 27(23), pp. 6128-6140 (2007).
Venkatesh, S. et al., "Role of the Development Scientist in Compound Lead Selection and Optimization", J. Pharm Sci, 89(2):145-154, Feb. 2000 (10 pages).
Venturini et al., "β-Amyloid inhibits NOS activity by subtracting NADPH availability," FASEB J., 16(14), pp. 1970-1972 (2002).
Vitolo et al., "Amyloid β-peptide inhibition of the PKA/CREB pathway and long-term potentiation: reversibility by drugs that enhance cAMP signaling," Proc. Natl. Acad. Sci. USA, 99(20), pp. 13217-13221 (2002).
Walsh et al., "Certain Inhibitors of Synthetic Amyloid β-Peptide (Aβ) Fibrillogenesis Block Oligomerization of Natural Aβ and Thereby Rescue Long-Term Potentiation," The Journal of Neuroscience, 25(10), pp. 2455-2462 (2005).
Walsh et al., "Naturally secreted oligomers of amyloid β protein potently inhibit hippocampal long-term potentiation in vivo," Nature, 416(6880), pp. 535-539 (2002).
Wang et al., "ATP-Sensitive potassium channel openers and 2,3-dimethyl-2-butylamine derivatives," Curr. Med. Chem., 14(2), pp. 133-155 (2007).
Wang et al., "β-Amyloid-mediated inhibition of NMDA receptor-dependent long-term potentiation induction involves activation of microglia and stimulation of inducible nitric oxide synthase and superoxide," J. Neurosci., 24(27), pp. 6049-6056 (2004).
Werner et al., "Joining high-throughput technology with in silico modelling advances genome-wide screening towards targeted discovery," Brief Funct. Genomic Proteomic, 5(1), pp. 32-36 (2006).
Wirtz-Brugger et al., "Guanosine 3',5'-cyclic monophosphate mediated inhibition of cell death induced by nerve growth factor withdrawal and β-amyloid: protective effects of propentofylline," Neuroscience, 99(4), pp. 737-750 (2000).
Wong et al., "Advanced glycation endproducts co-localize with inducible nitric oxide synthase in Alzheimer's disease," Brain Research, 920, pp. 32-40 (2001).
Wu et al., "β-Amyloid-(1-40) increases long-term potentiation in rat hippocampus in vitro," European Journal of Pharmacology, 284, pp. R1-R3 (1995).
Wulff, "Molecular recognition in polymers prepared by imprinting with templates," Ford, ACS Symposium Series No. 308, American Chemical Society, pp. 186-230 (1986).
Xie et al., "Peroxynitrite Mediates Neurotoxicity of Amyloid β-Peptide 1-42- and Lipopolysaccharide-Activated Microglia," The Journal of Neuroscience, 22(9), pp. 3484-3492 (2002).
Yang et al., "HATs and HDACs: from structure, function and regulation to novel strategies for therapy and prevention," Oncogene, 26(37), pp. 5310-5318 (2007).
Yin et al., "Induction of a dominant negative CREB transgene specifically blocks long-term memory in *Drosophila*," Cell, 79(1), pp. 49-58 (1994).
Consiglio, G. et al., "Linear Free Energy ortho-Correlations in the Thiophen Series. Part 7. Kinetics of the Reaction of Some 3-Substituted 2-Thenoyl Chlorides with Aniline in Benzene", Journal of the Chemical Society, Perkin Transactions 2: Physical Organic Chemistry, No. 8, pp. 1153-1155, Jan. 1, 1980 (3 pages).
Extended European Search Report issued in European Patent Application No. 19205945.9, dated Feb. 19, 2020 (8 pages).

\* cited by examiner

A
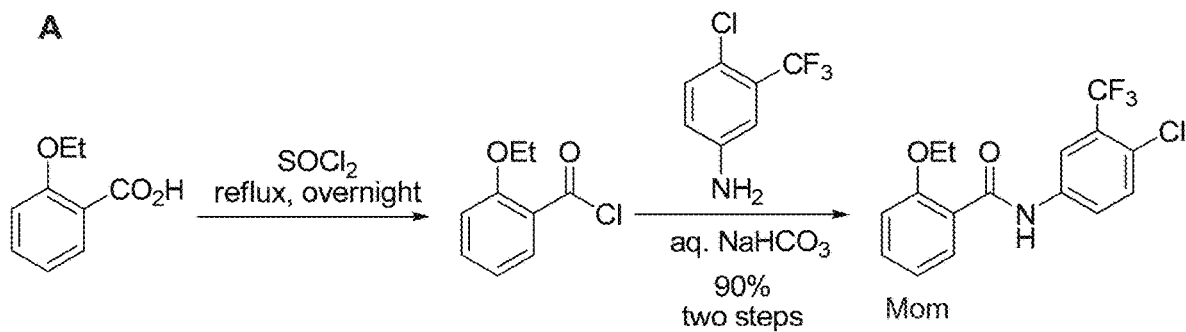
B
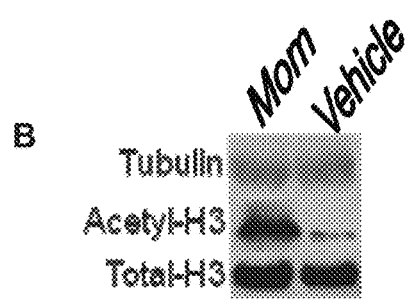
FIG. 26
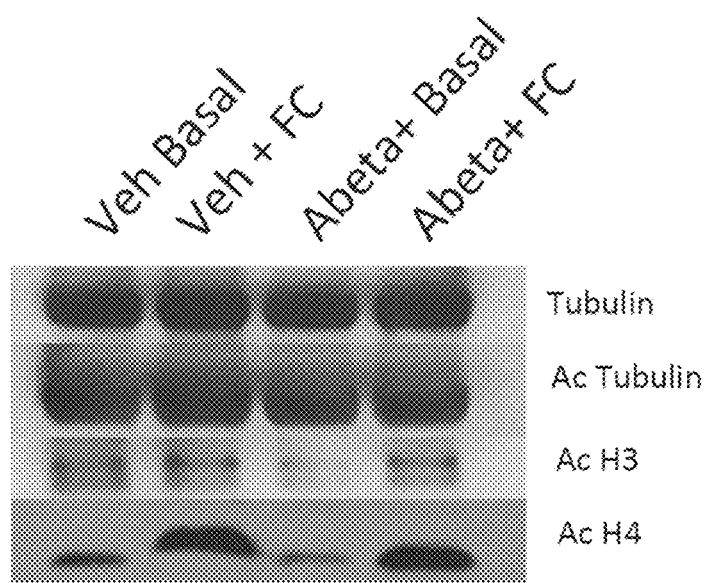
FIG. 27

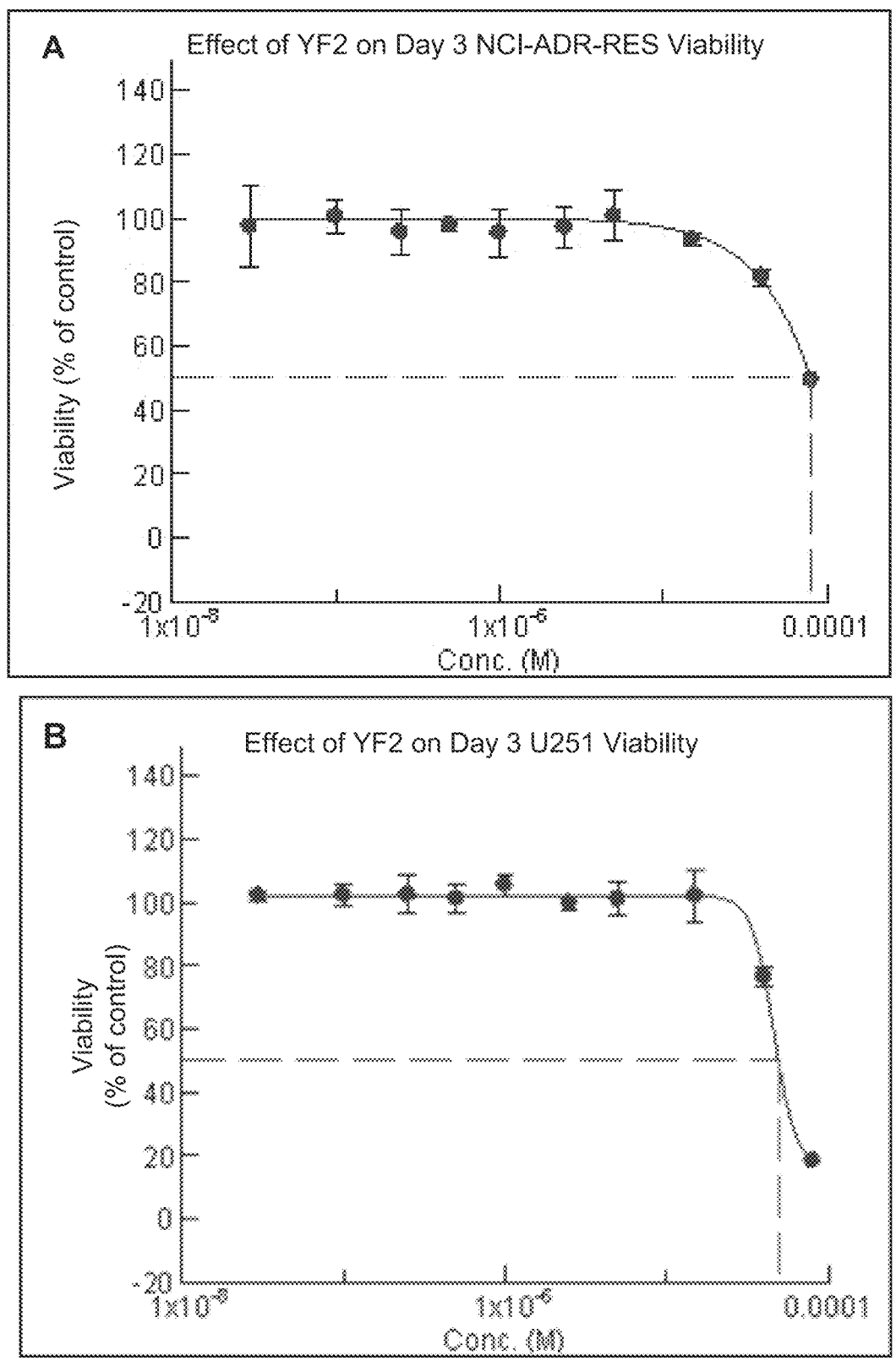
Figs. 31A-B

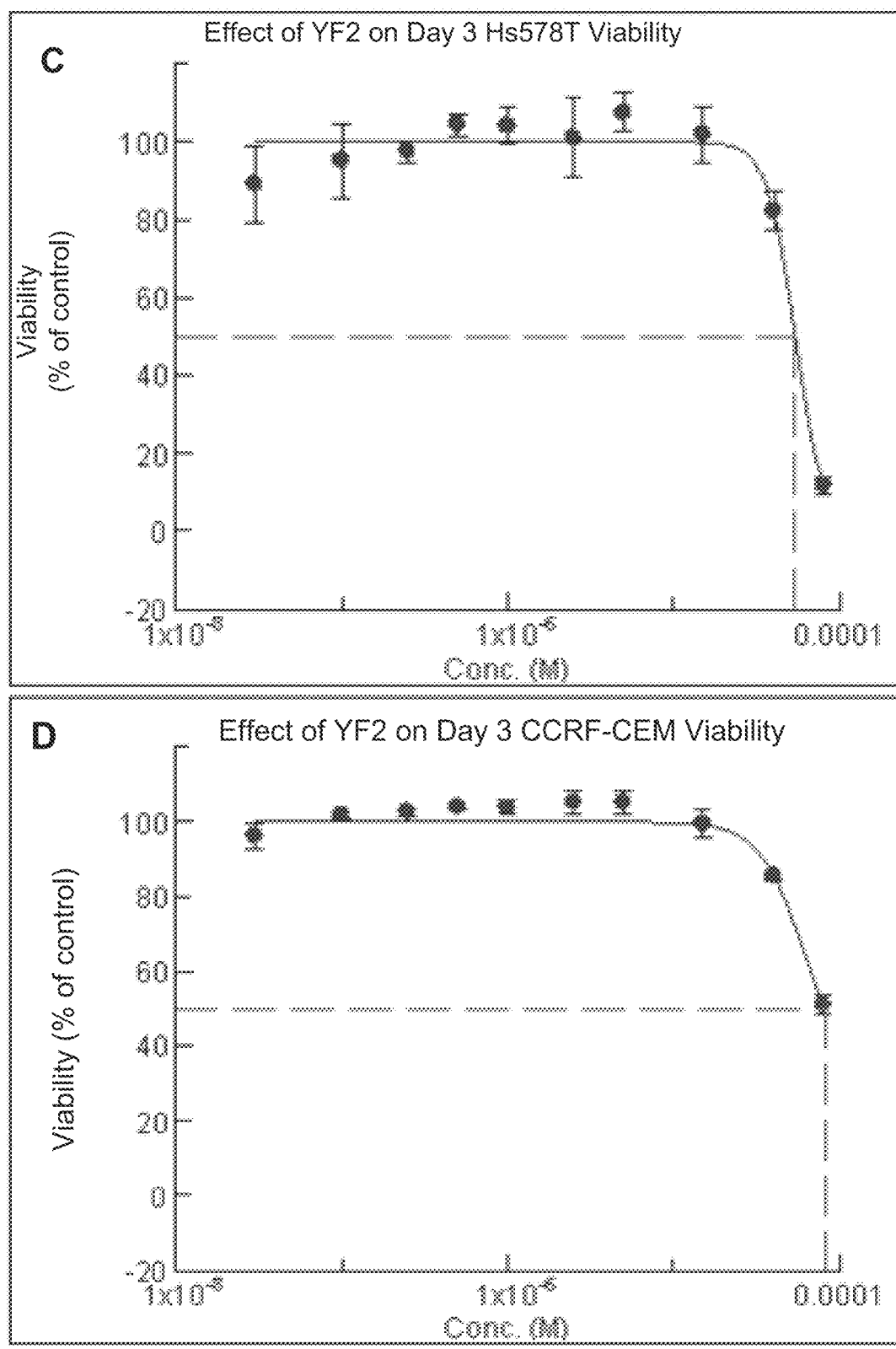
Figs. 31C-D

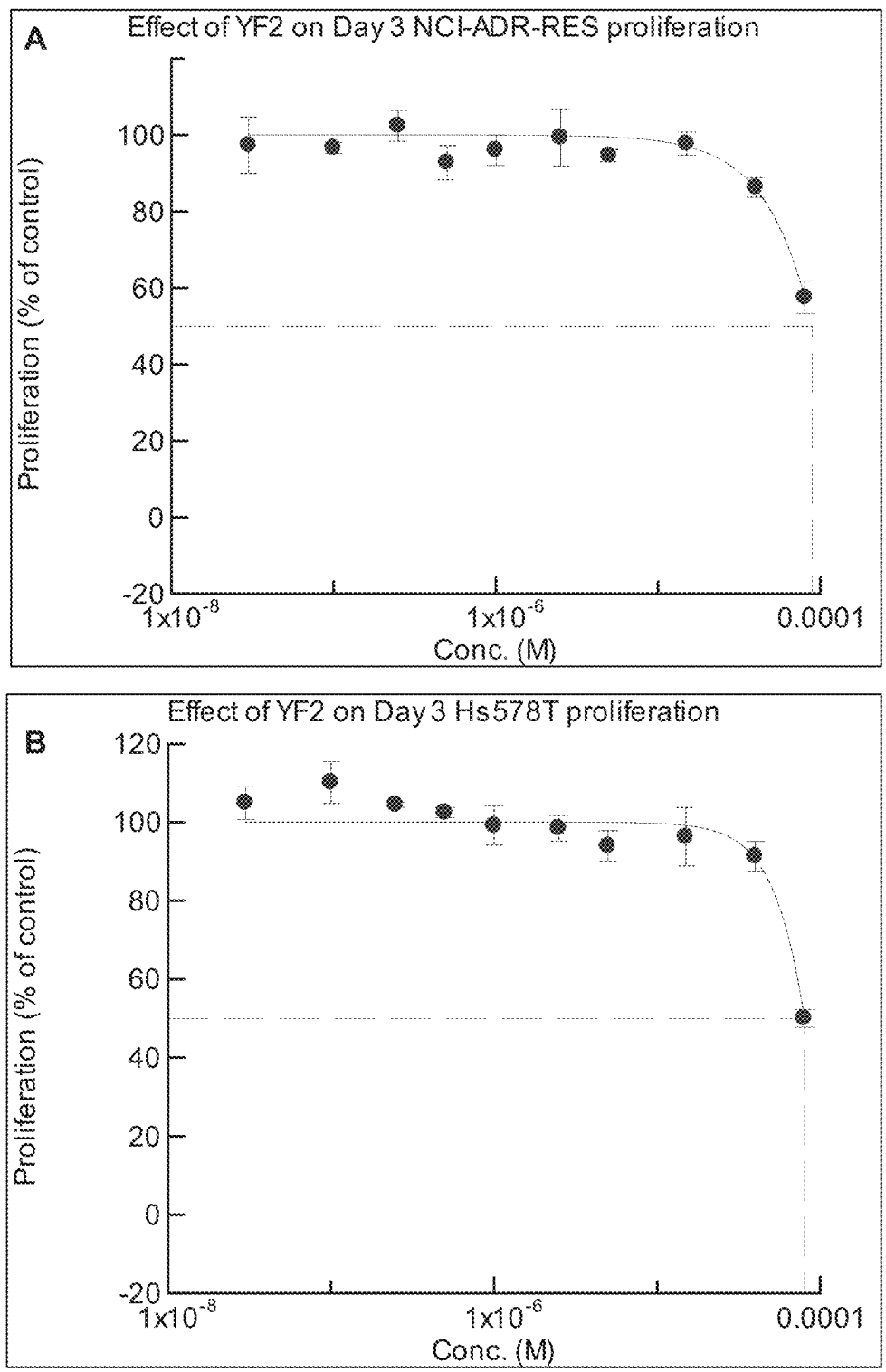
FIGS. 32A-B

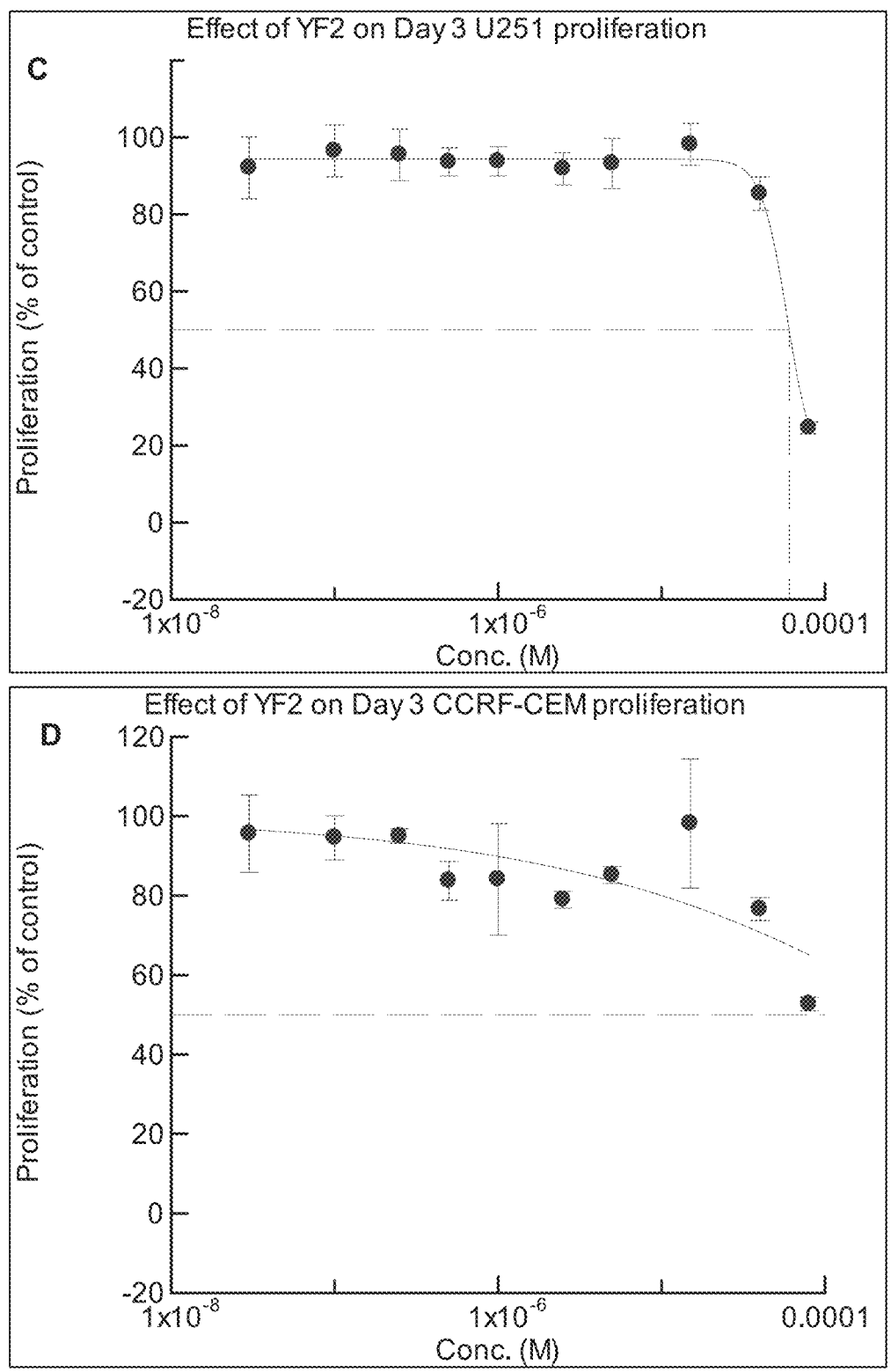
FIGS. 32C-D

| Drug ▶          | YF2           |            | VBL           |            |
| --------------- | ------------- | ---------- | ------------- | ---------- |
| Cell Line ▼     | Cell Titer Glo™ | Cyquant™ | Cell Titer Glo™ | Cyquant™ |
| ACHN            | 2.04E-1M      | 2.94E-1M   | 2.15E-9M      | 2.03E-9M   |
| U251            | 4.55E-5M      | 4.87E-5M   | 1.32E-9M      | 1.31E-9M   |
| NCI-ADR-RES     | 2.86E-4M      | 4.46E-5M   | 9.70E-9M      | 1.20E-8M   |
| A549            | 2.48E-4M      | ND         | 1.48E-9M      | 1.62E-9M   |
| Hs578T          | 4.71E-5M      | 7.16E-4M   | 6.97E-10M     | 1.10E-9M   |
| CCRF-CEM        | 8.87E-5M      | 4.25E-5M   | 1.56E-9M      | 1.11E-9M   |

*FIG. 33*

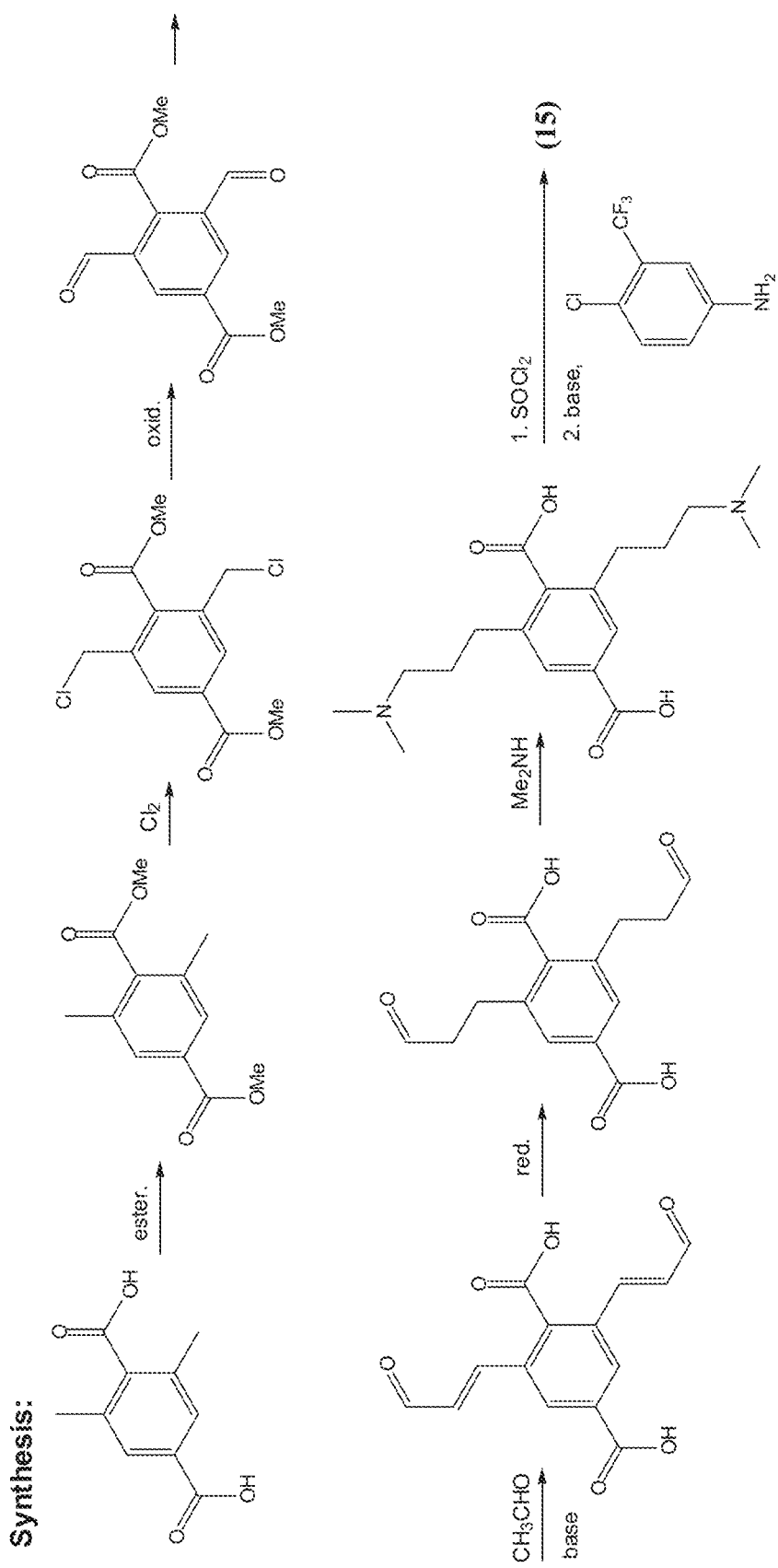
FIG. 43 – Cont.

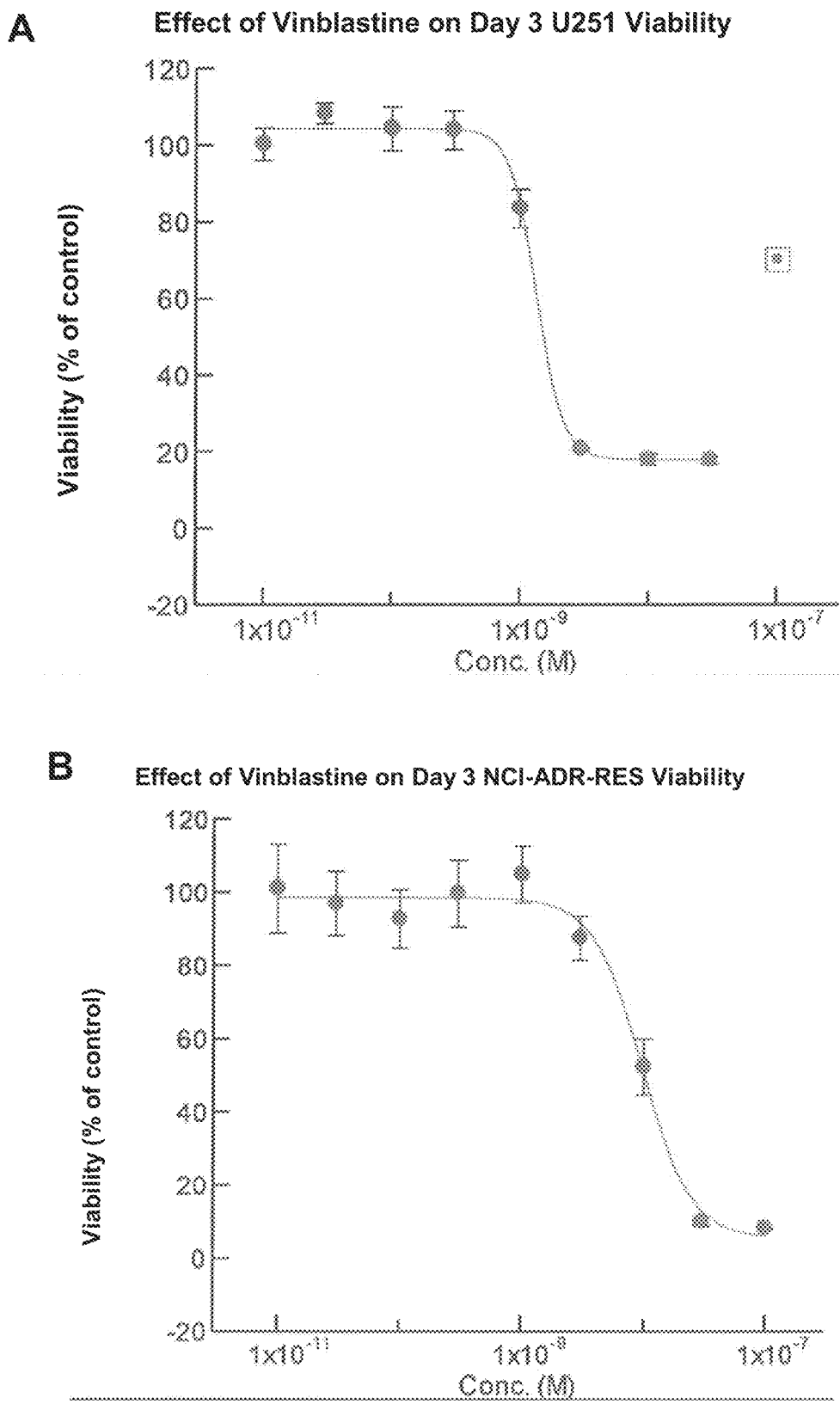
*FIGS. 47 A-B*

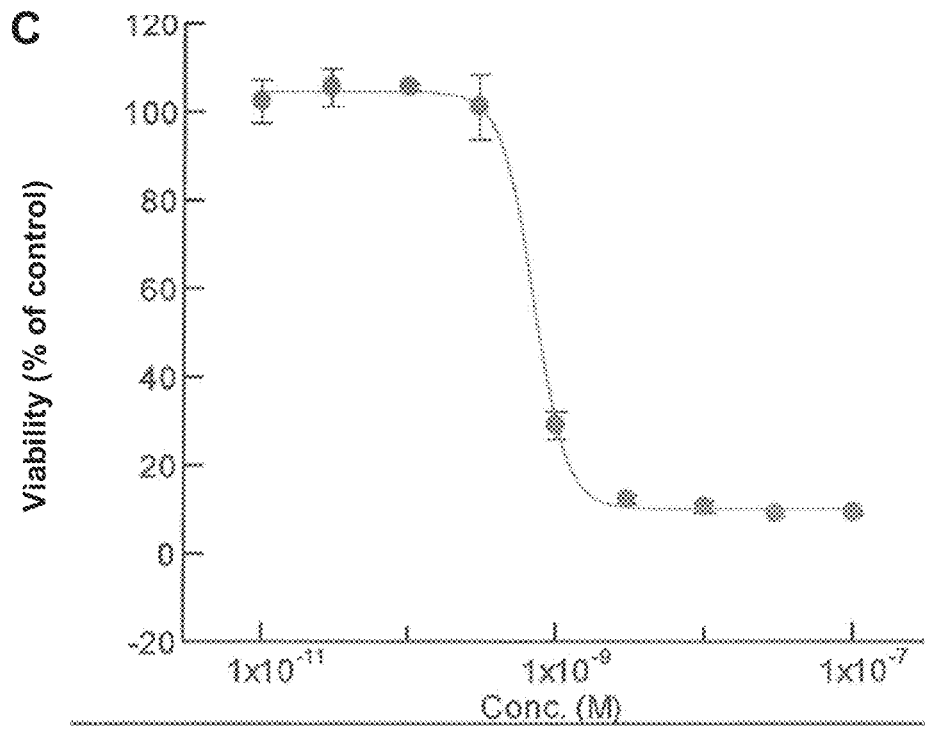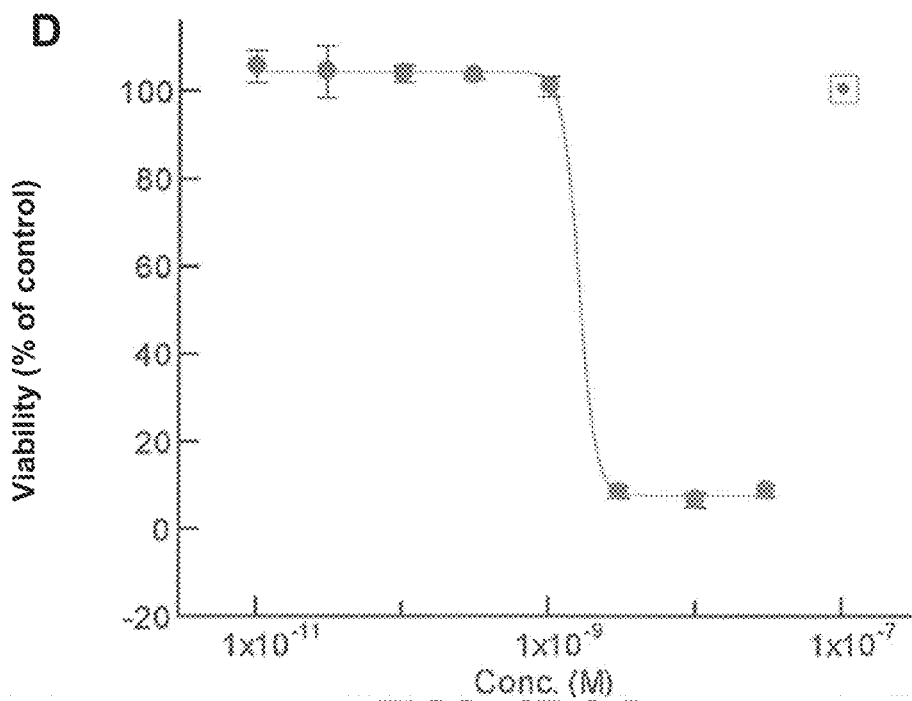
FIGS. 47 C-D

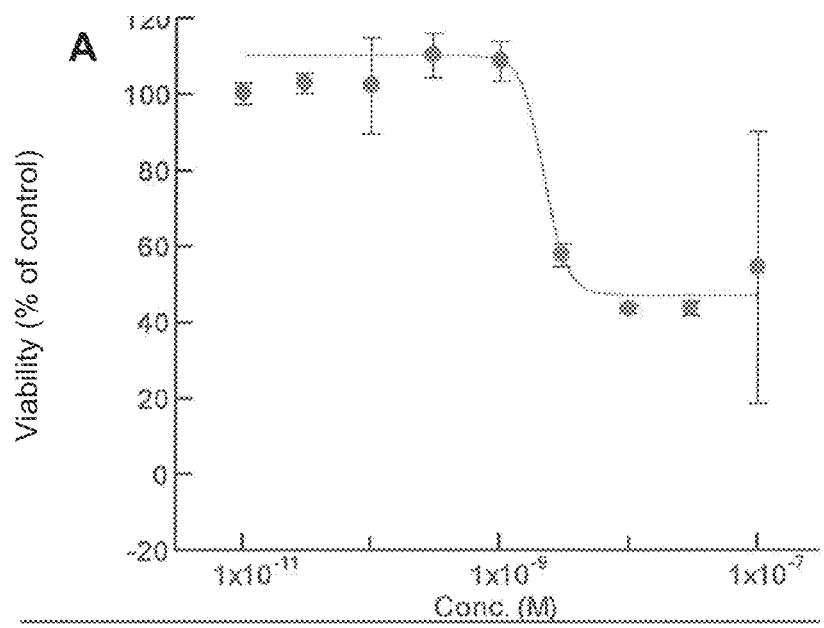
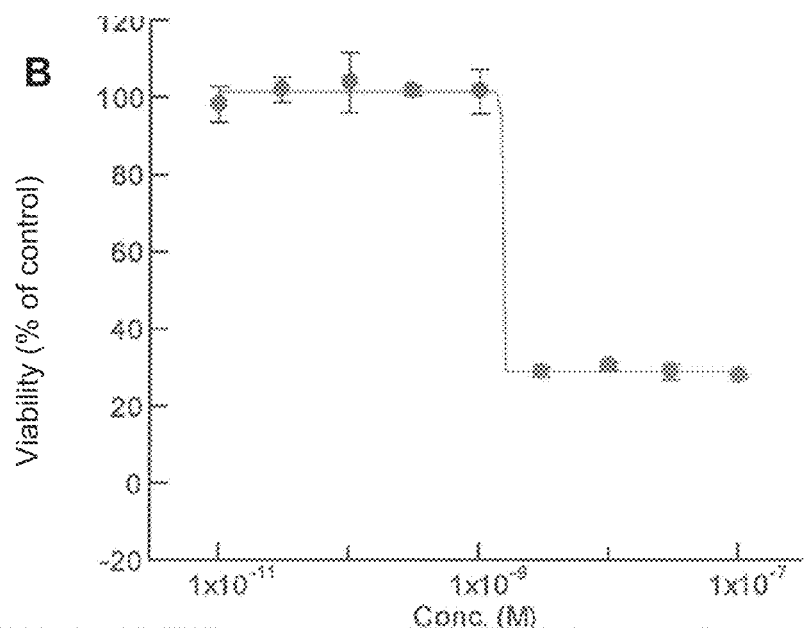
FIG. 48

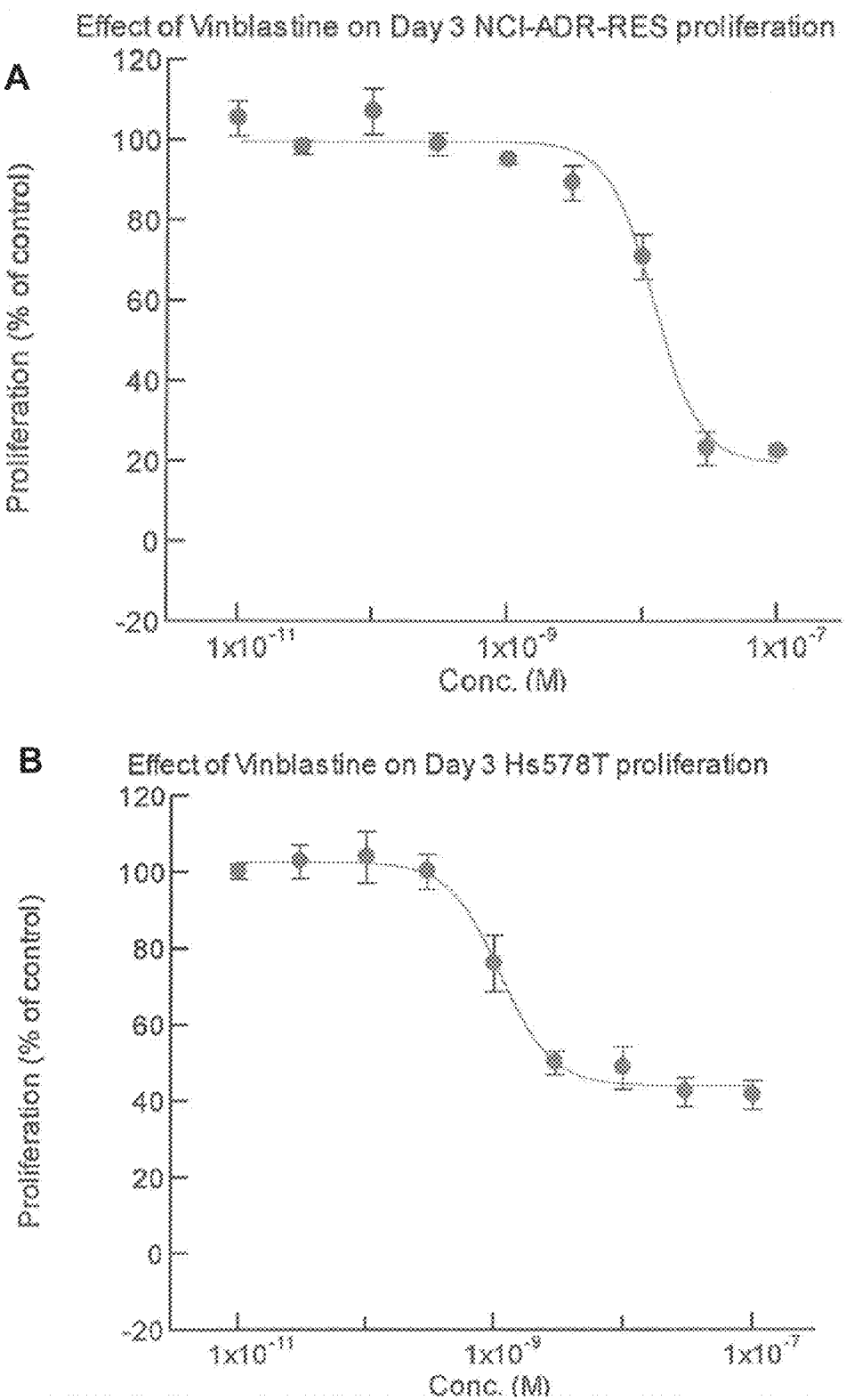
FIGS. 49A-B

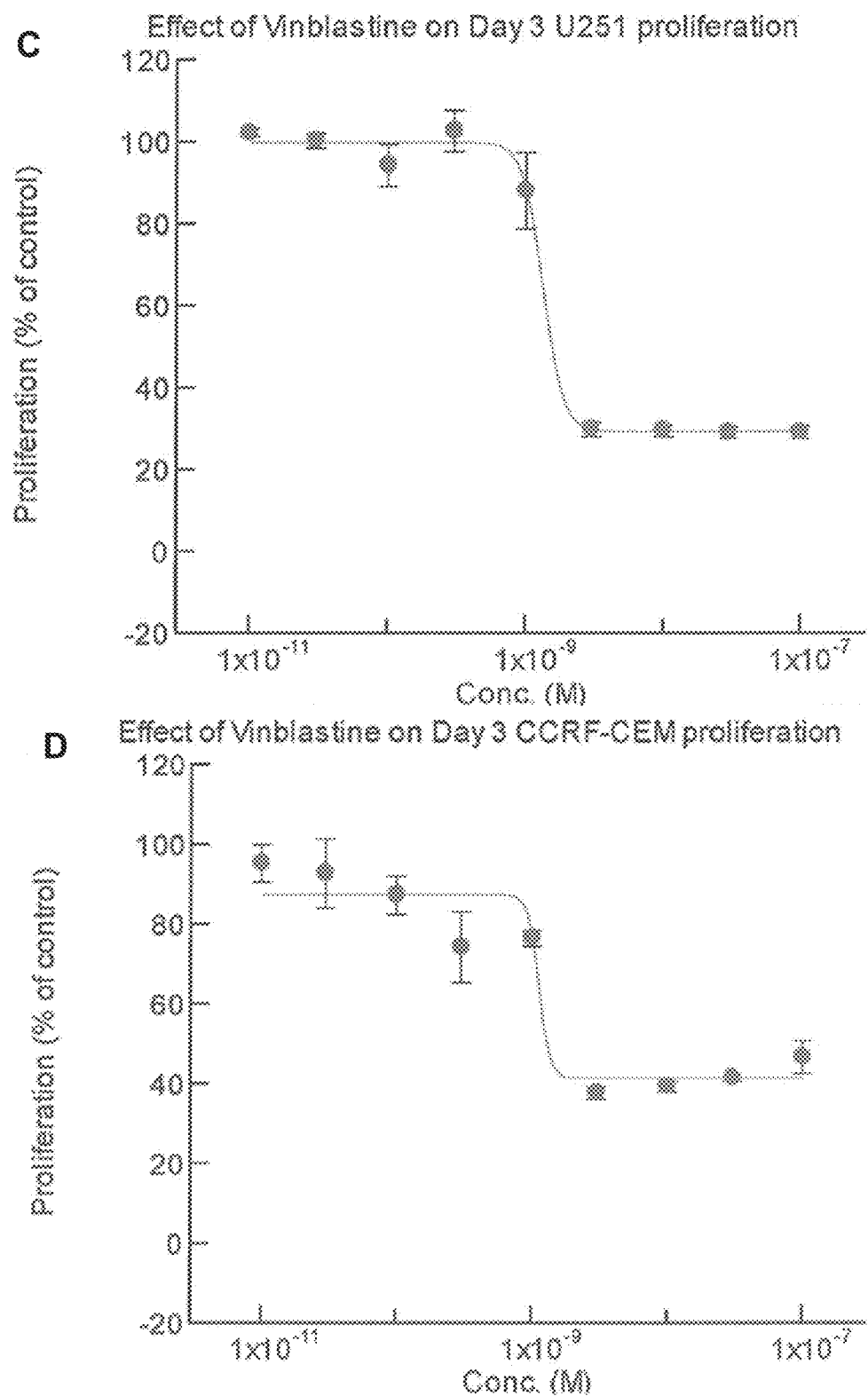
FIGS. 49C-D

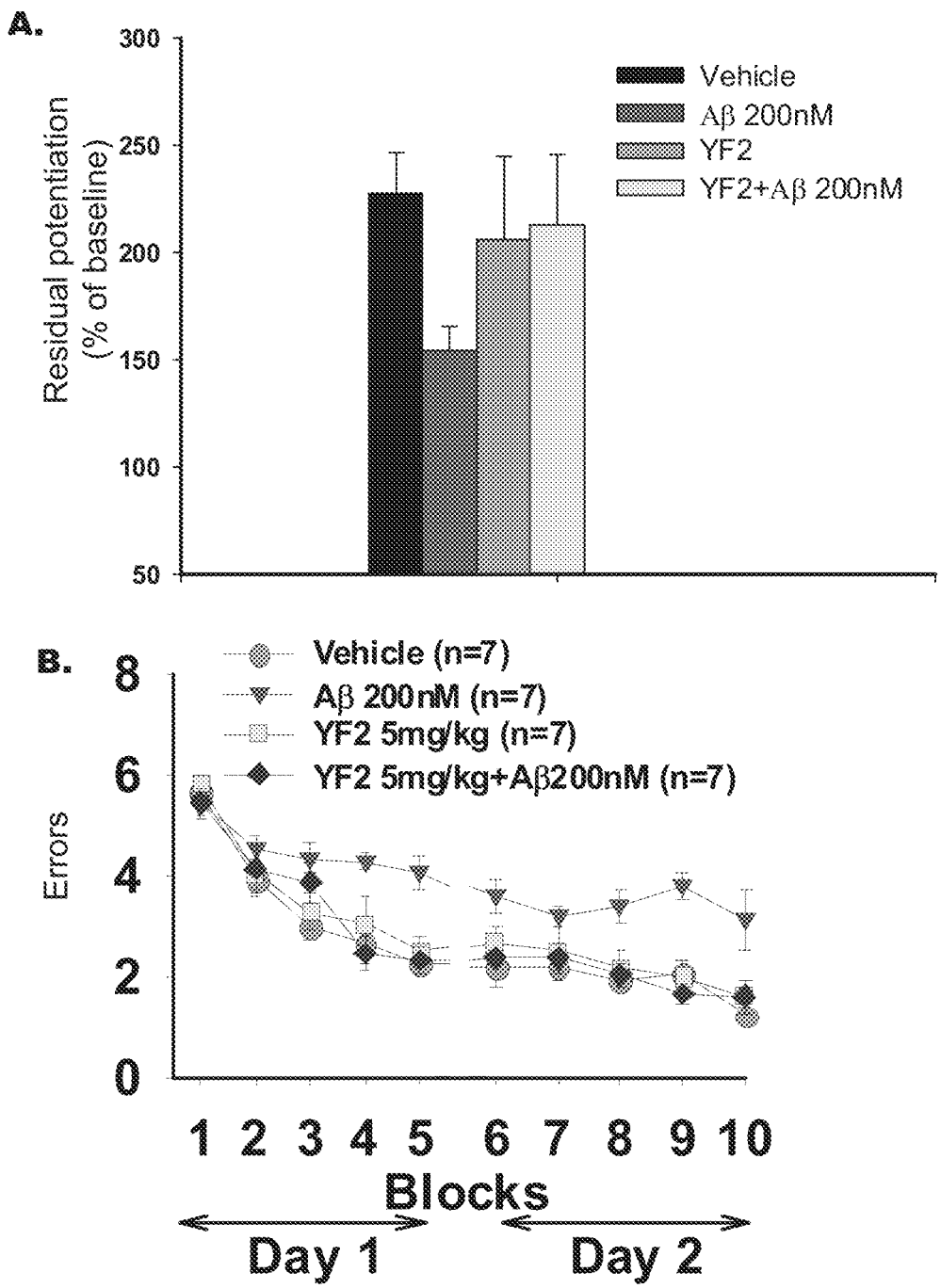
*FIGS. 66A-B*

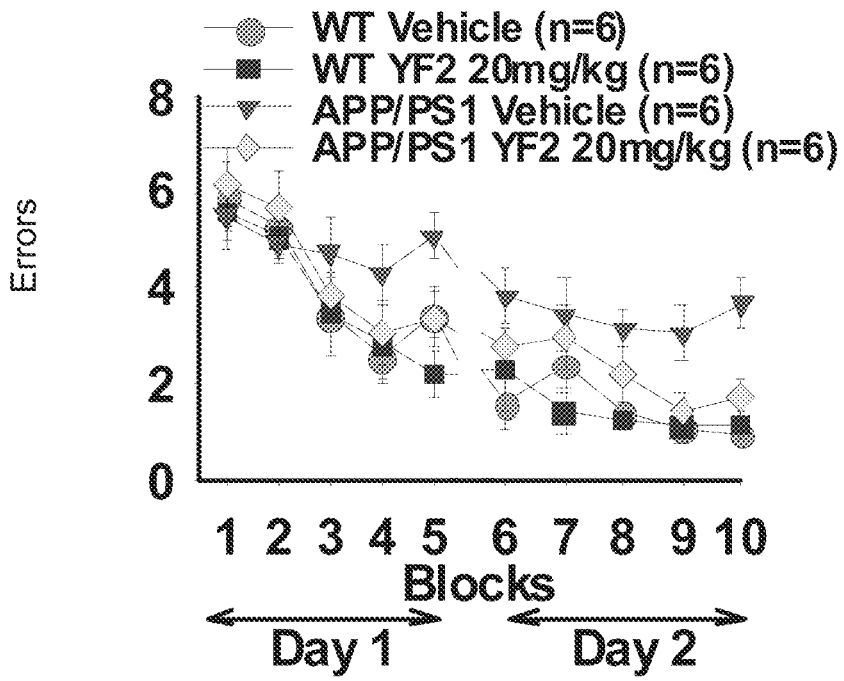
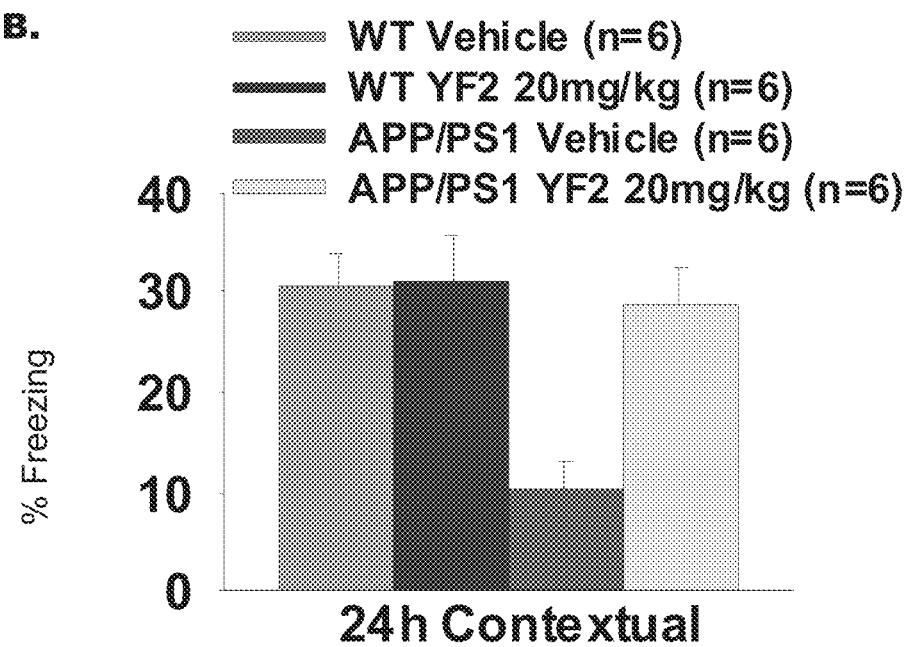
FIG. 67

A
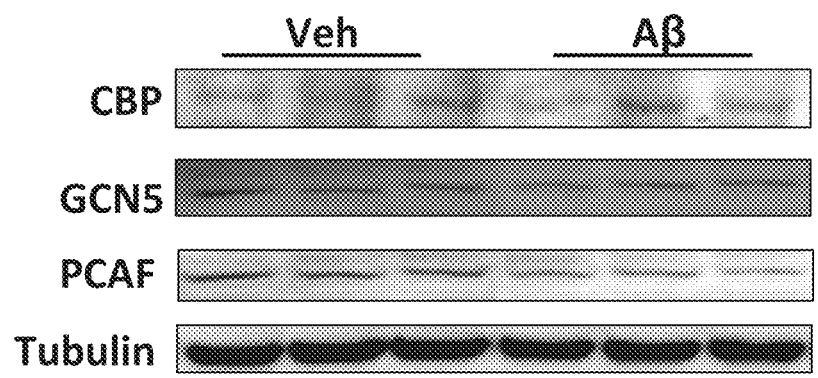
B
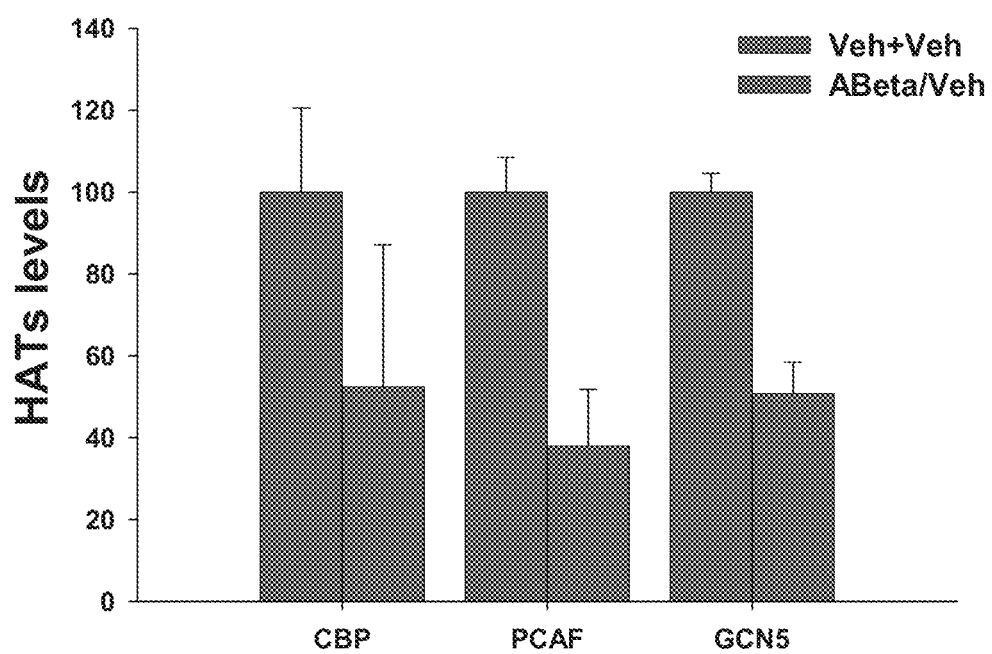
FIG. 76

A
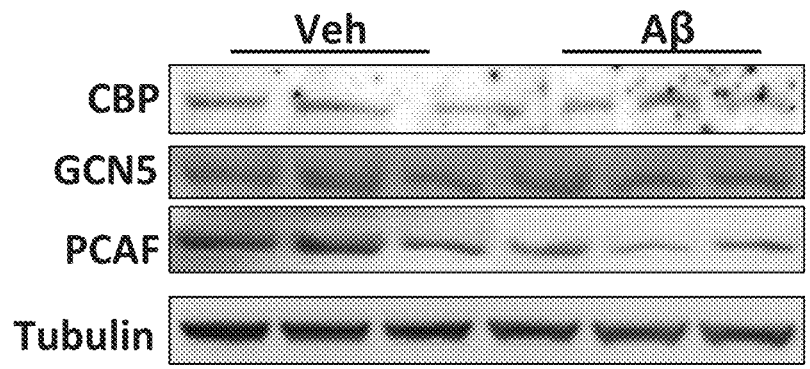
B
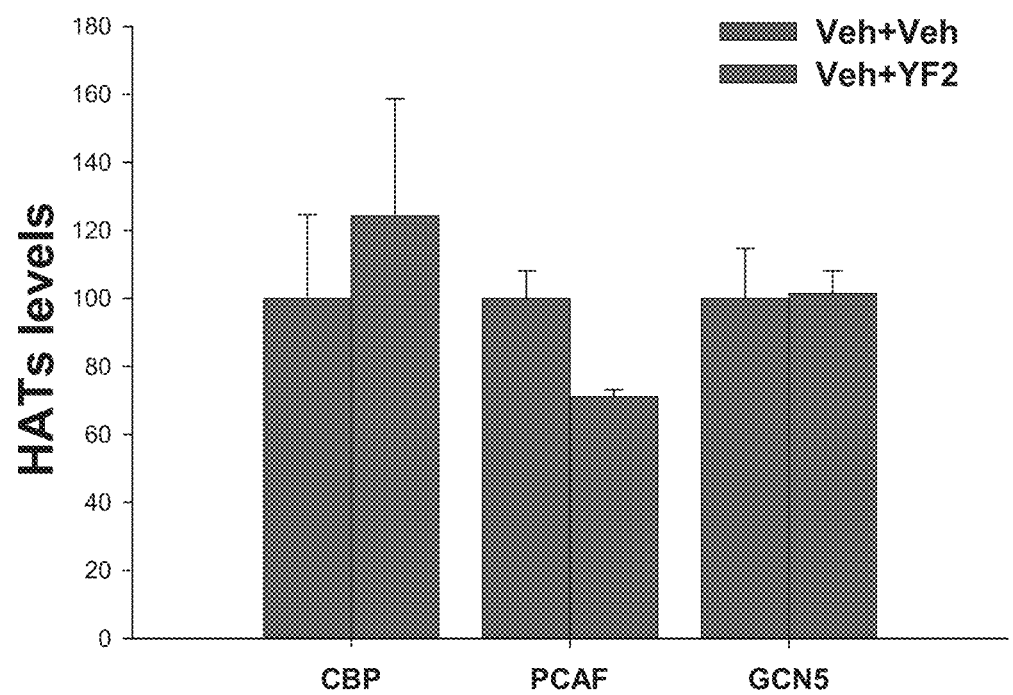
*FIG. 77*

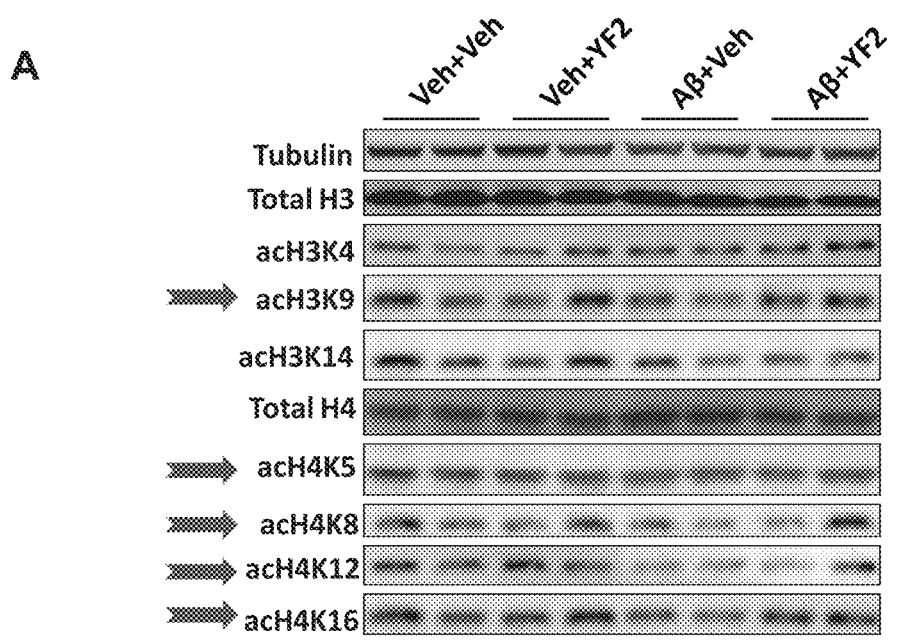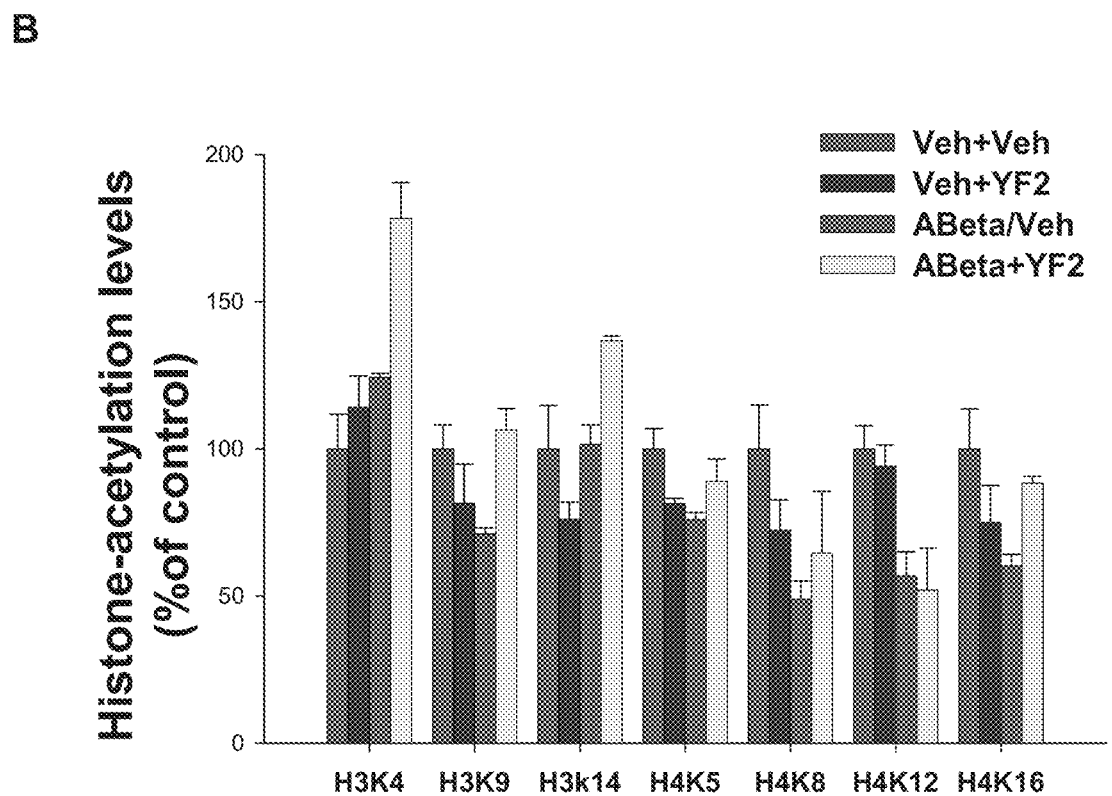
FIG. 80

DISTANCE TRAVELLED IN CENTER
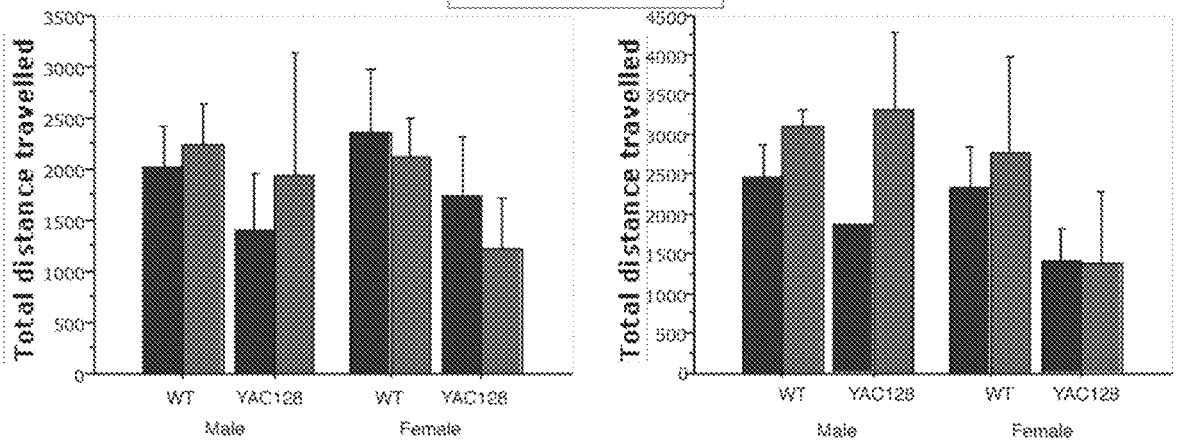
DISTANCE TRAVELLED IN PERIPHERY
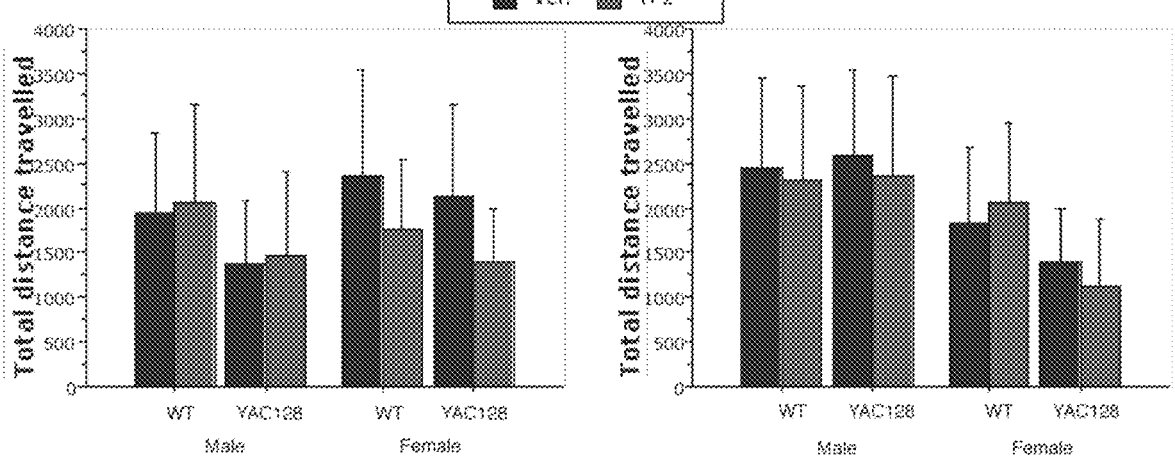
*FIG. 85*

SEQUENCE LISTING

```
<160> NUMBER OF SEQ ID NOS: 6

<210> SEQ ID NO 1
<211> LENGTH: 419
<212> TYPE: PRT
<213> ORGANISM: Homo sapiens

<400> SEQUENCE: 1

Met Ala Gly Phe Gly Ala Met Glu Lys Phe Leu Val Glu Tyr Lys Ser
1               5                   10                  15

Ala Val Glu Lys Lys Leu Ala Glu Tyr Lys Cys Asn Thr Asn Thr Ala
            20                  25                  30

Ile Glu Leu Lys Leu Val Arg Phe Pro Glu Asp Leu Glu Asn Asp Ile
        35                  40                  45

Arg Thr Phe Phe Pro Glu Tyr Thr His Gln Leu Phe Gly Asp Asp Glu
    50                  55                  60

Thr Ala Phe Gly Tyr Lys Gly Leu Lys Ile Leu Leu Tyr Tyr Ile Ala
65                  70                  75                  80

Gly Ser Leu Ser Thr Met Phe Arg Val Glu Tyr Ala Ser Lys Val Asp
                85                  90                  95

Glu Asn Phe Asp Cys Val Glu Ala Asp Asp Val Glu Gly Lys Ile Arg
            100                 105                 110

Gln Ile Ile Pro Pro Gly Phe Cys Thr Asn Thr Asn Asp Phe Leu Ser
        115                 120                 125

Leu Leu Glu Lys Glu Val Asp Phe Lys Pro Phe Gly Thr Leu Leu His
    130                 135                 140

Thr Tyr Ser Val Leu Ser Pro Thr Gly Gly Glu Asn Phe Thr Phe Gln
145                 150                 155                 160

Ile Tyr Lys Ala Asp Met Thr Cys Arg Gly Phe Arg Glu Tyr His Glu
                165                 170                 175

Arg Leu Gln Thr Phe Leu Met Trp Phe Ile Glu Thr Ala Ser Phe Ile
            180                 185                 190

Asp Val Asp Asp Glu Arg Trp His Tyr Phe Leu Val Phe Glu Lys Tyr
        195                 200                 205
```

Asn Lys Asp Gly Ala Thr Leu Phe Ala Thr Val Gly Tyr Met Thr Val
210                 215                 220

Tyr Asn Tyr Tyr Val Tyr Pro Asp Lys Thr Arg Pro Arg Val Ser Gln
225                 230                 235                 240

Met Leu Ile Leu Thr Pro Phe Gln Gly Gln Gly His Gly Ala Gln Leu
            245                 250                 255

Leu Glu Thr Val His Arg Tyr Tyr Thr Glu Phe Pro Thr Val Leu Asp
            260                 265                 270

Ile Thr Ala Glu Asp Pro Ser Lys Ser Tyr Val Lys Leu Arg Asp Phe
            275                 280                 285

Val Leu Val Lys Leu Cys Gln Asp Leu Pro Cys Phe Ser Arg Glu Lys
            290                 295                 300

Leu Met Gln Gly Phe Asn Glu Asp Met Ala Ile Glu Ala Gln Lys
305                 310                 315                 320

Phe Lys Ile Asn Lys Gln His Ala Arg Arg Val Tyr Glu Ile Leu Arg
            325                 330                 335

Leu Leu Val Thr Asp Met Ser Asp Ala Glu Gln Tyr Arg Ser Tyr Arg
            340                 345                 350

Leu Asp Ile Lys Arg Arg Leu Ile Ser Pro Tyr Lys Lys Lys Gln Arg
            355                 360                 365

Asp Leu Ala Lys Met Arg Lys Cys Leu Arg Pro Glu Glu Leu Thr Asn
370                 375                 380

Gln Met Asn Gln Ile Glu Ile Ser Met Gln His Glu Gln Leu Glu Glu
385                 390                 395                 400

Ser Phe Gln Glu Leu Val Glu Asp Tyr Arg Arg Val Ile Glu Arg Leu
            405                 410                 415

Ala Gln Glu

<210> SEQ ID NO 2
<211> LENGTH: 1682
<212> TYPE: DNA
<213> ORGANISM: Homo sapiens

<400> SEQUENCE: 2

```
ctgtgcggtc acttccggcc cgggagcgcg cgggttgatt cgtccttcct cagccgcggg      60
tgatcgtagc tcggaaatgg cgggatttgg tgctatggag aaattttggt agaatataa     120 gagtgcagtg gagaagaaac tggcagagta caaatgtaac accaacacag caattgaact    180
aaaattagtt cgtttttcctg aagatcttga aaatgacatt gaactttct ttcctgagta    240 tacccatcaa ctctttgggg atgatgaaac tgcttttggt tacaagggtc taaagatcct    300
gttatactat attgctggta gcctgtcaac aatgttccgt gttgaatatg catctaaagt    360
tgatgagaac tttgactgtg tagaggcaga tgatgttgag ggcaaaatta gacaaatcat    420
tccacctgga ttttgcacaa acacgaatga tttccttcct ttactggaaa aggaagttga    480
tttcaagcca ttcggaacct tacttcatac ctactcagtt ctcagtccaa caggaggaga    540
aaactttacc tttcagatat ataaggctga catgacatgt agaggctttc gagaatatca    600
tgaaaggctt cagaccttttt tgatgtggtt tattgaaact gctagcttta ttgacgtgga    660
tgatgaaaga tggcactact ttctagtatt tgagaagtat aataaggatg gagctacgct    720
ctttgcgacc gtaggctaca tgacagtcta taattactat gtgtacccag acaaaacccg    780
gccacgtgta agtcagatgc tgattttgac tccatttcaa ggtcaaggcc atggtgctca    840
acttcttgaa acagttcata gatactacac tgaatttcct acagttcttg atattacagc    900
```

```
ggaagatcca tccaaaagct atgtgaaatt acgagacttt gtgcttgtga agctttgtca    960
agatttgccc tgttttcccc gggaaaaatt aatgcaagga ttcaatgaag atatggcgat   1020
agaggcacaa cagaagttca aaataaataa gcaacacgct agaagggttt atgaaattct   1080
tcgactactg gtaactgaca tgagtgatgc cgaacaatac agaagctaca gactggatat   1140
taaaagaaga ctaattagcc catataagaa aaagcagaga gatcttgcta agatgagaaa   1200
atgtctcaga ccagaagaac tgacaaacca gatgaaccaa atagaaataa gcatgcaaca   1260
tgaacagctg gaagagagtt ttcaggaact agtggaagat taccggcgtg ttattgaacg   1320
acttgctcaa gagtaaagat tatactgctc tgtacaggaa gcttgcaaat tttctgtaca   1380
atgtgctgtg aaaaatctga tgactttaat tttaaaatct tgtgacattt tgcttatact   1440
aaaagttatc tatctttagt tgaatatttt cttttggaga gattgtatat tttaaaatac   1500
tgtttagagt ttatgagcat atattgcatt taaagaaaga taaagcttct gaaatactac   1560
tgcaattgct tcccttctta aacagtataa taaatgctta gttgtgatat gttaatgtgt   1620
gatgatatga ttcttaaata cttacaataa acctcattct taaatactta aaaaaaaaaa   1680
aa                                                                 1682
```

<210> SEQ ID NO 3
<211> LENGTH: 832
<212> TYPE: PRT
<213> ORGANISM: Homo sapiens

<400> SEQUENCE: 3

```
Met Ser Glu Ala Gly Gly Ala Gly Pro Gly Gly Cys Gly Ala Gly Ala
1               5                   10                  15

Gly Ala Gly Ala Gly Pro Gly Ala Leu Pro Pro Gln Pro Ala Ala Leu
            20                  25                  30

Pro Pro Ala Pro Pro Gln Gly Ser Pro Cys Ala Ala Ala Gly Gly
        35                  40                  45

Ser Gly Ala Cys Gly Pro Ala Thr Ala Val Ala Ala Ala Gly Thr Ala
    50                  55                  60

Glu Gly Pro Gly Gly Gly Ser Ala Arg Ile Ala Val Lys Lys Ala
65                  70                  75                  80

Gln Leu Arg Ser Ala Pro Arg Ala Lys Lys Leu Glu Lys Leu Gly Val
                85                  90                  95

Tyr Ser Ala Cys Lys Ala Glu Glu Ser Cys Lys Cys Asn Gly Trp Lys
            100                 105                 110

Asn Pro Asn Pro Ser Pro Thr Pro Pro Arg Ala Asp Leu Gln Gln Ile
        115                 120                 125

Ile Val Ser Leu Thr Glu Ser Cys Arg Ser Cys Ser His Ala Leu Ala
    130                 135                 140

Ala His Val Ser His Leu Glu Asn Val Ser Glu Glu Met Asn Arg
145                 150                 155                 160

Leu Leu Gly Ile Val Leu Asp Val Glu Tyr Leu Phe Thr Cys Val His
                165                 170                 175

Lys Glu Glu Asp Ala Asp Thr Lys Gln Val Tyr Phe Tyr Leu Phe Lys
            180                 185                 190

Leu Leu Arg Lys Ser Ile Leu Gln Arg Gly Lys Pro Val Val Glu Gly
        195                 200                 205

Ser Leu Glu Lys Lys Pro Pro Phe Glu Lys Pro Ser Ile Glu Gln Gly
    210                 215                 220
```

Val Asn Asn Phe Val Gln Tyr Lys Phe Ser His Leu Pro Ala Lys Glu
225                 230                 235                 240

Arg Gln Thr Ile Val Glu Leu Ala Lys Met Phe Leu Asn Arg Ile Asn
            245                 250                 255

Tyr Trp His Leu Glu Ala Pro Ser Gln Arg Arg Leu Arg Ser Pro Asn
        260                 265                 270

Asp Asp Ile Ser Gly Tyr Lys Glu Asn Tyr Thr Arg Trp Leu Cys Tyr
            275                 280                 285

Cys Asn Val Pro Gln Phe Cys Asp Ser Leu Pro Arg Tyr Glu Thr Thr
        290                 295                 300

Gln Val Phe Gly Arg Thr Leu Leu Arg Ser Val Phe Thr Val Met Arg
305                 310                 315                 320

Arg Gln Leu Leu Glu Gln Ala Arg Gln Glu Lys Asp Lys Leu Pro Leu
            325                 330                 335

Glu Lys Arg Thr Leu Ile Leu Thr His Phe Pro Lys Phe Leu Ser Met
            340                 345                 350

Leu Glu Glu Glu Val Tyr Ser Gln Asn Ser Pro Ile Trp Asp Gln Asp
        355                 360                 365

Phe Leu Ser Ala Ser Ser Arg Thr Ser Gln Leu Gly Ile Gln Thr Val
    370                 375                 380

Ile Asn Pro Pro Val Ala Gly Thr Ile Ser Tyr Asn Ser Thr Ser
385                 390                 395                 400

Ser Ser Leu Glu Gln Pro Asn Ala Gly Ser Ser Pro Ala Cys Lys
            405                 410                 415

Ala Ser Ser Gly Leu Glu Ala Asn Pro Gly Glu Lys Arg Lys Met Thr
            420                 425                 430

Asp Ser His Val Leu Glu Glu Ala Lys Lys Pro Arg Val Met Gly Asp
        435                 440                 445

Ile Pro Met Glu Leu Ile Asn Glu Val Met Ser Thr Ile Thr Asp Pro
    450                 455                 460

Ala Ala Met Leu Gly Pro Glu Thr Asn Phe Leu Ser Ala His Ser Ala
465                 470                 475                 480

Arg Asp Glu Ala Ala Arg Leu Glu Glu Arg Arg Gly Val Ile Glu Phe
            485                 490                 495

His Val Val Gly Asn Ser Leu Asn Gln Lys Pro Asn Lys Lys Ile Leu
        500                 505                 510

Met Trp Leu Val Gly Leu Gln Asn Val Phe Ser His Gln Leu Pro Arg
    515                 520                 525

Met Pro Lys Glu Tyr Ile Thr Arg Leu Val Phe Asp Pro Lys His Lys
530                 535                 540

Thr Leu Ala Leu Ile Lys Asp Gly Arg Val Ile Gly Gly Ile Cys Phe
545                 550                 555                 560

Arg Met Phe Pro Ser Gln Gly Phe Thr Glu Ile Val Phe Cys Ala Val
            565                 570                 575

Thr Ser Asn Glu Gln Val Lys Gly Tyr Gly Thr His Leu Met Asn His
        580                 585                 590

Leu Lys Glu Tyr His Ile Lys His Asp Ile Leu Asn Phe Leu Thr Tyr
    595                 600                 605

Ala Asp Glu Tyr Ala Ile Gly Tyr Phe Lys Lys Gln Gly Phe Ser Lys
        610                 615                 620

Glu Ile Lys Ile Pro Lys Thr Lys Tyr Val Gly Tyr Ile Lys Asp Tyr
625                 630                 635                 640

Glu Gly Ala Thr Leu Met Gly Cys Glu Leu Asn Pro Arg Ile Pro Tyr

|  |  | 645 |  |  |  | 650 |  |  |  | 655 |  |
|---|---|---|---|---|---|---|---|---|---|---|---|
| Thr | Glu | Phe | Ser | Val | Ile | Ile | Lys | Lys | Gln | Lys | Glu | Ile | Ile | Lys | Lys |
|  |  |  | 660 |  |  |  | 665 |  |  |  | 670 |

Leu Ile Glu Arg Lys Gln Ala Gln Ile Arg Lys Val Tyr Pro Gly Leu
            675                 680                 685

Ser Cys Phe Lys Asp Gly Val Arg Gln Ile Pro Ile Glu Ser Ile Pro
    690                 695                 700

Gly Ile Arg Glu Thr Gly Trp Lys Pro Ser Gly Lys Glu Lys Ser Lys
705                 710                 715                 720

Glu Pro Arg Asp Pro Asp Gln Leu Tyr Ser Thr Leu Lys Ser Ile Leu
                725                 730                 735

Gln Gln Val Lys Ser His Gln Ser Ala Trp Pro Phe Met Glu Pro Val
            740                 745                 750

Lys Arg Thr Glu Ala Pro Gly Tyr Tyr Glu Val Ile Arg Phe Pro Met
        755                 760                 765

Asp Leu Lys Thr Met Ser Glu Arg Leu Lys Asn Arg Tyr Tyr Val Ser
    770                 775                 780

Lys Lys Leu Phe Met Ala Asp Leu Gln Arg Val Phe Thr Asn Cys Lys
785                 790                 795                 800

Glu Tyr Asn Pro Pro Glu Ser Glu Tyr Tyr Lys Cys Ala Asn Ile Leu
                805                 810                 815

Glu Lys Phe Phe Phe Ser Lys Ile Lys Glu Ala Gly Leu Ile Asp Lys
            820                 825                 830

<210> SEQ ID NO 4
<211> LENGTH: 4824
<212> TYPE: DNA
<213> ORGANISM: Homo sapiens

<400> SEQUENCE: 4

```
gcggaaaaga ggccgtgggg ggcctcccag cgctggcaga caccgtgagg ctggcagccg      60
ccggcacgca cacctagtcc gcagtcccga ggaacatgtc cgcagccagg gcgcggagca     120
gagtcccggg caggagaacc aagggagggc gtgtgctgtg gcggcggcgg cagcggcagc     180
ggagccgcta gtccctccc tcctggggga gcagctgccg ccgctgccgc cgccgccacc     240
accatcagcg cgcggggccc ggccagagcg agccgggcga gcggcgcgct agggggaggg     300
cggggggcggg gaggggggtg ggcgaagggg gcggagggc gtgggggggag ggtctcgctc     360
tcccgactac cagagcccga gagggagacc ctggcggcgg cggcggcgcc tgacactcgg     420
cgcctcctgc cgtgctccgg ggcggcatgt ccgaggctgg cggggccggg ccgggcgggct     480
gcggggcagg agccggggca ggggccgggc ccggggcgct gccccgcag cctgcggcgc     540
ttccgcccgc gccccgcag ggctcccct gcgccgctgc cgccggggc tcgggcgcct     600
gcggtccggc gacggcagtg gctgcagcgg gcacggccga aggaccggga ggcggtggct     660
cggcccgaat cgccgtgaag aaagcgcaac tacgctccgc tccgcgggcc aagaaactgg     720
agaaactcgg agtgtactcc gcctgcaagg ccgaggagtc ttgtaaatgt aatggctgga     780
aaaaccctaa ccctcaccc actccccca gagccgacct gcagcaaata attgtcagtc     840
taacagaatc ctgtcggagt tgtagccatg ccctagctgc tcatgtttcc cacctggaga     900
atgtgtcaga ggaagaaatg aacagactcc tgggaatagt attggatgtg aatatctct     960
ttacctgtgt ccacaaggaa gaagatgcag ataccaaaca gtttatttc tatctattta    1020
agctcttgag aaagtctatt ttacaaagag gaaaacctgt ggttgaaggc tctttggaaa    1080
```

```
agaaaccccc atttgaaaaa cctagcattg aacagggtgt gaataacttt gtgcagtaca      1140
aatttagtca cctgccagca aaagaaaggc aaacaatagt tgagttggca aaaatgttcc      1200
taaaccgcat caactattgg catctggagg caccatctca acgaagactg cgatctccca      1260
atgatgatat ttctggatac aaagagaact acacaaggtg gctgtgttac tgcaacgtgc      1320
cacagttctg cgacagtcta cctcggtacg aaaccacaca ggtgtttggg agaacattgc      1380
ttcgctcggt cttcactgtt atgaggcgac aactcctgga acaagcaaga caggaaaaag      1440
ataaactgcc tcttgaaaaa cgaactctaa tcctcactca tttcccaaaa tttctgtcca      1500
tgctagaaga agaagtatat agtcaaaact ctcccatctg ggatcaggat tttctctcag      1560
cctcttccag aaccagccag ctaggcatcc aaacagttat caatccacct cctgtggctg      1620
ggacaatttc atacaattca acctcatctt cccttgagca gccaaacgca gggagcagca      1680
gtcctgcctg caaagcctct tctggacttg aggcaaaccc aggagaaaag aggaaaatga      1740
ctgattctca tgttctggag gaggccaaga accccgagt tatgggggat attccgatgg       1800
aattaatcaa cgaggttatg tctaccatca cggaccctgc agcaatgctt ggaccagaga      1860
ccaattttct gtcagcacac tcggccaggg atgaggcggc aaggttggaa gagcgcaggg      1920
gtgtaattga atttcacgtg gttggcaatt ccctcaacca gaaaccaaac aagaagatcc      1980
tgatgtggct ggttggccta cagaacgttt tctcccacca gctgccccga atgccaaaag      2040
aatacatcac acggctcgtc tttgacccga acacaaaac ccttgcttta attaaagatg       2100
gccgtgttat tggtggtatc tgtttccgta tgttcccatc tcaaggattc acagagattg      2160
tcttctgtgc tgtaacctca aatgagcaag tcaagggcta tggaacacac ctgatgaatc      2220
atttgaaaga atatcacata aagcatgaca tcctgaactt cctcacatat gcagatgaat      2280
atgcaattgg atactttaag aaacagggtt tctccaaaga aattaaaata cctaaaacca      2340
aatatgttgg ctatatcaag gattatgaag gagccacttt aatgggatgt gagctaaatc      2400
cacggatccc gtacacagaa ttttctgtca tcattaaaaa gcagaaggag ataattaaaa      2460
aactgattga agaaaacag gcacaaattc gaaaagttta ccctggactt tcatgtttta       2520
aagatggagt tcgacagatt cctatagaaa gcattcctgg aattagagag acaggctgga      2580
aaccgagtgg aaaagagaaa agtaaagagc ccagagaccc tgaccagctt tacagcacgc      2640
tcaagagcat cctccagcag gtgaagagcc atcaaagcgc ttggcccttc atggaacctg      2700
tgaagagaac agaagctcca ggatattatg aagttataag gttccccatg gatctgaaaa      2760
ccatgagtga acgcctcaag aataggtact acgtgtctaa gaaattattc atggcagact      2820
tacagcgagt ctttaccaat tgcaaagagt acaaccccc tgagagtgaa tactacaaat       2880
gtgccaatat cctggagaaa ttcttcttca gtaaaattaa ggaagctgga ttaattgaca      2940
agtgattttt tttccccctct gcttcttaga aactcaccaa gcagtgtgcc taaagcaagg      3000
tggtttagtt tttacaaag aattggacat gatgtattga agagacttgt aaatgtaata       3060
attagcactt ttgaaaaaac aaaaaaccte cttttagctt ttcagatatg tatttaaatt      3120
gaagtcatag gacattttta ttttatggaa tagattttaa tctatttact actattaagg      3180
taaatttcct atggcatgtc cattagctat ttcatgatag atgattaggg gtttcctcaa      3240
aacctgtgtg tgaggaaatt gcacacagta gcaaaatttg gggaaatcca taacattttc      3300
agaccatgaa tgaatgtttc catttttttc taatggaatg tgagagttta cttttatttt      3360
attctgaagg acttttaagga agggatacat gattttaaaa aagcctgtaa gaggtgaaat     3420
atgtgatgtt tgaagtctct ttatagactt tttatatata tttttttaaaa cactcatcta    3480
```

```
gatgaggtgc tttgagcagt tctgaaaaat gcagttccag gaaagcaact gctttggttc    3540
ctaaggaaga aattctaaat aatgcaaact tttaaaataa gcatctaggt ttttgataat    3600
tctgtctact tacaacaaac ttgttagtac ataaccacta ttttaataat tattttctct    3660
acacaaatgt gtaatatcat atttgacttt gcttatgcag gccataagtt ccaaaagata    3720
atttccctgc ccacaaaggc ataaacttga aaacacatga gattgaatca acatgcttta    3780
ataggaaaag atgtatggtc tatatatgta tcaatctggt gaatcctcgt tctaataaag    3840 gttcttttc ttttctatga tacacacagc cacgctgata atatgcaaat gaacattttc    3900
ctttatgtct ctccagataa tgtttattgt ctgaggtaaa ttaaattccc accagggttt    3960
gctgtcagta ttttaacacc cacattagta tatgcgtcca gggtcataac cccctaaaat    4020
ccatcatgca accttattaa tctgtcttgg gattccagtt tagtgcttgg atttatttcc    4080
tgattacact acatagaaaa gtgagacatc tgccattccc aactctggga aaaccaacta    4140
atatacaacc atataaatga aggccatctt gatggtctca acactaattt ttatgatgca    4200
aatttataca ctgattttg taaaggacaa agttttaaaa gcgtatttaa cttgatgttt    4260
tctatcagca taaataaaat ggtcatgaat agtcattaaa aacagttgcc agtgataatc    4320
tgcatgaagg aaaaagaacc ctgcaaatgg ctattgagtt ggaagtattg ttttgatat    4380 gtaagagata ttcagaatgc tcacactgaa aatgcctcaa cttttaaaag tgtaagaaac    4440
caccatgagt ggtgtctaga tttctaatga agaatcatga tacagtttgg attaagtatc    4500
ttggactggt tttaaacagt gctttgtacc ggatctgctg aagcatctgt ccagctggta    4560
tcctgtgaaa gtttgttatt ttctgagtag acattcttat agagtattgt ctttaaaatc    4620
agattgtctc ttctatattg aaagcatttt tatgttttct aatttaaaaa ttaatatttt    4680
cttatagata ttgtgcaata aagctgaagt agaatgtgtg gttttgcaa atgctttaac    4740 agctgataaa aattttacat ttgtaaaatt aatatattgt actggtacaa atagttttta    4800
aattatattt taaaaagctt ccaa                                           4824
```

<210> SEQ ID NO 5  
<211> LENGTH: 837  
<212> TYPE: PRT  
<213> ORGANISM: Homo sapiens

<400> SEQUENCE: 5

```
Met Ala Glu Pro Ser Gln Ala Pro Thr Pro Ala Pro Ala Ala Gln Pro
1               5                   10                  15

Arg Pro Leu Gln Ser Pro Ala Pro Ala Pro Thr Pro Thr Pro Ala Pro
            20                  25                  30

Ser Pro Ala Ser Ala Pro Ile Pro Thr Pro Thr Pro Ala Pro Ala Pro
        35                  40                  45

Ala Pro Ala Ala Ala Pro Ala Gly Ser Thr Gly Thr Gly Gly Pro Gly
    50                  55                  60

Val Gly Ser Gly Gly Ala Gly Ser Gly Gly Asp Pro Ala Arg Pro Gly
65                  70                  75                  80

Leu Ser Gln Gln Gln Arg Ala Ser Gln Arg Lys Ala Gln Val Arg Gly
                85                  90                  95

Leu Pro Arg Ala Lys Lys Leu Glu Lys Leu Gly Val Phe Ser Ala Cys
            100                 105                 110

Lys Ala Asn Glu Thr Cys Lys Cys Asn Gly Trp Lys Asn Pro Lys Pro
        115                 120                 125
```

```
Pro Thr Ala Pro Arg Met Asp Leu Gln Gln Pro Ala Asn Leu Ser
    130                 135                 140

Glu Leu Cys Arg Ser Cys Glu His Pro Leu Ala Asp His Val Ser His
145                 150                 155                 160

Leu Glu Asn Val Ser Glu Asp Glu Ile Asn Arg Leu Leu Gly Met Val
                165                 170                 175

Val Asp Val Glu Asn Leu Phe Met Ser Val His Lys Glu Glu Asp Thr
            180                 185                 190

Asp Thr Lys Gln Val Tyr Phe Tyr Leu Phe Lys Leu Leu Arg Lys Cys
        195                 200                 205

Ile Leu Gln Met Thr Arg Pro Val Val Glu Gly Ser Leu Gly Ser Pro
    210                 215                 220

Pro Phe Glu Lys Pro Asn Ile Glu Gln Gly Val Leu Asn Phe Val Gln
225                 230                 235                 240

Tyr Lys Phe Ser His Leu Ala Pro Arg Glu Arg Gln Thr Met Phe Glu
                245                 250                 255

Leu Ser Lys Met Phe Leu Leu Cys Leu Asn Tyr Trp Lys Leu Glu Thr
            260                 265                 270

Pro Ala Gln Phe Arg Gln Arg Ser Gln Ala Glu Asp Val Ala Thr Tyr
        275                 280                 285

Lys Val Asn Tyr Thr Arg Trp Leu Cys Tyr Cys His Val Pro Gln Ser
    290                 295                 300

Cys Asp Ser Leu Pro Arg Tyr Glu Thr Thr His Val Phe Gly Arg Ser
305                 310                 315                 320

Leu Leu Arg Ser Ile Phe Thr Val Thr Arg Arg Gln Leu Leu Glu Lys
                325                 330                 335

Phe Arg Val Glu Lys Asp Lys Leu Val Pro Glu Lys Arg Thr Leu Ile
            340                 345                 350

Leu Thr His Phe Pro Lys Phe Leu Ser Met Leu Glu Glu Glu Ile Tyr
        355                 360                 365

Gly Ala Asn Ser Pro Ile Trp Glu Ser Gly Phe Thr Met Pro Pro Ser
    370                 375                 380

Glu Gly Thr Gln Leu Val Pro Arg Pro Ala Ser Val Ser Ala Ala Val
385                 390                 395                 400

Val Pro Ser Thr Pro Ile Phe Ser Pro Ser Met Gly Gly Ser Asn
                405                 410                 415

Ser Ser Leu Ser Leu Asp Ser Ala Gly Ala Glu Pro Met Pro Gly Glu
            420                 425                 430

Lys Arg Thr Leu Pro Glu Asn Leu Thr Leu Glu Asp Ala Lys Arg Leu
        435                 440                 445

Arg Val Met Gly Asp Ile Pro Met Glu Leu Val Asn Glu Val Met Leu
    450                 455                 460

Thr Ile Thr Asp Pro Ala Ala Met Leu Gly Pro Glu Thr Ser Leu Leu
465                 470                 475                 480

Ser Ala Asn Ala Ala Arg Asp Glu Thr Ala Arg Leu Glu Glu Arg Arg
                485                 490                 495

Gly Ile Ile Glu Phe His Val Ile Gly Asn Ser Leu Thr Pro Lys Ala
            500                 505                 510

Asn Arg Arg Val Leu Leu Trp Leu Val Gly Leu Gln Asn Val Phe Ser
        515                 520                 525

His Gln Leu Pro Arg Met Pro Lys Glu Tyr Ile Ala Arg Leu Val Phe
    530                 535                 540

Asp Pro Lys His Lys Thr Leu Ala Leu Ile Lys Asp Gly Arg Val Ile
```

Gly Gly Ile Cys Phe Arg Met Phe Pro Thr Gln Gly Phe Thr Glu Ile
545                 550                 555                 560

Val Phe Cys Ala Val Thr Ser Asn Glu Gln Val Lys Gly Tyr Gly Thr
            565                 570                 575

His Leu Met Asn His Leu Lys Glu Tyr His Ile Lys His Asn Ile Leu
        580                 585                 590

Tyr Phe Leu Thr Tyr Ala Asp Glu Tyr Ala Ile Gly Tyr Phe Lys Lys
    595                 600                 605

Gln Gly Phe Ser Lys Asp Ile Lys Val Pro Lys Ser Arg Tyr Leu Gly
610                 615                 620

Tyr Ile Lys Asp Tyr Glu Gly Ala Thr Leu Met Glu Cys Glu Leu Asn
625                 630                 635                 640

Pro Arg Ile Pro Tyr Thr Glu Leu Ser His Ile Ile Lys Lys Gln Lys
            645                 650                 655

Glu Ile Ile Lys Lys Leu Ile Glu Arg Lys Gln Ala Gln Ile Arg Lys
        660                 665                 670

Val Tyr Pro Gly Leu Ser Cys Phe Lys Glu Gly Val Arg Gln Ile Pro
    675                 680                 685

Val Glu Ser Val Pro Gly Ile Arg Glu Thr Gly Trp Lys Pro Leu Gly
690                 695                 700

Lys Glu Lys Gly Lys Glu Leu Lys Asp Pro Asp Gln Leu Tyr Thr Thr
705                 710                 715                 720

Leu Lys Asn Leu Leu Ala Gln Ile Lys Ser His Pro Ser Ala Trp Pro
            725                 730                 735

Phe Met Glu Pro Val Lys Lys Ser Glu Ala Pro Asp Tyr Tyr Glu Val
        740                 745                 750

Ile Arg Phe Pro Ile Asp Leu Lys Thr Met Thr Glu Arg Leu Arg Ser
    755                 760                 765

Arg Tyr Tyr Val Thr Arg Lys Leu Phe Val Ala Asp Leu Gln Arg Val
770                 775                 780

Ile Ala Asn Cys Arg Glu Tyr Asn Pro Pro Asp Ser Glu Tyr Cys Arg
785                 790                 795                 800

Cys Ala Ser Ala Leu Glu Lys Phe Phe Tyr Phe Lys Leu Lys Glu Gly
            805                 810                 815

Gly Leu Ile Asp Lys
        820                 825                 830

<210> SEQ ID NO 6
<211> LENGTH: 3127
<212> TYPE: DNA
<213> ORGANISM: Homo sapiens

<400> SEQUENCE: 6
ggttgcccat gcggccctag ggctgggagc gcggcgccgc tctccgctgc gggggaggcc     60
atggcggaac cttcccaggc cccgaccccg gccccggctg cgcagcccg gcccccttcag    120 tccccagccc ctgccccaac tccgactcct gcacccagcc cggcttcagc ccgattccg    180 actcccaccc cggcaccagc ccctgcccca gctgcagccc cagccggcag cacagggact    240
ggggggcccg gggtaggaag tgggggggcc gggagcgggg gggatccggc tcgacctggc    300
ctgagccagc agcagcgcgc cagtcagagg aaggcgcaag tccgggggct gccgcgcgcc    360
aagaagcttg agaagctagg ggtcttctcg gcttgcaagg ccaatgaaac ctgtaagtgt    420
aatggctgga aaaaccccaa gccccccact gcaccccgca tggatctgca gcagccagct    480

```
gccaacctga gtgagctgtg ccgcagttgt gagcacccct tggctgacca cgtatcccac    540
ttggagaatg tgtcagagga tgagataaac cgactgctgg ggatggtggt ggatgtggag    600
aatctcttca tgtctgttca caaggaagag gacacagaca ccaagcaggt ctatttctac    660
ctcttcaagc tactgcggaa atgcatcctg cagatgaccc ggcctgtggt ggaggggtcc    720
ctgggcagcc ctccatttga gaaacctaat attgagcagg gtgtgctgaa ctttgtgcag    780
tacaagttta gtcacctggc tccccgggag cggcagacga tgttcgagct ctcaaagatg    840
ttcttgctct gccttaacta ctggaagctt gagacacctg cccagtttcg gcagaggtct    900
caggctgagg acgtggctac ctacaaggtc aattacacca tgatggctctg ttactgccac    960 gtgccccaga gctgtgatag cctccccccgc tacgaaacca ctcatgtctt tgggcgaagc   1020
cttctccggt ccattttcac cgttacccgc cggcagctgc tggaaaagtt ccgagtggag   1080
aaggacaaat tggtgcccga aagaggacc ctcatcctca ctcacttccc caaattcctg    1140
tccatgctgg aggaggagat ctatggggca aactctccaa tctggagtc aggcttcacc    1200 atgccaccct cagagggag acagctggtt ccccggccag cttcagtcag tgcagcggtt    1260
gttcccagca cccccatctt cagccccagc atgggtgggg gcagcaacag ctccctgagt   1320
ctggattctg caggggccga gcctatgcca ggcgagaaga ggacgctccc agagaacctg   1380
accctggagg atgccaagcg gctccgtgtg atgggtgaca tccccatgga gctggtcaat   1440
gaggtcatgc tgaccatcac tgaccctgct gccatgctgg ggcctgagac gagcctgctt   1500
tcggccaatg cggcccggga tgagacagcc cgcctggagg agcgccgcgg catcatcgag   1560
ttccatgtca tcggcaactc actgacgccc aaggccaacc ggcgggtgtt gctgtggctc   1620
gtggggctgc agaatgtctt tcccaccag ctgccgcgca tgcctaagga gtatatcgcc   1680
cgcctcgtct ttgacccgaa gcacaagact ctggccttga tcaaggatgg gcgggtcatc   1740
ggtggcatct gcttccgcat gttccccacc cagggcttca cggagattgt cttctgtgct   1800
gtcacctcga atgagcaggt caagggttat gggacccacc tgatgaacca cctgaaggag   1860
tatcacatca gcacaacat tctctacttc ctcacctacg ccgacgagta cgccatcggc   1920
tacttcaaaa agcagggttt ctccaaggac atcaaggtgc ccaagagccg ctacctgggc   1980
tacatcaagg actacgaggg agcgacgctg atggagtgtg agctgaatcc ccgcatcccc   2040
tacacggagc tgtcccacat catcaagaag cagaaagaga tcatcaagaa gctgattgag   2100
cgcaaacagg cccagatccg caaggtctac ccgggggctca gctgcttcaa ggagggcgtg   2160
aggcagatcc ctgtggagag cgttcctggc attcgagaga caggctggaa gccattgggg   2220
aaggagaagg ggaaggagct gaaggacccc gaccagctct acacaaccct caaaaacctg   2280
ctggcccaaa tcaagtctca ccccagtgcc tggcccttca tggagcctgt gaagaagtcg   2340
gaggcccctg actactacga ggtcatccgc ttccccattg acctgaagac catgactgag   2400
cggctgcgaa gccgctacta cgtgacccgg aagctctttg tggccgacct gcagcgggtc   2460
atcgccaact gtcgcgagta caaccccccg gacagcgagt actgccgctg tgccagcgcc   2520
ctggagaagt tcttctactt caagctcaag gagggaggcc tcattgacaa gtaggcccat   2580
ctttgggccg cagccctgac ctggaatgtc tccacctcgg attctgatct gatccttagg   2640
gggtgccctg gccccacgga cccgactcag cttgagacac tccagccaag ggtcctccgg   2700
acccgatcct gcagctcttt ctggaccttc aggcacccccc aagcgtgcag ctctgtccca   2760
gccttcactg tgtgtgagag gtctcctggg ttggggccca gccctctag agtagctggt    2820
```

-continued

```
ggccagggat gaaccttgcc cagccgtggt ggcccccagg cctggtcccc aagagctttg    2880
gaggcttgga ttcctgggcc tggcccaggt ggctgtttcc ctgaggacca gaactgctca    2940
ttttagcttg agtgatggct tcaggggttg gaagttcagc ccaaactgaa gggggccatg    3000
ccttgtccag cactgttctg tcagtctccc ccaggggtgg ggggtatggg gaccattcat    3060
tccctggcat taatcccttg gagggaataa taaagctttt tatttctctg tgaaaaaaaa    3120
aaaaaaa                                                             3127
```

HISTONE ACETYLTRANSFERASE ACTIVATORS AND USES THEREOF

This application is a divisional of U.S. patent application Ser. No. 13/493,490, filed Jun. 11, 2012, which is a continuation-in-part of International Patent Application No. PCT/US2010/059925, filed Dec. 10, 2010, which claims priority to U.S. Provisional Patent Application Nos. 61/285,287, filed Dec. 10, 2009, 61/317,765, filed Mar. 26, 2010, 61/354,964, filed Jun. 15, 2010, 61/355,110, filed Jun. 15, 2010, 61/363,009, filed Jul. 9, 2010. U.S. patent application Ser. No. 13/439,490 also claims priority to U.S. Provisional Patent Application No. 61/539,697, filed Sep. 27, 2011, the contents of each of which are hereby incorporated by reference in their entireties.

All patents, patent applications and publications cited herein are hereby incorporated by reference in their entirety. The disclosures of these publications in their entireties are hereby incorporated by reference into this application in order to more fully describe the state of the art as known to those skilled therein as of the date of the invention described and claimed herein.

GOVERNMENT SUPPORT

This invention was made with government support under NS049442, AG017490, AG031294 and AG14351 awarded by the NIH. The government has certain rights in the invention.

This patent disclosure contains material that is subject to copyright protection. The copyright owner has no objection to the facsimile reproduction by anyone of the patent document or the patent disclosure as it appears in the U.S. Patent and Trademark Office patent file or records, but otherwise reserves any and all copyright rights.

BACKGROUND OF THE INVENTION

Cognitive neurodegenerative disorders are characterized by synaptic dysfunction, cognitive abnormalities, and/or the presence of inclusion bodies throughout the CNS containing, for example, but not limited to native beta-amyloid fragments, native and phosphorylated Tau, native and phosphorylated alpha-synuclein, lipofuscin, cleaved TARDBP (TDB-43), in various percentages and in relation to the specific disease.

Alzheimer's disease (AD) is a neurodegenerative disorder characterized by memory loss, synaptic dysfunction and accumulation of amyloid β-peptides (Aβ). It is caused in part by increased levels of amyloid-β-peptide 1-42 (Aβ42). Although Alzheimer's Disease (AD) was described almost a century ago, the molecular mechanisms that lead to its development are still unknown. From a neuropathological point of view it is characterized by the presence of amyloid plaques and neurofibrillary tangles associated with neuronal degeneration, whereas the clinical hallmark is a progressive memory loss associated with a number of neuropsychiatric symptoms Histone Acetyltransferases (HATs) are involved in histone acetylation (leading to gene activation), chromosome decondensation, DNA repair and non-histone substrate modification.

SUMMARY OF THE INVENTION

The invention is directed to compounds with histone acetyltransferase (HAT) activity, high selectivity, and blood-brain-barrier (BBB) permeability. In one aspect, the compound is a compound of Formula (I),

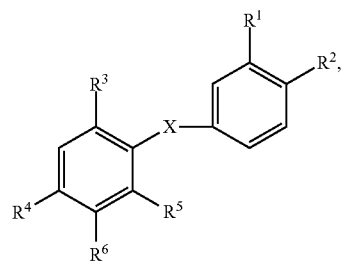

wherein,
$R^1$ is H, or $CF_3$;
$R^2$ is H, Cl, or CN;
$R^3$ is H, O-methyl, O-ethyl, S-ethyl, O-cyclopentyl, $OCH_2CH_2N(CH_3)_2$, or $CH_2CH_2CH_2N(CH_3)_2$;
$R^4$ is H; C(=O)NH-phenyl, wherein phenyl is substituted with one or more halo or $CF_3$;
$R^5$ is H, $C_1$-$C_5$-alkyl, OH, $OCH_3$, O-ethyl, $OCH_2CH_2N(CH_3)_2$, $CH_2CH_2CH_2N(CH_3)_2$, $SCH_2CH_2N(CH_3)_2$, or $OCH_2C(=O)O$-alkyl; $R^6$ is H, O-methyl, O-ethyl, $OCH_2CH_2N(CH_3)_2$; and
X is CONH, SONH, $SO_2NH$, NHC(=O)NH, or NHCO, or a pharmaceutically acceptable salt or hydrate thereof.

In one aspect of the invention, the compound is a compound of Formula (II),

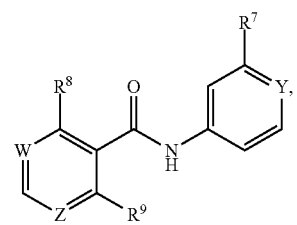

wherein,
$R^7$ is H or $CF_3$;
$R^8$ is O-ethyl or S-methyl;
$R^9$ is butyl or $OCH_2CH_2N(CH_3)_2$;
Y is C—Cl, C—CN, C—$NO_2$, or N;
W is CH or N; and
Z is CH or N, or a pharmaceutically acceptable salt or hydrate thereof.

In one aspect, the compound is a compound of Formula (III),

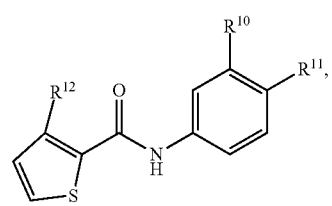

wherein
  $R^{10}$ is $CF_3$;
  $R^{11}$ is CN; and
  $R^{12}$ is O-ethyl, or a pharmaceutically acceptable salt or hydrate thereof.

In another aspect, the compound is a compound of Formula (IV),

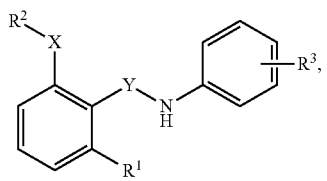

Formula IV wherein
  X is S, $S(O)_2$, NH, O, or C;
  Y is —C(O), $S(O)_2$, or NH—C(O);
  $R^1$ is H, Methyl, Ethyl, n-Propyl, Isopropyl, n-butyl, t-butyl, $C_8H_{18}$, $C_{15}H_{26}$, $C_{15}H_{28}$, $C_{15}H_{30}$, $C_{15}H_{32}$, $SR^4$, or $OR^4$;
  $R^2$ is H, methyl, ethyl, n-propyl, isopropyl, n-butyl, t-butyl, or $(C_1-C_6$ alkyl$)-CO_2R^6$;
  $R^3$ is H, methyl, ethyl, n-propyl, isopropyl, n-butyl, t-butyl, $CF_3$, $CCl_3$, $Cl_3$, F, Cl, I, $NO_2$, or CN;
  $R^4$ is $(C_1-C_6$ alkyl$)-N(R^5)_2$— or $C_1-C_6$ alkyl;
  $R^5$ is independently hydrogen, $C_1-C_6$ alkyl, or $C_3-C_8$ cycloalkyl; and
  $R^6$ is hydrogen, $C_1-C_6$ alkyl, or $C_3-C_8$ cycloalkyl, or a pharmaceutically acceptable salt or hydrate thereof.

In a further aspect, the compound is a compound of Formula (V),

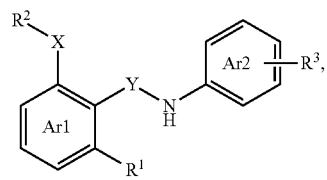

Formula V wherein
  X is S, $S(O)_2$, NH, O, or C;
  Y is —C(O), $S(O)_2$, or NH—C(O);
  AR1 is a 5-membered aromatic ring or a 6-membered aromatic ring containing 1-2 Nitrogens;
  AR2 is a 5-membered aromatic ring, a 6-membered aromatic ring or a 6-membered aromatic ring containing 1-2 Nitrogens;
  $R^1$ is H, Methyl, Ethyl, n-Propyl, Isopropyl, n-butyl, t-butyl, $C_8H_{18}$, $C_{15}H_{26}$, $C_{15}H_{28}$, $C_{15}H_{30}$, $C_{15}H_{32}$, $SR^4$, or $OR^4$;
  $R^2$ is H, methyl, ethyl, n-propyl, isopropyl, n-butyl, t-butyl, or $(C_1-C_6$ alkyl$)-CO_2R^6$;
  $R^3$ is H, methyl, ethyl, n-propyl, isopropyl, n-butyl, t-butyl, $CF_3$, $CCl_3$, $Cl_3$, F, Cl, I, $NO_2$, or CN;
  $R^4$ is $(C_1-C_6$ alkyl$)-N(R^5)_2$— or $C_1-C_6$ alkyl;
  $R^5$ is independently hydrogen, $C_1-C_6$ alkyl, or $C_3-C_8$ cycloalkyl; and
  $R^6$ is hydrogen, $C_1-C_6$ alkyl, or $C_3-C_8$ cycloalkyl, or a pharmaceutically acceptable salt or hydrate thereof.

In one embodiment, the compound of Formula (I) is YF2 compound:

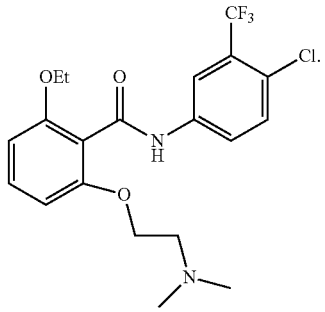 [SMILES: CCOc1cccc(OCCN(C)C)c1C(=O)Nc1ccc(Cl)c(C(F)(F)F)c1]

In other embodiments, the compound of Formula (I) is:

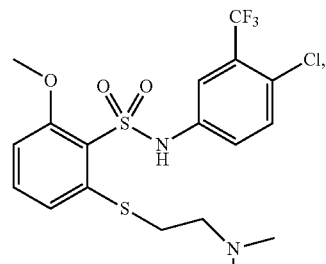

1

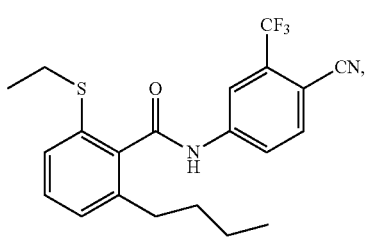

2

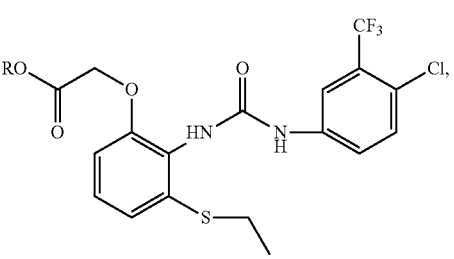

3

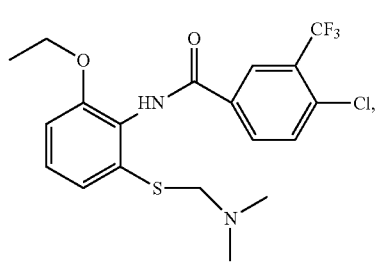

4

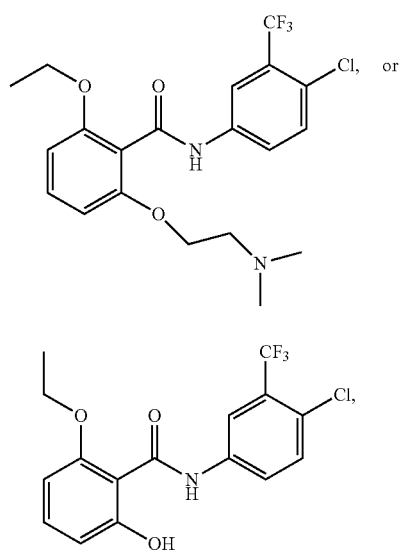
wherein R of compound 3 is H, methyl, ethyl, n-propyl, isopropyl, n-butyl, t-butyl, $C_8H_{18}$, $C_{15}H_{26}$, $C_{15}H_{28}$, $C_{15}H_{30}$, or $C_{15}H_{32}$.
In some embodiments, the compound of Formula (I) is:
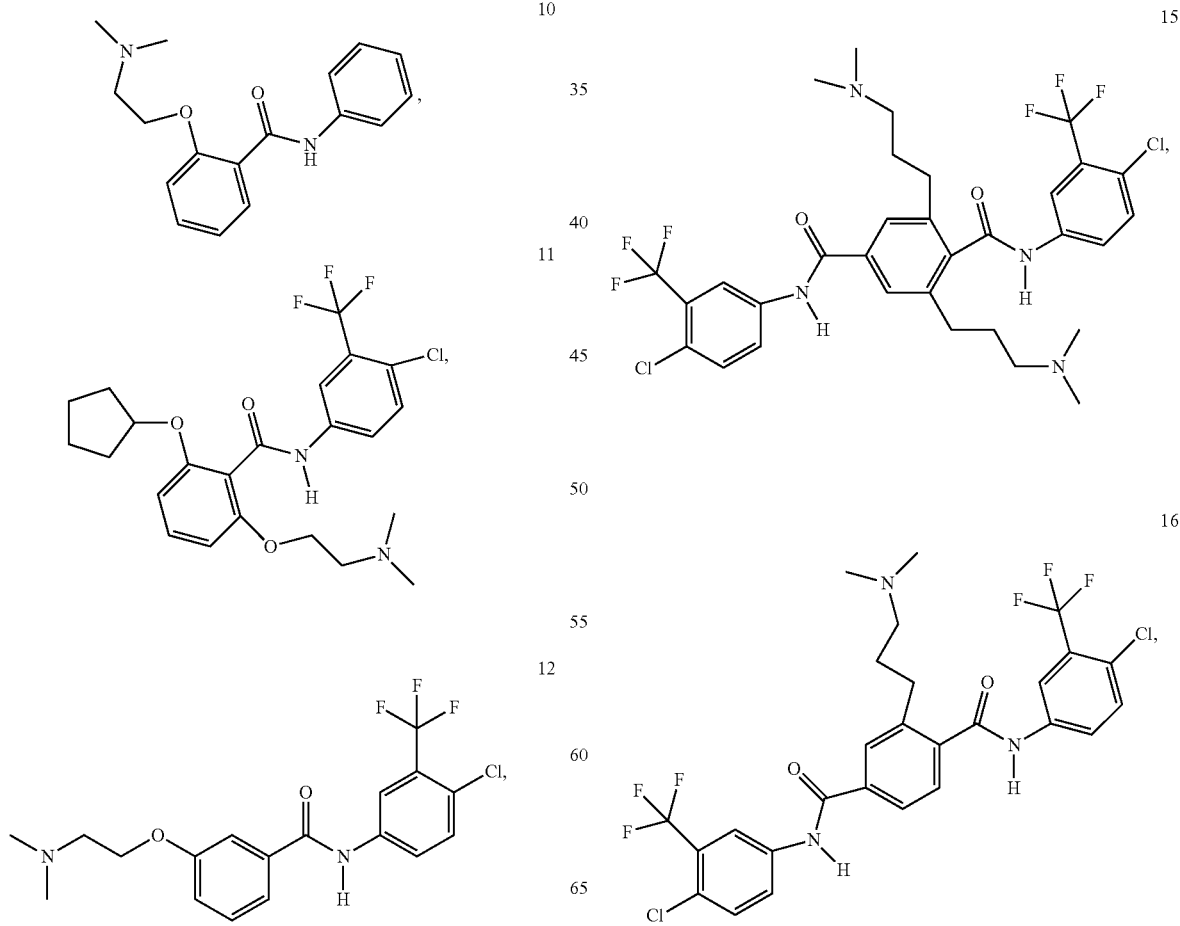
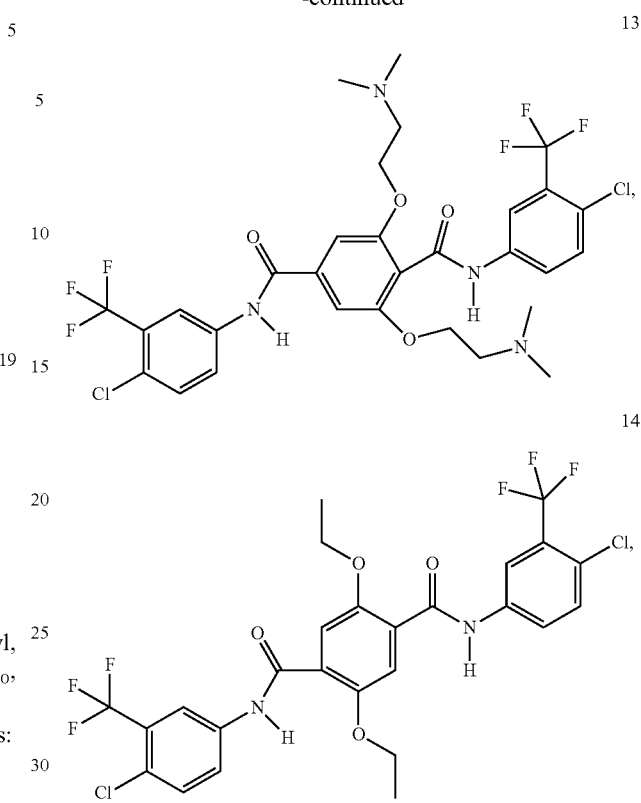

17

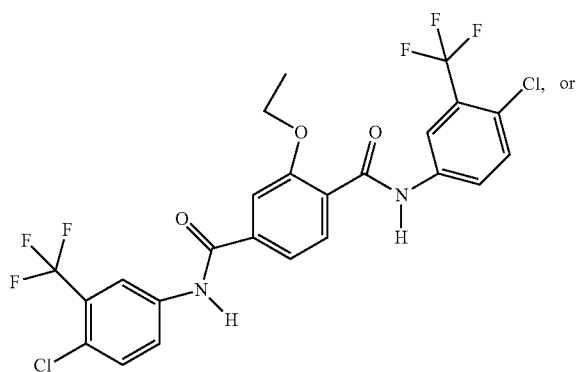

5

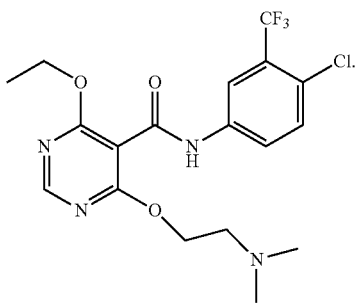

In some embodiments, the compound of Formula (V) is:

18

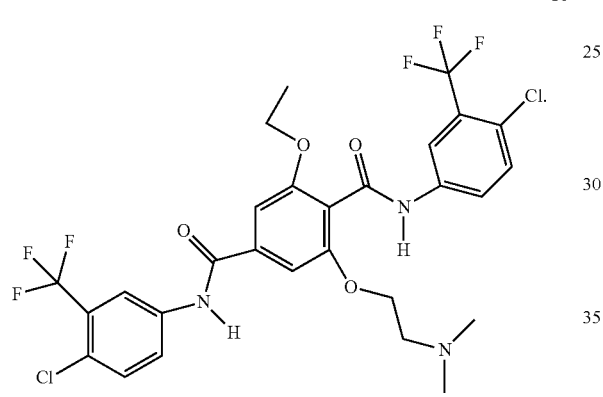

6

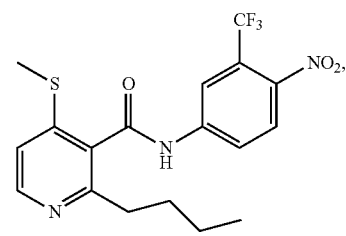

7

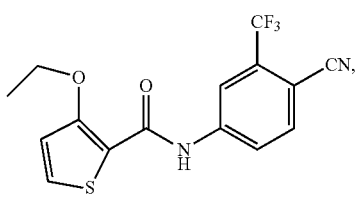

8

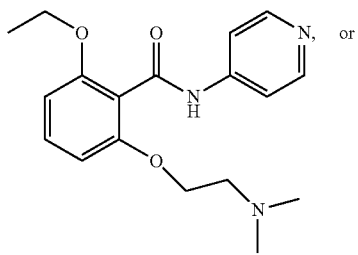

In some embodiments, the compound of Formula (II) is:

6

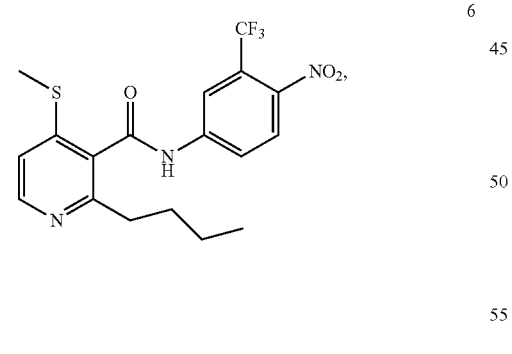

9

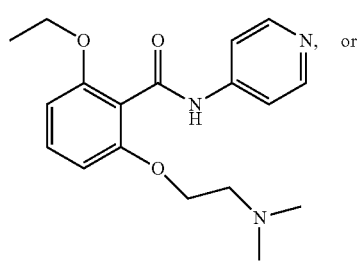

8

An aspect of the invention provides a method for screening compounds of Formula (I), Formula (II), Formula (III), Formula (IV), Formula (V), or Formula (VI) to treat conditions associated with accumulated amyloid-beta peptide deposits. The method comprises (a) administering a HAT Activator compound of Formula (I), Formula (II), Formula (III), Formula (IV), Formula (V), or Formula (VI) to an animal model of amyloid-beta peptide deposit accumulation; and (b) selecting a HAT Activator compound of Formula (I), Formula (II), Formula (III), Formula (IV), Formula (V), or Formula (VI) that can modulate histone acetylation after administration of the HAT Activator compound in an animal model of amyloid-beta peptide deposit accumulation.

An aspect of the invention further provides a method for identifying a histone acetyltransferase (HAT) activator compound of Formula (I), Formula (II), Formula (III), Formula (IV), Formula (V), or Formula (VI) to treat conditions associated with accumulated amyloid-beta peptide deposits, wherein the method comprises selecting a HAT Activator compound of Formula (I), Formula (II), Formula (III), Formula (IV), Formula (V), or Formula (VI) having one or more of the following features: (a) the $EC_{50}$ of the compound is no more than about 1000 nM; (b) the histone acetylation activity in vitro targets histone protein H2, H3, and/or H4; (c) the compound penetrates the blood brain barrier; (d) or a combination thereof. In one embodiment, the compound has a molecular mass less than about 500 Da, has a polar surface area less than about 90 $Å^2$, has less than 8 hydrogen bonds, or a combination thereof, in order to penetrate the blood brain barrier.

An aspect of the invention provides a method for reducing amyloid beta (Aβ) protein deposits in a subject wherein the method comprises administering to the subject an effective amount of a composition comprising a HAT Activator compound of Formula (I), Formula (II), Formula (III), Formula (IV), Formula (V), or Formula (VI), thereby decreasing Aβ protein deposits in the subject. In one embodiment, the subject exhibits abnormally elevated levels of amyloid beta plaques. In another embodiment, the subject is afflicted with Alzheimer's disease, Lewy body dementia, inclusion body myositis, or cerebral amyloid angiopathy. In a further embodiment, the Aβ protein deposit comprises an $Aβ_{40}$ isomer, an $Aβ_{42}$ isomer, or a combination of isomers. In one embodiment, the compound is YF2. In other embodiments, the effective amount is at least about 1 mg/kg body weight, at least about 2 mg/kg body weight, at least about 3 mg/kg body weight, at least about 4 mg/kg body weight, at least about 5 mg/kg body weight, at least about 6 mg/kg body weight, at least about 7 mg/kg body weight, at least about 8 mg/kg body weight, at least about 9 mg/kg body weight, at least about 10 mg/kg body weight, at least about 15 mg/kg body weight, at least about 20 mg/kg body weight, at least about 25 mg/kg body weight, at least about 30 mg/kg body weight, at least about 40 mg/kg body weight, at least about 50 mg/kg body weight, at least about 75 mg/kg body weight, or at least about 100 mg/kg body weight. In some embodiments, the composition crosses the blood brain barrier. In some embodiments, the compound is compound 1, compound 2, compound 3, compound 4, compound 5, compound 6, compound 7, compound 8, compound 9, compound 10, compound 11, compound 12, compound 13, compound 14, compound 15, compound 16, compound 17, compound 18, or compound 19. In other embodiments, the compound increases histone acetylation. In further embodiments, histone acetylation comprises acetylation of histones H2B, H3, H4, or a combination thereof. In further embodiments, histone acetylation comprises acetylation of histone lysine residues H3K4, H3K9, H3K14, H4K5, H4K8, H4K12, H4K16, or a combination thereof.

An aspect of the invention further provides a method for treating Alzheimer's Disease in a subject, the method comprising administering to a subject a therapeutic amount of a pharmaceutical composition comprising a HAT activator compound. In one embodiment, the compound is YF2. In other embodiments, the effective amount is at least about 1 mg/kg body weight, at least about 2 mg/kg body weight, at least about 3 mg/kg body weight, at least about 4 mg/kg body weight, at least about 5 mg/kg body weight, at least about 6 mg/kg body weight, at least about 7 mg/kg body weight, at least about 8 mg/kg body weight, at least about 9 mg/kg body weight, at least about 10 mg/kg body weight, at least about 15 mg/kg body weight, at least about 20 mg/kg body weight, at least about 25 mg/kg body weight, at least about 30 mg/kg body weight, at least about 40 mg/kg body weight, at least about 50 mg/kg body weight, at least about 75 mg/kg body weight, or at least about 100 mg/kg body weight. In some embodiments, the composition crosses the blood brain barrier. In some embodiments, the compound is compound 1, compound 2, compound 3, compound 4, compound 5, compound 6, compound 7, compound 8, compound 9, compound 10, compound 11, compound 12, compound 13, compound 14, compound 15, compound 16, compound 17, compound 18, or compound 19. In other embodiments, the compound increases histone acetylation. In further embodiments, histone acetylation comprises acetylation of histones H2B, H3, H4, or a combination thereof. In further embodiments, histone acetylation comprises acetylation of histone lysine residues H3K4, H3K9, H3K14, H4K5, H4K8, H4K12, H4K16, or a combination thereof.

An aspect of the invention further provides a method for treating Alzheimer's Disease in a subject, the method comprising administering to a subject a therapeutic amount of a pharmaceutical composition comprising a compound of Formula (I), Formula (II), Formula (III), Formula (IV), Formula (V), or Formula (VI). In one embodiment, the compound is YF2. In other embodiments, the effective amount is at least about 1 mg/kg body weight, at least about 2 mg/kg body weight, at least about 3 mg/kg body weight, at least about 4 mg/kg body weight, at least about 5 mg/kg body weight, at least about 6 mg/kg body weight, at least about 7 mg/kg body weight, at least about 8 mg/kg body weight, at least about 9 mg/kg body weight, at least about 10 mg/kg body weight, at least about 15 mg/kg body weight, at least about 20 mg/kg body weight, at least about 25 mg/kg body weight, at least about 30 mg/kg body weight, at least about 40 mg/kg body weight, at least about 50 mg/kg body weight, at least about 75 mg/kg body weight, or at least about 100 mg/kg body weight. In some embodiments, the composition crosses the blood brain barrier. In some embodiments, the compound is compound 1, compound 2, compound 3, compound 4, compound 5, compound 6, compound 7, compound 8, compound 9, compound 10, compound 11, compound 12, compound 13, compound 14, compound 15, compound 16, compound 17, compound 18, or compound 19. In other embodiments, the compound increases histone acetylation. In further embodiments, histone acetylation comprises acetylation of histones H2B, H3, H4, or a combination thereof. In further embodiments, histone acetylation comprises acetylation of histone lysine residues H3K4, H3K9, H3K14, H4K5, H4K8, H4K12, H4K16, or a combination thereof.

Another aspect of the invention provides a method for increasing memory retention in a subject afflicted with a neurodegenerative disease, the method comprising administering to a subject a therapeutic amount of a pharmaceutical composition comprising a compound of Formula (I), Formula (II), Formula (III), Formula (IV), Formula (V), or Formula (VI). In one embodiment, the neurodegenerative disease comprises Adrenoleukodystrophy (ALD), Alcoholism, Alexander's disease, Alper's disease, Alzheimer's disease, Amyotrophic lateral sclerosis (Lou Gehrig's Disease), Ataxia telangiectasia, Batten disease (also known as Spielmeyer-Vogt-Sjögren-Batten disease), Bovine spongiform encephalopathy (BSE), Canavan disease, Cockayne syndrome, Corticobasal degeneration, Creutzfeldt-Jakob disease, Familial fatal insomnia, Frontotemporal lobar degeneration, Huntington's disease, HIV-associated dementia, Kennedy's disease, Krabbe's disease, Lewy body dementia, Neuroborreliosis, Machado-Joseph disease (Spinocerebellar ataxia type 3), Multiple System Atrophy, Multiple sclerosis, Narcolepsy, Niemann Pick disease, Parkinson's disease, Pelizaeus-Merzbacher Disease, Pick's disease, Primary lateral sclerosis, Prion diseasesm Progressive Supranuclear Palsy, Rett's syndrome, Tau-positive FrontoTemporal dementia, Tau-negative FrontoTemporal dementia, Refsum's disease, Sandhoff disease, Schilder's disease, Subacute combined degeneration of spinal cord secondary to Pernicious Anaemia, Spielmeyer-Vogt-Sjogren-Batten disease (also known as Batten disease), Spinocerebellar ataxia (multiple types with varying characteristics), Spinal muscular atrophy, Steele-Richardson-Olszewski disease, Tabes dorsalis, or Toxic encephalopathy. In one embodiment, the compound is YF2. In other embodiments, the effective amount is at least about 1 mg/kg body weight, at least about 2 mg/kg body weight, at least about 3 mg/kg body weight, at least about 4 mg/kg body weight, at least about 5 mg/kg body weight, at least about 6 mg/kg body weight, at least about 7 mg/kg body weight, at least about 8 mg/kg body weight, at least about 9 mg/kg body weight, at least about 10 mg/kg body weight, at least about 15 mg/kg body weight, at least about 20 mg/kg body weight, at least about 25 mg/kg body weight, at least about 30 mg/kg body weight, at least about 40 mg/kg body weight, at least about 50 mg/kg body weight, at least about 75 mg/kg body weight, or at least about 100 mg/kg body weight. In some embodiments, the composition crosses the blood brain barrier. In some embodiments, the compound is compound 1, compound 2, compound 3, compound 4, compound 5, compound 6, compound 7, compound 8, compound 9, compound 10, compound 11, compound 12, compound 13, compound 14, compound 15, compound 16, compound 17, compound 18, or compound 19. In other embodiments, the compound increases histone acetylation. In further embodiments, histone acetylation comprises acetylation of histones H2B, H3, H4, or a combination thereof. In further embodiments, histone acetylation comprises acetylation of histone lysine residues H3K4, H3K9, H3K14, H4K5, H4K8, H4K12, H4K16, or a combination thereof.

An aspect of the invention further provides a method for increasing synaptic plasticity in a subject afflicted with a neurodegenerative disease, the method comprising administering to a subject a therapeutic amount of a composition that increases histone acetylation in the subject, wherein the composition comprises a compound of Formula (I), Formula (II), Formula (III), Formula (IV), Formula (V), or Formula (VI). In one embodiment, the compound is YF2. In other embodiments, the effective amount is at least about 1 mg/kg body weight, at least about 2 mg/kg body weight, at least about 3 mg/kg body weight, at least about 4 mg/kg body weight, at least about 5 mg/kg body weight, at least about 6 mg/kg body weight, at least about 7 mg/kg body weight, at least about 8 mg/kg body weight, at least about 9 mg/kg body weight, at least about 10 mg/kg body weight, at least about 15 mg/kg body weight, at least about 20 mg/kg body weight, at least about 25 mg/kg body weight, at least about 30 mg/kg body weight, at least about 40 mg/kg body weight, at least about 50 mg/kg body weight, at least about 75 mg/kg body weight, body weight, or at least about 100 mg/kg body weight. In some embodiments, the composition crosses the blood brain barrier. In one embodiment, the neurodegenerative disease comprises Adrenoleukodystrophy (ALD), Alcoholism, Alexander's disease, Alper's disease, Alzheimer's disease, Amyotrophic lateral sclerosis (Lou Gehrig's Disease), Ataxia telangiectasia, Batten disease (also known as Spielmeyer-Vogt-Sjögren-Batten disease), Bovine spongiform encephalopathy (BSE), Canavan disease, Cockayne syndrome, Corticobasal degeneration, Creutzfeldt-Jakob disease, Familial fatal insomnia, Frontotemporal lobar degeneration, Huntington's disease, HIV-associated dementia, Kennedy's disease, Krabbe's disease, Lewy body dementia, Neuroborreliosis, Machado-Joseph disease (Spinocerebellar ataxia type 3), Multiple System Atrophy, Multiple sclerosis, Narcolepsy, Niemann Pick disease, Parkinson's disease, Pelizaeus-Merzbacher Disease, Pick's disease, Primary lateral sclerosis, Prion diseasesm Progressive Supranuclear Palsy, Rett's syndrome, Tau-positive FrontoTemporal dementia, Tau-negative FrontoTemporal dementia, Refsum's disease, Sandhoff disease, Schilder's disease, Subacute combined degeneration of spinal cord secondary to Pernicious Anaemia, Spielmeyer-Vogt-Sjogren-Batten disease (also known as Batten disease), Spinocerebellar ataxia (multiple types with varying characteristics), Spinal muscular atrophy, Steele-Richardson-Olszewski disease, Tabes dorsalis, or Toxic encephalopathy. In another embodiment, synaptic plasticity comprises learning, memory, or a combination thereof. In some embodiments, synaptic plasticity comprises long term potentiation (LTP). In some embodiments, the compound is compound 1, compound 2, compound 3, compound 4, compound 5, compound 6, compound 7, compound 8, compound 9, compound 10, compound 11, compound 12, compound 13, compound 14, compound 15, compound 16, compound 17, compound 18, or compound 19. In other embodiments, the compound increases histone acetylation. In further embodiments, histone acetylation comprises acetylation of histones H2B, H3, H4, or a combination thereof. In further embodiments, histone acetylation comprises acetylation of histone lysine residues H3K4, H3K9, H3K14, H4K5, H4K8, H4K12, H4K16, or a combination thereof.

An aspect of the invention further provides a method for treating Alzheimer's Disease in a subject, the method comprising administering to a subject a therapeutic amount of a pharmaceutical composition comprising a compound of Formula (I), Formula (II), Formula (III), Formula (IV), Formula (V), or Formula (VI). In one embodiment, the compound is YF2. In other embodiments, the effective amount is at least about 1 mg/kg body weight, at least about 2 mg/kg body weight, at least about 3 mg/kg body weight, at least about 4 mg/kg body weight, at least about 5 mg/kg body weight, at least about 6 mg/kg body weight, at least about 7 mg/kg body weight, at least about 8 mg/kg body weight, at least about 9 mg/kg body weight, at least about 10 mg/kg body weight, at least about 15 mg/kg body weight, at least about 20 mg/kg body weight, at least about 25 mg/kg body weight, at least about 30 mg/kg body weight, at least about 40 mg/kg body weight, at least about 50 mg/kg body weight, at least about 75 mg/kg body weight, or at least about 100 mg/kg body weight. In some embodiments, the composition crosses the blood brain barrier. In some embodiments, the compound is compound 1, compound 2, compound 3, compound 4, compound 5, compound 6, compound 7, compound 8, compound 9, compound 10, compound 11, compound 12, compound 13, compound 14, compound 15, compound 16, compound 17, compound 18, or compound 19. In other embodiments, the compound increases histone acetylation. In further embodiments, histone acetylation comprises acetylation of histones H2B, H3, H4, or a combination thereof. In further embodiments, histone acetylation comprises acetylation of histone lysine residues H3K4, H3K9, H3K14, H4K5, H4K8, H4K12, H4K16, or a combination thereof.

An aspect of the invention provides a method for ameliorating symptoms of Parkinson's Disease in a subject, the method comprising administering to a subject a therapeutic amount of a pharmaceutical composition comprising a HAT activator compound. In one embodiment, the HAT activator compound can be a compound of Formula (I), Formula (II), Formula (III), Formula (IV), Formula (V), or Formula (VI). In one embodiment, the compound is YF2. In other embodiments, the effective amount is at least about 1 mg/kg body weight, at least about 2 mg/kg body weight, at least about 3 mg/kg body weight, at least about 4 mg/kg body weight, at least about 5 mg/kg body weight, at least about 6 mg/kg body weight, at least about 7 mg/kg body weight, at least about 8 mg/kg body weight, at least about 9 mg/kg body weight, at least about 10 mg/kg body weight, at least about 15 mg/kg body weight, at least about 20 mg/kg body weight, at least about 25 mg/kg body weight, at least about 30 mg/kg body weight, at least about 40 mg/kg body weight, at least about 50 mg/kg body weight, at least about 75 mg/kg body weight, or at least about 100 mg/kg body weight. In some embodiments, the composition crosses the blood brain barrier. In some embodiments, the compound is compound 1, compound 2, compound 3, compound 4, compound 5, compound 6, compound 7, compound 8, compound 9, compound 10, compound 11, compound 12, compound 13, compound 14, compound 15, compound 16, compound 17, compound 18, or compound 19. In other embodiments, the compound increases histone acetylation. In further embodiments, histone acetylation comprises acetylation of histones H2B, H3, H4, or a combination thereof. In further embodiments, histone acetylation comprises acetylation of histone lysine residues H3K4, H3K9, H3K14, H4K5, H4K8, H4K12, H4K16, or a combination thereof. In one embodiment, the symptoms of Parkinson's Disease comprise tremor, bradykinesia, dyskinesia, rigidity, postural instability, dystonia, akathisia, dementia, impaired gross motor coordination, or a combination of the listed symptoms. In another embodiment, the postural instability comprises impaired imbalance, impaired coordination, or a combination thereof.

An aspect of the invention also provides a method for treating cancer in a subject, the method comprising administering to a subject a therapeutic amount of a pharmaceutical composition comprising a compound of Formula (I), Formula (II) or Formula (III). In one embodiment, the compound is YF2. In other embodiments, the effective amount is at least about 1 mg/kg body weight, at least about 2 mg/kg body weight, at least about 3 mg/kg body weight, at least about 4 mg/kg body weight, at least about 5 mg/kg body weight, at least about 6 mg/kg body weight, at least about 7 mg/kg body weight, at least about 8 mg/kg body weight, at least about 9 mg/kg body weight, at least about 10 mg/kg body weight, at least about 15 mg/kg body weight, at least about 20 mg/kg body weight, at least about 25 mg/kg body weight, at least about 30 mg/kg body weight, at least about 40 mg/kg body weight, at least about 50 mg/kg body weight, at least about 75 mg/kg body weight, or at least about 100 mg/kg body weight. In some embodiments, the composition crosses the blood brain barrier. In one embodiment, the cancer comprises B cell lymphoma, colon cancer, lung cancer, renal cancer, bladder cancer, T cell lymphoma, myeloma, leukemia, chronic myeloid leukemia, acute myeloid leukemia, chronic lymphocytic leukemia, acute lymphocytic leukemia, hematopoietic neoplasias, thymoma, lymphoma, sarcoma, lung cancer, liver cancer, non-Hodgkins lymphoma, Hodgkins lymphoma, uterine cancer, renal cell carcinoma, hepatoma, adenocarcinoma, breast cancer, pancreatic cancer, liver cancer, prostate cancer, head and neck carcinoma, thyroid carcinoma, soft tissue sarcoma, ovarian cancer, primary or metastatic melanoma, squamous cell carcinoma, basal cell carcinoma, brain cancer, angiosarcoma, hemangiosarcoma, bone sarcoma, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, testicular cancer, uterine cancer, cervical cancer, gastrointestinal cancer, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, Waldenstroom's macroglobulinemia, papillary adenocarcinomas, cystadenocarcinoma, bronchogenic carcinoma, bile duct carcinoma, choriocarcinoma, seminoma, embryonal carcinoma, Wilms' tumor, lung carcinoma, epithelial carcinoma, cervical cancer, testicular tumor, glioma, astrocytoma, medulloblastoma, craniopharyngioma, ependymoma, pinealoma, hemangioblastoma, acoustic neuroma, oligodendroglioma, meningioma, retinoblastoma, leukemia, melanoma, neuroblastoma, small cell lung carcinoma, bladder carcinoma, lymphoma, multiple myeloma, or medullary carcinoma. In some embodiments, the compound is compound 1, compound 2, compound 3, compound 4, compound 5, compound 6, compound 7, compound 8, compound 9, compound 10, compound 11, compound 12, compound 13, compound 14, compound 15, compound 16, compound 17, compound 18, or compound 19.

An aspect of the invention provides a method for treating Huntington's Disease in a subject, the method comprising administering to a subject a therapeutic amount of a pharmaceutical composition comprising a HAT activator compound. In one embodiment, the HAT activator compound can be a compound of Formula (I), Formula (II), Formula (III), Formula (IV), Formula (V), or Formula (VI). In one embodiment, the compound is YF2. In other embodiments, the effective amount is at least about 1 mg/kg body weight, at least about 2 mg/kg body weight, at least about 3 mg/kg body weight, at least about 4 mg/kg body weight, at least about 5 mg/kg body weight, at least about 6 mg/kg body weight, at least about 7 mg/kg body weight, at least about 8 mg/kg body weight, at least about 9 mg/kg body weight, at least about 10 mg/kg body weight, at least about 15 mg/kg body weight, at least about 20 mg/kg body weight, at least about 25 mg/kg body weight, at least about 30 mg/kg body weight, at least about 40 mg/kg body weight, at least about 50 mg/kg body weight, at least about 75 mg/kg body weight, or at least about 100 mg/kg body weight. In some embodiments, the composition crosses the blood brain barrier. In some embodiments, the compound is compound 1, compound 2, compound 3, compound 4, compound 5, compound 6, compound 7, compound 8, compound 9, compound 10, compound 11, compound 12, compound 13, compound 14, compound 15, compound 16, compound 17, compound 18, or compound 19. In other embodiments, the compound increases histone acetylation. In further embodiments, histone acetylation comprises acetylation of histones H2B, H3, H4, or a combination thereof. In further embodiments, histone acetylation comprises acetylation of histone lysine residues H3K4, H3K9, H3K14, H4K5, H4K8, H4K12, H4K16, or a combination thereof.

An aspect of the invention provides for a method of treating a neurodegenerative disease in a subject, the method comprising administering to a subject a therapeutic amount of a pharmaceutical composition comprising a compound of Formula (I), Formula (II), Formula (III), or Formula (V), thereby treating the neurodegenerative disease in the subject. In one embodiment, the compound is YF2. In other embodiments, the effective amount is at least about 1 mg/kg body weight, at least about 2 mg/kg body weight, at least about 3 mg/kg body weight, at least about 4 mg/kg body weight, at least about 5 mg/kg body weight, at least about 6 mg/kg body weight, at least about 7 mg/kg body weight, at least about 8 mg/kg body weight, at least about 9 mg/kg body weight, at least about 10 mg/kg body weight, at least about 15 mg/kg body weight, at least about 20 mg/kg body weight, at least about 25 mg/kg body weight, at least about 30 mg/kg body weight, at least about 40 mg/kg body weight, at least about 50 mg/kg body weight, at least about 75 mg/kg body weight, or at least about 100 mg/kg body weight. In some embodiments, the composition crosses the blood brain barrier. In one embodiment, the neurodegenerative disease comprises Adrenoleukodystrophy (ALD), Alcoholism, Alexander's disease, Alper's disease, Alzheimer's disease, Amyotrophic lateral sclerosis (Lou Gehrig's Disease), Ataxia telangiectasia, Batten disease (also known as Spielmeyer-Vogt-Sjögren-Batten disease), Bovine spongiform encephalopathy (BSE), Canavan disease, Cockayne syndrome, Corticobasal degeneration, Creutzfeldt-Jakob disease, Familial fatal insomnia, Frontotemporal lobar degeneration, Huntington's disease, HIV-associated dementia, Kennedy's disease, Krabbe's disease, Lewy body dementia, Neuroborreliosis, Machado-Joseph disease (Spinocerebellar ataxia type 3), Multiple System Atrophy, Multiple sclerosis, Narcolepsy, Niemann Pick disease, Parkinson's disease, Pelizaeus-Merzbacher Disease, Pick's disease, Primary lateral sclerosis, Prion diseasesm Progressive Supranuclear Palsy, Rett's syndrome, Tau-positive FrontoTemporal dementia, Tau-negative FrontoTemporal dementia, Refsum's disease, Sandhoff disease, Schilder's disease, Subacute combined degeneration of spinal cord secondary to Pernicious Anaemia, Spielmeyer-Vogt-Sjogren-Batten disease (also known as Batten disease), Spinocerebellar ataxia (multiple types with varying characteristics), Spinal muscular atrophy, Steele-Richardson-Olszewski disease, Tabes dorsalis, or Toxic encephalopathy. In another embodiment, synaptic plasticity comprises learning, memory, or a combination thereof. In some embodiments, synaptic plasticity comprises long term potentiation (LTP). In some embodiments, the compound is compound 1, compound 2, compound 3, compound 4, compound 5, compound 6, compound 7, compound 8, compound 9, compound 10, compound 11, compound 12, compound 13, compound 14, compound 15, compound 16, compound 17, compound 18, or compound 19. In other embodiments, the compound increases histone acetylation. In further embodiments, histone acetylation comprises acetylation of histones H2B, H3, H4, or a combination thereof. In further embodiments, histone acetylation comprises acetylation of histone lysine residues H3K4, H3K9, H3K14, H4K5, H4K8, H4K12, H4K16, or a combination thereof.

An aspect of the invention provides for a method of decreasing inclusion bodies in a subject afflicted with a neurodegenerative disorder, the method comprising administering to the subject an effective amount of a composition comprising a HAT Activator compound of Formula (I), Formula (II), Formula (III), or Formula (V), thereby decreasing inclusion bodies in the subject. In one embodiment, the inclusion bodies comprise beta-amyloid peptides, native and phosphorylated Tau proteins, native and phosphorylated alpha-synuclein, lipofuscin, cleaved TARDBP (TDB-43), or a combination thereof. In another embodiment, the subject exhibits abnormally elevated levels of amyloid beta plaques. In a further embodiment, the beta-amyloid peptides comprise an A1340 isomer, an Aβ42 isomer, or a combination of isomers. In one embodiment, the compound is YF2. In other embodiments, the effective amount is at least about 1 mg/kg body weight, at least about 2 mg/kg body weight, at least about 3 mg/kg body weight, at least about 4 mg/kg body weight, at least about 5 mg/kg body weight, at least about 6 mg/kg body weight, at least about 7 mg/kg body weight, at least about 8 mg/kg body weight, at least about 9 mg/kg body weight, at least about 10 mg/kg body weight, at least about 15 mg/kg body weight, at least about 20 mg/kg body weight, at least about 25 mg/kg body weight, at least about 30 mg/kg body weight, at least about 40 mg/kg body weight, at least about 50 mg/kg body weight, at least about 75 mg/kg body weight, or at least about 100 mg/kg body weight. In some embodiments, the composition crosses the blood brain barrier. In one embodiment, the neurodegenerative disease comprises Adrenoleukodystrophy (ALD), Alcoholism, Alexander's disease, Alper's disease, Alzheimer's disease, Amyotrophic lateral sclerosis (Lou Gehrig's Disease), Ataxia telangiectasia, Batten disease (also known as Spielmeyer-Vogt-Sjögren-Batten disease), Bovine spongiform encephalopathy (BSE), Canavan disease, Cockayne syndrome, Corticobasal degeneration, Creutzfeldt-Jakob disease, Familial fatal insomnia, Frontotemporal lobar degeneration, Huntington's disease, HIV-associated dementia, Kennedy's disease, Krabbe's disease, Lewy body dementia, Neuroborreliosis, Machado-Joseph disease (Spinocerebellar ataxia type 3), Multiple System Atrophy, Multiple sclerosis, Narcolepsy, Niemann Pick disease, Parkinson's disease, Pelizaeus-Merzbacher Disease, Pick's disease, Primary lateral sclerosis, Prion diseasesm Progressive Supranuclear Palsy, Rett's syndrome, Tau-positive FrontoTemporal dementia, Tau-negative FrontoTemporal dementia, Refsum's disease, Sandhoff disease, Schilder's disease, Subacute combined degeneration of spinal cord secondary to Pernicious Anaemia, Spielmeyer-Vogt-Sj ogren-Batten disease (also known as Batten disease), Spinocerebellar ataxia (multiple types with varying characteristics), Spinal muscular atrophy, Steele-Richardson-Olszewski disease, Tabes dorsalis, or Toxic encephalopathy. In another embodiment, synaptic plasticity comprises learning, memory, or a combination thereof. In some embodiments, synaptic plasticity comprises long term potentiation (LTP). In some embodiments, the compound is compound 1, compound 2, compound 3, compound 4, compound 5, compound 6, compound 7, compound 8, compound 9, compound 10, compound 11, compound 12, compound 13, compound 14, compound 15, compound 16, compound 17, compound 18, or compound 19. In other embodiments, the compound increases histone acetylation. In further embodiments, histone acetylation comprises acetylation of histones H2B, H3, H4, or a combination thereof. In further embodiments, histone acetylation comprises acetylation of histone lysine residues H3K4, H3K9, H3K14, H4K5, H4K8, H4K12, H4K16, or a combination thereof.

BRIEF DESCRIPTION OF THE FIGURES

The present application includes the following figures:

FIG. 20A depicts the relative luciferase activity in F11 cells cotransfected with 2 µg of a promoter-reporter construct containing Gal4 DNA binding sites upstream of the luciferase gene and constructs containing either functional CBP (WT-CBP) or a mutant lacking HAT activity (WY-CBP) linked to the DNA binding domain of Gal4. Cells were transfected with WT or mutated PS1. Values are expressed relative to the level of luciferase in control, neural cells transfected with Gal-luciferase and Gal-CBP. n=3 per each group. t=7.788, p=0.0015 vs. control; *p<0.05 vs. control. FIG. 20B shows basal luciferase activity in F11 cells co-transfected with 2 µg of Gal4 DNA binding sites upstream of the luciferase gene and constructs containing either WT-CBP or WY-CBP linked to the DNA binding domain of Gal4. No significant difference was found.

FIG. 24A is a schematic representation of cannulas implanted bilaterally into the dorsal hippocampi. FIG. 24B is a photograph of a Tris-Tricine PAGE Western blot depicting the analysis of Aβ preparation in non-denaturing/non-reducing conditions, showing different bands corresponding to monomers (4.5 kDa), trimers (13.5 kDa) and tetramers (18 kDa). FIG. 24C is a graph that represents: (Baseline) Bilateral infusions of human Aβ42 (200 nM in a final volume of 1 µl slowly over 1 min) into dorsal hippocampi, 15 min prior to training, do not affect immediate freezing in the training chamber either in conjunction with TSA or vehicle injected (i.p) 2 hrs before training. (24 hrs) Contextual fear conditioning performed 24 hrs after training shows a reduction of freezing in Aβ-infused mice injected with vehicle compared to vehicle-infused mice injected with vehicle. Treatment with TSA ameliorates deficit in freezing responses in Aβ-infused mice, and has no effect in vehicle-infused mice. (Aβ-infused mice with TSA injection: n=14, Aβ-infused mice with vehicle injection: n=12, vehicle-infused mice with TSA injection: n=8 and vehicle-infused mice with vehicle injection: n=11).

FIG. 25A is photograph of a western blot (top) and the normalized results in graphic form (bottom). Western blotting of protein extracts from APP/PS1 and WT mice, which were injected with vehicle and TSA 2 hours before training, and euthanized 1 hour after contextual fear conditioning. Vehicle-treated APP/PS1 animals showed a decrease in acetylated H4 levels. However, TSA-treated APP/PS1 mice showed an enhancement of H4 acetylation, reaching the same levels of acetylation as TSA-treated WT mice. Results were normalized against vehicle-treated WT mice. n=4 per each group except for TSA-treated WT mice with n=5. FIG. 25B is photograph of a western blot (top) and the normalized results in graphic form (bottom). Basal acetylation levels of H4 in APP/PS1 mice and WT littermates, which were exposed to the context without receiving an electrical shock, were similar n=3 per each group. The data shown in FIG. 25A and FIG. 25B are presented as a ratio of acetylated-H4 to total H4.

FIG. 26 is a synthetic scheme showing the synthesis and HAT activity assessment of the agonist MOM. FIG. 26A shows that the o-ethoxybenzolic acid was refluxed in $SOCl_2$ (1.66 g, 10 mmol) overnight. Removal of the organic solvent in vacuum gave the corresponding benzoyl chloride, which was dissolved in 20 mL of $CH_2C_{12}$, followed by addition of 4-chloro-3-trifluoromethylaniline (1.96 g, 10 mmol). The resulting solution was put in an ice-$H_2O$ bath and added 20 mL of saturated $NaHCO_3$ aqueous solution dropwise. The mixture was then allowed to react at room temperature for 4 hours. The organic phase was separated and washed with 2N HCl, $H_2O$ and brine. After dried over $Na_2SO_4$, the organic solvent was removed in vacuum to yield an off-white crystalline as the desired product (3.1 g, yield 90%). FIG. 26B is a photograph of a western blot showing that endogenous levels of acetylated H3 are increased by MOM (100 μg in 1 μl infused into dorsal hippocampi through cannulas) in mouse hippocampi which were harvested 2 hrs after the agonist administration.

FIG. 27 is a photograph of a western blot showing that histone acetylation is reduced in Aβ (A-beta) infused mice. Vehicle-treated A-beta infused animals showed a decrease in acetylated H3/4 levels both before and after following associative memory.

FIG. 31 are graphs showing the effect of YF2 on cancer cell viability in NCI-ADR-RES cells (FIG. 31A; ovarian cancer), U251 cells (FIG. 31B; glioblastoma cells), Hs578T cells (FIG. 31C; breast cancer cells), and CCRF-CEM cell (FIG. 31D; leukemia cells). Values represent an average of 3 wells. Error bars represent standard deviations.

FIGS. 32A-B are graphs showing the effect of YF2 on cancer cell proliferation in NCI-ADR-RES cells (FIG. 32A; ovarian cancer) and U251 cells (FIG. 32B; glioblastoma cells).

FIGS. 32C-D are graphs showing the effect of YF2 on cancer cell proliferation in Hs578T cells (FIG. 32C; breast cancer cells) and CCRF-CEM cell (FIG. 32D; leukemia cells).

FIG. 33 is a table showing the $IC_{50}$ measurements for YF2 and Vinblastine (VBL) on cell viability (Cell Titer Glo column) and cell proliferation (Cyquant column) in NCI-ADR-RES cells (ovarian cancer), U251 cells (glioblastoma cells), Hs578T cells (breast cancer cells), CCRF-CEM cells (leukemia cells), ACHN cells (human renal carcinoma cells), and A549 cells (human lung carcinoma cells).

FIG. 47 are graphs showing the effect of Vinblastine on cancer cell viability in NCI-ADR-RES cells (FIG. 47A; ovarian cancer), U251 cells (FIG. 47B; glioblastoma cells), Hs578T cells (FIG. 47C; breast cancer cells), and CCRF-CEM cell (FIG. 47D; leukemia cells). Values represent an average of 3 wells. Error bars represent standard deviations.

FIG. 48 are graphs showing the effect of Vinblastine on cancer cell viability in ACHN cells (FIG. 48A; human renal carcinoma cells) and A549 cells (FIG. 48B; human lung carcinoma cells). Values represent an average of 3 wells. Error bars represent standard deviations.

FIGS. 49A-B are graphs showing the effect of Vinblastine on cancer cell proliferation in NCI-ADR-RES cells (FIG. 49A; ovarian cancer) and U251 cells (FIG. 49B; glioblastoma cells). Values represent an average of 3 wells. Error bars represent standard deviations.

FIGS. 49C-D are graphs showing the effect of Vinblastine on cancer cell proliferation in Hs578T cells (FIG. 49C; breast cancer cells) and CCRF-CEM cell (FIG. 49D; leukemia cells). Values represent an average of 3 wells. Error bars represent standard deviations.

FIGS. 66A-B are graphs that show the beneficial effect of YF2 on A1342-induced synaptic and cognitive dysfunction. YF2 ameliorates the LTP deficit in A1342-treated slices (FIG. 66A; the graph represents the average of the last 5 min of recording at 60 min after the tetanus) P<0.05. YF2 ameliorates the contextual fear memory deficit in Aβ42-infused mice, P<0.01 (FIG. 66B).

FIG. 67 shows graphs depicting the beneficial effect of YF2 against memory defect in APP/PS1 mice using fear conditioning or reference memory tests. YF2 ameliorates the reference (FIG. 67A) and contextual fear (FIG. 67B) memory deficit in APP/PS1 mice compared to WT littermates (P<0.02 for both tests).

FIG. 76 is (A) a Western blot and (B) a graph showing histone acetylation levels are reduced following Aβ elevation in basal conditions.

FIG. 77 is (A) a Western blot and (B) a graph showing histone acetylation levels are not reduced following Aβ elevation and foot shock.

FIG. 80 is (A) a Western blot and (B) a graph showing that YF2 restores histone acetylation levels following Aβ elevation after foot shock.

FIG. 85 shows total locomotion in the center of the maze versus periphery in wild-type and Huntington's Disease mice models treated with YF2. Distance travelled in center is shown at (A) 6 months and (B) 8 months of age. Distance travelled in periphery is shown at (C) 6 months and (D) 8 months of age.

DETAILED DESCRIPTION OF THE INVENTION

Figure 1:
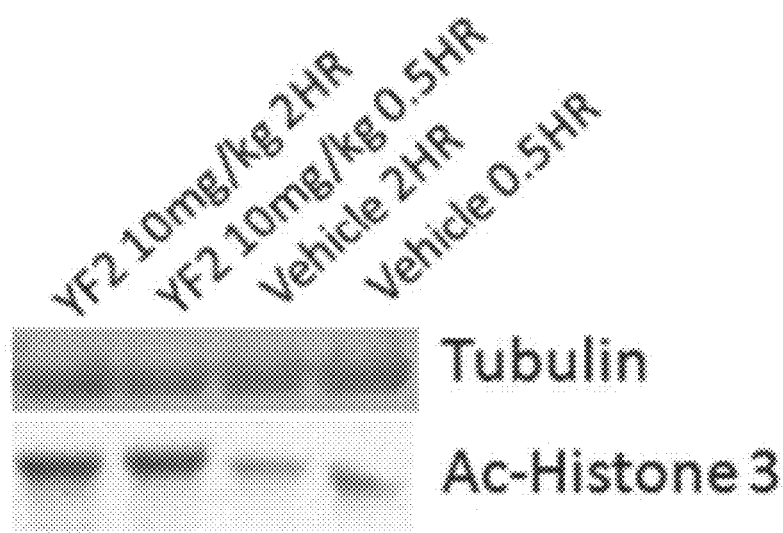
FIG. 1 is photograph of a western blot that shows histone 3 acetylation levels of mice hippocampus.

Early amnesic changes in Alzheimer's disease (AD) are thought to be linked to synaptic dysfunction. β-amyloid (Aβ), a peptide that is present in high amounts in the disease, has been found to inhibit memory[P1, P2] (each herein incorporated by reference in its entirety) and its electrophysiological model, long-term potentiation (LTP)[P3-P8] (each herein incorporated by reference in its entirety). Memory is known to be modulated by epigenetics through regulation of gene expression. Epigenetics is defined as the mechanism that changes gene expression by 'marking' DNA or its associated proteins, through processes such as DNA methylation and histone (H) modification, without changing the DNA sequence itself[P9] (each herein incorporated by reference in its entirety). Modification of histones by, for example, the addition or removal of acetyl or methyl functional groups causes the chromatin structure to open or close, so that the information contained within the DNA is made more or less accessible to transcription factors. Hence, it is not surprising that deregulation of one of the epigenetic mechanisms might lead to memory disruption. For instance, reduction of histone acetylation causes the chromatin structure to close, so that the information contained within the DNA might be less accessible to transcription factors and memory formation[P9] (each herein incorporated by reference in its entirety).

The main strategy that is currently used to up-regulate histone acetylation involves inhibition of histone deacetylases (HDACs), enzymes that remove an acetyl group from histones. However, the pleiotropic effect of nonspecific HDAC inhibition may hamper the therapeutic potential of HDAC inhibitors[P10-P13] (each herein incorporated by reference in its entirety).

HATs share a highly conserved motif containing an acetyl-CoA binding site. HATs can be involved in the pathology of cancer, asthma, neurodegenerative diseases and viral infection. This indicates that specific HAT activators are potential tools for pharmacological research and might find therapeutic applications. So far only one group has reported HAT activators. However, their compounds are neither soluble, nor membrane permeant, which makes them not good drug candidates for the treatment for the diseases described above.

This invention is about the synthesis of a new class of HAT activators, which have good potency, excellent solubility, reasonable pharmacokinetic profiles and good membrane and Blood-brain-Barrier (BBB) permeability, hence can be used as a new medicine with minimum amount of side effect for patients with neurodegenerative diseases and cancers.

The invention provides for compounds with histone acetyltransferase activity, HAT activation potency, high selectivity, reasonable pharmacokinetics and good permeability across the blood-brain-barrier (BBB). These compounds may be used to minimize the side effects for AD patients, the third most costly disease in the U.S., such as improving cognition or memory in AD and Alzheimer's-like pathologies, as well as minimize the side effects for subjects afflicted with other neurodegenerative diseases. The compounds of the invention may also be developed as anti-cancer drugs.

In some embodiments, the invention provides methods for identifying HAT activators that can acetylate histone proteins thus increasing gene expression in a subject resulting in enhanced memory and cognition.

In further embodiments, the invention provides for the utilization of HAT agonists as memory enhancers in normal subjects (for example, a subject not afflicted with a neurodegenerative disease). In further embodiments, the invention provides for the utilization of HAT agonists as memory enhancers in aging subjects (for example, a subject who is >55 years old). In further embodiments, the invention provides for the utilization of HAT agonists as memory enhancers for other conditions associated with cognitive decrease/impairment. Non-limiting examples of conditions associated with cognitive decrease/impairment include a variety of syndromes associated with mental retardation and syndromes associated with learning disabilities, Parkinson's disease, Pick's disease, a Lewy body disease, amyotrophic lateral sclerosis, Huntington's disease, Creutzfeld-Jakob disease, Down syndrome, multiple system atrophy, neuronal degeneration with brain iron accumulation type I (Hallervorden-Spatz disease), pure autonomic failure, REM sleep behavior disorder, mild cognitive impairment (MCI), cerebral amyloid angiopathy (CAA), mild cognitive deficits, aging, vascular dementias mixed with Alzheimer's disease, a neurodegenerative disease characterized by abnormal amyloid deposition, and any combination thereof.

To shrink the candidate pool of HAT activator compounds to be tested in animal models of neurodegenerative diseases, such as animals that exhibit elevated levels of inclusion bodies, for example Aβ accumulation animal models (e.g., animal models of AD), or, for example, a mouse model for Huntington's disease, HAT activators can first be screened or selected based on their possession of certain characteristics, such as having one or more of: an $EC_{50}$ no greater than about 100 nM; a histone acetylation activity in vitro; and the ability to penetrate the BBB.

In some embodiments, the candidate pool of HAT activators to be tested in animal models of neurodegenerative diseases, such as, but not limited to, animals that exhibit elevated levels of inclusion bodies, for example Aβ accumulation animal models (e.g., animal models of AD), or, for example, a mouse model for Huntington's disease, can first be screened or selected based on "medicinal chemistry" strategies. For example, based on the structure analysis of reported HAT activators, a class of structurally related, but nevertheless formally independent scaffolds, can be generated to be deemed as HAT activator candidates. Compounds derived from these scaffolds can first be screened and optimized on computational models. Compounds with highest score will be synthesized and tested for potency. At this stage, the synthetic effort will be guided by the testing results of potency/selectivity. Compounds with satisfactory potency and selectivity (lead compounds) will be further studied for PK, bioavailability/brain penetration and off-target activities (safety). Selected compounds can be tested in the animal models of neurodegenerative diseases, such as, but not limited to, animals that exhibit elevated levels of inclusion bodies, for example Aβ accumulation animal models (e.g., animal models of AD), or a mouse model for Huntington's disease to determine whether they increase gene expression in a subject resulting in enhanced memory and cognition. As used herein, a HAT activator compound does not necessarily preclude the possibility that the compound may also be able to inhibit other HATs.

Acetylation and Methylation of DNA and Histones

Figure 28:
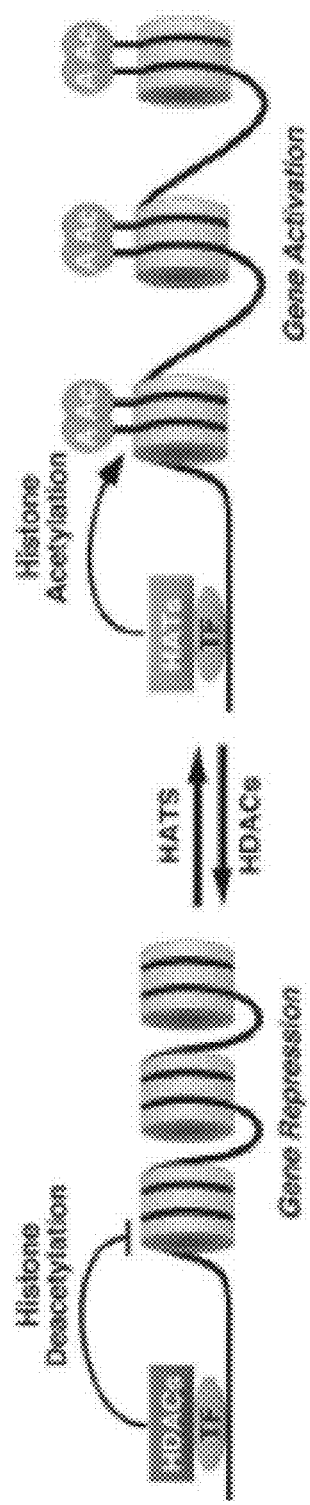
FIG. 28 is a schematic of histone acetylation and the role of HATs in such. YF2 is an example of a compound that activates HAT.

Eukaryotic DNA is highly organized and packaged into the nucleus. The organization and packaging are achieved through the addition of proteins, including core histones H2A, H2B, H3 and H4, which form a complex structure, the chromatin, together with DNA (see FIG. 28). The modification of core histones is of fundamental importance to conformational changes of the chromatin. The level of acetylation is related to transcription activity, and then the acetylation induces an open chromatin confirmation that allows the transcription machinery access to promoters. Histone deacetylase (HDAC) and histone acetyltransferase (HAT) are enzymes that influence transcription by selectively deacetylating or acetylating the ε-amino groups of lysine located near the amino termini of core histone proteins. Chromatin acetylation correlates with transcriptional activity (euchromatin), whereas deacetylation correlates with gene silencing. Interestingly, it was shown that increased acetylation of H3 in area CA1 of the hippocampus (an area in the brain that plays an important role in long-tem memory) occurs following associative memory. Additionally, by inhibiting HDAC, they were able to manipulate changes in the chromatin and enhance the formation of long-tem memory.

Histone acetylation and deacetylation are increasingly recognized for their contribution to the tight regulation of gene activation and silencing, respectively. Hence, it is not surprising that deregulation of these mechanisms might lead to the disruption of memory-associated gene expression, resulting in a number of syndromes associated with mental retardation.

Histones.

The DNA is firstly wrapped around an octamer complex of histones (H) to form nucleosomal units, giving the appearance of beads on a string [B31] (herein incorporated by reference in its entirety). In turn, these nucleosomal units, fold into a higher-order chromatin fiber [B32] (herein incorporated by reference in its entirety). Each histone-octamer complex contains two copies of histones H3 and H4 bordered by two copies of histones 2A and 2B [B32] (herein incorporated by reference in its entirety). H1 and its avian variant H5 are linker histones that bind the nucleosome and both the entry and exit sites of the DNA, thus locking the DNA into place and allowing the formation of higher order structure. Every histone has a globular domain, which mediates histone-histone interactions, and an N-terminal 'tail' extension. The histone cores and in particular their tails, are targets for a considerable number of covalent modifications, such as acetylation, ubiquitination, sumoylation, phosphorylation, citrullination, ADP-ribosylation, and methylation [B33] (herein incorporated by reference in its entirety). Histone modifications associated with active gene transcription, such as H3 Lys4 methylation and H3 Lys56 acetylation, were found to lead to gene expression. On the other hand, histone modifications associated with the inactivation of gene transcription, such as H3 Lys27 methylation and H2A Lys119 ubiquitination were found to cause gene silencing. Of particular interest for this application are histone 2B, 3 and 4 because they have been shown to be involved in memory processes [B19, B25] (each herein incorporated by reference in its entirety).

HATs and HDACs.

Histone modifications and their combinations have been proposed to be involved in gene regulation by modifying the chromatin accessibility and by acting as docking sites for transcription factors and modifying enzymes [B34, B35] (each herein incorporated by reference in its entirety). One of the most studied histone modifications is the acetylation of the evolutionary-conserved lysine residues on the histone N-termini by histone acetyltransferase (HAT). In contrast, histone deacetylation, catalyzed by histone deacetylase (HDAC), was found to package the DNA into a more condensed form, limiting the access of transcription factors and thus acting as a gene silencer [B36] (herein incorporated by reference in its entirety). The HATs involved in the regulation of gene expression include at least three groups of enzymes [B37] (herein incorporated by reference in its entirety). The general control non-derepressible 5 (Gcn5) is the founding member of the Gcn5 N-acetyltransferases (GNATs). The GNAT family members include Gcn5, PCAF, Elp3, HAT1m Hpa2 and Nutl. The MYST family is named after the founding members of the family: Morf, Ybf2, Sas2 and Tip60 [B37] (herein incorporated by reference in its entirety). In addition, other proteins including CBP/p300, Taf1 and a number of nuclear receptor co-activators have been shown to possess intrinsic HAT activity. However, these proteins do not contain a consensus domain and therefore represent an 'orphan class' of HAT enzymes [B37] (herein incorporated by reference in its entirety).

HDACs form repressor complexes with transcription activators and with other HDACs [B38] (herein incorporated by reference in its entirety). Mammalian HDACs can be divided into the classical and the silent information regulator 2 (Sir2)-related protein (sirtruin) families [B39] (herein incorporated by reference in its entirety). In humans, members of the classical family have another subdivision, which include class I, II and IV, that share sequence similarity and require Zn+ for deacetylase activity. Class I HDACs (HDAC1-3, HDAC8) are related to the yeast gene repressor Rpd3p, and are subunits of at least two distinct co-repressor complexes, the Sin3 complex and the NuRD complex. Class II HDACs (HDAC4-7, 9 and 10) are similar to the yeast Hda1p HDAC, they act as gene repressors and have been implicated in various roles in cell differentiation and development. Class IV comprises HDAC11, which has some features of both class I and II HDACs. The sirtruin family includes class III HDACs (SIRT1-7), which are similar to yeast Sir2. Class III HDACs are biochemically and structurally distinct from the classical family and require $NAD^+$ as a cofactor. HDACs appear to be involved in gene silencing and heterochromatin formation at centromeres and telomeres (for a review see [B40] (herein incorporated by reference in its entirety)).

Figure 3:
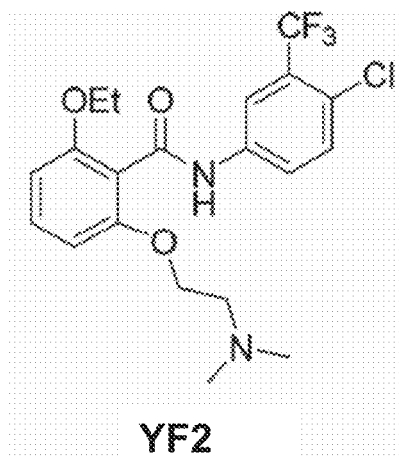
FIG. 3 is the chemical structure of lead compound YF2, a HAT agonist/activator.

Alterations in epigenetic modifications including acetylation and methylation of DNA and histones may contribute to gene expression changes in cancer and neurological diseases. Addition of acetyl group on histones by Histone Acetyltransferases (HATs) enhances gene expression, while its removal by Histone Deacytylases (HDAC) reduces gene expression. Reduction in histone acetylation has been found in a variety of ailments such as tumors, mood disorders, and neurodegenerative diseases. Examples of HATs include, but are not limited to GCN5, GCN5L, PCAF, HAT1, ELP3, HPA2, ESA1, SAS2, SAS3, TIP60, HBO1, MOZ, MORF, MOF, SRC1, SRC3, TIF2, GRIP1, ATF-2 [see Lee and Workman (2007) Nat Rev Mol Cell Biol., 8(4):284-95, Marmorstein (2001) J Molec Biol. 311: 433-444; and Kimura et al., (2005) J Biochem. 138(6): 647-662, which are each hereby incorporated by reference in their entireties]. In one embodiment, the HAT activator compound of the invention is directed to GCN5, GCN5L, HAT1, PCAF, or a combination thereof. In some embodiments, the HAT activator compound of the invention is directed to proteins that possess intrinsic HAT activity, such as nuclear receptor co-activators (for example, CBP/p300 and Taf1). In another embodiment, the acetylation of H2, H3, and/or H4 histones is increased. In some embodiments, the HAT Activator compound is YF2, depicted in FIG. 3.

Increasing histone acetylation has been shown to improve outcome in a wide variety of diseases as diverse as asthma, infectious disease and psychiatric diseases. Although clinical trials of several HDAC inhibitors are currently underway, the alternative strategy where by histone acetylation is increased by HAT activation has not been extensively explored. For example, compounds in U.S. Patent Publication No. US2009076155 and PCT Publication No. WO2004053140 (each herein incorporated by reference in its entirety) have poor solubility and membrane permeability. Furthermore, the compounds disclosed in the patent applications do not disclose any data for the treatment of any diseases.

No HAT activator is currently in drug trials, however several HDAC inhibitors are currently in clinical trials. Some of these HDAC inhibitors (HDACi) have shown therapeutic efficacy in preclinical trials. Without being bound by theory, HAT activators can be a useful drug candidate with a role similar to HDACi. However, previously available HAT activators had little solubility and membrane permeability, making them unsuitable as drugs.

Several HDACi are in trials for cancer some of which are, for example, 4SC-202 (Nycomed, Germany), which is in a Preclinical stage; AR-42 (Arno therapeutics, Parsippany, N.J.) which is in a Preclinical stage; Belinostat (TopoTarget, Rockaway, N.J.) which is in Phase II clinical trials; and Entinostat (Bayer Schering) which is in Phase II clinical trials. For example, in Table 3 of Lane and Chabner (2009, J Clin Oncol., 27(32):5459-68; incorporated by reference in its entirety), selected clinical trials of HDAC inhibitors are discussed, which include Vorinostat, Depsipeptide, and MGCD0103. In Table 2 of Lane and Chabner (2009, J Clin Oncol., 27(32):5459-68; incorporated by reference in its entirety), selected HDAC inhibitors in clinical use or development are discussed, which include hydroxamic acid compounds (e.g., Vorinostat, Trichostatin A, LAQ824, Panobinostat, Belinostat, and ITF2357), cyclic tetrapeptide compounds (e.g., Depsipeptide), benzamide compounds (e.g., Entinostat and MGCD0103), and short-chain aliphatic acid compounds (e.g., valproic acid, phenyl butyrate, and pivanex).

Some HDACi are or were being developed for neurological diseases, such as an HDACi from Merck (Whitehouse Station, N.J.) that is being used for the treatment of neurodegenerative diseases; and HDACi from TopoTarget (Rockaway, N.J.) that was being used for the treatment of Huntington's disease, now discontinued; isovaleramide NPS-1776 (NPS Pharmaceutical, Bedminster, N.J.) that was being used for bipolar disorder, epilepsy, and migraines, now discontinued; and a histone acetyltransferase inhibitor for cancer from TopoTarget A/S (Kobenhavn, Denmark), which was discontinued in the preclinical stage.

Here, the synthesis of a new class of HAT activators with improved solubility and membrane permeability are described and its potency in-vitro as well as in an animal model are shown (see EXAMPLES). In vitro and behavioral data show that a HAT activator compound of the invention, YF2, can acetylate histone H3 in brain and ameliorate memory deficits in a mouse model of Alzheimer's disease. For example, the HAT activator shown in FIG. 3 can be used as adjuvant therapy in several cancers, psychiatric and neurodegenerative diseases and may improve efficacy and safety of treatment for these disorders. Furthermore, the HAT activator compound, YF2, has a moiety which was not mentioned in the above-referenced patent applications that significantly improves the solubility and membrane and Blood-brain-Barrier (BBB) permeability. See Abel and Zukin (2008) Current Opinion in Pharmacology 8:57-64; and Lee and Workman (2007) Nat Rev Mol Cell Biol 8:284-295 (each herein incorporated by reference in its entirety).

In one embodiment, a HAT activator compound can be used to treat a cancer in a subject in need thereof. Non-limiting examples of cancers include B cell lymphoma, colon cancer, lung cancer, renal cancer, bladder cancer, T cell lymphoma, myeloma, leukemia, chronic myeloid leukemia, acute myeloid leukemia, chronic lymphocytic leukemia, acute lymphocytic leukemia, hematopoietic neoplasias, thymoma, lymphoma, sarcoma, lung cancer, liver cancer, non-Hodgkins lymphoma, Hodgkins lymphoma, uterine cancer, renal cell carcinoma, hepatoma, adenocarcinoma, breast cancer, pancreatic cancer, liver cancer, prostate cancer, head and neck carcinoma, thyroid carcinoma, soft tissue sarcoma, ovarian cancer, primary or metastatic melanoma, squamous cell carcinoma, basal cell carcinoma, brain cancer, angiosarcoma, hemangiosarcoma, bone sarcoma, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, testicular cancer, uterine cancer, cervical cancer, gastrointestinal cancer, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, Waldenstroom's macroglobulinemia, papillary adenocarcinomas, cystadenocarcinoma, bronchogenic carcinoma, bile duct carcinoma, choriocarcinoma, seminoma, embryonal carcinoma, Wilms' tumor, lung carcinoma, epithelial carcinoma, cervical cancer, testicular tumor, glioma, astrocytoma, medulloblastoma, craniopharyngioma, ependymoma, pinealoma, hemangioblastoma, acoustic neuroma, oligodendroglioma, meningioma, retinoblastoma, leukemia, melanoma, neuroblastoma, small cell lung carcinoma, bladder carcinoma, lymphoma, multiple myeloma, and medullary carcinoma.

In one embodiment, the cancer is colon cancer, lung cancer, renal cancer, leukemia, CNS cancer, melanoma, ovarian cancer, breast cancer, or prostate cancer.

In one embodiment, the cancer is colon cancer, renal cancer, T cell leukemia, myeloma, leukemia, acute myeloid leukemia, acute lymphocytic leukemia, renal cell carcinoma, adenocarcinoma, glioblastoma, breast carcinoma, prostate carcinoma, or lung carcinoma.

In one embodiment, a HAT activator compound can be used to treat a neurodegenerative disease in a subject in need thereof. Non-limiting examples of neurodegenerative diseases include Adrenoleukodystrophy (ALD), Alcoholism, Alexander's disease, Alper's disease, Alzheimer's disease, Amyotrophic lateral sclerosis (Lou Gehrig's Disease), Ataxia telangiectasia, Batten disease (also known as Spielmeyer-Vogt-Sjögren-Batten disease), Bovine spongiform encephalopathy (BSE), Canavan disease, Cockayne syndrome, Corticobasal degeneration, Creutzfeldt-Jakob disease, Familial fatal insomnia, Frontotemporal lobar degeneration, Huntington's disease, HIV-associated dementia, Kennedy's disease, Krabbe's disease, Lewy body dementia, Neuroborreliosis, Machado-Joseph disease (Spinocerebellar ataxia type 3), Multiple System Atrophy, Multiple sclerosis, Narcolepsy, Niemann Pick disease, Parkinson's disease, Pelizaeus-Merzbacher Disease, Pick's disease, Primary lateral sclerosis, Prion diseasesm Progressive Supranuclear Palsy, Refsum's disease, Rett's syndrome, Tau-positive FrontoTemporal dementia, Tau-negative FrontoTemporal dementia, Sandhoff disease, Schilder's disease, Subacute combined degeneration of spinal cord secondary to Pernicious Anaemia, Spielmeyer-Vogt-Sj ogren-Batten disease (also known as Batten disease), Spinocerebellar ataxia (multiple types with varying characteristics), Spinal muscular atrophy, Steele-Richardson-Olszewski disease, Tabes dorsalis, and Toxic encephalopathy.

Gene Transcription and Memory

Figure 23:
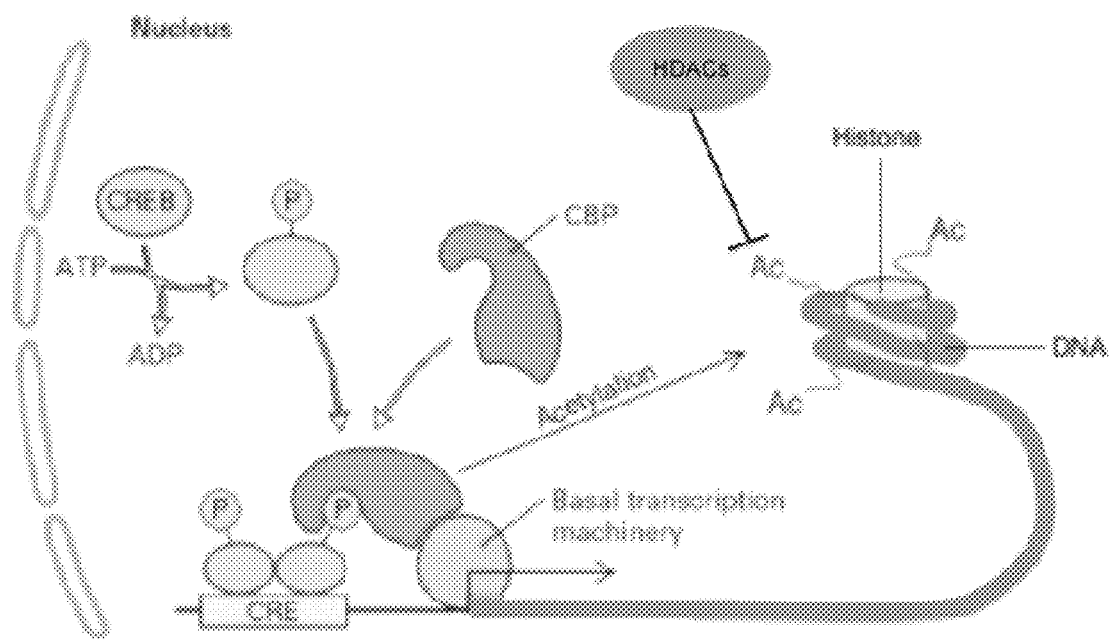
FIG. 23 is a schematic showing that CBP is recruited to act as a bridge between DNA-bound phosphorylated CREB and the basal transcription machinery located at the start site of transcription. In addition, CBP acts as a HAT, making the chromatin more accessible and increasing the transcription of memory associated genes. Unlike CBP, HDACs remove an acetyl group from histones, thus restricting access of the transcriptional machinery to the DNA (figure was modified from [B1]; herein incorporated by reference in its entirety).

A schematic representation of the processes involved in gene transcription and memory is shown in FIG. 23. In the brain, CREB phosphorylation is required for CREB ability to bind to CBP and to stimulate memory associated gene expression. CBP functions as a co-activator that facilitates interactions with the basal transcription machinery and through its HAT activity catalyzes acetylation of the histones, causing a loss in chromosomal repression and increase in the transcription of memory associated genes. In agreement with this scheme, mutations in HAT domain CBP were found to cause LTM impairment. For instance, Korzus et al. demonstrated that inducible dominant-negative CBP mice, with no CBP HAT activity, exhibited normal short-tem memory while LTM was impaired [B8] (herein incorporated by reference in its entirety). Moreover, the impaired LTM was rescued by suppression of the transgene expression and by HDAC inhibitor administration [B8] (herein incorporated by reference in its entirety).

The relevance of histone deacetylation in memory processes is underscored by a study from Levenson et al. [B26] (herein incorporated by reference in its entirety). In this work acetylation of H3 in area CA1 of the hippocampus (an area in the brain that plays important roles in LTM) was found to be increased following training for contextual fear conditioning, a form of associative memory in which mice associate a novel context with an aversive stimulus. However, HDAC inhibition enhanced LTM [B26] (herein incorporated by reference in its entirety). In agreement with this study, HDAC inhibition may be beneficial in certain neurodegenerative disorders, such as Huntington's disease, spinal muscular atrophy, amyotrophic lateral sclerosis, ischemia and Rubinstein-Taybi syndrome [B19, B25, B41, B42] (each herein incorporated by reference in its entirety). Interestingly, the effect of HDAC inhibitors are likely to depend upon specific HDACs, as neuron-specific overexpression of HDAC2, but not that of HDAC1, reduced dendritic spine density, synapse number, synaptic plasticity and memory formation [B43] (herein incorporated by reference in its entirety). Conversely, HDAC2 deficiency increased synapse number and facilitated memory, similar to chronic treatment with HDAC inhibitors in mice [B43] (herein incorporated by reference in its entirety). Taken together, these findings indicate that HDAC inhibition may provide a therapeutic avenue for memory impairment in neurodegenerative diseases characterized by cognitive disorders such as AD.

Transcriptional Machinery and AD

Recent studies have linked CREB/CBP dysfunction to AD. APP(K670N:M671L) transgenic animals showed a decrease in CREB phosphorylation at the downstream level of the $\alpha$-7-nicotinic-receptor ($\alpha$7-nAChR)/ERK/MAPK cascade [B44, B45] (each herein incorporated by reference in its entirety). Perfusion of hippocampal slices with a preparation containing oligomeric A$\beta$42 revealed a reduction of the tetanus-induced increase in CREB phosphorylation, providing a clue to the mechanisms underlying the A$\beta$-mediated changes in LTP [B12] (herein incorporated by reference in its entirety). Consistent with these results A$\beta$ blocked the glutamate-induced increase in CREB phosphorylation in rat hippocampal cultures [B11] (herein incorporated by reference in its entirety). Gong et al. also found that rolipram, a selective PDE IV inhibitor which increases cAMP levels and therefore CREB phosphorylation, ameliorates deficits in both LTP and contextual learning in the APP/PS1 double-transgenic mouse [B46] (herein incorporated by reference in its entirety). This protective effect is possibly due to CREB activation that might lead to CBP recruitment and thus histone acetylation. Another investigation demonstrated that in PS1 and 2 conditional double knockout (PS cDKO) mice showed impaired memory and LTP that were amplified with age. In addition PS cDKO mice showed a reduction in CBP levels and in CRE-dependent gene expression in the cerebral cortex, which is likely to contribute to subsequent neuronal degeneration [B15] (herein incorporated by reference in its entirety). In addition, a recent study has demonstrated that wild-type (WT) PS1 stimulates the transcriptional ability of CBP and p300, whereas the AD associated mutant of PS1 (M146L) does not have this effect [B18, B47] (each herein incorporated by reference in its entirety). In these experiments a response to WT PS1 was observed with a construct containing the 721-1679 region of CBP, which contains the CBP acetyltransferase domain [B18] (herein incorporated by reference in its entirety). Moreover, it was shown that CBP loss and histone deacetylation takes place during neuronal death, which was induced by an APP-directed antibody in primary cortical neurons [B48] (herein incorporated by reference in its entirety).

Alzheimer's Disease—an Example of a Neurodegenerative Disease

An emerging view of the processes involved in memory impairment indicates that the subtlety and variability of the earliest amnesic symptoms, occurring in the absence of any other clinical signs of brain injury, could be due to discrete changes in the function of a single synapse, produced at least in part, by A$\beta$ [B11, B27-B29] (each herein incorporated by reference in its entirety).

Several evidences have shown that LTM and synaptic plasticity rely on gene expression after an early induction phase characterized by the activation of a number of pathways (for a review, see [B30] (herein incorporated by reference in its entirety)). More recently, a fine regulation of memory-related genes and long-term synaptic plasticity has been discovered to involve epigenetic factors [B6] (herein incorporated by reference in its entirety). Indeed, epigenetic modifications, such as DNA methylation and histone post-translational modifications, profoundly affect the ability of polymerases to interact with the open reading frame of DNA without changing the DNA sequence itself. Hence, it would not be surprising that deregulation of epigenetic mechanisms might lead to the disruption of memory-associated gene expression and synaptic plasticity [B6] (herein incorporated by reference in its entirety), contributing to the pathogenesis of diseases characterized by cognitive disorders, such as AD.

The process of memory storage has been described as a dialogue between genes and synapses [B2] (herein incorporated by reference in its entirety). The formation of long-term memory (LTM) is dependent upon gene transcription [B3] (herein incorporated by reference in its entirety), synthesis of new proteins [B4] (herein incorporated by reference in its entirety) and structural changes of the synapse [B5] (herein incorporated by reference in its entirety). In addition, the proper regulation of gene expression in LTM is modulated by epigenetics [B6] (herein incorporated by reference in its entirety). Epigenetics is defined as the mechanism that changes gene expression by 'marking' DNA or its associated proteins, through processes such as histone modification and DNA methylation, without changing the DNA sequence itself [B7] (herein incorporated by reference in its entirety). The N-terminal tails of histone proteins are known to undergo posttranslational modifications, such as histone acetylation, ubiquitination, sumoylation, phosphorylation, citrullination, ADP-ribosylation, and methylation that can dictate the transitions between transcriptionally active or transcriptionally silent chromatin states [B7] (herein incorporated by reference in its entirety). Hence, it is not surprising that deregulation of one of these mechanisms might lead to disruption of memory associated gene expression and cognitive disorders.

Alzheimer's disease (AD) is characterized by neuronal loss, extracellular senile plaques and intracellular neurofibrillary tangles, leading to memory loss. AD purportedly begins as a synaptic disorder produced at least in part, by Aβ (Selkoe, D. J. Alzheimer's disease is a synaptic failure. Science (New York, N.Y. 298, 789-791 (2002)); herein incorporated by reference in its entirety. Aβ-induced reduction in long-term-potentiation (LTP), a physiological correlate of synaptic plasticity that is thought to underlie learning and memory, and phosphorylation of the memory transcription factor CREB, are ameliorated by nitric oxide (NO) donors and cGMP-analogs (Puzzo, D., et al. Amyloid-beta peptide inhibits activation of the nitric oxide/cGMP/cAMP-responsive element-binding protein pathway during hippocampal synaptic plasticity. *J Neurosci* 25, 6887-6897 (2005)); herein incorporated by reference in its entirety. Vice-versa, genetic ablation of NO-synthase 2 (NOS2) results in worsening of the AD phenotype in mice expressing mutated amyloid precursor protein (APP) (Colton, C. A., et al. NO synthase 2 (NOS2) deletion promotes multiple pathologies in a mouse model of Alzheimer's disease. *Proceedings of the National Academy of Sciences of the United States of America* 103, 12867-12872 (2006); herein incorporated by reference in its entirety). These findings show that up-regulation of the NO pathway can be protective in AD.

Alzheimer's disease (AD) is a chronic progressive neurodegenerative disorder, in which the earliest stages are thought to be linked to synaptic dysfunction leading to memory disorders. In this regard, β-amyloid (Aβ) has been found to inhibit memory[41,42] (each herein incorporated by reference in its entirety) and its cellular model, long-term potentiation (LTP)[43-48] (each herein incorporated by reference in its entirety). Aβ is the proteolytic product of a larger precursor protein, the amyloid precursor protein (APP), which in its mutant form has been found to be implicated in familial AD (FAD)[49] (herein incorporated by reference in its entirety). Subsequently, two AD associated genes, presenilin 1 (PS1) and presenilin 2 (PS2)[410, 411] (each herein incorporated by reference in its entirety), were found to be involved in FAD as well[412] (herein incorporated by reference in its entirety). Presenilins are part of the γ-secretase complex responsible for cleaving APP and producing the Aβ42 peptide[413] (herein incorporated by reference in its entirety).

AD is characterized neuropathologically by neuronal loss, extracellular senile plaques (SPs) and intracellular neurofibrillary tangles (NFTs). SPs are chiefly comprised of Aβ aggregates. The major component of NFTs is the microtubule binding protein tau. Clinically, AD is characterized by cognitive dysfunction and begins as a synaptic disorder that involves progressively larger areas of the brain over time [51] (herein incorporated by reference in its entirety). An emerging view of the processes involved in synaptic impairment shows that the subtlety and variability of the earliest amnesic symptoms, occurring in the absence of any other clinical signs of brain injury, can be due to discrete changes in the function of a single synapse, produced at least in part, by Aβ [S5, S7, S10, S11] (each herein incorporated by reference in its entirety).

An important target for developing a causal therapy for Alzheimer's disease is represented by synapses. Synaptic alterations are highly correlated with the severity of clinical dementia [S1, S2] (each herein incorporated by reference in its entirety), whereas other important variables such as senile plaques and neurofibrillary tangles are involved to a lesser extent [S1] (herein incorporated by reference in its entirety). The importance of synaptic alterations in AD has been confirmed by studies of transgenic (Tg) mouse models of AD [S3] (herein incorporated by reference in its entirety) as well as of long-term potentiation (LTP), a widely studied cellular model of learning and memory (L&M) [S4] (herein incorporated by reference in its entirety), which is impaired following application of amyloid-(Aβ) both in slices and in vivo [S3, S5-S12] (each herein incorporated by reference in its entirety). Aβ has been found to markedly inhibit LTP. Electrophysiological studies using Tg, human Aβ producing mice have often revealed significant deficits in basal synaptic transmission and/or LTP in the hippocampus [S23-S30] (each herein incorporated by reference in its entirety).

Regulation of gene expression in long-term memory is known to be modulated by epigenetics. Epigenetics is defined as the mechanism that changes gene expression by 'marking' DNA or its associated proteins, through processes such as DNA methylation and histone modification, without changing the DNA sequence itself[414]. Modification of histones by, for example, the addition or removal of acetyl or methyl functional groups causes the chromatin structure to open or close, so that the information contained within the DNA is made more or less accessible to transcription factors. Hence, it is not surprising that deregulation of one of the epigenetic mechanisms might lead to disruption of memory associated gene expression. Studies of the mechanisms underlying synaptic and memory dysfunction in AD have indicated central roles for the transcription factor CREB (CRE binding protein) and the coactivator CREB binding protein (CBP).

Recent studies have linked the transcriptional machinery to Alzheimer's disease (AD), a pathology characterized by profound memory disorders. Both the transcription factor CREB (CRE binding protein) and the coactivator CREB binding protein (CBP), two molecules that are known to be associated with chromatin and memory processes [B8-B10] (each herein incorporated by reference in its entirety), are likely to play central roles in the mechanisms underlying synaptic and memory dysfunction in AD. Drugs enhancing CREB phosphorylation were shown to ameliorate memory and long-term potentiation (LTP), a type of synaptic plasticity that is thought to underlie learning and memory, both in mouse models of AD and following exposure to sublethal doses of Aβ42, a proteolytic product of the amyloid precursor protein (APP) [B11-B14] (each herein incorporated by reference in its entirety). In addition, cerebral CBP levels are reduced in mice lacking functional presenilin 1 (PS1) and presenilin 2 (PS2) [B15] (herein incorporated by reference in its entirety), two genes that have been implicated in AD [B16, B17] (each herein incorporated by reference in its entirety). Moreover, wild-type (WT) PS1 stimulates CBP transcriptional ability, whereas PS1(M146L) mutation does not have this effect [B18] (herein incorporated by reference in its entirety).

Following exposure to sublethal doses of $A\beta_{42}$ and in mouse models of AD, drugs enhancing CREB phosphorylation were shown to ameliorate LTP and memory[45, 415-417] (each herein incorporated by reference in its entirety). Dysregulation of CBP histone acetyltransferase (HAT) activity disrupts memory associated gene expression[418] (herein incorporated by reference in its entirety). In addition, cerebral CBP levels are reduced in mice lacking functional PS1 and PS2[419] (herein incorporated by reference in its entirety). Moreover, wild-type (WT)

PS1 stimulates CBP transcriptional ability, whereas PS1 (M146L) mutation does not have this effect[420] (herein incorporated by reference in its entirety).

NO is a central molecule in cellular biochemical processes. The gas has been established as an important messenger molecule in various steps of brain physiology, from development to synaptic plasticity and learning and memory. In AD research, NO has been found to have a protective effect on Aβ-induced damage of the nervous system [S38-S40] (herein incorporated by reference in its entirety). Studies performed on PC12 cells, sympathetic neurons and hippocampal neurons, have shown that treatment with the NO generator S-nitroso penicillamine exerts a neuroprotective effect due to the inhibition of the pro-apoptotic factor caspase-2 by nitrosylation [S39] (herein incorporated by reference in its entirety), whereas inhibition of NO synthesis by N-nitro-L-arginine methyl ester does not protect against Aβ-induced neurotoxicity. Aβ has been found to impair NO generation by decreasing NMDA receptor signal transduction [S38] (herein incorporated by reference in its entirety), by subtracting NADPH availability to NO-synthase (NOS) [S41], or by inhibiting the phosphorylation of the serine-threonine kinase Akt [S42]. Moreover, i-NOS deletion enhances AD pathology in the APP mice [S43]. Thus, drugs enhancing the NO-cascade have a beneficial effect against AD [S44] (herein incorporated by reference in its entirety).

Despite the neuroprotective function of NO is clear and indisputable, the gas has also been viewed as a major agent of neuropathology and cell death when it is produced in high quantity. High amounts of NO lead to generation of significant quantity of peroxinitrites that are responsible for oxidative and nitrosative stress in Aβ-induced cell death [S45-S51] (each herein incorporated by reference in its entirety). In fact, release of low amounts of NO by the constitutive forms of NOS that include both the neuronal and the endothelial isoforms, n-NOS and e-NOS, promotes synaptic plasticity and learning, whereas uncontrolled production of high amounts of the gas by the inducible form of NOS (i-NOS) can promote oxidative and nitrosative stress via production of peroxinitrite [S45-S51] (each herein incorporated by reference in its entirety). Thus, both Aβ-induced downregulation of the NO cascade which blocks plasticity and memory and generation of peroxinitrites leading to cell death, can play roles in AD. The current status of drug research exploiting these discoveries is focused both on finding ways to upregulate the NO cascade and therefore elicit neuroprotection, as well as on finding ways to block peroxinitrite toxic effects in order to limit neuropathology [S52] (herein incorporated by reference in its entirety).

HAT Activators Optimized for CNS Diseases and Cancer

None of the commercially available HAT activators were developed to have the characteristics required for administration in a chronic disease of the CNS, for example neurodegenerative diseases (such as AD, Parkinson's Disease, Huntington's Disease), or for cancer. Thus, in some embodiments, the invention provides methods for identifying an agent or compound for the treatment of neurodegenerative diseases (such as AD, Huntington's Disease, Parkinson's Disease, other Aβ-accumulation related neurodegenerative disorders or diseases characterized by elevated levels of inclusion bodies) that comprise selecting the agent or compound on the basis of having one or more characteristics that make the compound optimized for treating CNS diseases. For example, the characteristics can comprise: an $EC_{50}$ no greater than about 100 nM; histone acetylation activity in vitro; the ability to penetrate the BBB; or a combination thereof. In one embodiment, the HAT Activator compound is YF2, depicted in FIG. 3.

In some embodiments, the invention provides methods for identifying or designing agents or compounds for the treatment of neurodegenerative diseases, treatment of conditions associated with, but not limited to, elevated inclusion bodies, (e.g., conditions associated with Aβ, alpha-synuclein, lipofuscin, cleaved TARDBP-TDP-43, and/or Tau protein accumulation), where computer aided-medicinal chemistry methods are used to identify and/or design agents or compounds tailored to satisfy one or more of the characteristics mentioned above and/or to suit the strengths of various bioassays described herein.

The invention generally provides methods for identifying compounds which can be used for treating a neurodegenerative disease in a subject. The invention provides methods for identifying compounds which can be used for treating subjects that exhibit abnormally elevated amyloid beta plaques, or elevated Tau protein levels, or elevated alpha-synuclein levels, or inclusions, or lipofuscin level or inclusions, or cleaved TARDBP-TDP-43 level or inclusion, or accumulation of cleaved TARDBP/TDP-43 inclusions. In addition, the invention provides methods for identifying compounds which can be used for the treatment of Alzheimer's disease, Lewy body dementia, inclusion body myositis, cerebral amyloid angiopathy, Huntington's Disease, Parkinson's Disease, and cancer. The methods can comprise the identification of test compounds or agents (e.g., peptides (such as antibodies or fragments thereof), small molecules, nucleic acids (such as siRNA or antisense RNA), or other agents) that can bind to a HAT polypeptide molecule and/or activate or enhance the biological activity of a HAT polypeptide or its expression. In one embodiment, the compound is a HAT activator (for example a HAT activator compound having Formula (I), (II), (III), (IV), (V), or (VI). In another embodiment, the HAT Activator compound is YF2, depicted in FIG. 3.

The term "modulate", as it appears herein, refers to a change in the activity or expression of a protein molecule. For example, modulation can cause an increase or a decrease in protein activity, binding characteristics, or any other biological, functional, or immunological properties of a secretase protein molecule.

In one embodiment, a HAT activator compound can be a peptide fragment of a HAT protein that binds to a histone acetyltransferase protein. For example, the HAT activator molecule can encompass any portion of at least about 8 consecutive amino acids of SEQ ID NO: 1, 3, or 5. The fragment can comprise at least about 10 amino acids, a least about 20 amino acids, at least about 30 amino acids, at least about 40 amino acids, a least about 50 amino acids, at least about 60 amino acids, or at least about 75 amino acids of SEQ ID NO: 1, 3, or 5. In one embodiment, the peptide fragment is directed to a HAT protein, such as GCN5, GCN5L, HAT1, or PCAF.

The polypeptide sequence of a HAT protein, human HAT1, is depicted in SEQ ID NO: 1. The nucleotide sequence of human HAT1 is shown in SEQ ID NO: 2. Sequence information related to HAT1 is accessible in public databases by GenBank Accession numbers NM 003642 (for mRNA) and NP 003633 (for protein). HAT1 is also known as KAT1 (K(lysine) acetyltransferase 1). The protein encoded by this gene is a type B histone acetyltransferase (HAT) that is involved in the rapid acetylation of newly synthesized cytoplasmic histones, which are in turn imported into the nucleus for de novo deposition onto nascent DNA chains. Histone acetylation, particularly of histone H4, plays an important role in replication-dependent chromatin assembly.

SEQ ID NO: 1 is the human wild type amino acid sequence corresponding to the HAT protein, the HAT1 enzyme (residues 1-419):

```
  1  MAGFGAMEKF LVEYKSAVEK KLAEYKCNTN TAIELKLVRF PEDLENDIRT FFPEYTHQLF
 61  GDDETAFGYK GLKILLYYIA GSLSTMFRVE YASKVDENFD CVEADDVEGK IRQIIPPGFC
121  TNTNDFLSLL EKEVDFKPFG TLLHTYSVLS PTGGENFTFQ IYKADMTCRG FREYHERLQT
181  FLMWFIETAS FIDVDDERWH YFLVFEKYNK DGATLFATVG YMTVYNYYVY PDKTRPRVSQ
241  MLILTPFQGQ GHGAQLLETV HRYYTEFPTV LDITAEDPSK SYVKLRDFVL VKLCQDLPCF
301  SREKLMQGFN EDMAIEAQQK FKINKQHARR VYEILRLLVT DMSDAEQYRS YRLDIKRRLI
361  SPYKKKQRDL AKMRKCLRPE ELTNQMNQIE ISMQHEQLEE SFQELVEDYR RVIERLAQE
```

SEQ ID NO: 2 is the human wild type nucleotide sequence corresponding to HAT protein, the HAT1 enzyme (residues 1-1682), wherein the underscored ATG denotes the beginning of the open reading frame:

```
   1  ctgtgcggtc acttccggcc cgggagcgcg cgggttgatt cgtccttcct cagccgcggg
  61  tgatcgtagc tcggaaatgg cgggatttgg tgctatggag aaattttggg tagaatataa
 121  gagtgcagtg gagaagaaac tggcagagta caaatgtaac accaacacag caattgaact
 181  aaaattagtt cgttttcctg aagatcttga aaatgacatt agaacttttct ttcctgagta
 241  tacccatcaa ctctttgggg atgatgaaac tgcttttggt tacaagggtc taaagatcct
 301  gttatactat attgctggta gcctgtcaac aatgttccgt gttgaatatg catctaaagt
 361  tgatgagaac tttgactgtg tagaggcaga tgatgttgag ggcaaaatta gacaaatcat
 421  tccacctgga ttttgcacaa acacgaatga tttcctttct ttactggaaa aggaagttga
 481  tttcaagcca ttcggaacct tacttcatac ctactcagtt ctcagtccaa caggaggaga
 541  aaactttacc tttcagatat ataaggctga catgacatgt agaggctttc gagaatatca
 601  tgaaaggctt cagaccttttt tgatgtggtt tattgaaact gctagcttta ttgacgtgga
 661  tgatgaaaga tggcactact ttctagtatt tgagaagtat aataaggatg gagctacgct
 721  ctttgcgacc gtaggctaca tgacagtcta taattactat gtgtacccag acaaaacccg
 781  gccacgtgta agtcagatgc tgattttgac tccatttcaa ggtcaaggcc atggtgctca
 841  acttcttgaa acagttcata gatactacac tgaatttcct acagttcttg atattacagc
 901  ggaagatcca tccaaaagct atgtgaaatt acgagacttt gtgcttgtga agctttgtca
 961  agatttgccc tgttttttccc gggaaaaatt aatgcaagga ttcaatgaag atatggcgat
1021  agaggcacaa cagaagttca aaataaataa gcaacacgct agaagggttt atgaaattct
1081  tcgactactg gtaactgaca tgagtgatgc cgaacaatac agaagctaca gactggatat
1141  taaagaaga ctaattagcc catataagaa aaagcagaga gatcttgcta agatgagaaa
1201  atgtctcaga ccagaagaac tgacaaacca gatgaaccaa atagaaataa gcatgcaaca
1261  tgaacagctg gaagagagtt ttcaggaact agtggaagat taccggcgtg ttattgaacg
1321  acttgctcaa gagtaaagat tatactgctc tgtacaggaa gcttgcaaat tttctgtaca
1381  atgtgctgtg aaaaatctga tgactttaat tttaaaatct tgtgacattt tgcttatact
1441  aaaagttatc tatctttagt tgaatatttt cttttggaga gattgtatat tttaaaatac
1501  tgtttagagt ttatgagcat atattgcatt taagaaaaga taaagcttct gaaatactac
1561  tgcaattgct tcccttctta aacagtataa taaatgctta gttgtgatat gttaatgtgt
1621  gatgatatga ttcttaaata cttacaataa acctcattct taaatactta aaaaaaaaaa
1681  aa
```

The polypeptide sequence of a HAT protein, human PCAF, is depicted in SEQ ID NO: 3. The nucleotide sequence of human PCAF is shown in SEQ ID NO: 4. Sequence information related to PCAF is accessible in public databases by GenBank Accession numbers NM 003884 (for mRNA) and NP 003875 (for protein). PCAF is also known as KAT2B (K(lysine) acetyltransferase 2B). CBP and p300 are large nuclear proteins that bind to many sequence-specific factors involved in cell growth and/or differentiation, including c-jun and the adenoviral oncoprotein E1A. The protein encoded by this gene associates with p300/CBP. It has in vitro and in vivo binding activity with CBP and p300, and competes with E1A for binding sites in p300/CBP. It has histone acetyl transferase activity with core histones and nucleosome core particles, indicating that this protein plays a direct role in transcriptional regulation SEQ ID NO: 3 is the human wild type amino acid sequence corresponding to the HAT protein, the PCAF enzyme (residues 1-832):

```
  1   MSEAGGAGPG  GCGAGAGAGA  GPGALPPQPA  ALPPAPPQGS  PCAAAAGGSG  ACGPATAVAA
 61   AGTAEGPGGG  GSARIAVKKA  QLRSAPRAKK  LEKLGVYSAC  KAEESCKCNG  WKNPNPSPTP
121   PRADLQQIIV  SLTESCRSCS  HALAAHVSHL  ENVSEEEMNR  LLGIVLDVEY  LFTCVHKEED
181   ADTKQVYFYL  FKLLRKSILQ  RGKPVVEGSL  EKKPPFEKPS  IEQGVNNFVQ  YKFSHLPAKE
241   RQTIVELAKM  FLNRINYWHL  EAPSQRRLRS  PNDDISGYKE  NYTRWLCYCN  VPQFCDSLPR
301   YETTQVFGRT  LLRSVFTVMR  RQLLEQARQE  KDKLPLEKRT  LILTHFPKFL  SMLEEEVYSQ
361   NSPIWDQDFL  SASSRTSQLG  IQTVINPPPV  AGTISYNSTS  SSLEQPNAGS  SSPACKASSG
421   LEANPGEKRK  MTDSHVLEEA  KKPRVMGDIP  MELINEVMST  ITDPAAMLGP  ETNFLSAHSA
481   RDEAARLEER  RGVIEFHVVG  NSLNQKPNKK  ILMWLVGLQN  VFSHQLPRMP  KEYITRLVFD
541   PKHKTLALIK  DGRVIGGICF  RMFPSQGFTE  IVFCAVISNE  QVKGYGTHLM  NHLKEYHIKH
601   DILNFLTYAD  EYAIGYFKKQ  GFSKEIKIPK  TKYVGYIKDY  EGATLMGCEL  NPRIPYTEFS
661   VIIKKQKEII  KKLIERKQAQ  IRKVYPGLSC  FKDGVRQIPI  ESIPGIRETG  WKPSGKEKSK
721   EPRDPDQLYS  TLKSILQQVK  SHQSAWPFME  PVKRTEAPGY  YEVIRFPMDL  KTMSERLKNR
781   YYVSKKLFMA  DLQRVFTNCK  EYNPPESEYY  KCANILEKFF  FSKIKEAGLI  DK
```

SEQ ID NO: 4 is the human wild type nucleotide sequence corresponding to HAT protein, the PCAF enzyme (residues 1-4824), wherein the underscored ATG denotes the beginning of the open reading frame:

```
  1   gcggaaaaga  ggccgtgggg  ggcctcccag  cgctggcaga  caccgtgagg  ctggcagccg
 61   ccggcacgca  cacctagtcc  gcagtcccga  ggaacatgtc  cgcagccagg  gcgcggagca
121   gagtcccggg  caggagaacc  aagggagggc  gtgtgctgtg  gcggcggcgg  cagcggcagc
181   ggagccgcta  gtcccctccc  tcctggggga  gcagctgccg  ccgctgccgc  cgccgccacc
241   accatcagcg  cgcggggccc  ggccagagcg  agccgggcga  gcggcgcgct  agggggaggg
301   cggggcggg   gaggggggtg  ggcgaagggg  gcgggagggc  gtgggggag   ggtctcgctc
361   tcccgactac  cagagcccga  gagggagacc  ctggcggcgg  cggcggcgcc  tgacactcgg
421   cgcctcctgc  cgtgctccgg  ggcggcatgt  ccgaggctgg  cggggccggg  ccgggcggct
481   gcggggcagg  agccggggca  ggggccgggc  ccggggcgct  gccccgcag   cctgcgcgc
541   ttccgcccgc  gccccgcag   ggctccccct  gcgccgctgc  cgccggggc   tcgggcgcct
601   gcggtccggc  gacggcagtg  gctgcagcgg  gcacggccga  aggaccggga  ggcggtggct
661   cggcccgaat  cgccgtgaag  aaagcgcaac  tacgctccgc  tccgcgggcc  aagaaactgg
721   agaaactcgg  agtgtactcc  gcctgcaagg  ccgaggagtc  ttgtaaatgt  aatggctgga
781   aaaacctaa   cccctcaccc  actccccca   gagccgacct  gcagcaaata  attgtcagtc
841   taacagaatc  ctgtcggagt  tgtagccatg  ccctagctgc  tcatgtttcc  cacctggaga
901   atgtgtcaga  ggaagaaatg  aacagactcc  tgggaatagt  attggatgtg  gaatatctct
```

-continued

```
 961 ttacctgtgt ccacaaggaa gaagatgcag ataccaaaca agtttatttc tatctattta
1021 agctcttgag aaagtctatt ttacaaagag gaaacctgt ggttgaaggc tctttggaaa
1081 agaaaccccc atttgaaaaa cctagcattg aacagggtgt gaataacttt gtgcagtaca
1141 aatttagtca cctgccagca aaagaaaggc aaacaatagt tgagttggca aaaatgttcc
1201 taaaccgcat caactattgg catctggagg caccatctca acgaagactg cgatctccca
1261 atgatgatat ttctggatac aaagagaact acacaaggtg gctgtgttac tgcaacgtgc
1321 cacagttctg cgacagtcta cctcggtacg aaaccacaca ggtgtttggg agaacattgc
1381 ttcgctcggt cttcactgtt atgaggcgac aactcctgga caagcaaga caggaaaaag
1441 ataaactgcc tcttgaaaaa cgaactctaa tcctcactca tttcccaaaa tttctgtcca
1501 tgctagaaga agaagtatat agtcaaaact ctcccatctg ggatcaggat tttctctcag
1561 cctcttccag aaccagccag ctaggcatcc aaacagttat caatccacct cctgtggctg
1621 ggacaatttc atacaattca acctcatctt cccttgagca gccaaacgca gggagcagca
1681 gtcctgcctg caaagcctct tctggacttg aggcaaaccc aggagaaaag aggaaaatga
1741 ctgattctca tgttctggag gaggccaaga accccgagt tatgggggat attccgatgg
1801 aattaatcaa cgaggttatg tctaccatca cggaccctgc agcaatgctt ggaccagaga
1861 ccaattttct gtcagcacac tcggccaggg atgaggcggc aaggttggaa gagcgcaggg
1921 gtgtaattga atttcacgtg gttggcaatt ccctcaacca gaaaccaaac aagaagatcc
1981 tgatgtggct ggttggccta cagaacgttt tctcccacca gctgccccga atgccaaaag
2041 aatacatcac acggctcgtc tttgacccga acacaaaac ccttgcttta attaaagatg
2101 gccgtgttat tggtggtatc tgtttccgta tgttcccatc tcaaggattc acagagattg
2161 tcttctgtgc tgtaacctca aatgagcaag tcaagggcta tggaacacac ctgatgaatc
2221 atttgaaaga atatcacata aagcatgaca tcctgaactt cctcacatat gcagatgaat
2281 atgcaattgg atactttaag aaacagggtt tctccaaaga aattaaaata cctaaaacca
2341 aatatgttgg ctatatcaag gattatgaag gagccacttt aatgggatgt gagctaaatc
2401 cacgatccc gtacacagaa ttttctgtca tcattaaaaa gcagaaggag ataattaaaa
2461 aactgattga agaaaacag gcacaaattc gaaaagttta ccctggactt tcatgtttta
2521 aagatggagt tcgacagatt cctatagaaa gcattcctgg aattagagag acaggctgga
2581 aaccgagtgg aaaagagaaa agtaaagagc ccagagaccc tgaccagctt tacagcacgc
2641 tcaagagcat cctccagcag gtgaagagcc atcaaagcgc ttggcccttc atggaacctg
2701 tgaagagaac agaagctcca ggatattatg aagttataag gttccccatg gatctgaaaa
2761 ccatgagtga acgcctcaag aataggtact acgtgtctaa gaaattattc atggcagact
2821 tacagcgagt ctttaccaat tgcaaagagt acaaccccc tgagagtgaa tactacaaat
2881 gtgccaatat cctggagaaa ttcttcttca gtaaaattaa ggaagctgga ttaattgaca
2941 agtgatttttt tttcccctct gcttcttaga aactccaa gcagtgtgcc taaagcaagg
3001 tggtttagtt ttttacaaag aattggacat gatgtattga agagacttgt aaatgtaata
3061 attagcactt ttgaaaaaac aaaaaacctc cttttagctt ttcagatatg tatttaaatt
3121 gaagtcatag gacatttta ttttatggaa tagattttaa tctatttact actattaagg
3181 taaattttct atggcatgtc cattagctat ttcatgatag atgattaggg gtttcctcaa
3241 aacctgtgtg tgaggaaatt gcacacagta gcaaaatttg gggaaatcca taacattttc
3301 agaccatgaa tgaatgtttc cattttttc taatggaatg tgagagttta cttttatttt
3361 attctgaagg actttaagga agggatacat gatttttaaaa aagcctgtaa gaggtgaaat
```

```
3421  atgtgatgtt tgaagtctct ttatagactt tttatatata ttttttaaaa cactcatcta
3481  gatgaggtgc tttgagcagt tctgaaaaat gcagttccag gaaagcaact gctttggttc
3541  ctaaggaaga aattctaaat aatgcaaact tttaaaataa gcatctaggt ttttgataat
3601  tctgtctact tacaacaaac ttgttagtac ataaccacta ttttaataat tattttctct
3661  acacaaatgt gtaatatcat atttgacttt gcttatgcag gccataagtt ccaaaagata
3721  atttccctgc ccacaaaggc ataaacttga aaacacatga gattgaatca acatgcttta
3781  ataggaaaag atgtatggtc tatatatgta tcaatctggt gaatcctcgt tctaataaag
3841  gttcttttc ttttctatga tacacacagc cacgctgata atatgcaaat gaacattttc
3901  ctttatgtct ctccagataa tgtttattgt ctgaggtaaa ttaaattccc accagggttt
3961  gctgtcagta ttttaacacc cacattagta tatgcgtcca gggtcataac cccctaaaat
4021  ccatcatgca accttattaa tctgtcttgg gattccagtt tagtgcttgg atttatttcc
4081  tgattacact acatagaaaa gtgagacatc tgccattccc aactctggga aaaccaacta
4141  atatacaacc atataaatga aggccatctt gatggtctca acactaattt ttatgatgca
4201  aatttataca ctgattttg taaaggacaa agtttttaaaa gcgtatttaa cttgatgttt
4261  tctatcagca taaataaaat ggtcatgaat agtcattaaa aacagttgcc agtgataatc
4321  tgcatgaagg aaaaagaacc ctgcaaatgg ctattgagtt ggaagtattg tttttgatat
4381  gtaagagata ttcagaatgc tcacactgaa aatgcctcaa cttttaaag tgtaagaaac
4441  caccatgagt ggtgtctaga tttctaatga agaatcatga tacagtttgg attaagtatc
4501  ttggactggt tttaaacagt gctttgtacc ggatctgctg aagcatctgt ccagctggta
4561  tcctgtgaaa gtttgttatt ttctgagtag acattcttat agagtattgt ctttaaaatc
4621  agattgtctc ttctatattg aaagcatttt tatgtttct aatttaaaaa ttaatatttt
4681  cttatagata ttgtgcaata aagctgaagt agaatgtgtg gttttgcaa atgctttaac
4741  agctgataaa aattttacat ttgtaaaatt aatatattgt actggtacaa aatagtttta
4801  aattatattt taaaaagctt ccaa
```

The polypeptide sequence of a HAT protein, human GCN5L, is depicted in SEQ ID NO: 5. The nucleotide sequence of human GCN5L is shown in SEQ ID NO: 6. Sequence information related to GCN5L is accessible in its public databases by GenBank Accession numbers NM_021078 (for mRNA) and NP_066564.2 (for protein). GCN5L is also known as KAT2A (K(lysine) acetyltransferase 2A). KAT2A, or GCN5, is a histone acetyltransferase (HAT) that functions primarily as a transcriptional activator. It also functions as a repressor of NF-kappa-B by promoting ubiquitination of the NF-kappa-B subunit RELA in a HAT-independent manner (Mao et al., Genes Dev. 2009 Apr. 1; 23(7):849-61; herein incorporated by reference in its entirety).

SEQ ID NO: 5 is the human wild type amino acid sequence corresponding to the HAT protein, the GCN5L enzyme (residues 1-837):

```
  1   MAEPSQAPTP APAAQPRPLQ SPAPAPTPTP APSPASAPIP TPTPAPAPAP AAAPAGSTGT
 61   GGPGVGSGGA GSGGDPARPG LSQQQRASQR KAQVRGLPRA KKLEKLGVFS ACKANETCKC
121   NGWKNPKPPT APRMDLQQPA ANLSELCRSC EHPLADHVSH LENVSEDEIN RLLGMVVDVE
181   NLFMSVHKEE DTDTKQVYFY LFKLLRKCIL QMTRPVVEGS LGSPPFEKPN IEQGVLNFVQ
241   YKFSHLAPRE RQTMFELSKM FLLCLNYWKL ETPAQFRQRS QAEDVATYKV NYTRWLCYCH
301   VPQSCDSLPR YETTHVFGRS LLRSIFTVTR RQLLEKFRVE KDKLVPEKRT LILTHFPKFL
361   SMLEEEIYGA NSPIWESGFT MPPSEGTQLV PRPASVSAAV VPSTPIFSPS MGGGSNSSLS
421   LDSAGAEPMP GEKRTLPENL TLEDAKRLRV MGDIPMELVN EVMLTITDPA AMLGPETSLL
481   SANAARDETA RLEERRGIIE FHVIGNSLTP KANRRVLLWL VGLQNVFSHQ LPRMPKEYIA
```

```
541  RLVFDPKHKT LALIKDGRVI GGICERMEPT QGFTEIVFCA VTSNEQVKGY GTHLMNHLKE
601  YHIKHNILYF LTYADEYAIG YFKKQGFSKD IKVPKSRYLG YIKDYEGATL MECELNPRIP
661  YTELSHIIKK QKEIIKKLIE RKQAQIRKVY PGLSCFKEGV RQIPVESVPG IRETGWKPLG
721  KEKGKELKDP DQLYTTLKNL LAQIKSHPSA WPFMEPVKKS EAPDYYEVIR FPIDLKTMTE
781  RLRSRYYVTR KLFVADLQRV IANCREYNPP DSEYCRCASA LEKFFYFKLK EGGLIDK
```

SEQ ID NO: 6 is the human wild type nucleotide sequence corresponding to HAT protein, the GCN5L enzyme (residues 1-3127), wherein the underscored ATG denotes the beginning of the open reading frame:

```
   1  ggttgcccat gcggccctag ggctgggagc gcggcgccgc tctccgctgc gggggaggcc
  61  atggcggaac cttcccaggc cccgaccccg gccccggctg cgcagccccg gccccttcag
 121  tccccagccc ctgccccaac tccgactcct gcacccagcc cggcttcagc cccgattccg
 181  actcccaccc cggcaccagc ccctgcccca gctgcagccc agccggcag cacagggact
 241  gggggccccg gggtaggaag tgggggggcc gggagcgggg gggatccggc tcgacctggc
 301  ctgagccagc agcagcgcgc cagtcagagg aaggcgcaag tccggggggct gccgcgcgcc
 361  aagaagcttg agaagctagg ggtcttctcg gcttgcaagg ccaatgaaac ctgtaagtgt
 421  aatggctgga aaaaccccaa gcccccccact gcaccccgca tggatctgca gcagccagct
 481  gccaacctga gtgagctgtg ccgcagttgt gagcacccct tggctgacca cgtatcccac
 541  ttggagaatg tgtcagagga tgagataaac cgactgctgg ggatggtggt ggatgtggag
 601  aatctcttca tgtctgttca caggaagag acacagaca ccaagcaggt ctatttctac
 661  ctcttcaagc tactgcgaa atgcatcctg cagatgaccc ggcctgtggt ggaggggtcc
 721  ctgggcagcc ctccatttga gaaacctaat attgagcagg gtgtgctgaa cttttgtcag
 781  tacaagttta gtcacctggc tccccgggag cggcagacga tgttcgagct ctcaaagatg
 841  ttcttgctct gccttaacta ctggaagctt gagacacctg cccagtttcg gcagaggtct
 901  caggctgagg acgtggctac ctacaaggtc aattacacca gatggctctg ttactgccac
 961  gtgccccaga gctgtgatag cctccccgc tacgaaacca ctcatgtctt tgggcgaagc
1021  cttctccggt ccatttttcac cgttacccgc cggcagctgc tggaaaagtt ccgagtggag
1081  aaggacaaat tggtgcccga agaggacc ctcatcctca ctcacttccc caaattcctg
1141  tccatgctgg aggaggagat ctatgggca aactctccaa tctgggagtc aggcttcacc
1201  atgccaccct cagagggac acagctggtt ccccggccag cttcagtcag tgcagcggtt
1261  gttcccagca ccccatcatt cagccccagc atgggtgggg gcagcaacag ctccctgagt
1321  ctggattctg caggggccga gcctatgcca ggcgagaaga ggacgctccc agagaacctg
1381  accctggagg atgccaagcg gctccgtgtg atgggtgaca tccccatgga gctggtcaat
1441  gaggtcatgc tgaccatcac tgaccctgct gccatgctgg ggcctgagac gagcctgctt
1501  tcggccaatg cggcccggga tgagacagcc cgcctggagg agcgccgcgg catcatcgag
1561  ttccatgtca tcgcaactc actgacgccc aaggccaacc ggcgggtgtt gctgtggctc
1621  gtgggggctgc agaatgtctt ttcccaccag ctgccgcgca tgcctaagga gtatatcgcc
1681  cgcctcgtct ttgacccgaa gcacaagact ctggccttga tcaaggatgg gcgggtcatc
1741  ggtggcatct gcttccgcat gtttcccacc cagggcttca ggagattgt cttctgtgct
1801  gtcacctcga atgagcaggt caagggttat gggacccacc tgatgaacca cctgaaggag
1861  tatcacatca gcacaacat tctctacttc ctcacctacg ccgacgagta cgccatcggc
1921  tacttcaaaa agcagggttt ctccaaggac atcaaggtgc caagagccg ctacctgggc
```

```
-continued
1981  tacatcaagg  actacgaggg  agcgacgctg  atggagtgtg  agctgaatcc  ccgcatcccc 2041  tacacggagc  tgtcccacat  catcaagaag  cagaaagaga  tcatcaagaa  gctgattgag 2101  cgcaaacagg  cccagatccg  caaggtctac  ccggggctca  gctgcttcaa  ggagggcgtg 2161  aggcagatcc  ctgtggagag  cgttcctggc  attcgagaga  caggctggaa  gccattgggg 2221  aaggagaagg  ggaaggagct  gaaggacccc  gaccagctct  acacaaccct  caaaaacctg 2281  ctggcccaaa  tcaagtctca  ccccagtgcc  tggcccttca  tggagcctgt  gaagaagtcg 2341  gaggccctg   actactacga  ggtcatccgc  ttccccattg  acctgaagac  catgactgag 2401  cggctgcgaa  gccgctacta  cgtgacccgg  aagctctttg  tggccgacct  gcagcgggtc 2461  atcgccaact  gtcgcgagta  caacccccg   gacagcgagt  actgccgctg  tgccagcgcc 2521  ctggagaagt  tcttctactt  caagctcaag  gagggaggcc  tcattgacaa  gtaggcccat 2581  ctttgggccg  cagccctgac  ctggaatgtc  tccacctcgg  attctgatct  gatccttagg 2641  gggtgccctg  gccccacgga  cccgactcag  cttgagacac  tccagccaag  ggtcctccgg 2701  acccgatcct  gcagctcttt  ctggaccttc  aggcaccccc  aagcgtgcag  ctctgtccca 2761  gccttcactg  tgtgtgagag  gtctcctggg  ttggggccca  gcccctctag  agtagctggt 2821  ggccagggat  gaaccttgcc  cagccgtggt  ggcccccagg  cctggtcccc  aagagctttg 2881  gaggcttgga  ttcctgggcc  tggcccaggt  ggctgtttcc  ctgaggacca  gaactgctca 2941  ttttagcttg  agtgatggct  tcaggggttg  gaagttcagc  ccaaactgaa  ggggccatg 3001  ccttgtccag  cactgttctg  tcagtctccc  ccaggggtgg  ggggtatggg  gaccattcat 3061  tccctggcat  taatccctta  gagggaataa  taaagctttt  tatttctctg  tgaaaaaaaa 3121  aaaaaaa
```

Fragments include all possible amino acid lengths between and including about 8 and 100 about amino acids, for example, lengths between about 10 and 100 amino acids, between about 15 and 100 amino acids, between about 20 and 100 amino acids, between about 35 and 100 amino acids, between about 40 and 100 amino acids, between about 50 and 100 amino acids, between about 70 and 100 amino acids, between about 75 and 100 amino acids, or between about 80 and 100 amino acids. These peptide fragments can be obtained commercially or synthesized via liquid phase or solid phase synthesis methods (Atherton et al., (1989) *Solid Phase Peptide Synthesis: a Practical Approach*. IRL Press, Oxford, England; herein incorporated by reference in its entirety). The HAT peptide fragments can be isolated from a natural source, genetically engineered, or chemically prepared. These methods are well known in the art.

A HAT Activator compound can also be a protein, such as an antibody (monoclonal, polyclonal, humanized, and the like), or a binding fragment thereof, directed against a histone acetyltransferase enzyme, such as GCN5, GCN5L, PCAF, or HAT1. An antibody fragment can be a form of an antibody other than the full-length form and includes portions or components that exist within full-length antibodies, in addition to antibody fragments that have been engineered. Antibody fragments can include, but are not limited to, single chain Fv (scFv), diabodies, Fv, and (Fab')$_2$, triabodies, Fc, Fab, CDR1, CDR2, CDR3, combinations of CDR's, variable regions, tetrabodies, bifunctional hybrid antibodies, framework regions, constant regions, and the like (see, Maynard et al., (2000) *Ann. Rev. Biomed. Eng.* 2:339-76; Hudson (1998) *Curr. Opin. Biotechnol.* 9:395-402; each herein incorporated by reference in its entirety). Antibodies can be obtained commercially, custom generated, or synthesized against an antigen of interest according to methods established in the art (Janeway et al., (2001) *Immunobiology*, 5th ed., Garland Publishing, herein incorporated by reference in its entirety).

Inhibition of RNA encoding a HAT protein can effectively modulate the expression of a HAT gene (e.g., GCN5, GCN5L, PCAF, or HAT1) from which the RNA is transcribed. Inhibitors are selected from the group comprising: siRNA, interfering RNA or RNAi; dsRNA; RNA Polymerase III transcribed DNAs; ribozymes; and antisense nucleic acid, which can be RNA, DNA, or artificial nucleic acid.

Antisense oligonucleotides, including antisense DNA, RNA, and DNA/RNA molecules, act to directly block the translation of mRNA by binding to targeted mRNA and preventing protein translation. For example, antisense oligonucleotides of at least about 15 bases and complementary to unique regions of the DNA sequence encoding a HAT polypeptide can be synthesized, e.g., by conventional phosphodiester techniques (Dallas et al., (2006) *Med. Sci. Monit.* 12(4):RA67-74; Kalota et al., (2006) *Handb. Exp. Pharmacol.* 173:173-96; Lutzelburger et al., (2006) *Handb. Exp. Pharmacol.* 173:243-59; each herein incorporated by reference in its entirety).

siRNA comprises a double stranded structure containing from about 15 to about 50 base pairs, for example from about 21 to about 25 base pairs, and having a nucleotide sequence identical or nearly identical to an expressed target gene or RNA within the cell. Antisense nucleotide sequences include, but are not limited to: morpholinos, 2'-O-methyl polynucleotides, DNA, RNA and the like. RNA polymerase III transcribed DNAs contain promoters, such as the U6 promoter. These DNAs can be transcribed to produce small hairpin RNAs in the cell that can function as siRNA or linear RNAs that can function as antisense RNA. The HAT activator compound can contain ribonucleotides, deoxyribonucleotides, synthetic nucleotides, or any suitable combination such that the target RNA and/or gene is inhibited. In addition, these forms of nucleic acid can be single, double, triple, or quadruple stranded. (see for example Bass (2001) Nature, 411, 428 429; Elbashir et al., (2001) Nature, 411, 494 498; and PCT Publication Nos. WO 00/44895, WO 01/36646, WO 99/32619, WO 00/01846, WO 01/29058, WO 99/07409, WO 00/44914; each herein incorporated by reference in its entirety).

In some embodiments, a HAT Activator compound can be a small molecule that binds to a histone acetyltransferase enzyme, such as GCN5, GCN5L, PCAF, or HAT1, and disrupts its function. Small molecules are a diverse group of synthetic and natural substances generally having low molecular weights. They can be isolated from natural sources (for example, plants, fungi, microbes and the like), are obtained commercially and/or available as libraries or collections, or synthesized. Candidate small molecules that interact with a HAT protein can be identified via in silico screening or high-through-put (HTP) screening of combinatorial libraries. Most conventional pharmaceuticals, such as aspirin, penicillin, and many chemotherapeutics, are small molecules, can be obtained commercially, can be chemically synthesized, or can be obtained from random or combinatorial libraries as described below (Werner et al., (2006) *Brief Funct. Genomic Proteomic* 5(1):32-6; herein incorporated by reference in its entirety).

Knowledge of the primary sequence of a molecule of interest, such as a HAT polypeptide, and the similarity of that sequence with other proteins of the same histone acetyltransferase family (such as the GNAT family, the MYST family or the GCNS family [see Lee and Owrkman (2007) Nat Rev Mol Cell Biol., 8(4):284-95, Marmorstein (2001) J Molec Biol. 311: 433-444; and Kimura et al., (2005) J Biocehm. 138(6): 647-662; each herein incorporated by reference in its entirety], can provide information as to the inhibitors or antagonists of the protein of interest. Identification and screening antagonists can be further facilitated by determining structural features of the protein, e.g., using X-ray crystallography, neutron diffraction, nuclear magnetic resonance spectrometry, and other techniques for structure determination. These techniques provide for the rational design or identification of antagonists, in addition to protein agonists.

The invention provides methods for screening and identifying compounds useful for treating a neurodegenerative disease in a subject. The invention provides methods for identifying compounds which can be used for treating subjects that exhibit, for example, abnormally elevated amyloid beta plaques, or elevated Tau protein levels, or elevated alpha-synuclein levels, or inclusions, or lipofuscin level or inclusions, or cleaved TARDBP-TDP-43 level or inclusion, or accumulation of cleaved TARDBP/TDP-43 inclusions, or a combination thereof. In one embodiment, the method comprises selecting a HAT Activator compound that comprises one or both of the following features: (a) the $EC_{50}$ of the compound is no more than about 1000 nM; (b) the compound penetrates the blood brain barrier; (c) the compound enhances histone acetylation (for example acetylates histone protein H3 or H4), or a combination thereof. In a further embodiment, the compound, for example the HAT Activator, has an $EC_{50}$ of at least about 0.1 nM, at least about 1 nM, at least about 5 nM, at least about 10 nM, at least about 25 nM, at least about 50 nM, at least about 100 nM, at least about 200 nM, at least about 300 nM, at least about 400 nM, at least about 500 nM, at least about 600 nM, at least about 700 nM, at least about 800 nM, or at least about 900 nM. In some embodiments, the HAT Activator compound can have a molecular mass less than about 500 Da in order to penetrate the blood brain barrier. In other embodiments, the HAT Activator compound can have a polar surface area less than about 90 $Å^2$ and should have 8 or fewer hydrogen bonds in order to penetrate the blood brain barrier. The screening and identifying of the compound can comprise in silico screening, molecular docking, in vivo screening, in vitro screening, or a combination thereof.

Test compounds, such as HAT Activator compounds, can be screened from large libraries of synthetic or natural compounds (see Wang et al., (2007) *Curr Med Chem*, 14(2):133-55; Mannhold (2006) *Curr Top Med Chem*, 6 (10):1031-47; and Hensen (2006) *Curr Med Chem* 13(4): 361-76; each herein incorporated by reference in its entirety). Numerous means are currently used for random and directed synthesis of saccharide, peptide, and nucleic acid based compounds. Synthetic compound libraries are commercially available from Maybridge Chemical Co. (Trevillet, Cornwall, UK), Comgenex (Princeton, N.J.), Brandon Associates (Merrimack, N.H.), and Microsource (New Milford, Conn.). A rare chemical library is available from Aldrich (Milwaukee, Wis.). Alternatively, libraries of natural compounds in the form of bacterial, fungal, plant and animal extracts are available from e.g. Pan Laboratories (Bothell, Wash.) or MycoSearch (N.C.), or are readily producible. Additionally, natural and synthetically produced libraries and compounds are readily modified through conventional chemical, physical, and biochemical means (Blondelle et al., (1996) *Tib Tech* 14:60; herein incorporated by reference in its entirety).

Methods for preparing libraries of molecules are well known in the art and many libraries are commercially available. Libraries of interest in the invention include peptide libraries, randomized oligonucleotide libraries, synthetic organic combinatorial libraries, and the like. Degenerate peptide libraries can be readily prepared in solution, in immobilized form as bacterial flagella peptide display libraries or as phage display libraries. Peptide ligands can be selected from combinatorial libraries of peptides containing at least one amino acid. Libraries can be synthesized of peptoids and non-peptide synthetic moieties. Such libraries can further be synthesized which contain non-peptide synthetic moieties, which are less subject to enzymatic degradation compared to their naturally-occurring counterparts. Libraries are also meant to include for example but are not limited to peptide-on-plasmid libraries, polysome libraries, aptamer libraries, synthetic peptide libraries, synthetic small molecule libraries, neurotransmitter libraries, and chemical libraries. The libraries can also comprise cyclic carbon or heterocyclic structure and/or aromatic or polyaromatic structures substituted with one or more of the functional groups described herein.

Small molecule combinatorial libraries can also be generated and screened. A combinatorial library of small organic compounds is a collection of closely related analogs that differ from each other in one or more points of diversity and are synthesized by organic techniques using multi-step processes. Combinatorial libraries include a vast number of small organic compounds. One type of combinatorial library is prepared by means of parallel synthesis methods to produce a compound array. A compound array can be a collection of compounds identifiable by their spatial addresses in Cartesian coordinates and arranged such that each compound has a common molecular core and one or more variable structural diversity elements. The compounds in such a compound array are produced in parallel in separate reaction vessels, with each compound identified and tracked by its spatial address. Examples of parallel synthesis mixtures and parallel synthesis methods are provided in U.S. Ser. No. 08/177,497, filed Jan. 5, 1994 and its corresponding PCT published patent application WO95/18972, published Jul. 13, 1995 and U.S. Pat. No. 5,712,171 granted Jan. 27, 1998 and its corresponding PCT published patent application WO96/22529, each herein incorporated by reference in its entirety.

Examples of chemically synthesized libraries are described in Fodor et al., (1991) Science 251:767-773; Houghten et al., (1991) Nature 354:84-86; Lam et al., (1991) Nature 354:82-84; Medynski, (1994) BioTechnology 12:709-710; Gallop et al., (1994) J. Medicinal Chemistry 37(9):1233-1251; Ohlmeyer et al., (1993) Proc. Natl. Acad. Sci. USA 90:10922-10926; Erb et al., (1994) Proc. Natl. Acad. Sci. USA 91:11422-11426; Houghten et al., (1992) Biotechniques 13:412; Jayawickreme et al., (1994) Proc. Natl. Acad. Sci. USA 91:1614-1618; Salmon et al., (1993) Proc. Natl. Acad. Sci. USA 90:11708-11712; PCT Publication No. WO 93/20242, dated Oct. 14, 1993; and Brenner et al., (1992) Proc. Natl. Acad. Sci. USA 89:5381-5383; each herein incorporated by reference in its entirety.

Examples of phage display libraries are described in Scott et al., (1990) Science 249:386-390; Devlin et al., (1990) Science, 249:404-406; Christian, et al., (1992) J. Mol. Biol. 227:711-718; Lenstra, (1992) J. Immunol. Meth. 152:149-157; Kay et al., (1993) Gene 128:59-65; and PCT Publication No. WO 94/18318; each herein incorporated by reference in its entirety.

In vitro translation-based libraries include but are not limited to those described in PCT Publication No. WO 91/05058; and Mattheakis et al., (1994) Proc. Natl. Acad. Sci. USA 91:9022-9026; each herein incorporated by reference in its entirety.

In one non-limiting example, non-peptide libraries, such as a benzodiazepine library (see e.g., Bunin et al., (1994) Proc. Natl. Acad. Sci. USA 91:4708-4712; herein incorporated by reference in its entirety), can be screened. Peptoid libraries, such as that described by Simon et al., (1992) Proc. Natl. Acad. Sci. USA 89:9367-9371 (herein incorporated by reference in its entirety), can also be used. Another example of a library that can be used, in which the amide functionalities in peptides have been permethylated to generate a chemically transformed combinatorial library, is described by Ostresh et al. (1994), Proc. Natl. Acad. Sci. USA 91:11138-11142; herein incorporated by reference in its entirety.

The three dimensional geometric structure of an active site, for example that of a HAT polypeptide can be determined by known methods in the art, such as X-ray crystallography, which can determine a complete molecular structure. Solid or liquid phase NMR can be used to determine certain intramolecular distances. Any other experimental method of structure determination can be used to obtain partial or complete geometric structures. The geometric structures can be measured with a complexed ligand, natural or artificial, which can increase the accuracy of the active site structure determined. In one embodiment, a compound that binds to a HAT protein, such as GCN5, GCN5L, PCAF, or HAT1, can be identified via: (1) providing an electronic library of test compounds; (2) providing atomic coordinates listed in PDB Entry No. 1YGH or 2RC4, for at least 20 amino acid residues for the acetyltransferase active site of the HAT protein (the HAT domain), wherein the coordinates have a root mean square deviation therefrom, with respect to at least 50% of Ca atoms, of not greater than about 2 Å, in a computer readable format; (3) converting the atomic coordinates into electrical signals readable by a computer processor to generate a three dimensional model of the HAT protein; (4) performing a data processing method, wherein electronic test compounds from the library are docked onto the three dimensional model of the HAT protein; and determining which test compound fits into the active site of the three dimensional model of the HAT protein, thereby identifying which compound would bind to a HAT protein. In another embodiment, the method can further comprise: synthesizing or obtaining the compound determined to dock to the active site of the HAT protein; contacting the HAT protein with the compound under a condition suitable for binding; and determining whether the compound modulates HAT protein expression or mRNA expression, or HAT protein activity using a diagnostic assay.

Methods for predicting the effect on protein conformation of a change in protein sequence, are known in the art, and the skilled artisan can thus design a variant which functions as an antagonist according to known methods. One example of such a method is described by Dahiyat and Mayo in Science (1997) 278:82 87 (herein incorporated by reference in its entirety), which describes the design of proteins de novo. The method can be applied to a known protein to vary only a portion of the polypeptide sequence. Similarly, Blake (U.S. Pat. No. 5,565,325; herein incorporated by reference in its entirety) teaches the use of known ligand structures to predict and synthesize variants with similar or modified function.

Other methods for preparing or identifying peptides that bind to a target are known in the art. Molecular imprinting, for instance, can be used for the de novo construction of macromolecular structures such as peptides that bind to a molecule. See, for example, Kenneth J. Shea, *Molecular Imprinting of Synthetic Network Polymers: The De Novo synthesis of Macromolecular Binding and Catalytic Sites*, TRIP Vol. 2, No. 5, May 1994; Mosbach, (1994) *Trends in Biochem. Sci.,* 19(9); and Wulff, G., in *Polymeric Reagents and Catalysts* (Ford, W. T., Ed.) ACS Symposium Series No. 308, pp 186-230, American Chemical Society (1986); each herein incorporated by reference in its entirety. One method for preparing mimics of a HAT protein involves the steps of: (i) polymerization of functional monomers around a known substrate (the template) that exhibits a desired activity; (ii) removal of the template molecule; and then (iii) polymerization of a second class of monomers in, the void left by the template, to provide a new molecule which exhibits one or more desired properties which are similar to that of the template. Other binding molecules such as polysaccharides, nucleosides, drugs, nucleoproteins, lipoproteins, carbohydrates, glycoproteins, steroids, lipids, and other biologically active materials can also be prepared. This method is useful for designing various biological mimics that are more stable than their natural counterparts, because they are prepared by the free radical polymerization of functional monomers, resulting in a compound with a nonbiodegradable backbone. Other methods for designing such molecules include, e.g., drug design based on structure activity relationships, which require the synthesis and evaluation of a number of compounds and molecular modeling.

The invention also provides in vivo and in vitro methods for identifying a compound that binds to a HAT protein. In one embodiment, the method comprises: (a) obtaining a tissue and/or cells that express a HAT protein (such as GCNS, GCN5L, PCAF, or HAT1); (b) contacting the tissue and/or cell with a ligand source for an effective period of time; (c) measuring a secondary messenger response, wherein the response is indicative of a ligand binding to a HAT protein; (d) isolating the ligand from the ligand source; and (e) identifying the structure of the ligand that binds a HAT protein, thereby identifying which compound would bind to a HAT protein. As used herein, the term "ligand source" can be any compound library described herein, or a library of neurotransmitters that can be used to screen for compounds that would act as an agonist of a HAT protein (such as GCNS, GCN5L, PCAF, or HAT1). Screening compound libraries listed herein [also see U.S. Patent Application Publication No. 2005/0009163, which is hereby incorporated by reference in its entirety], in combination with in vivo animal studies and functional assays can be used to identify HAT Activator compounds that can be used to treat subjects afflicted with abnormal Aβ deposits, such as AD or to treat cancer.

A HAT Activator compound can be a compound that increases the activity and/or expression of a HAT molecule (e.g., GCN5, GCN5L, PCAF, or HAT1) in vivo and/or in vitro. HAT Activator compounds can be compounds that exert their effect on the activity of a HAT protein via the expression, via post-translational modifications, or by other means. In one embodiment, a HAT Activator compound can increase HAT protein or mRNA expression, or acetyltransferase activity by at least about 10%, at least about 20%, at least about 30%, at least about 40%, at least about 50%, at least about 60%, at least about 70%, at least about 75%, at least about 80%, at least about 85%, at least about 90%, at least about 95%, at least about 97%, at least about 99%, or 100%.

Test compounds or agents which bind to a HAT molecule (such as GCN5, GCN5L, PCAF, or HAT1), and/or have a stimulatory effect on the activity or the expression of a HAT molecule, can be identified by various assays. The assay can be a binding assay comprising direct or indirect measurement of the binding of a test compound or a known HAT ligand to the active site of a HAT protein. The assay can also be an activity assay comprising direct or indirect measurement of the activity of a HAT molecule. The assay can also be an expression assay comprising direct or indirect measurement of the expression of a HAT mRNA or protein. The various screening assays can be combined with an in vivo assay comprising measuring the effect of the test compound on cognitive and synaptic function in an animal model for neurodegenerative disorders, such as, but not imited to, AD or Huntington's Disease.

The diagnostic assay of the screening methods of the invention can also involve monitoring the expression of a HAT molecule. For example, inhibitors of the expression of a HAT molecule can be identified via contacting a HAT-positive cell or tissue with a test compound and determining the expression of a HAT protein or HAT mRNA in the cell. The protein or mRNA expression level of a HAT molecule in the presence of the test compound is compared to the protein or mRNA expression level of a HAT protein in the absence of the test compound. The test compound can then be identified as an inhibitor of expression of a HAT protein (such as GCN5, GCN5L, PCAF, or HAT1) based on this comparison. Acivators of the expression of a HAT molecule can also be identified via contacting a HAT-positive cell or tissue with a test compound and determining the expression of a HAT protein or HAT mRNA in the cell. The protein or mRNA expression level of a HAT molecule in the presence of the test compound is compared to the protein or mRNA expression level of a HAT protein in the absence of the test compound. The test compound can then be identified as an activator of expression of a HAT protein (such as GCN5, GCN5L, PCAF, or HAT1) based on this comparison. For example, when expression of HAT protein or mRNA is statistically or significantly more in the presence of the test compound than in its absence, the compound is identified as an activator of the expression of a HAT protein or mRNA. In other words, the test compound can also be said to be a HAT Activator compound (such as an agonist). The expression level of a HAT protein or mRNA in cells can be determined by methods described herein.

Determining the ability of a test compound to bind to a HAT molecule or a variant thereof can be accomplished using real-time Bimolecular Interaction Analysis (BIA) [McConnell, (1992); Sjolander, (1991); herein incorporated by reference in its entirety]. BIA is a technology for studying biospecific interactions in real time, without labeling any of the interactants (e.g., BIA-core™). Changes in optical phenomenon surface plasmon resonance (SPR) can be used as an indication of real-time reactions between biological molecules.

Exemplary HAT Activator Compounds Optimized for CNS Disorders and Cancer

The invention provides for compounds that bind to a HAT activator protein, such as GCN5, GCN5L, PCAF, or HAT1. These compounds can be identified by the screening methods and assays described herein, and enhance the activity or expression of HAT activator proteins. In one embodiment, the invention encompasses a compound of Formula (I):

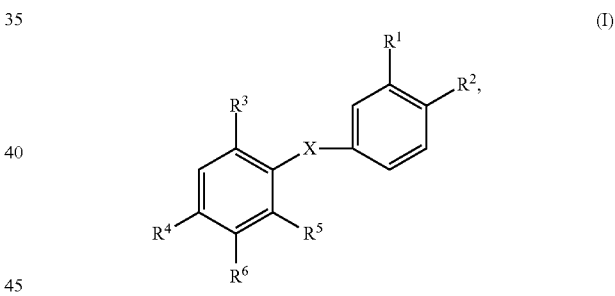

(I)

wherein,
R$^1$ is H, or CF$_3$;
R$^2$ is H, Cl, or CN;
R$^3$ is H, O-methyl, O-ethyl, S-ethyl, O-cyclopentyl, OCH$_2$CH$_2$N(CH$_3$)$_2$, or CH$_2$CH$_2$CH$_2$N(CH$_3$)$_2$;
R$^4$ is H; C(=O)NH-phenyl, wherein phenyl is substituted with one or more halo or CF$_3$;
R$^5$ is H, C$_1$-C$_5$-alkyl, OH, OCH$_3$, O-ethyl, OCH$_2$CH$_2$N(CH$_3$)$_2$, CH$_2$CH$_2$CH$_2$N(CH$_3$)$_2$, SCH$_2$CH$_2$N(CH$_3$)$_2$, or OCH$_2$C(=O)O-alkyl;
R$^6$ is H, O-methyl, O-ethyl, OCH$_2$CH$_2$N(CH$_3$)$_2$; and
X is CONH, SONH, SO$_2$NH, NHC(=O)NH, or NHCO, or a pharmaceutically acceptable salt or hydrate thereof.

In one embodiment of the compound of Formula (I),
R$^1$ is H, or CF$_3$;
R$^2$ is H, Cl, or CN;
R$^3$ is H, O-methyl, O-ethyl, S-ethyl, O-cyclopentyl, OCH$_2$CH$_2$N(CH$_3$)$_2$, or CH$_2$CH$_2$CH$_2$N(CH$_3$)$_2$;
R$^4$ is H; C(=O)NH-phenyl, wherein phenyl is substituted with one or more halo or CF$_3$;

$R^5$ is $C_1$-$C_5$-alkyl, OH, $OCH_3$, O-ethyl, $OCH_2CH_2N(CH_3)_2$, $CH_2CH_2CH_2N(CH_3)_2$, $SCH_2CH_2N(CH_3)_2$, or $OCH_2C(=O)O$-alkyl;

$R^6$ is H, O-methyl, O-ethyl, $OCH_2CH_2N(CH_3)_2$; and

X is CONH, SONH, $SO_2NH$, NHC(=O)NH, or NHCO.

In one embodiment of the compound of Formula (I), $R^1$ is H. In one embodiment of the compound of Formula (I), $R^1$ is $CF_3$.

In one embodiment of the compound of Formula (I), $R^2$ is H, Cl, or CN. In one embodiment of the compound of Formula (I), $R^2$ is Cl or CN. In one embodiment of the compound of Formula (I), $R^2$ is Cl. In one embodiment of the compound of Formula (I), $R^2$ is CN.

In one embodiment of the compound of Formula (I), $R^3$ is O-methyl, O-ethyl, S-ethyl, O-cyclopentyl, $OCH_2CH_2N(CH_3)_2$, or $CH_2CH_2CH_2N(CH_3)_2$. In one embodiment of the compound of Formula (I), $R^3$ is O-methyl, O-ethyl, S-ethyl, or O-cyclopentyl. In one embodiment of the compound of Formula (I), $R^3$ is O-methyl, O-ethyl, or S-ethyl. In one embodiment of the compound of Formula (I), $R^3$ is O-methyl or O-ethyl. In one embodiment of the compound of Formula (I), $R^3$ is O-ethyl, or S-ethyl. In one embodiment of the compound of Formula (I), $R^3$ is O-ethyl.

In one embodiment of the compound of Formula (I), $R^4$ is H. In one embodiment of the compound of Formula (I), $R^4$ is C(=O)NH-phenyl, wherein phenyl is substituted with one or more halo or $CF_3$.

In one embodiment of the compound of Formula (I), $R^5$ is $C_1$-$C_4$-alkyl, OH, $OCH_3$, O-ethyl, $OCH_2CH_2N(CH_3)_2$, $CH_2CH_2CH_2N(CH_3)_2$, $SCH_2CH_2N(CH_3)_2$, or $OCH_2C(=O)O$-alkyl. In one embodiment of the compound of Formula (I), $R^5$ is OH, $OCH_3$, O-ethyl, $OCH_2CH_2N(CH_3)_2$, $CH_2CH_2CH_2N(CH_3)_2$, $SCH_2CH_2N(CH_3)_2$, or $OCH_2C(=O)O$-alkyl. In one embodiment of the compound of Formula (I), $R^5$ is $OCH_3$, O-ethyl, $OCH_2CH_2N(CH_3)_2$, $CH_2CH_2CH_2N(CH_3)_2$, $SCH_2CH_2N(CH_3)_2$, or $OCH_2C(=O)O$-alkyl. In one embodiment of the compound of Formula (I), $R^5$ is $OCH_2CH_2N(CH_3)_2$, $CH_2CH_2CH_2N(CH_3)_2$, $SCH_2CH_2N(CH_3)_2$, or $OCH_2C(=O)O$-alkyl. In one embodiment of the compound of Formula (I), $R^5$ is $OCH_2CH_2N(CH_3)_2$, $CH_2CH_2CH_2N(CH_3)_2$, or $SCH_2CH_2N(CH_3)_2$. In one embodiment of the compound of Formula (I), $R^5$ is $OCH_2CH_2N(CH_3)_2$ or $SCH_2CH_2N(CH_3)_2$. In one embodiment of the compound of Formula (I), $R^5$ is $OCH_2CH_2N(CH_3)_2$.

In one embodiment of the compound of Formula (I), $R^6$ is H, O-methyl, O-ethyl, or $OCH_2CH_2N(CH_3)_2$. In one embodiment of the compound of Formula (I), $R^6$ is H or $OCH_2CH_2N(CH_3)_2$. In one embodiment of the compound of Formula (I), $R^6$ is H.

In one embodiment of the compound of Formula (I), X is CONH, SONH, $SO_2NH$, NHC(=O)NH, or NHCO. In one embodiment of the compound of Formula (I), X is CONH, SONH, or $SO_2NH$. In one embodiment of the compound of Formula (I), X is CONH or $SO_2NH$. In one embodiment of the compound of Formula (I), X is CONH. In one embodiment of the compound of Formula (I), X is $SO_2NH$.

In one embodiment of the compound of Formula (I),
$R^1$ is $CF_3$;
$R^2$ is H, Cl, or CN;
$R^3$ is H, O—($C_1$-$C_2$)-alkyl, O—($C_3$-$C_6$)-cycloalkyl, O—($C_1$-$C_2$)-alkyl-$OC_2$—($C_1$-$C_2$)-alkyl, or S—($C_1$-$C_2$)-alkyl;
$R^4$ is H;
$R^5$ is H, ($C_1$-$C_6$)-alkyl, OH, $OCH_2CH_2N(CH_3)_2$, S—($C_1$-$C_2$)-alkyl, or $SCH_2CH_2N(CH_3)_2$;
$R^6$ is H, or $OCH_2CH_2N(CH_3)_2$; and
X=$SO_2NH$, CONH, NHCO, or NHCONH, or a pharmaceutically acceptable salt or hydrate thereof.

In one embodiment of the compound of Formula (I),
$R^1$ is $CF_3$;
$R^2$ is H, Cl, or CN;
$R^3$ is H, O—($C_1$-$C_2$)-alkyl, O—($C_3$-$C_6$)-cycloalkyl, O—($C_1$-$C_2$)-alkyl-$OC_2$—($C_1$-$C_2$)-alkyl, or S—($C_1$-$C_2$)-alkyl;
$R^4$ is H;
$R^5$ is ($C_1$-$C_6$)-alkyl, OH, $OCH_2CH_2N(CH_3)_2$, S—($C_1$-$C_2$)-alkyl, or $SCH_2CH_2N(CH_3)_2$;
$R^6$ is H, or $OCH_2CH_2N(CH_3)_2$; and
X=$SO_2NH$, CONH, NHCO, or NHCONH, or a pharmaceutically acceptable salt or hydrate thereof.

In particular embodiments, the compound of Formula (I) is:

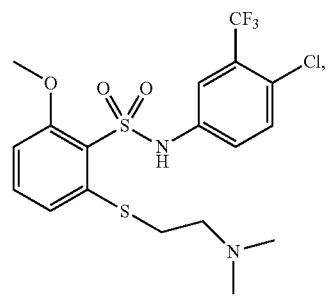

1

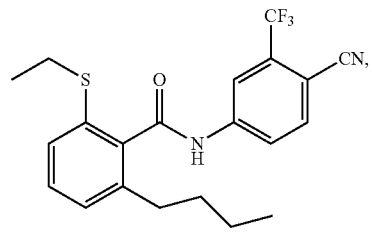

2

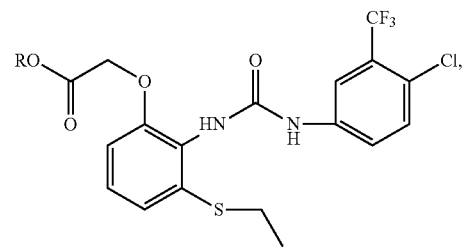

3

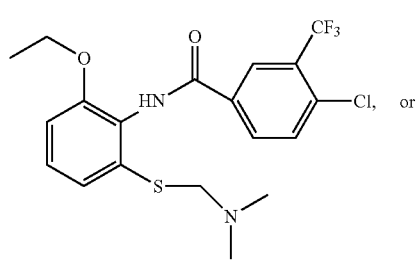

4

-continued

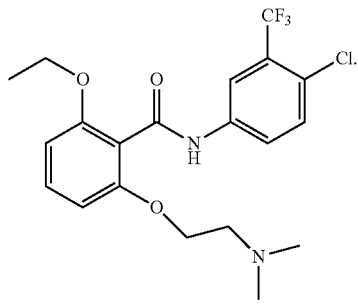

In some embodiments, the compound of Formula (I) is

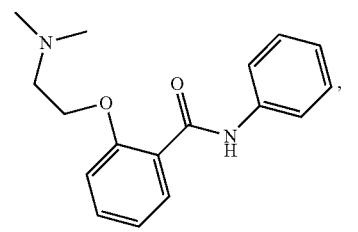

10

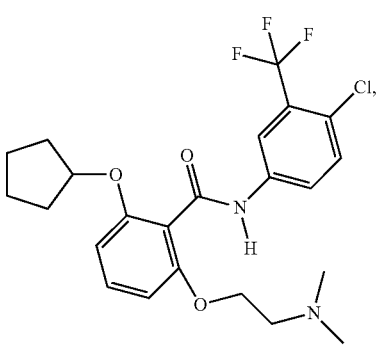

11

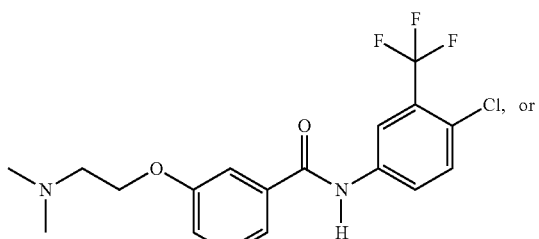

12

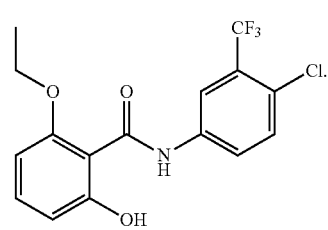

19

In another embodiment of the compound of Formula (I),
R¹ is CF₃;
R² is Cl; R³ is H, O—(C₁-C₂)-alkyl, O—(C₃-C₆)-cycloalkyl, or O—(C₁-C₂)-alkyl-OC₂—(C₁-C₂)-alkyl;
R⁴ is H;
R⁵ is H, (C₁-C₆)-alkyl, OH, OCH₂CH₂N(CH₃)₂, S—(C₁-C₂)-alkyl, or SCH₂CH₂N(CH₃)₂;
R⁶ is H, or OCH₂CH₂N(CH₃)₂; and
X is SO₂NH, CONH, NHCO, or NHCONH, or a pharmaceutically acceptable salt or hydrate thereof.

In another embodiment of the compound of Formula (I),
R¹ is CF₃;
R² is Cl;
R³ is H, O—(C₁-C₂)-alkyl, O—(C₃-C₆)-cycloalkyl, or O—(C₁-C₂)-alkyl-OC₂—(C₁-C₂)-alkyl;
R⁴ is H;
R⁵ is (C₁-C₆)-alkyl, OH, OCH₂CH₂N(CH₃)₂, S—(C₁-C₂)-alkyl, or SCH₂CH₂N(CH₃)₂;
R⁶ is H, or OCH₂CH₂N(CH₃)₂; and
X is SO₂NH, CONH, NHCO, or NHCONH, or a pharmaceutically acceptable salt or hydrate thereof.

In particular embodiments, the compound of Formula (I) is:

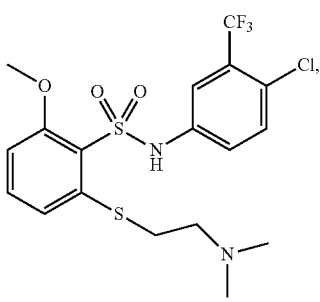

1

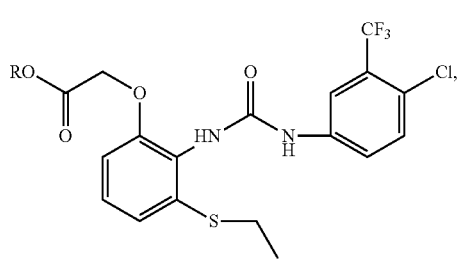

3

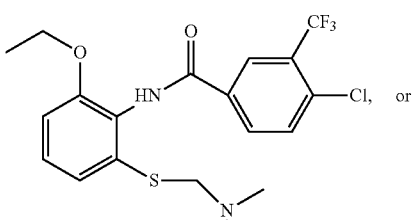

4

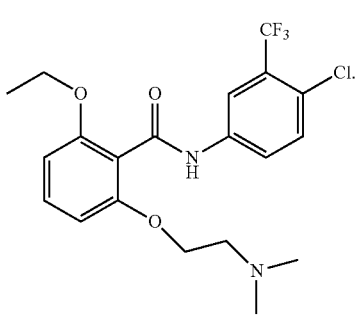

5

In some embodiments, the compound is,

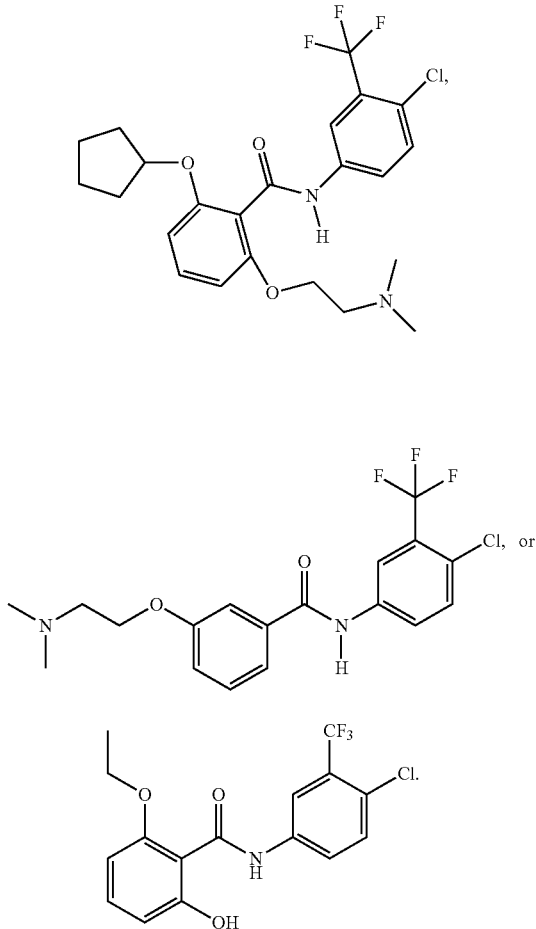

In a further embodiment of the compound of Formula (I), $R^1$ is $CF_3$;

$R^2$ is H, or CN;

$R^3$ is S—($C_1$-$C_2$)-alkyl, or $OCH_2CH_2N(CH_3)_2$;

$R^4$ is H;

$R^5$ is H, or ($C_1$-$C_4$)-alkyl;

$R^6$ is H; and

X is CONH, or a pharmaceutically acceptable salt or hydrate thereof.

In particular embodiments, the compound of Formula (I) is:

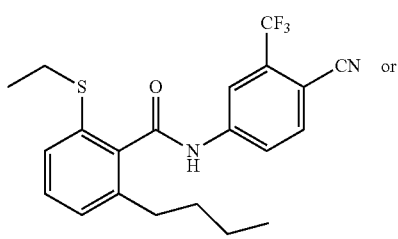

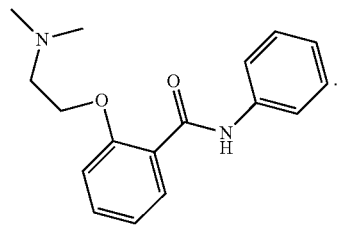

In some embodiments of the compound of Formula (I), $R_1$ is $CF_3$;

$R_2$ is $C_1$;

$R_3$ is H, O—($C_1$-$C_2$)-alkyl, $OCH_2CH_2N(CH_3)_2$, or $CH_2CH_2CH_2N(CH_3)_2$;

$R_4$ is $C(O)NH$-(3-$CF_3$, 4-Cl-phenyl);

$R^5$ is H, O—($C_1$-$C_2$)-alkyl, $OCH_2CH_2N(CH_3)_2$, or $CH_2CH_2CH_2N(CH_3)_2$;

$R^6$ is H, or O—($C_1$-$C_2$)-alkyl; and

X=CONH, or a pharmaceutically acceptable salt or hydrate thereof.

In some embodiments of the compound of Formula (I), $R_1$ is $CF_3$;

$R_2$ is $C_1$;

$R_3$ is H, O—($C_1$-$C_2$)-alkyl, $OCH_2CH_2N(CH_3)_2$, or $CH_2CH_2CH_2N(CH_3)_2$;

$R_4$ is $C(O)NH$-(3-$CF_3$, 4-Cl-phenyl);

$R^5$ is O—($C_1$-$C_2$)-alkyl, $OCH_2CH_2N(CH_3)_2$, or $CH_2CH_2CH_2N(CH_3)_2$;

$R^6$ is H, or O—($C_1$-$C_2$)-alkyl; and

X=CONH, or a pharmaceutically acceptable salt or hydrate thereof.

In particular embodiments, the compound of Formula (I) is:

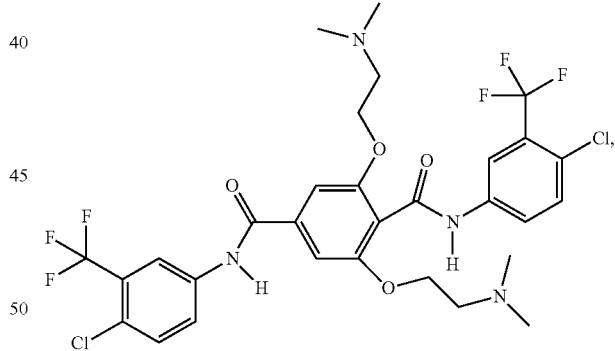

-continued

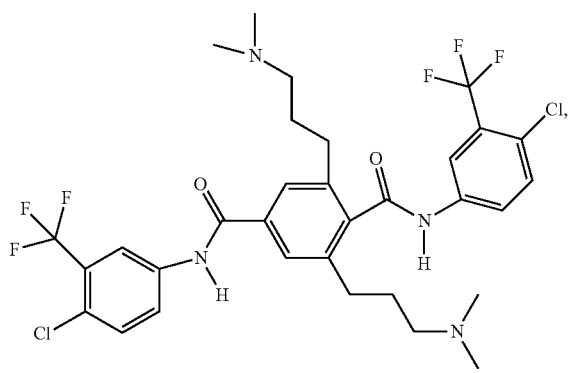
15

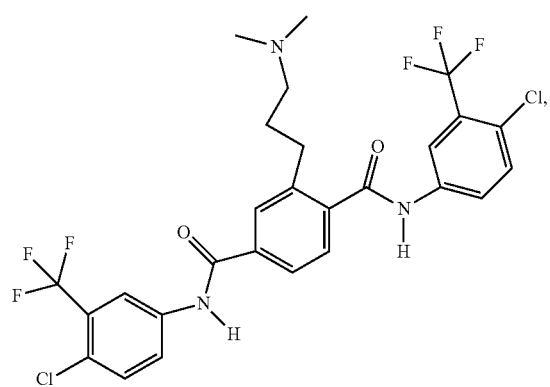
16

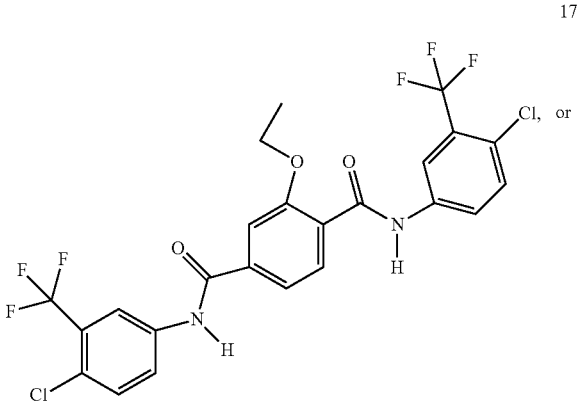
17

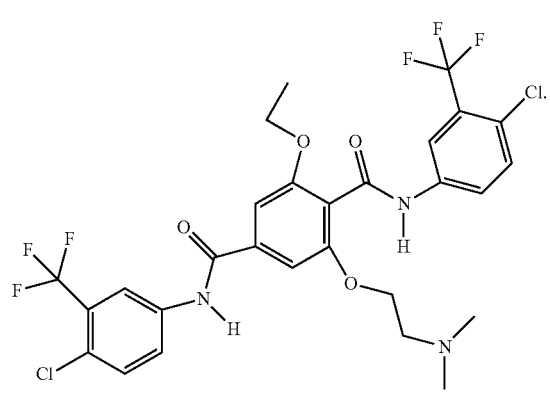
18

In one embodiment of the compound of Formula (I),
$R^1$ is $CF_3$;
$R^2$ is $C_1$;
$R^3$ is O—($C_1$-$C_2$)-alkyl;
$R^4$ is H;
$R^5$ is $OCH_2CH_2N(CH_3)_2$; and
X is CONH, or a pharmaceutically acceptable salt or hydrate thereof.

In another embodiment of the compound of Formula (I),
$R^1$ is $CF_3$;
$R^2$ is $C_1$;
$R^3$ is H, O—($C_1$-$C_2$)-alkyl;
$R^4$ is H;
$R^5$ is $SCH_2CH_2N(CH_3)_2$;
$R^6$ is H; and
X=$SO_2NH$, or a pharmaceutically acceptable salt or hydrate thereof.

In one embodiment, the invention encompasses HAT Activator compounds of Formula (II), wherein:

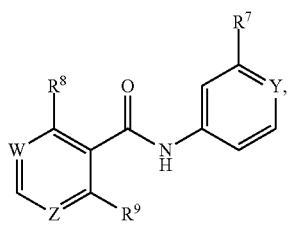

(II)

wherein,
$R^7$ is H or $CF_3$;
$R^8$ is O-ethyl or S-methyl;
$R^9$ is butyl or $OCH_2CH_2N(CH_3)_2$;
Y is C—Cl, C—CN, C—$NO_2$, or N;
W is CH or N; and
Z is CH or N, or a pharmaceutically acceptable salt or hydrate thereof.

In particular embodiments, the compound of Formula (II) is:

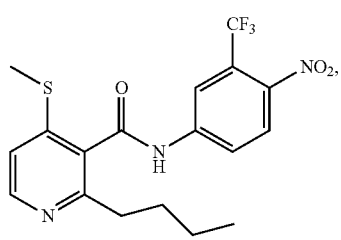
6

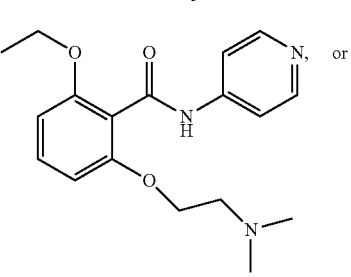
8

-continued

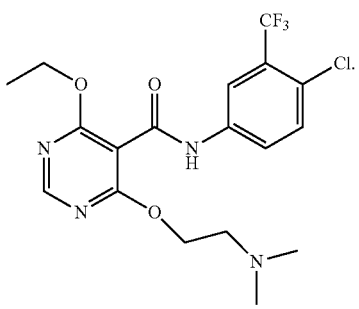

9

In one embodiment, the invention encompasses HAT Activator compounds of Formula (III), wherein:

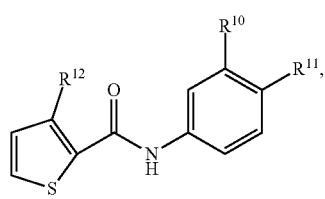

(III)

wherein
$R^{10}$ is $CF_3$;
$R^{11}$ is CN; and
$R^{12}$ is O-ethyl, or a pharmaceutically acceptable salt or hydrate thereof.

In one embodiment, the invention encompasses HAT Activator compounds of Formula (IV), wherein:

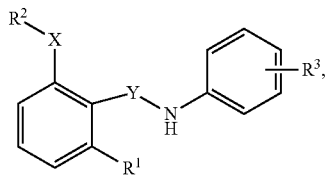

Formula IV wherein,
X is S, $S(O)_2$, NH, O, or C;
Y is —C(O), $S(O)_2$, or NH—C(O);
$R^1$ is H, methyl, ethyl, n-propyl, isopropyl, n-butyl, t-butyl, $C_8H_{18}$, $C_{15}H_{26}$, $C_{15}H_{28}$, $C_{15}H_{30}$, $C_{15}H_{32}$, $SR^4$, or $OR^4$;
$R^2$ is H, methyl, ethyl, n-propyl, isopropyl, n-butyl, t-butyl, or ($C_1$-$C_6$ alkyl)-$CO_2R^6$;
$R^3$ is H, methyl, ethyl, n-propyl, isopropyl, n-butyl, t-butyl, $CF_3$, $CCl_3$, $Cl_3$, F, Cl, I, $NO_2$, or CN;
$R^4$ is ($C_1$-$C_6$ alkyl)-$N(R^5)_2$ or $C_1$-$C_6$ alkyl;
$R^5$ is independently hydrogen, $C_1$-$C_6$ alkyl, or $C_3$-$C_8$ cycloalkyl; and $R^6$ is hydrogen, $C_1$-$C_6$ alkyl, or $C_3$-$C_8$ cycloalkyl, or a pharmaceutically acceptable salt or hydrate thereof.

In one embodiment, X is O, while Y is N—C=O. In another embodiment, X is S, while Y is N—C=O.

In specific embodiments, the compound is YF2:

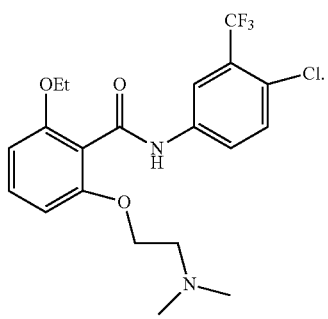 [SMILES: CCOc1cccc(OCCN(C)C)c1C(=O)Nc1ccc(Cl)c(C(F)(F)F)c1]

5

Figure 29:
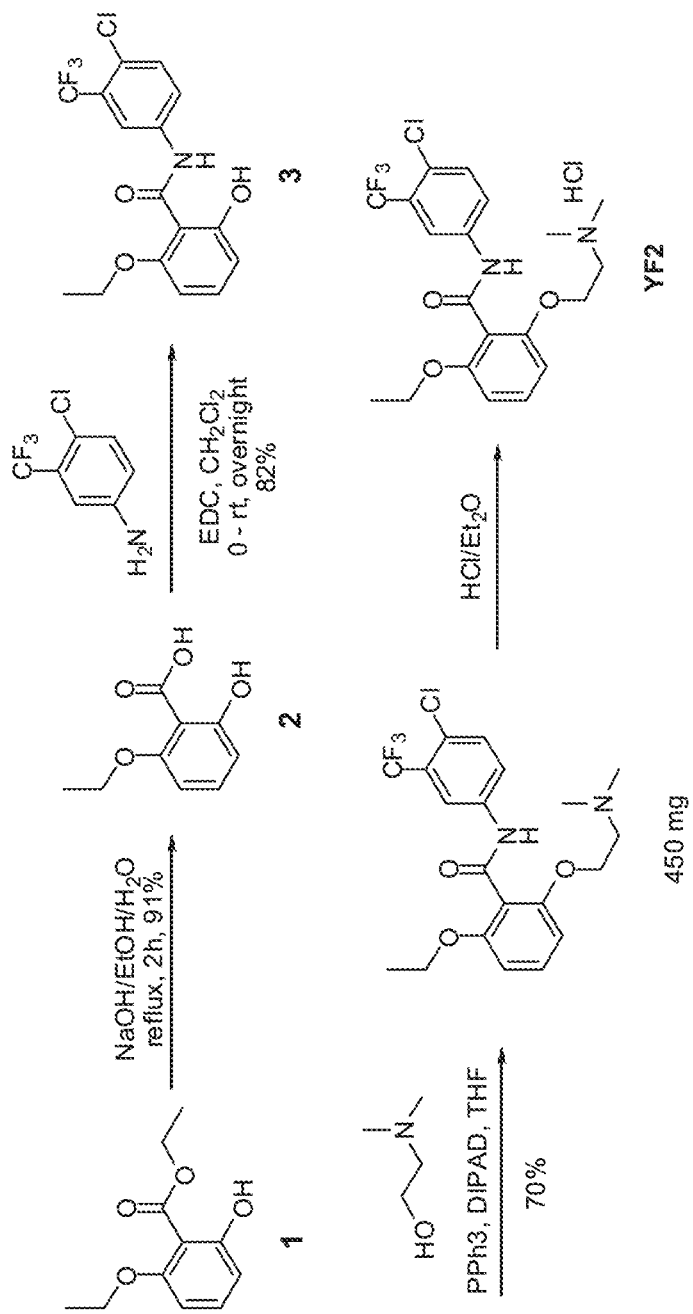
FIG. 29 is a synthetic scheme for the HAT Activator compound, YF2.
Figure 30:
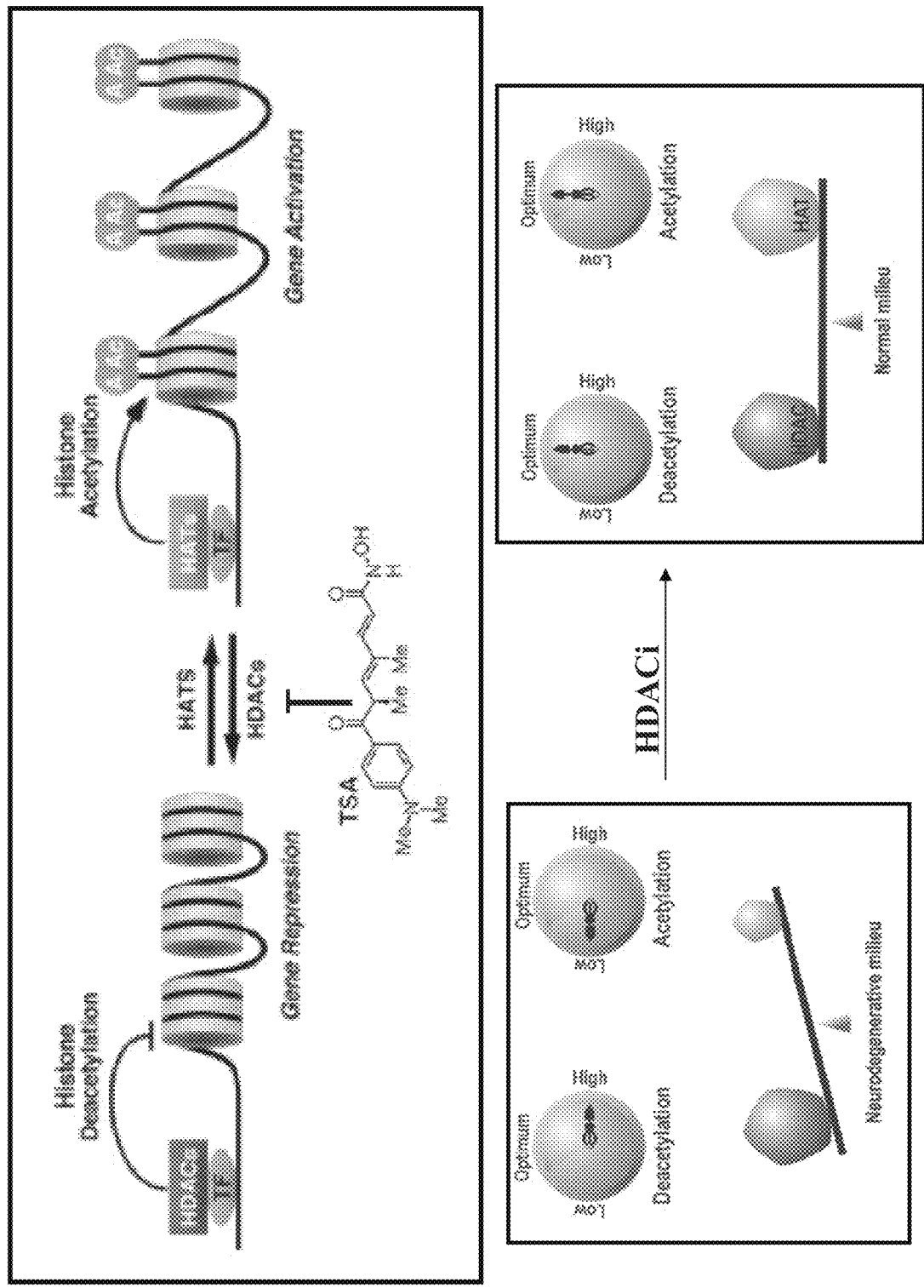
FIG. 30 is a schematic showing the role of a HDAC inhibitor (HDACi; e.g., TSA) in histone acetylation and deacetylation.
Figure 34:
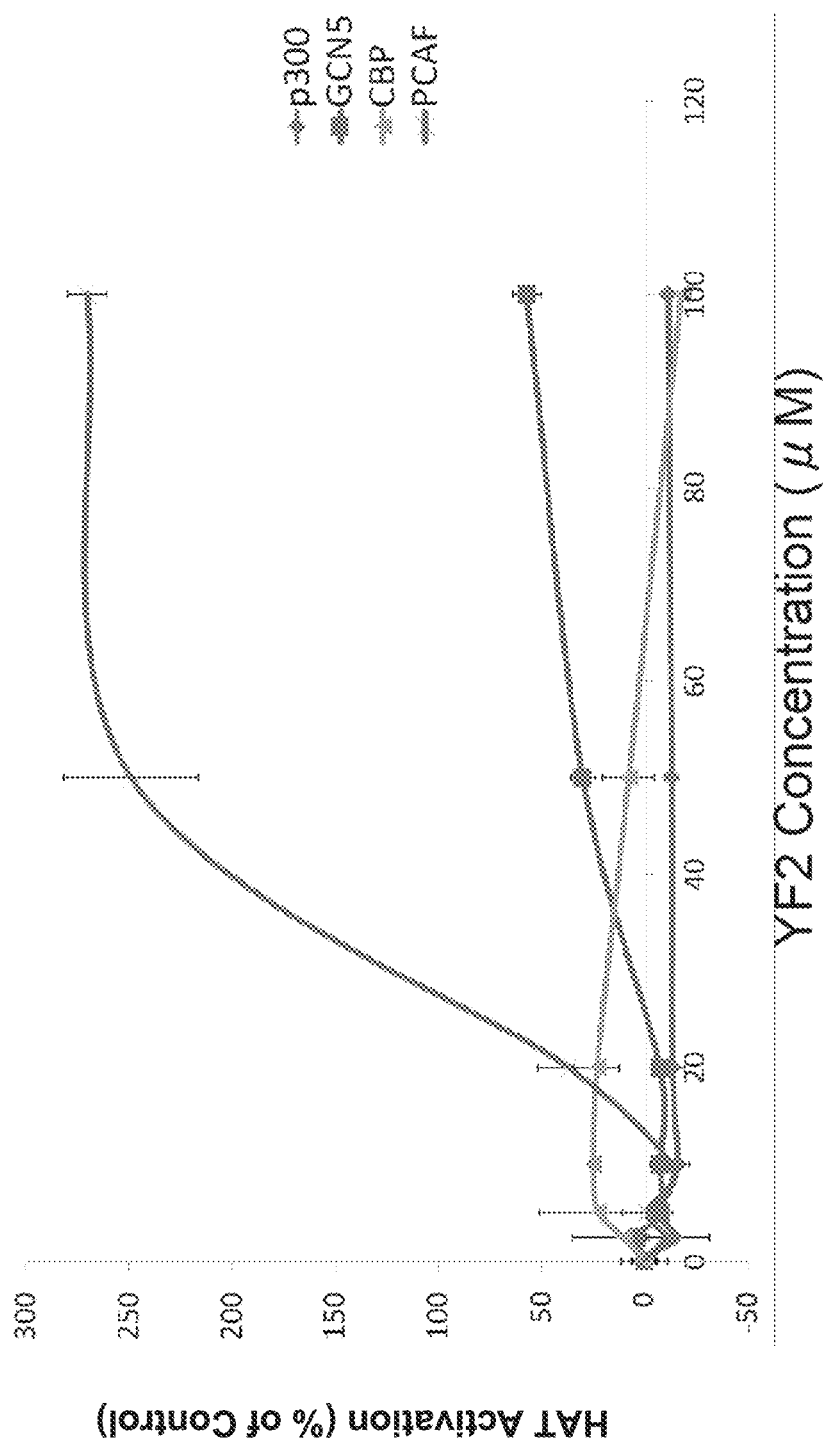
FIG. 34 is a graph showing YF2 specificity. YF2 activates CREB Binding Protein (CBP) and the histone acetyltransferase, GCN5.
Figure 35:
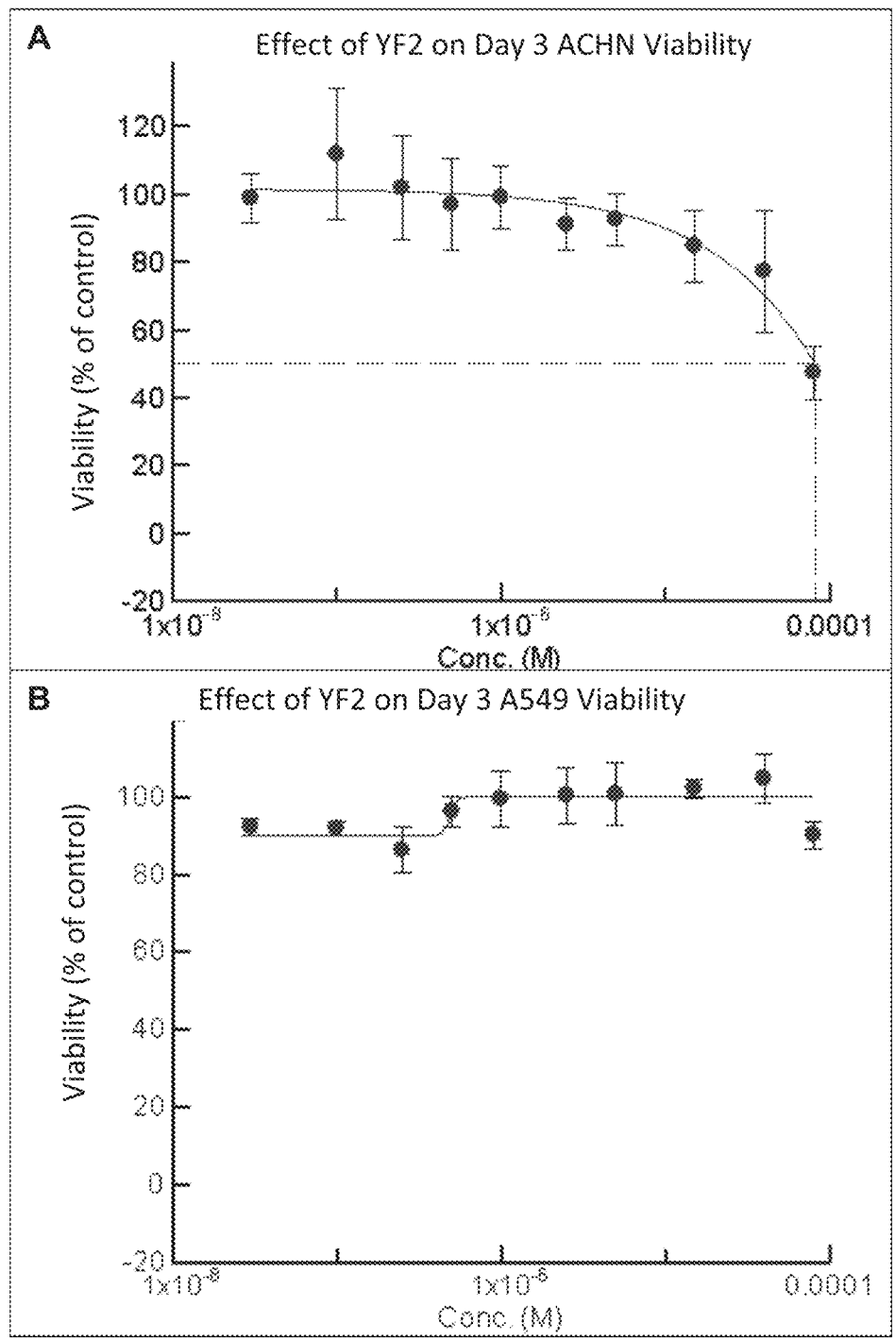
FIG. 35 are graphs showing the effect of YF2 on cancer cell viability in ACHN cells (FIG. 35A; human renal carcinoma cells) and A549 cells (FIG. 35B; human lung carcinoma cells). Values represent an average of 3 wells. Error bars represent standard deviations.
Figure 36:
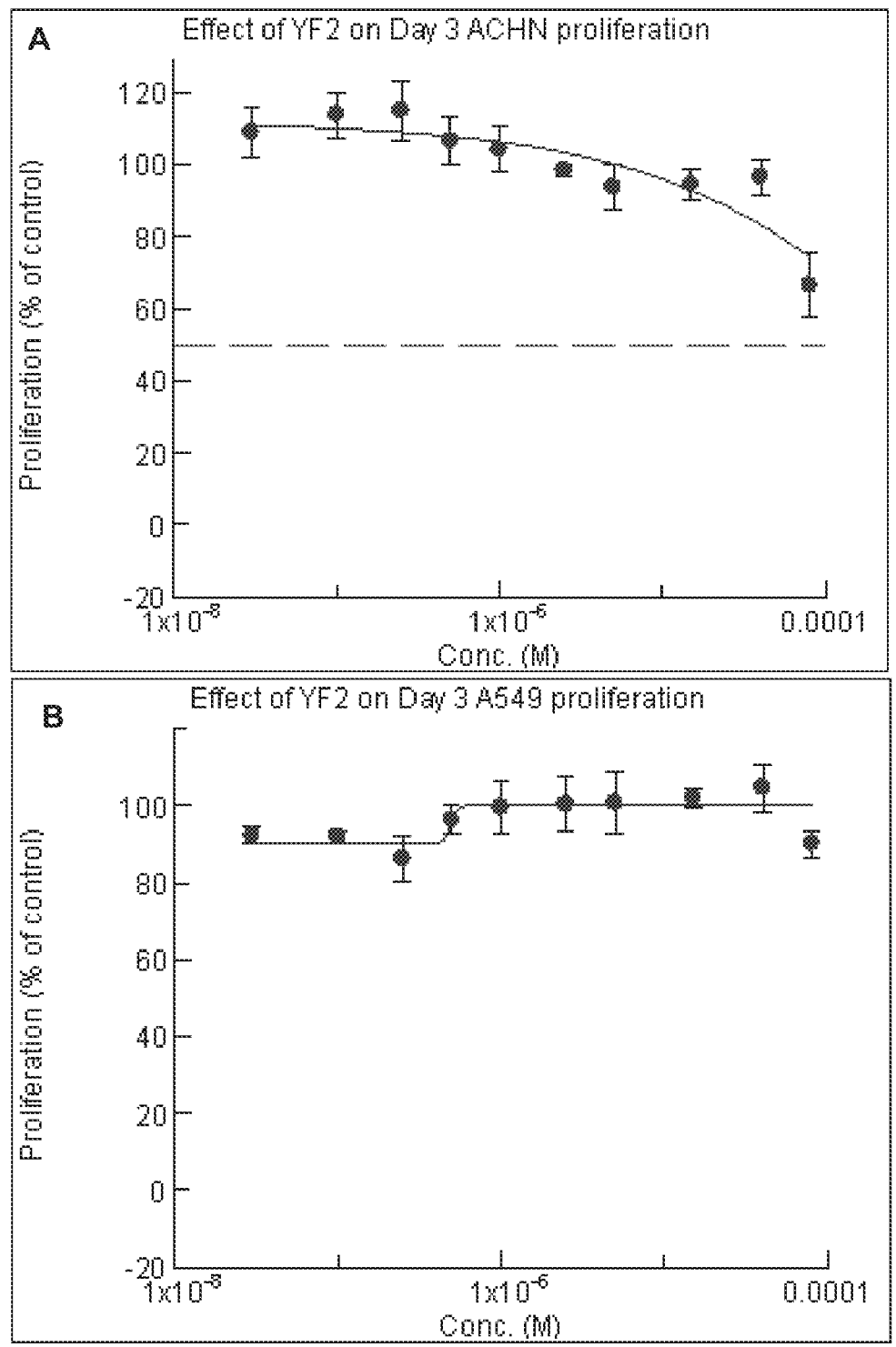
FIG. 36 are graphs showing the effect of YF2 on cancer cell proliferation in ACHN cells (FIG. 36A; human renal carcinoma cells) and A549 cells (FIG. 36B; human lung carcinoma cells).

In one embodiment, the HAT Activator compound, YF2, can be synthesized according to the scheme depicted in FIG. 29. Other analogs of HAT Activator compounds having Formula I can be similarly synthesized.

Figure 37:
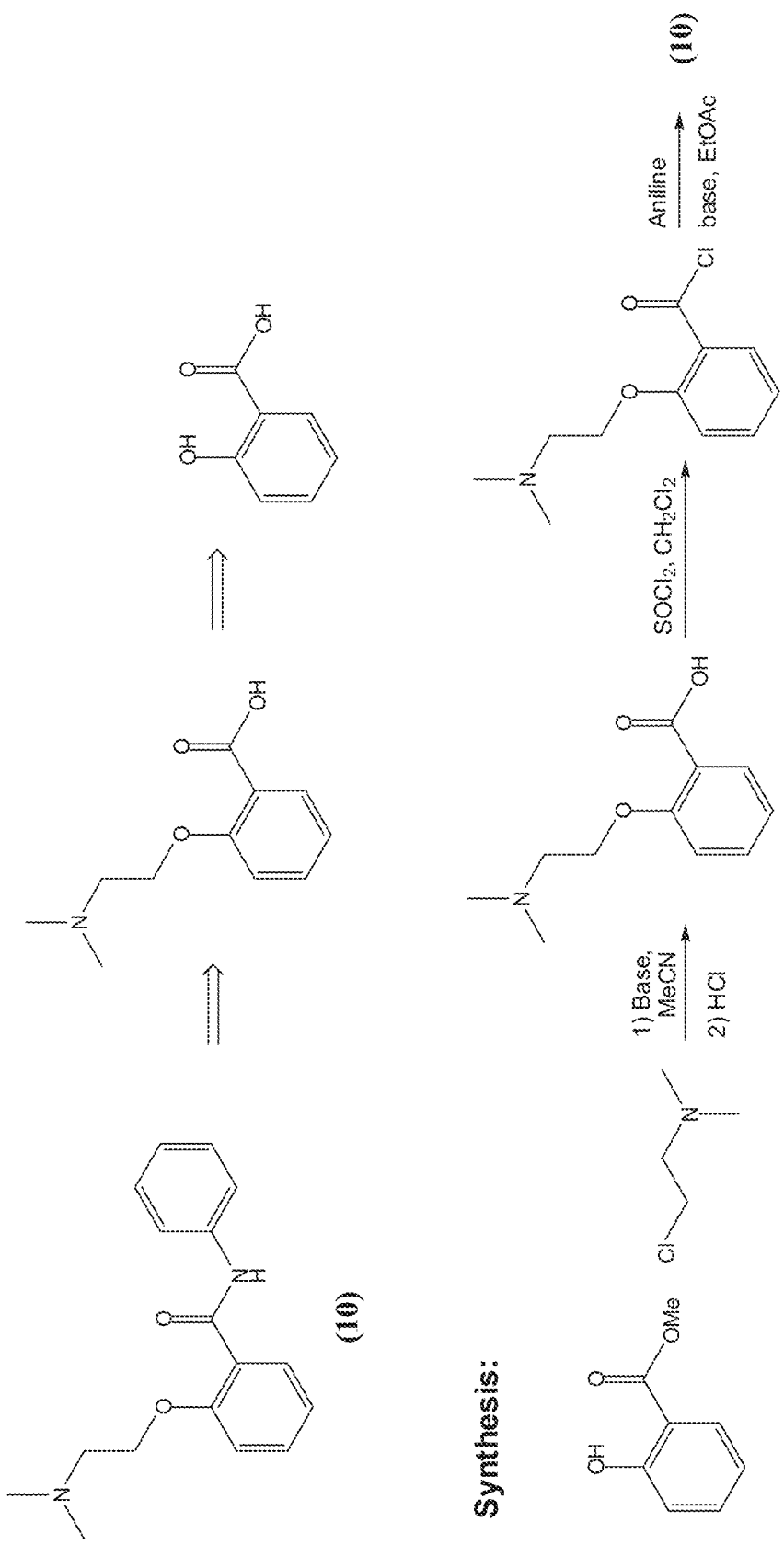
FIG. 37 is a synthetic scheme for the HAT Activator compound, 10.

In one embodiment, the HAT Activator compound, 10, can be synthesized according to the scheme depicted in FIG. 37.

Figure 39:
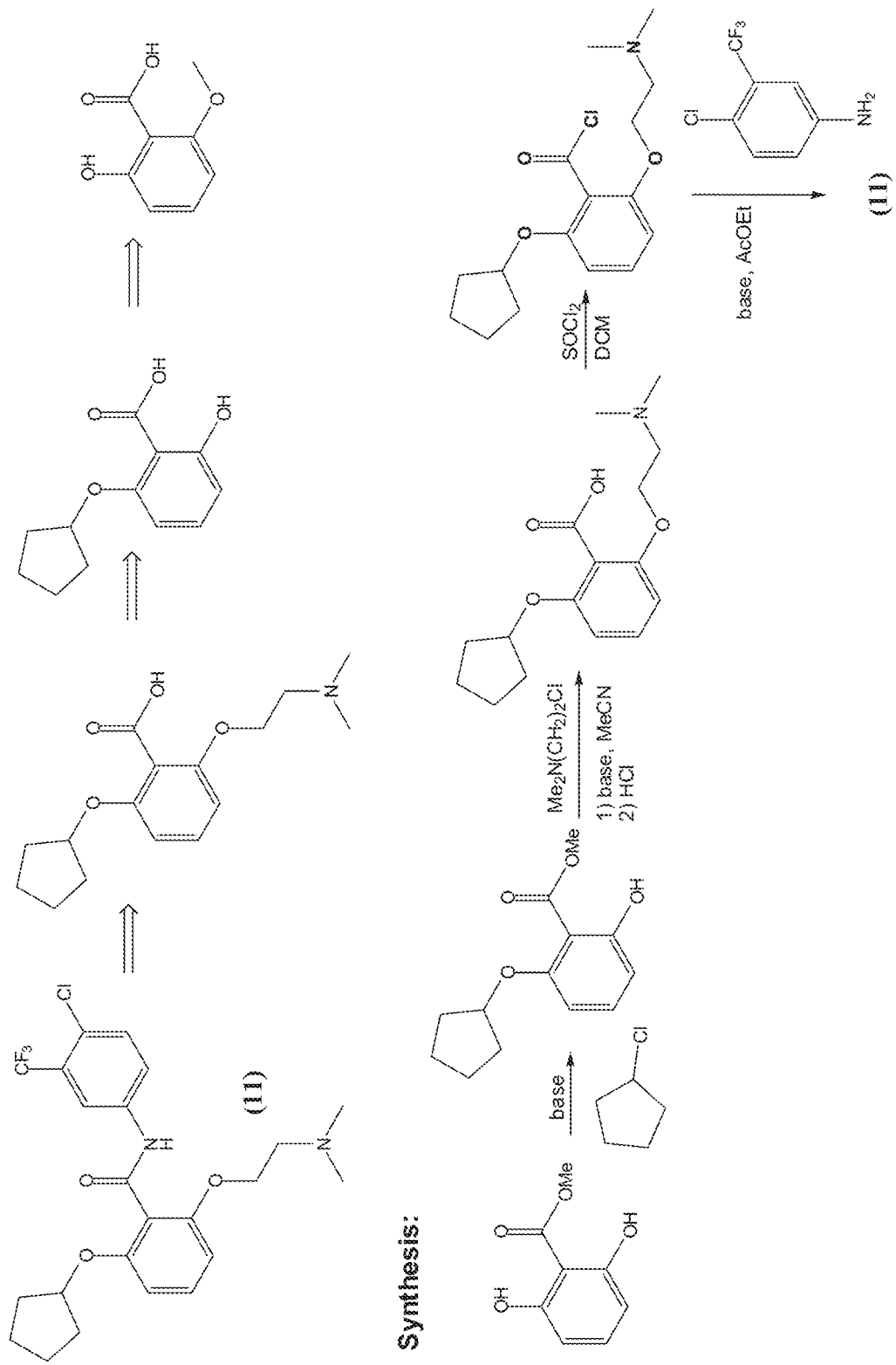
FIG. 39 is a synthetic scheme for the HAT Activator compound, 11.

In one embodiment, the HAT Activator compound, 11, can be synthesized according to the scheme depicted in FIG. 39.

Figure 40:
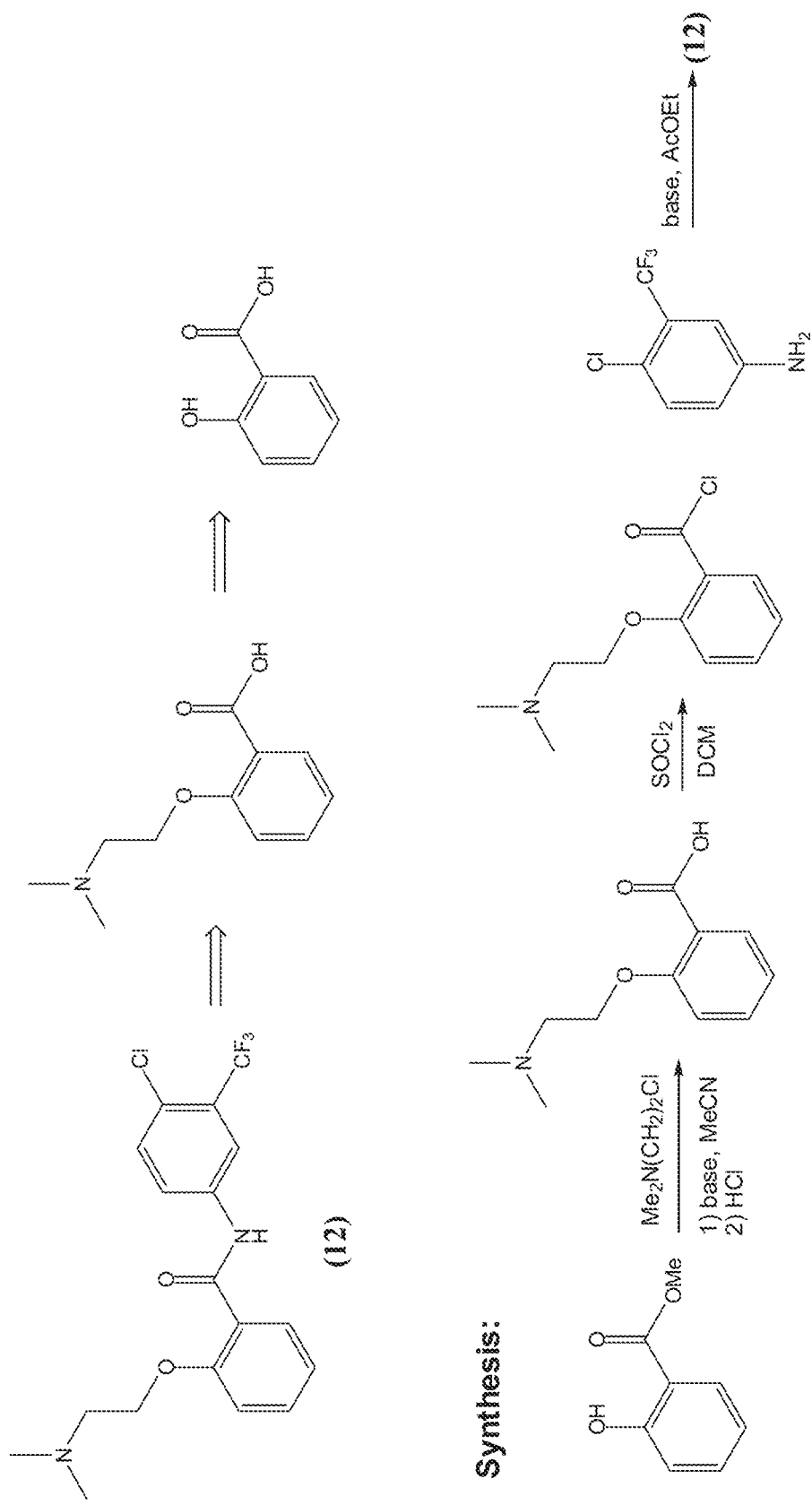
FIG. 40 is a synthetic scheme for the HAT Activator compound, 12.

In one embodiment, the HAT Activator compound, 12, can be synthesized according to the scheme depicted in FIG. 40.

Figure 42:
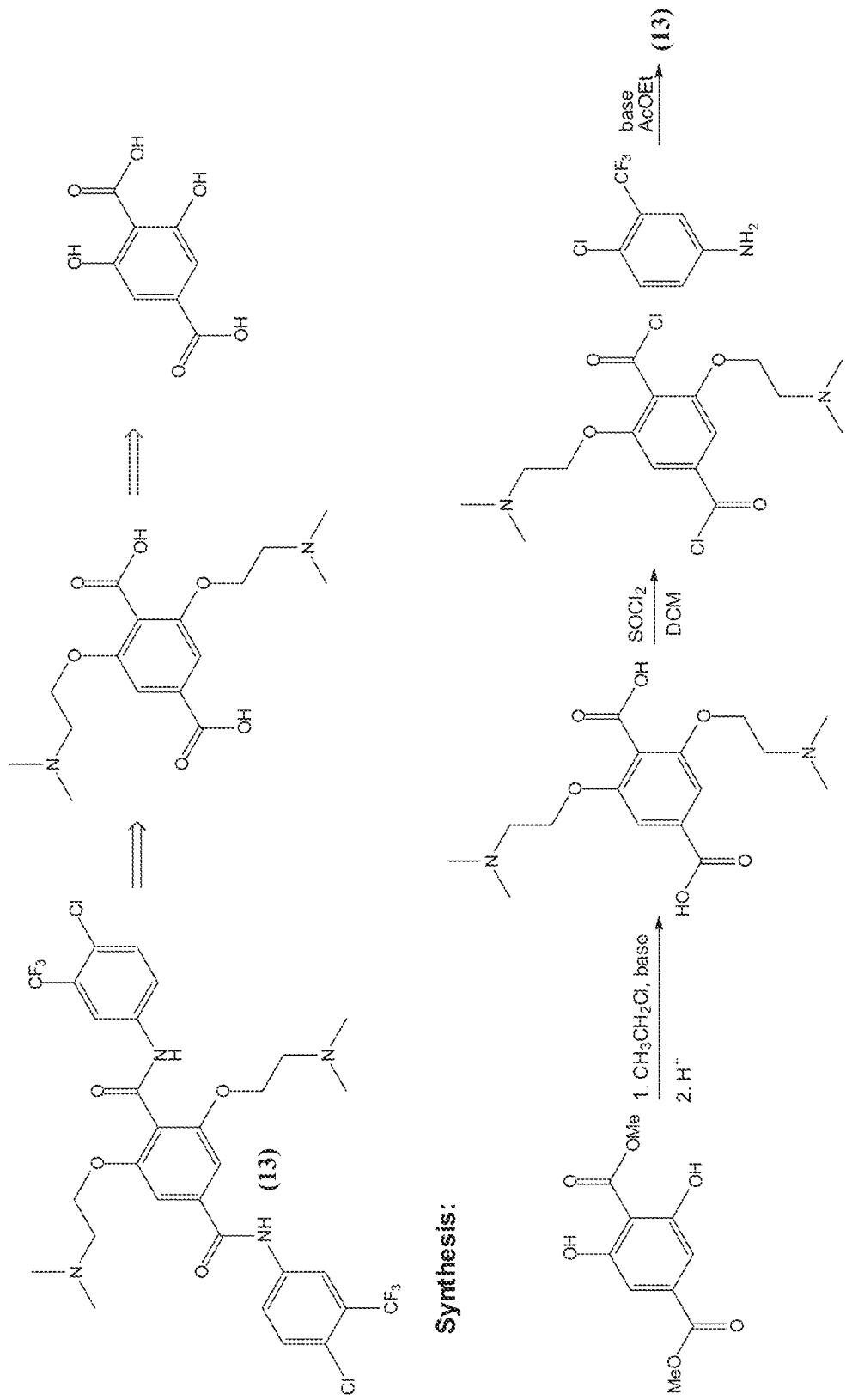
FIG. 42 is a synthetic scheme for the HAT Activator compound, 13.

In one embodiment, the HAT Activator compound, 13, can be synthesized according to the scheme depicted in FIG. 42.

Figure 41:
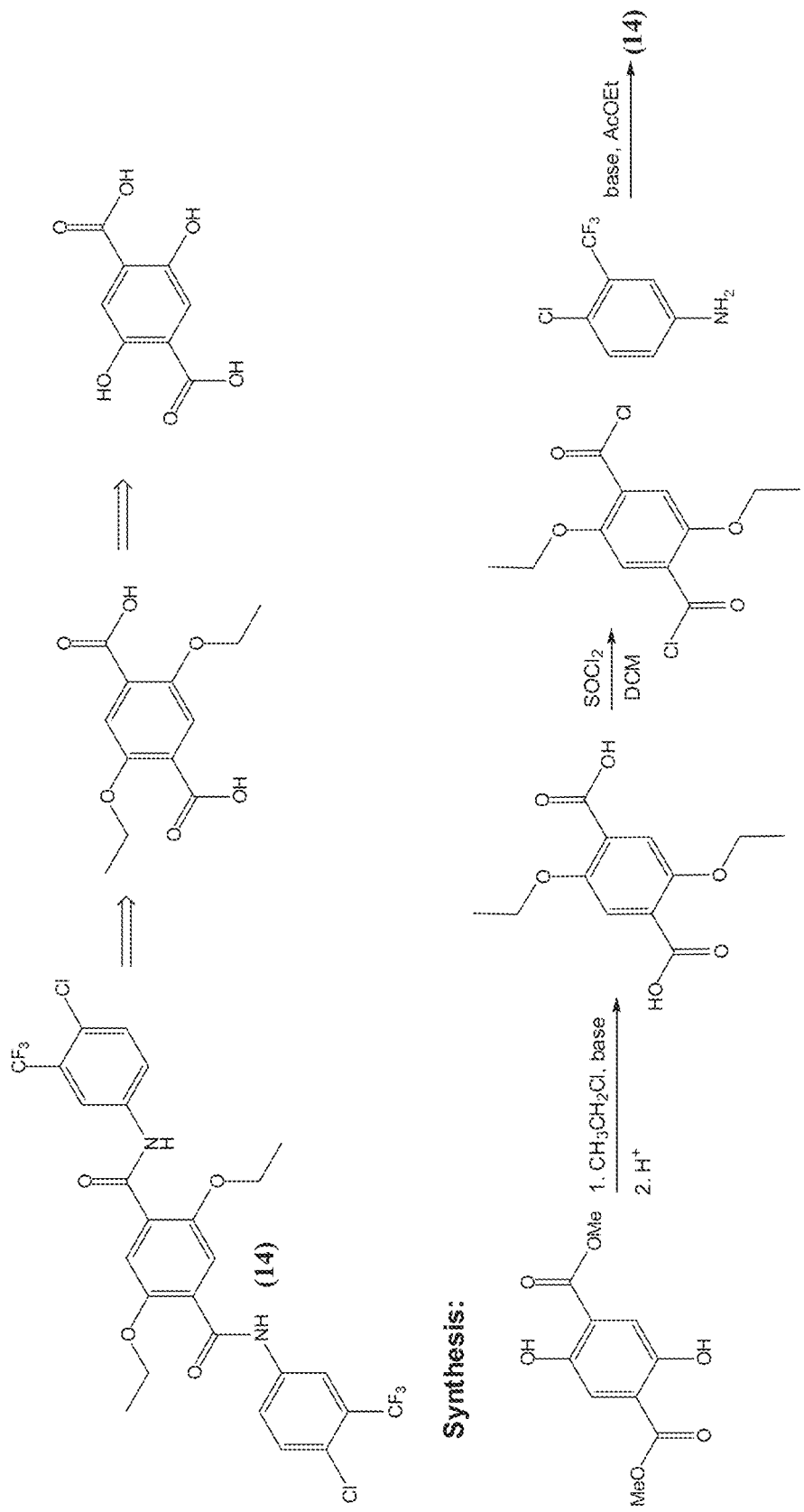
FIG. 41 is a synthetic scheme for the HAT Activator compound, 14.

In one embodiment, the HAT Activator compound, 14, can be synthesized according to the scheme depicted in FIG. 41.

Figure 43:
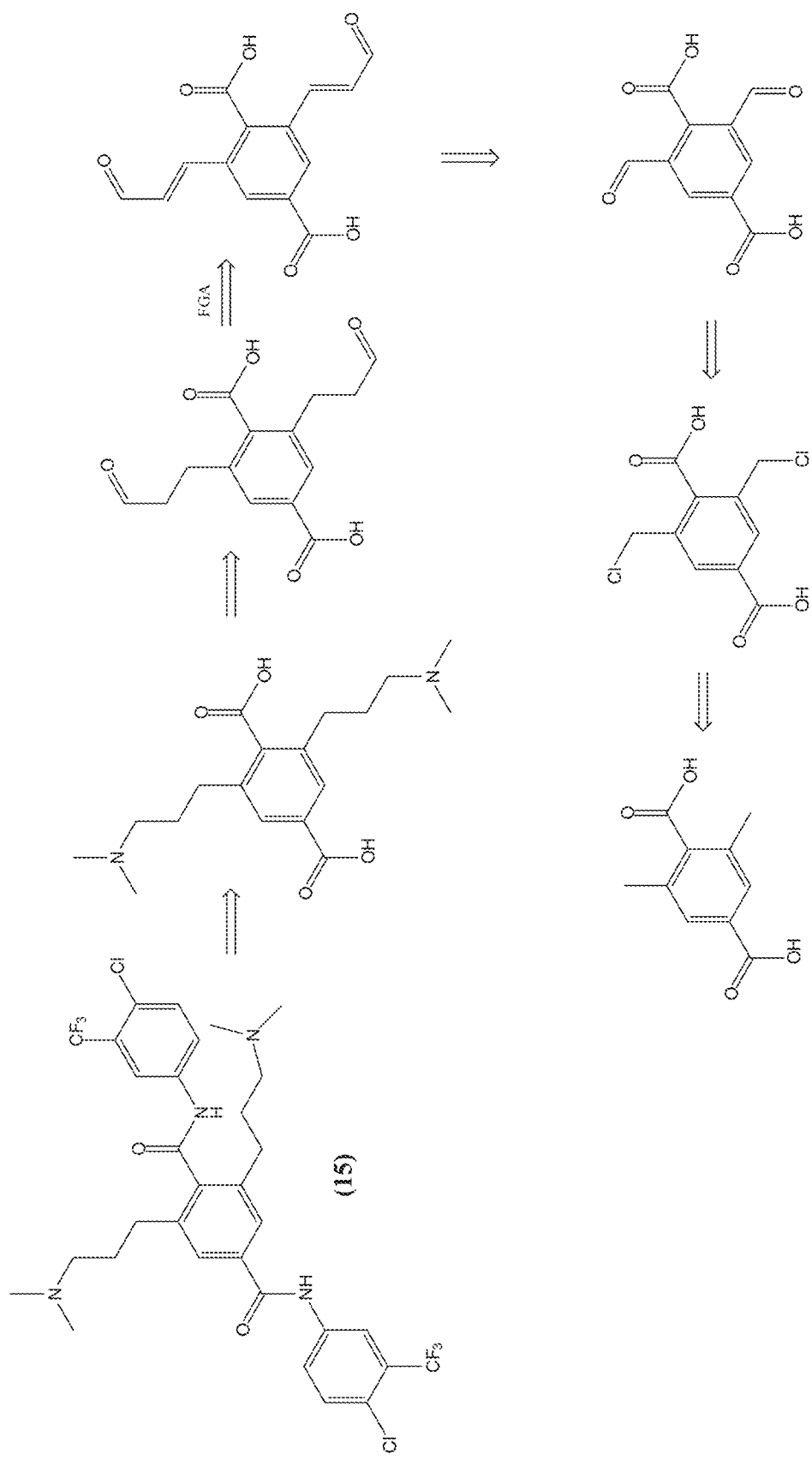
FIG. 43 is a synthetic scheme for the HAT Activator compound, 15. The synthetic scheme is continued to a second page at the hatched line.

In one embodiment, the HAT Activator compound, 15, can be synthesized according to the scheme depicted in FIG. 43.

Figure 44:
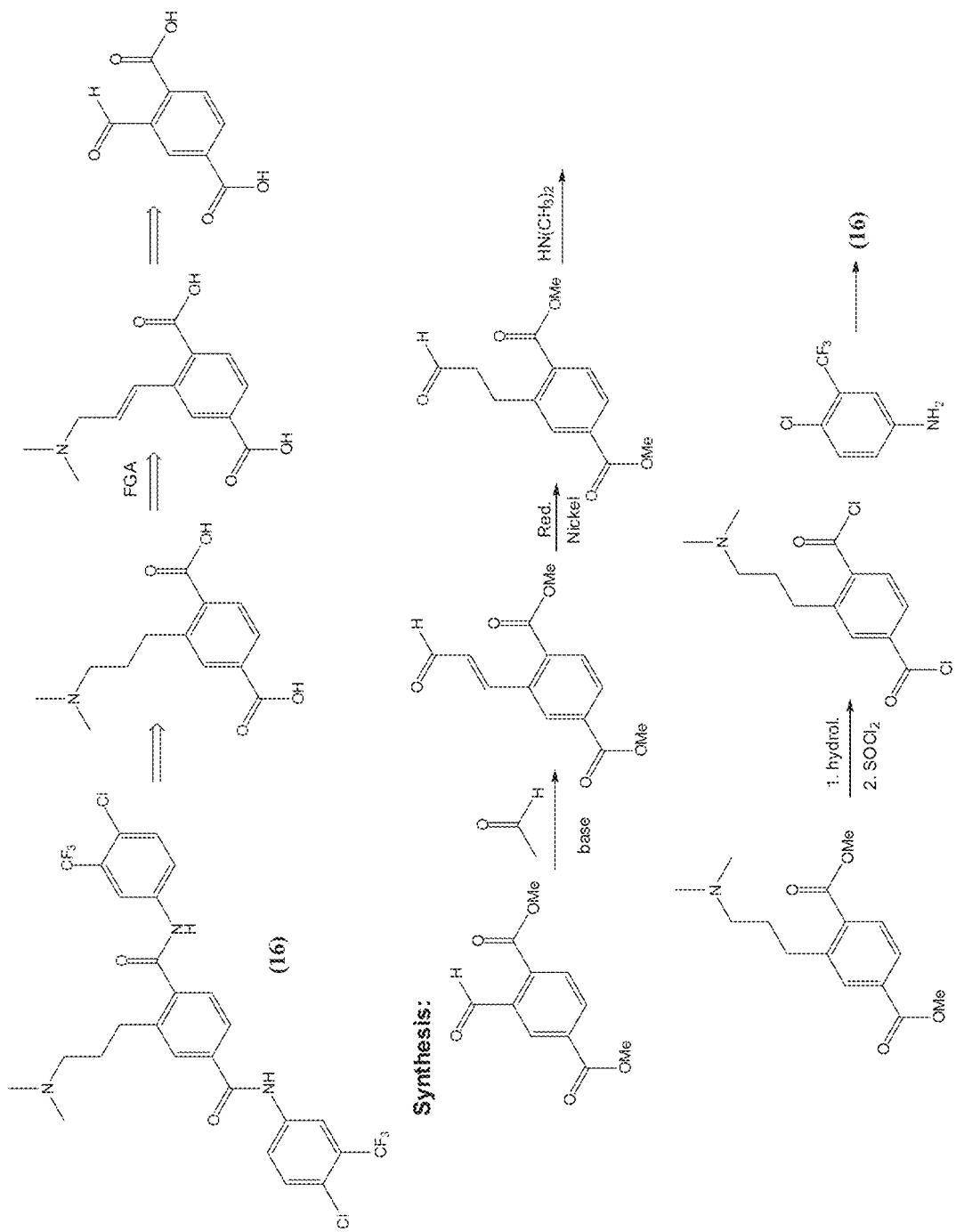
FIG. 44 is a synthetic scheme for the HAT Activator compound, 16.

In one embodiment, the HAT Activator compound, 16, can be synthesized according to the scheme depicted in FIG. 44.

Figure 45:
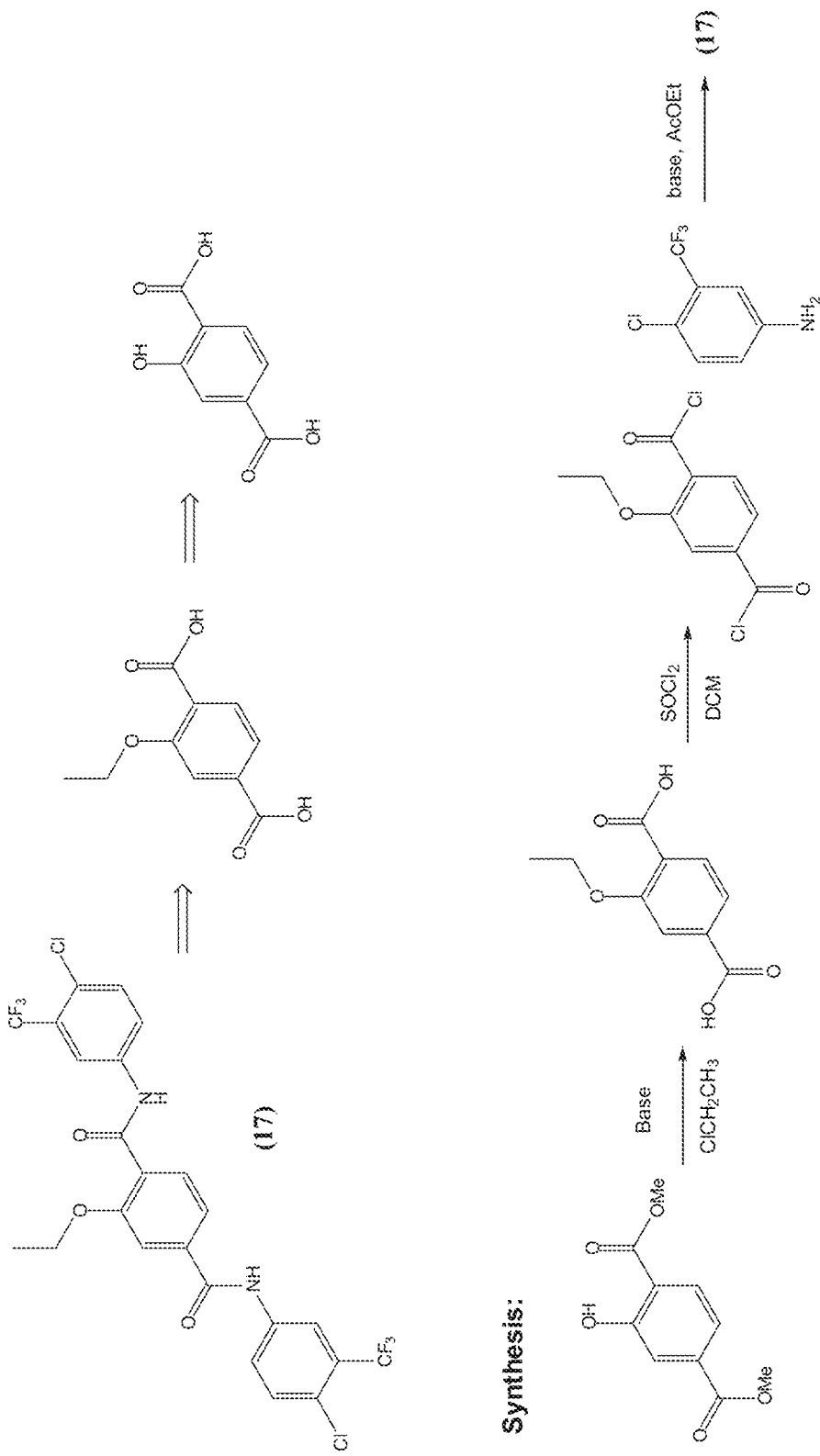
FIG. 45 is a synthetic scheme for the HAT Activator compound, 17.

In one embodiment, the HAT Activator compound, 17, can be synthesized according to the scheme depicted in FIG. 45.

Figure 46:
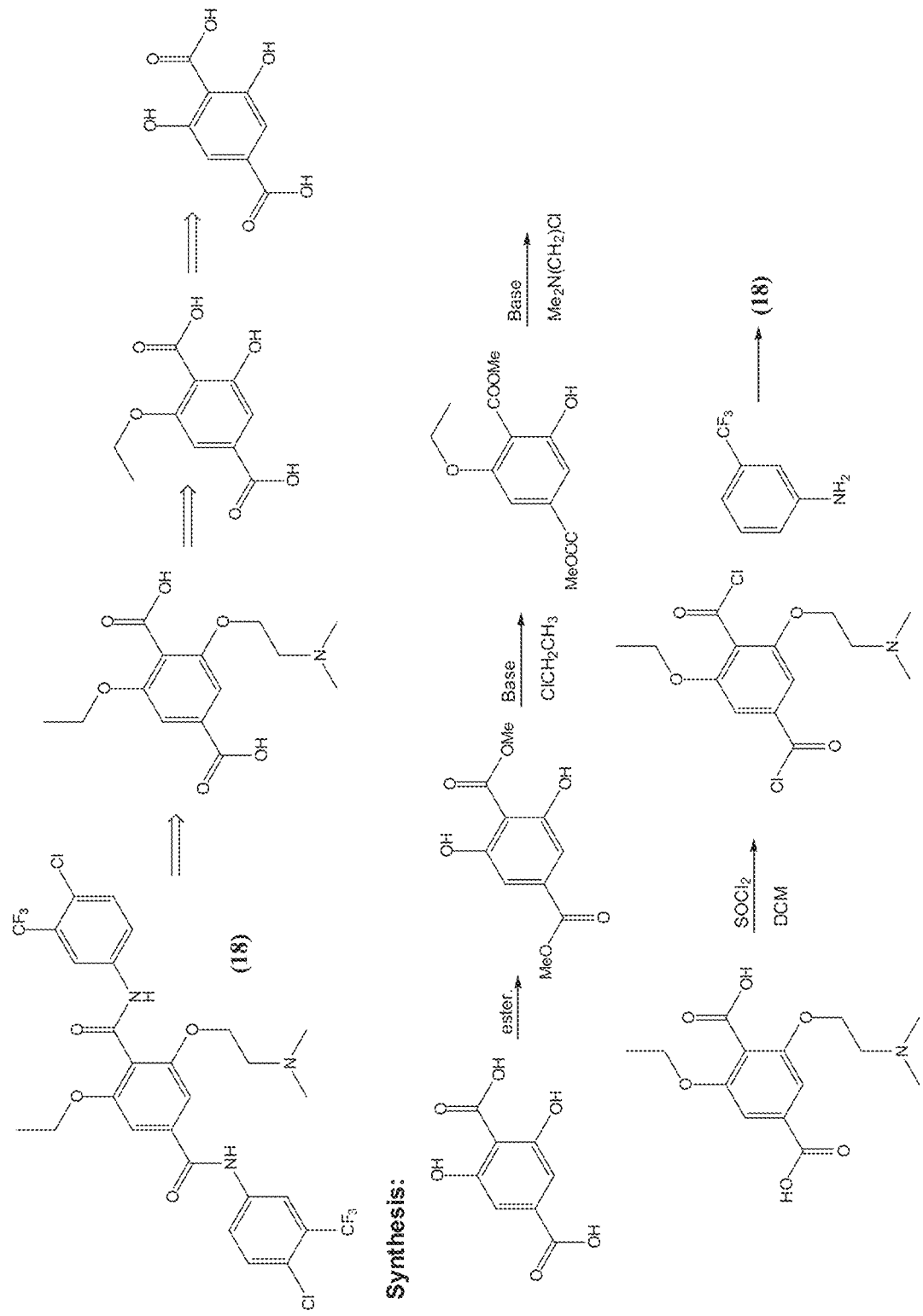
FIG. 46 is a synthetic scheme for the HAT Activator compound, 18.
Figure 50:
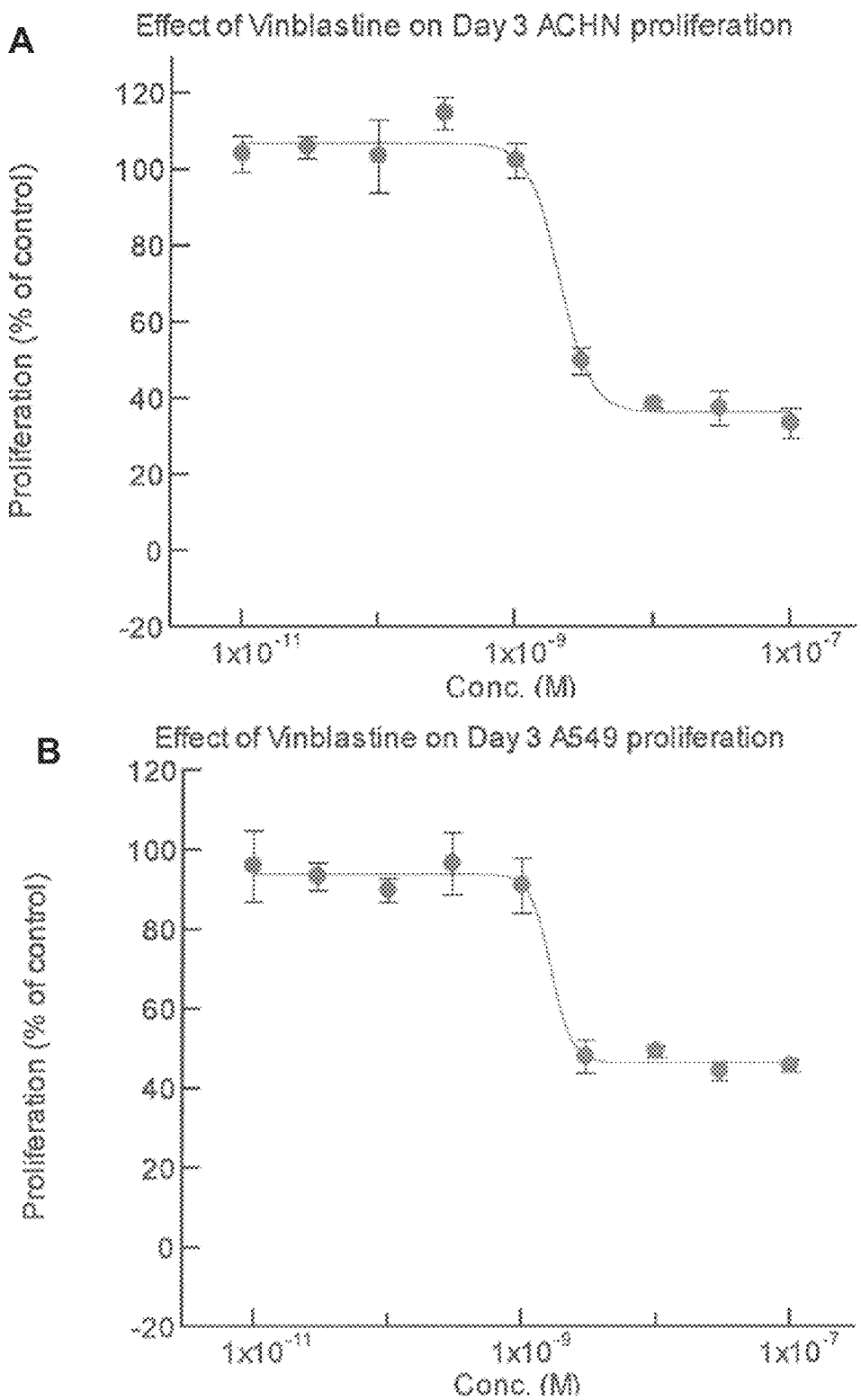
FIG. 50 are graphs showing the effect of Vinblastine on cancer cell proliferation in ACHN cells (FIG. 50A; human renal carcinoma cells) and A549 cells (FIG. 50B; human lung carcinoma cells). Values represent an average of 3 wells. Error bars represent standard deviations.

In one embodiment, the HAT Activator compound, 18, can be synthesized according to the scheme depicted in FIG. 46.

Figure 51:
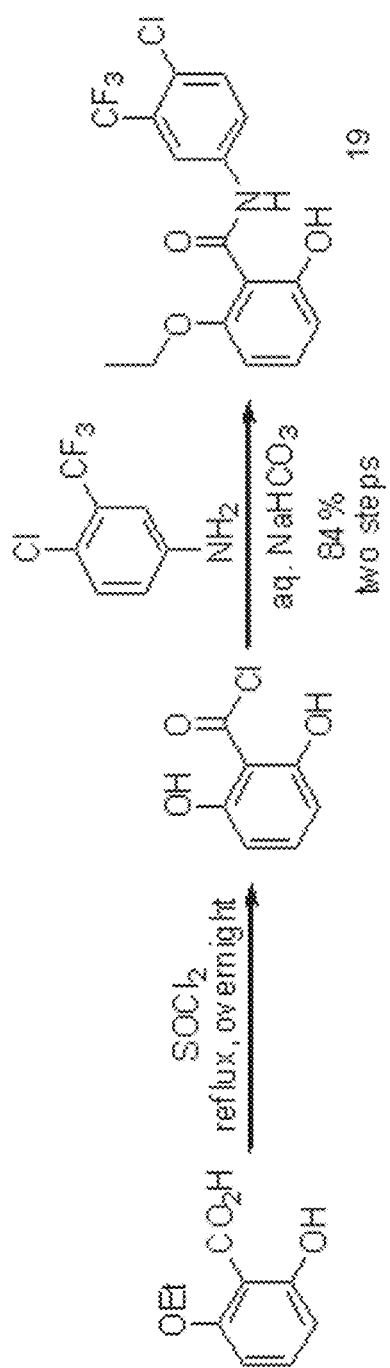
FIG. 51 is a synthetic scheme for the HAT Activator compound, 19.

In one embodiment, the HAT Activator compound, 19, can be synthesized according to the scheme depicted in FIG. 51.

Figure 38:
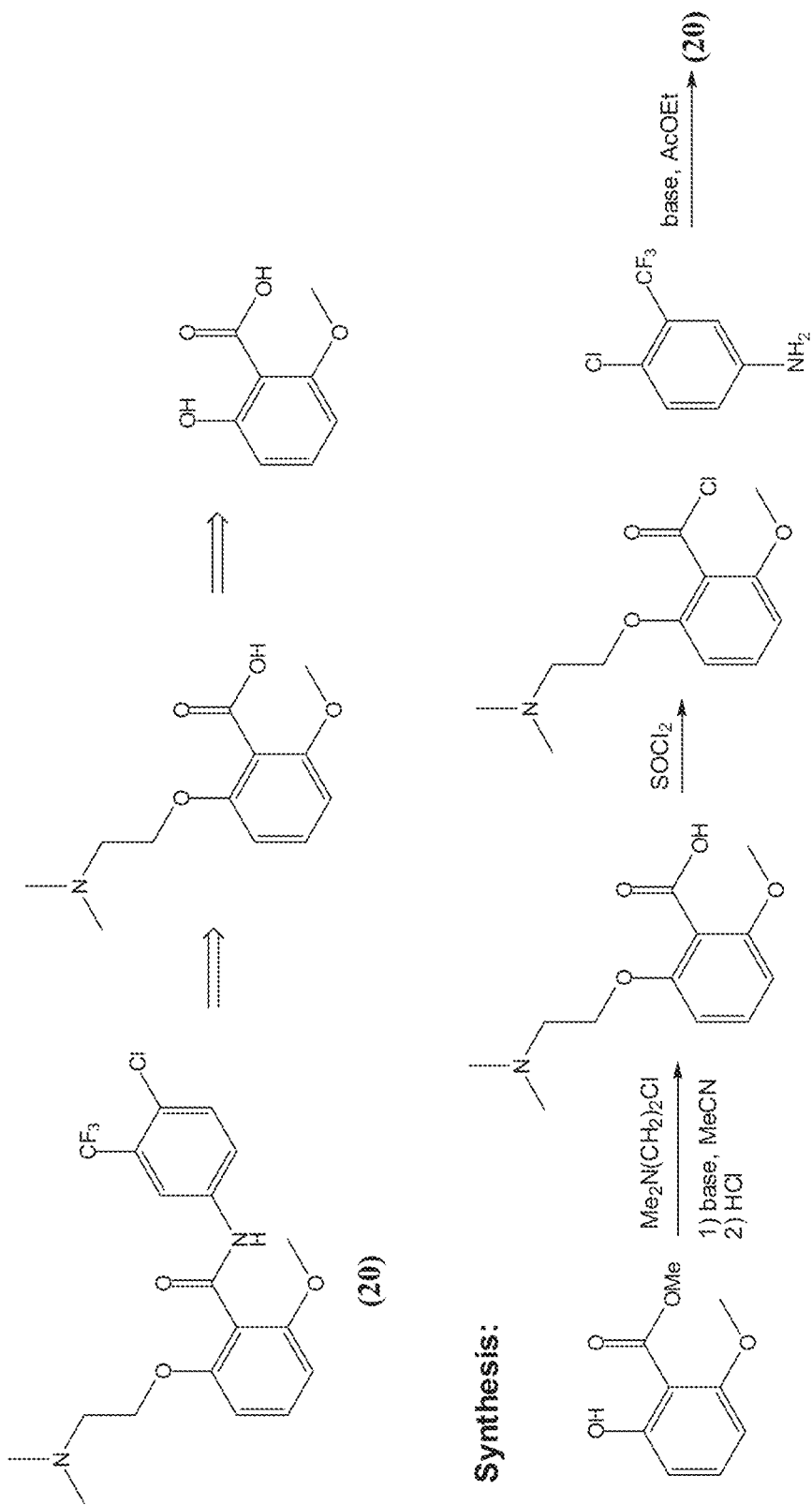
FIG. 38 is a synthetic scheme for the HAT Activator compound, 20.

In one embodiment, the HAT Activator compound, 20, can be synthesized according to the scheme depicted in FIG. 38.

In one embodiment, the invention encompasses HAT Activator compounds of Formula (V),

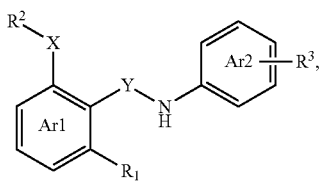

Formula V wherein,
X is S, $S(O)_2$, NH, O, or C;
Y is —C(O), $S(O)_2$, or NH—C(O);

Ar1 is a 5-membered aromatic ring or a 6-membered aromatic ring containing 1-2 Nitrogens;

Ar2 is a 5-membered aromatic ring, a 6-membered aromatic ring or a 6-membered aromatic ring containing 1-2 Nitrogens;

$R^1$ is H, methyl, ethyl, n-propyl, isopropyl, n-butyl, t-butyl, $C_8H_{18}$, $C_{15}H_{26}$, $C_{15}H_{28}$, $C_{15}H_{30}$, $C_{15}H_{32}$, $SR^4$, or $OR^4$;

$R^2$ is H, methyl, ethyl, n-propyl, isopropyl, n-butyl, t-butyl, or $(C_1$-$C_6$ alkyl)-$CO_2R^6$;

$R^3$ is H, methyl, ethyl, n-propyl, isopropyl, n-butyl, t-butyl, $CF_3$, $CCl_3$, $Cl_3$, F, Cl, I, $NO_2$, or CN;

$R^4$ is $(C_1$-$C_6$ alkyl)-$N(R^5)_2$— or $C_1$-$C_6$ alkyl;

$R^5$ is independently hydrogen, $C_1$-$C_6$ alkyl, or $C_3$-$C_8$ cycloalkyl; and $R^6$ is hydrogen, $C_1$-$C_6$ alkyl, or $C_3$-$C_8$ cycloalkyl, or a pharmaceutically acceptable salt or hydrate thereof.

In one embodiment, X is O, while Y is N—C=O. In another embodiment, X is S, while Y is N—C=O.

In particular embodiments, the compound of Formula (V) is:

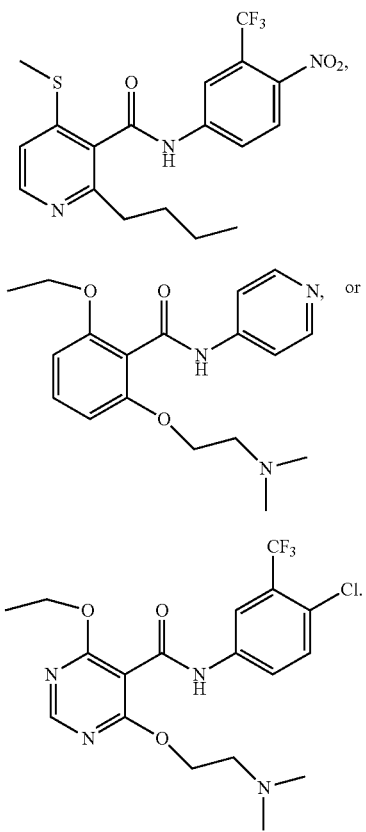

The compounds of the invention can be generally synthesized according to the scheme based on the diagram depicted in FIG. 29.

Pharmaceutically acceptable salts are known in the art, and may be selected from those listed in Berge, et al. ["Pharmaceutical Salts," J. Pharm. Sci., 66(1):1-19 (January 1977); herein incorporated by reference in its entirety]. In one embodiment, a pharmaceutically acceptable salt of a compound of Formula (I) is an acid addition salt, for example a hydrochloride, sulfate, or phosphate salt. In another embodiment, a pharmaceutically acceptable salt of a compound of Formula (I) is a base addition salt, for example a sodium, potassium, calcium, or ammonium salt. In another embodiment, the base addition salt is a tetrafluoroboro salt. In one embodiment, a pharmaceutically acceptable salt of a compound of Formula (II) is an acid addition salt, for example a hydrochloride, sulfate, or phosphate salt. In another embodiment, a pharmaceutically acceptable salt of a compound of Formula (II) is a base addition salt, for example a sodium, potassium, calcium, or ammonium salt. In another embodiment, the base addition salt is a tetrafluoroboro salt. In one embodiment, a pharmaceutically acceptable salt of a compound of Formula (III) is an acid addition salt, for example a hydrochloride, sulfate, or phosphate salt. In another embodiment, a pharmaceutically acceptable salt of a compound of Formula (III) is a base addition salt, for example a sodium, potassium, calcium, or ammonium salt. In another embodiment, the base addition salt is a tetrafluoroboro salt. In one embodiment, a pharmaceutically acceptable salt of a compound of Formula (IV) is an acid addition salt, for example a hydrochloride, sulfate, or phosphate salt. In another embodiment, a pharmaceutically acceptable salt of a compound of Formula (IV) is a base addition salt, for example a sodium, potassium, calcium, or ammonium salt. In another embodiment, the base addition salt is a tetrafluoroboro salt. In one embodiment, a pharmaceutically acceptable salt of a compound of Formula (V) is an acid addition salt, for example a hydrochloride, sulfate, or phosphate salt. In another embodiment, a pharmaceutically acceptable salt of a compound of Formula (V) is a base addition salt, for example a sodium, potassium, calcium, or ammonium salt. In another embodiment, the base addition salt is a tetrafluoroboro salt.

The invention provides methods for reducing inclusion bodies (e.g., amyloid beta (Aβ) protein deposits, native and phosphorylated Tau proteins, native and phosphorylated alpha-synuclein, lipofuscin, cleaved TARDBP (TDB-43), or a combination thereof) in a subject afflicted with a neurodegenerative disease (e.g., a AD, Huntington's Disease, or Parkinson's Disease) by administering any one of the HAT Activator compounds having Formula (I), Formula (II), Formula (III), Formula (IV), or Formula (V). The invention also provides methods for treating a neurodegenerative disease in a subject by administering any one of the HAT Activator compounds having Formula (I), Formula (II), Formula (III), Formula (IV), or Formula (V). The invention further provides methods for treating cancer in a subject by administering any one of the HAT Activator compounds having Formula (I), Formula (II), Formula (III), Formula (IV), or Formula (V). In some embodiments, the compound administered to a subject is any one of compounds 1-9. In specific embodiments, the HAT Activator compound is YF2, depicted in FIG. 3. In some embodiments, the compound administered is a HAT Activator compound of Formula (VI):

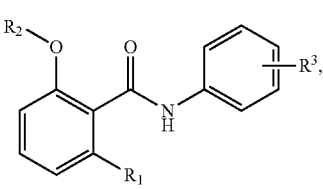

Formula VI wherein:

$R^1$ is H, methyl, ethyl, n-propyl, isopropyl, n-butyl, t-butyl, $C_8H_{18}$, $C_{15}H_{26}$, $C_{15}H_{28}$, $C_{15}H_{30}$, $C_{15}H_{32}$, S, O, $SR^4$, or $OR^4$;

$R^2$ is H, methyl, ethyl, n-propyl, isopropyl, n-butyl, t-butyl, or —C(O)$R^6$;

$R^3$ is H, methyl, ethyl, n-propyl, isopropyl, n-butyl, t-butyl, $CF_3$, $CCl_3$, $Cl_3$, F, Cl, I, $NO_2$, or CN;

$R^4$ is —$NR^5$;

$R^5$ is hydrogen, $C_1$-$C_6$ alkyl, or $C_3$-$C_8$ cycloalkyl;

$R^6$ is hydrogen, $C_1$-$C_6$ alkyl, or $C_3$-$C_8$ cycloalkyl, C(O)$R^7$; and $R^7$ is hydrogen, $C_1$-$C_6$ alkyl, or $C_3$-$C_8$ cycloalkyl, or a pharmaceutically acceptable salt or hydrate thereof.

In one embodiment, a pharmaceutically acceptable salt of a compound of Formula (VI) is an acid addition salt, for example a hydrochloride, sulfate, or phosphate salt. In another embodiment, a pharmaceutically acceptable salt of a compound of Formula (VI) is a base addition salt, for example a sodium, potassium, calcium, or ammonium salt. In another embodiment, the base addition salt is a tetrafluoroboro salt.

In some embodiments, HAT activator compounds having Formula (I), Formula (II), Formula (III), Formula (IV), Formula (V), or Formula (VI) are first screened for their ability to satisfy one or more of the following characteristics: an $EC_{50}$ no greater than about 100 nM; a histone acetylation activity in vitro; the ability to penetrate the BBB; or a combination thereof.

In one embodiment, the method comprises administering to the subject an effective amount of a composition comprising a HAT Activator compound. In another embodiment, the subject exhibits abnormally elevated amyloid beta plaques, or elevated Tau protein levels, or accumulations of alpha-synuclein, or accumulations of lipofuscin, or accumulation of cleaved TARDBP (TDB-43) levels, or a combination thereof. In some embodiments, the Aβ protein deposit comprises an $Aβ_{40}$ isomer, an $Aβ_{42}$ isomer, or a combination thereof. In a further embodiment, the subject is afflicted with Alzheimer's disease, Lewy body dementia, inclusion body myositis, Huntington's Disease, Parkinson's Disease, or cerebral amyloid angiopathy. In further embodiments, the subject is afflicted with cancer.

The dosage administered can be a therapeutically effective amount of the composition sufficient to result in amelioration of symptoms of a neurogenerative disease such as, but not limited to reducing inclusion bodies (e.g., amyloid beta (Aβ) protein deposits, native and phosphorylated Tau proteins, native and phosphorylated alpha-synuclein, lipofuscin, cleaved TARDBP (TDB-43), or a combination thereof), or reducing memory loss in a subject. For example, observing at least, about a 25% reduction, at least about a 30% reduction, at least about a 40% reduction, at least about a 50% reduction, at least about a 60% reduction, at least about a 70% reduction, at least about a 80% reduction, at least about a 85% reduction, at least about a 90% reduction, at least about a 95% reduction, at least about a 97% reduction, at least about a 98% reduction, or a 100% reduction in inclusion bodies or memory loss in a subject is indicative of amelioration of symptoms of a neurogenerative disease (for example, including, but not limited to, AD, Huntington's Disease, Parkinson's Disease). This efficacy in reducing inclusion occurrence, can be, for example, a meaure of ameliorating symptoms of a neurogenerative disease.

In one embodiment, the therapeutically effective amount is at least about 0.1 mg/kg body weight, at least about 0.25 mg/kg body weight, at least about 0.5 mg/kg body weight, at least about 0.75 mg/kg body weight, at least about 1 mg/kg body weight, at least about 2 mg/kg body weight, at least about 3 mg/kg body weight, at least about 4 mg/kg body weight, at least about 5 mg/kg body weight, at least about 6 mg/kg body weight, at least about 7 mg/kg body weight, at least about 8 mg/kg body weight, at least about 9 mg/kg body weight, at least about 10 mg/kg body weight, at least about 15 mg/kg body weight, at least about 20 mg/kg body weight, at least about 25 mg/kg body weight, at least about 30 mg/kg body weight, at least about 40 mg/kg body weight, at least about 50 mg/kg body weight, at least about 75 mg/kg body weight, at least about 100 mg/kg body weight, at least about 200 mg/kg body weight, at least about 250 mg/kg body weight, at least about 300 mg/kg body weight, at least about 3500 mg/kg body weight, at least about 400 mg/kg body weight, at least about 450 mg/kg body weight, at least about 500 mg/kg body weight, at least about 550 mg/kg body weight, at least about 600 mg/kg body weight, at least about 650 mg/kg body weight, at least about 700 mg/kg body weight, at least about 750 mg/kg body weight, at least about 800 mg/kg body weight, at least about 900 mg/kg body weight, or at least about 1000 mg/kg body weight.

A HAT activator compound can be administered to the subject one time (e.g., as a single injection or deposition). Alternatively, a HAT activator compound of the invention can be administered once or twice daily to a subject in need thereof for a period of from about 2 to about 28 days, or from about 7 to about 10 days, or from about 7 to about 15 days. It can also be administered once or twice daily to a subject for a period of 1, 2, 3, 4, 5, 6, 7, 8, 9, 10, 11, 12 times per year, or a combination thereof.

The dosage administered can vary depending upon known factors such as the pharmacodynamic characteristics of the active ingredient and its mode and route of administration; time of administration of active ingredient; age, sex, health and weight of the recipient; nature and extent of symptoms; kind of concurrent treatment, frequency of treatment and the effect desired; and rate of excretion.

Toxicity and therapeutic efficacy of therapeutic compositions of the present invention can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio $LD_{50}/ED_{50}$. Therapeutic agents that exhibit large therapeutic indices are useful. Therapeutic compositions that exhibit some toxic side effects can be used.

A therapeutically effective dose of a HAT activator compound can depend upon a number of factors known to those of ordinary skill in the art. The dose(s) of a HAT activator compound, for example a compound of Formula (I), Formula (II), Formula (III), Formula (IV), Formula (V), or Formula (VI), can vary, for example, depending upon the identity, size, and condition of the subject or sample being treated, further depending upon the route by which the composition is to be administered, if applicable, and the effect which the practitioner desires the HAT activator compound to have upon a HAT protein or a protein exhibiting intrinsic HAT activity. These amounts can be readily determined by a skilled artisan.

HAT activator compounds of the invention can be incorporated into pharmaceutical compositions suitable for administration. Such compositions can comprise a HAT activator compound (e.g., a compound of HAT activator compounds having Formula (I), Formula (II), Formula (III), Formula (IV), Formula (V), or Formula (VI), or compound YF2 depicted in FIG. 3) and a pharmaceutically acceptable carrier. The compositions can be administered alone or in combination with at least one other agent, such as a stabilizing compound, which can be administered in any sterile, biocompatible pharmaceutical carrier including, but not limited to, saline, buffered saline, dextrose, and water. The compositions can be administered to a patient alone, or in combination with other agents, drugs or hormones.

According to the invention, a pharmaceutically acceptable carrier can comprise any and all solvents, dispersion media, coatings, antibacterial and antifungal agents, isotonic and absorption delaying agents, and the like, compatible with pharmaceutical administration. The use of such media and agents for pharmaceutically active substances is well known in the art. Any conventional media or agent that is compatible with the active compound can be used. Supplementary active compounds can also be incorporated into the compositions.

Any of the therapeutic applications described herein can be applied to any subject in need of such therapy, including, for example, a mammal such as a dog, a cat, a cow, a horse, a rabbit, a monkey, a pig, a sheep, a goat, or a human.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersions. For intravenous administration, suitable carriers include physiological saline, bacteriostatic water, Cremophor EM™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, a pharmaceutically acceptable polyol like glycerol, propylene glycol, liquid polyetheylene glycol, and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, and thimerosal. In many cases, it can be useful to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the HAT Activator compound in the required amount in an appropriate solvent with one or a combination of ingredients enumerated herein, as required, followed by filtered sterilization. Generally, dispersions are prepared by incorporating the active compound into a sterile vehicle which contains a basic dispersion medium and the required other ingredients from those enumerated herein. In the case of sterile powders for the preparation of sterile injectable solutions, examples of useful preparation methods are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed.

Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or sterotes; a glidant such as colloidal silicon dioxide; a sweetening agent such as sucrose or saccharin; or a flavoring agent such as peppermint, methyl salicylate, or orange flavoring.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

REFERENCES

S1. Masliah, E., *Mechanisms of synaptic dysfunction in Alzheimer's disease.* Histol Histopathol, 1995. 10(2): p. 509-19.

S2. Selkoe, D. J., *Alzheimer's disease is a synaptic failure.* Science, 2002. 298(5594): p. 789-91.

S3. Sant'Angelo, A., F. Trinchese, and O. Arancio, *Usefulness of behavioral and electrophysiological studies in transgenic models of Alzheimer's disease.* Neurochem Res, 2003. 28(7): p. 1009-15.

S4. Bliss, T. V. and G. L. Collingridge, *A synaptic model of memory: long-term potentiation in the hippocampus.* Nature, 1993. 361(6407): p. 31-9.

S5. Cullen, W. K., et al., *Block of LTP in rat hippocampus in vivo by beta-amyloid precursor protein fragments.* Neuroreport, 1997. 8(15): p. 3213-7.

S6. Freir, D. B., C. Holscher, and C. E. Herron, *Blockade of long-term potentiation by beta-amyloid peptides in the CA1 region of the rat hippocampus in vivo.* J Neurophysiol, 2001. 85(2): p. 708-13.

S7. Itoh, A., et al., *Impairments of long-term potentiation in hippocampal slices of beta-amyloid-infused rats.* Eur J Pharmacol, 1999. 382(3): p. 167-75.

S8. Kim, J. H., et al., *Use-dependent effects of amyloidogenic fragments of (beta)-amyloid precursor protein on synaptic plasticity in rat hippocampus in vivo.* J Neurosci, 2001. 21(4): p. 1327-33.

S9. Stephan, A., S. Laroche, and S. Davis, *Generation of aggregated beta-amyloid in the rat hippocampus impairs synaptic transmission and plasticity and causes memory deficits.* J Neurosci, 2001. 21(15): p. 5703-14.

S10. Vitolo, O. V., et al., *Amyloid beta-peptide inhibition of the PKA/CREB pathway and long-term potentiation: reversibility by drugs that enhance cAMP signaling.* Proc Natl Acad Sci USA, 2002. 99(20): p. 13217-21.

S11. Walsh, D. M., et al., *Naturally secreted oligomers of amyloid beta protein potently inhibit hippocampal long-term potentiation in vivo.* Nature, 2002. 416(6880): p. 535-9.

S12. Puzzo, D., et al., *Amyloid-beta peptide inhibits activation of the nitric oxide/cGMP/cAMP-responsive element-binding protein pathway during hippocampal synaptic plasticity.* J Neurosci, 2005. 25(29): p. 6887-97.

S13. Selig, D. K., et al., *Examination of the role of cGMP in long-term potentiation in the CA1 region of the hippocampus.* Learn Mem, 1996. 3(1): p. 42-8.

S14. Prickaerts, J., et al., *cGMP, but not cAMP, in rat hippocampus is involved in early stages of object memory consolidation.* Eur J Pharmacol, 2002. 436(1-2): p. 83-7.

S15. Paakkari, I. and P. Lindsberg, *Nitric oxide in the central nervous system.* Ann Med, 1995. 27(3): p. 369-77.

S16. Baratti, C. M. and M. M. Boccia, *Effects of sildenafil on long-term retention of an inhibitory avoidance response in mice.* Behav Pharmacol, 1999. 10(8): p. 731-7.

S17. van Staveren, W. C., et al., *Species differences in the localization of cGMP-producing and NO-responsive elements in the mouse and rat hippocampus using cGMP immunocytochemistry.* Eur J Neurosci, 2004. 19(8): p. 2155-68.

S18. Van Staveren, W. C., et al., *mRNA expression patterns of the cGMP-hydrolyzing phosphodiesterases types 2, 5, and 9 during development of the rat brain.* J Comp Neurol, 2003. 467(4): p. 566-80.

S19. Schultheiss, D., et al., *Central effects of sildenafil (Viagra)on auditory selective attention and verbal recognition memory in humans: a study with event-related brain potentials.* World J Urol, 2001. 19(1): p. 46-50.

S20. Kemenes, I., et al., *Critical time-window for NO-cGMP-dependent long-term memory formation after one-trial appetitive conditioning.* J Neurosci, 2002. 22(4): p. 1414-25.

S21. Baltrons, M. A., et al., *Regulation of NO-dependent cyclic GMP formation by inflammatory agents in neural cells.* Toxicol Lett, 2003. 139(2-3): p. 191-8.

S22. Bon, C. L. and J. Garthwaite, *On the role of nitric oxide in hippocampal long-term potentiation.* J Neurosci, 2003. 23(5): p. 1941-8.

S23. Trinchese, F., et al., *Progressive age-related development of Alzheimer-like pathology in APP/PS1 mice.* Ann Neurol, 2004. 55(6): p. 801-14.

S24. Chapman, P. F., et al., *Impaired synaptic plasticity and learning in aged amyloid precursor protein transgenic mice.* Nat Neurosci, 1999. 2(3): p. 271-6.

S25. Fitzjohn, S. M., et al., *Age-related impairment of synaptic transmission but normal long-term potentiation in transgenic mice that overexpress the human APP695SWE mutant form of amyloid precursor protein.* J Neurosci, 2001. 21(13): p. 4691-8.

S26. Hsia, A. Y., et al., *Plaque-independent disruption of neural circuits in Alzheimer's disease mouse models.* Proc Natl Acad Sci USA, 1999. 96(6): p. 3228-33.

S27. Jolas, T., et al., *Long-term potentiation is increased in the CA1 area of the hippocampus of APP(swe/ind) CRND8 mice.* Neurobiol Dis, 2002. 11(3): p. 394-409.

S28. Larson, J., et al., *Alterations in synaptic transmission and long-term potentiation in hippocampal slices from young and aged PDAPP mice.* Brain Res, 1999. 840(1-2): p. 23-35.

S29. Moechars, D., et al., *Early phenotypic changes in transgenic mice that overexpress different mutants of amyloid precursor protein in brain.* J Biol Chem, 1999. 274(10): p. 6483-92.

S30. Nalbantoglu, J., et al., *Impaired learning and LTP in mice expressing the carboxy terminus of the Alzheimer amyloid precursor protein.* Nature, 1997. 387(6632): p. 500-5.

S31. Dineley, K. T., et al., *Beta-amyloid activates the mitogen-activated protein kinase cascade via hippocampal alpha7 nicotinic acetylcholine receptors: In vitro and in vivo mechanisms related to Alzheimer's disease.* J Neurosci, 2001. 21(12): p. 4125-33.

S32. Dineley, K. T., et al., *Accelerated plaque accumulation, associative learning deficits, and up-regulation of alpha 7 nicotinic receptor protein in transgenic mice co-expressing mutant human presenilin 1 and amyloid precursor proteins.* J Biol Chem, 2002. 277(25): p. 22768-80.

S33. Gong, B., et al., *Persistent improvement in synaptic and cognitive functions in an Alzheimer mouse model following rolipram treatment.* J. Clin. Invest., 2004. 114: p. 1624-1634.

S34. Yin, J. C., et al., *Induction of a dominant negative CREB transgene specifically blocks long-term memory in Drosophila.* Cell, 1994. 79(1): p. 49-58.

S35. Bourtchuladze, R., et al., *Deficient long-term memory in mice with a targeted mutation of the cAMP-responsive element-binding protein.* Cell, 1994. 79(1): p. 59-68.

S36. Bach, M. E., et al., *Age-related defects in spatial memory are correlated with defects in the late phase of hippocampal long-term potentiation in vitro and are attenuated by drugs that enhance the cAMP signaling pathway.* Proc Natl Acad Sci USA, 1999. 96(9): p. 5280-5.

S37. Lu, Y. F., E. R. Kandel, and R. D. Hawkins, *Nitric oxide signaling contributes to late-phase LTP and CREB phosphorylation in the hippocampus.* J Neurosci, 1999. 19(23): p. 10250-61.

S38. McCarty, M. F., *Vascular nitric oxide may lessen Alzheimer's risk.* Med Hypotheses, 1998. 51(6): p. 465-76.

S39. Troy, C. M., et al., *Caspase-2 mediates neuronal cell death induced by beta-amyloid.* J Neurosci, 2000. 20(4): p. 1386-92.

S40. Wirtz-Brugger, F. and A. Giovanni, *Guanosine 3',5'-cyclic monophosphate mediated inhibition of cell death induced by nerve growth factor withdrawal and beta-amyloid: protective effects of propentofylline.* Neuroscience, 2000. 99(4): p. 737-50.

S41. Venturini, G., et al., *Beta-amyloid inhibits NOS activity by subtracting NADPH availability*. Faseb J, 2002. 16(14): p. 1970-2.

S42. Suhara, T., et al., *Abeta42 generation is toxic to endothelial cells and inhibits eNOS function through an Akt/GSK-3beta signaling-dependent mechanism*. Neurobiol Aging, 2003. 24(3): p. 437-51.

S43. Colton, C. A., et al., *NO synthase 2 (NOS2) deletion promotes multiple pathologies in a mouse model of Alzheimer's disease*. Proc Natl Acad Sci USA, 2006. 103(34): p. 12867-72.

S44. Thatcher, G. R., B. M. Bennett, and J. N. Reynolds, *Nitric oxide mimetic molecules as therapeutic agents in Alzheimer's disease*. Curr Alzheimer Res, 2005. 2(2): p. 171-82.

S45. Haas, J., et al., *Inducible nitric oxide synthase and argininosuccinate synthetase: co-induction in brain tissue of patients with Alzheimer's dementia and following stimulation with beta-amyloid 1-42 in vitro*. Neurosci Lett, 2002. 322(2): p. 121-5.

S46. Tran, M. H., et al., *Amyloid beta-peptide induces nitric oxide production in rat hippocampus: association with cholinergic dysfunction and amelioration by inducible nitric oxide synthase inhibitors*. Faseb J, 2001. 15(8): p. 1407-9.

S47. McCann, S. M., *The nitric oxide hypothesis of brain aging*. Exp Gerontol, 1997. 32(4-5): p. 431-40.

S48. Xie, Z., et al., *Peroxynitrite mediates neurotoxicity of amyloid beta-peptide 1-42-and lipopolysaccharide-activated microglia*. J Neurosci, 2002. 22(9): p. 3484-92.

S49. Wong, A., et al., *Advanced glycation endproducts co-localize with inducible nitric oxide synthase in Alzheimer's disease*. Brain Res, 2001. 920(1-2): p. 32-40.

S50. Wang, Q., M. J. Rowan, and R. Anwyl, *Beta-amyloid-mediated inhibition of NMDA receptor-dependent long-term potentiation induction involves activation of microglia and stimulation of inducible nitric oxide synthase and superoxide*. J Neurosci, 2004. 24(27): p. 6049-56.

S51. Monsonego, A., et al., *Microglia-mediated nitric oxide cytotoxicity of T cells following amyloid beta-peptide presentation to Th1 cells*. J Immunol, 2003. 171(5): p. 2216-24.

S52. Contestabile, A., et al., *Brain nitric oxide and its dual role in neurodegeneration/neuroprotection: understanding molecular mechanisms to devise drug approaches*. Curr Med Chem, 2003. 10(20): p. 2147-74.

EXAMPLES

Examples are provided below to facilitate a more complete understanding of the invention. The following examples illustrate the exemplary modes of making and practicing the invention. However, the scope of the invention is not limited to specific embodiments disclosed in these Examples, which are for purposes of illustration only, since alternative methods can be utilized to obtain similar results.

Example 1—a HAT Activator Compound

Figure 2:
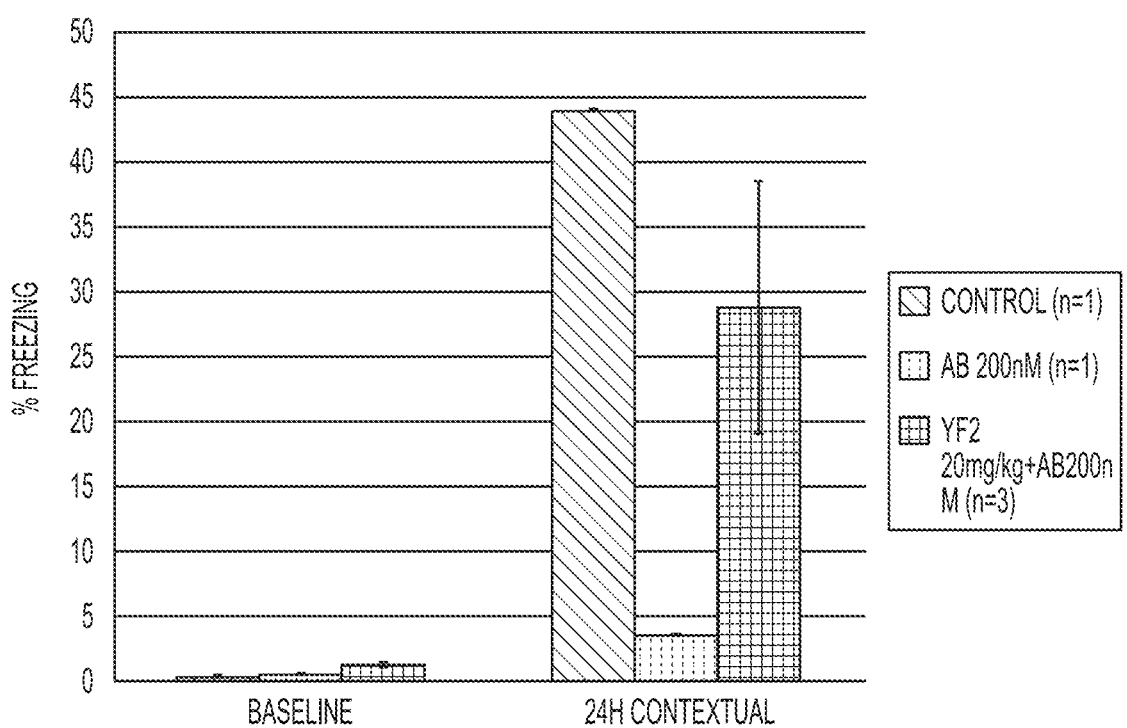
FIG. 2 is a bar graph showing that contextual fear conditioning of $A\beta_{42}$ infused memory deficit mice.

YF2, a Histone Acetyltransferase (HAT) Activator of the invention (FIG. 3), is a good drug candidate to ameliorate memory in neurodegenerative diseases (i.e. Alzheimer's disease and Huntington's disease) and treatment for a variety of cancers. When the YF2 compound was administrated to mice (i.p.), the western blot showed that it not only crosses the BBB, but also increases histone 3 acetylation levels of the hippocampus (FIG. 1). In the behavior experiments, the title compound ameliorates the contextual fear memory deficit in Aβ42-infused mice (FIG. 2). Aβ42 is a protein that is produced in high amount in AD and is responsible for the impairment of synaptic functions and memory.

Example 2—HAT Activator Compound Characteristics

Figure 4:
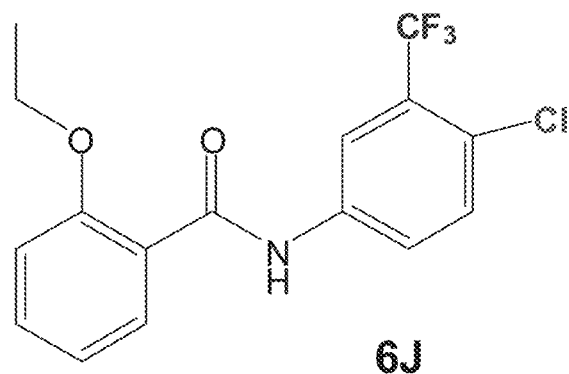
FIG. 4 is the chemical structure of compound 6J (CTB), N-(4-chloro-3-trifluoromethyl-phenyl)-2-ethoxy-benzamide. 6J had no solubility and precipitated as soon as it was put in $H_2O$.
Figure 5:
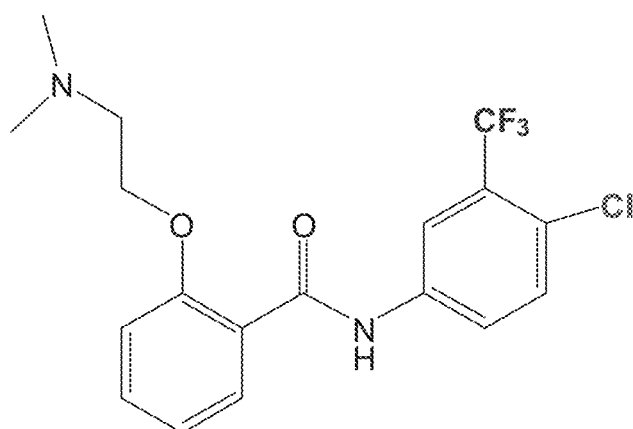
FIG. 5 is the chemical structure of compound MOM (YF1). YF1 was administered 25 mg/kg to WT mice (i.p.). The mice liver and hippocampus were extracted 1 hr after treatment. Hippocampus and liver had no increase in AcH3 levels.

Compound 6J, from Mantelingu et al, was synthesized (FIG. 4). However, compound 6J had no solubility and precipitated as soon as it was put in $H_2O$. However, concerns existed that the drug (even if dissolved in 100% DMSO) would precipitate as soon as it was administrated. Thus, a new drug that was soluble was synthesized, "MOM" (FIG. 5).

Figure 6:
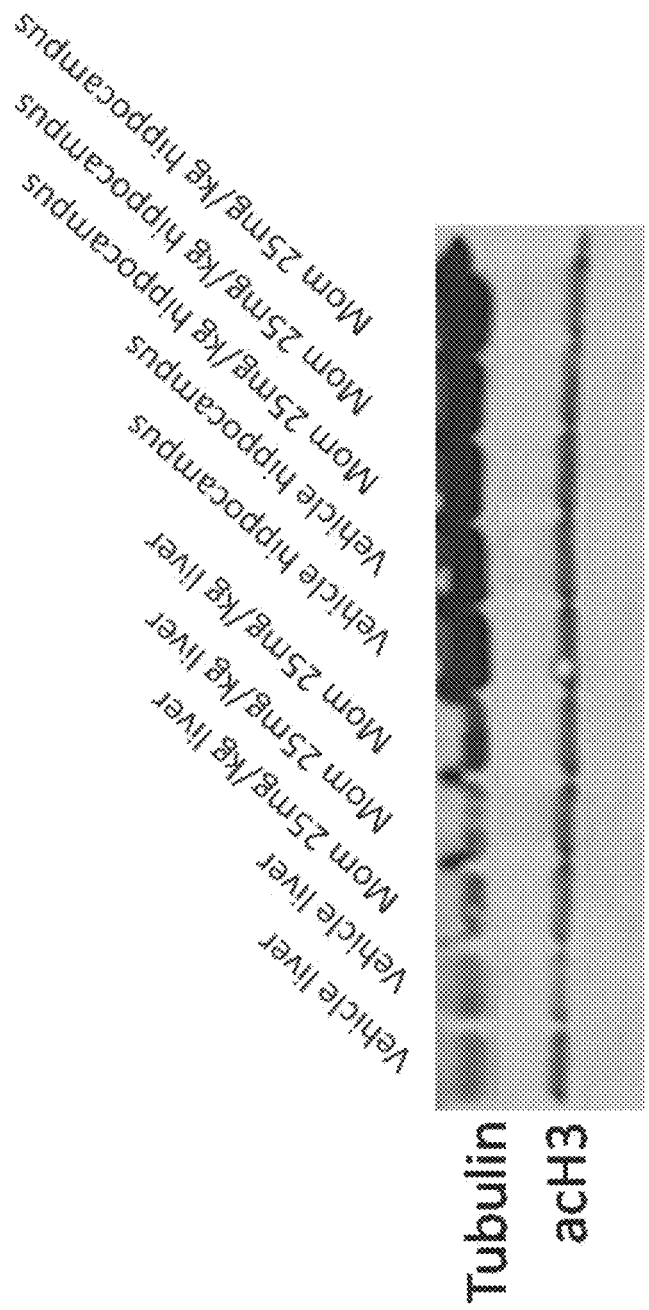
FIG. 6 is a photograph of a western blot showing acetylation levels of H3 in the liver and hippocampus.
Figure 7:
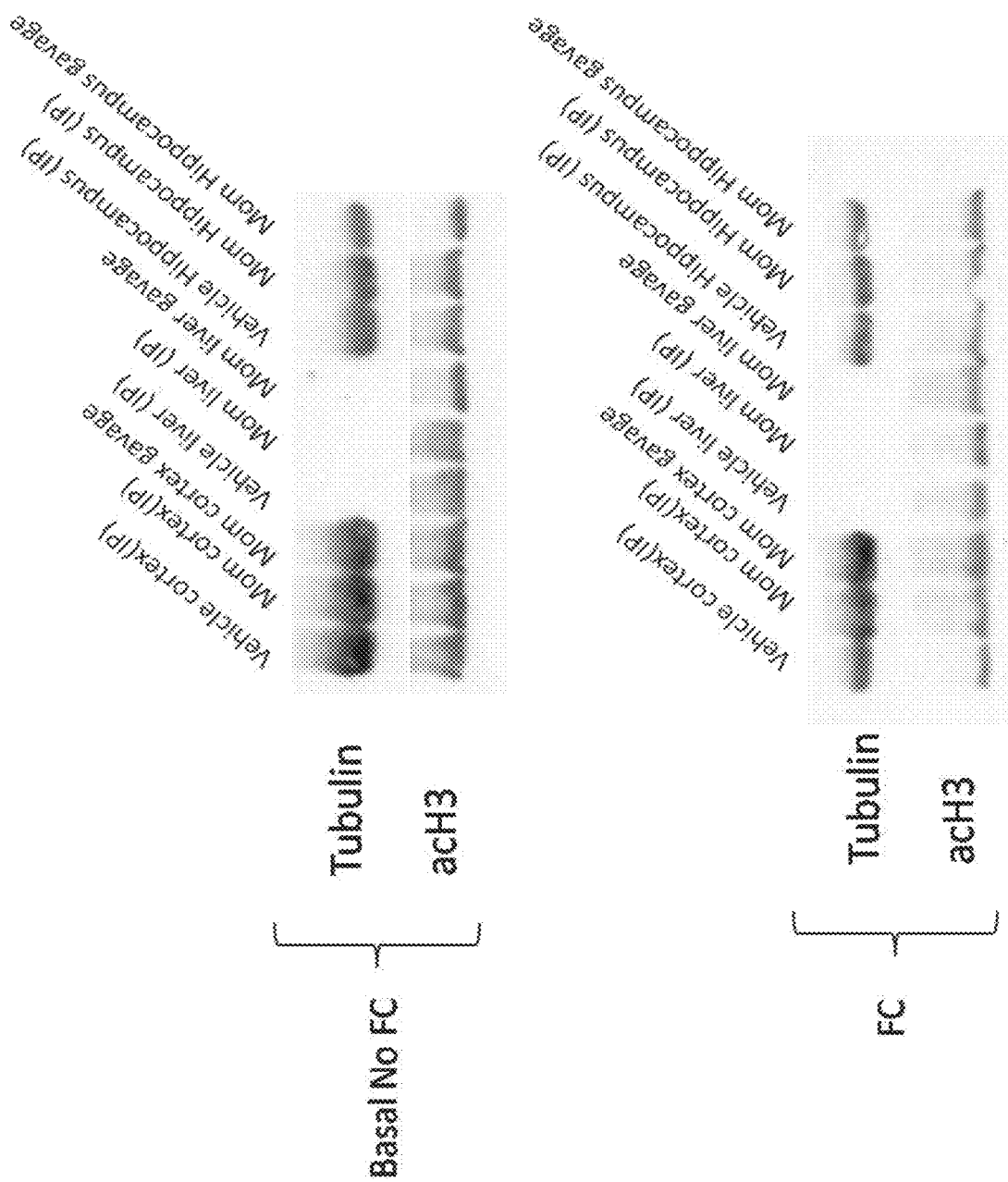
FIG. 7 is a photograph of a western blot showing acetylation levels of H3 in the liver, cortex, and hippocampus of mice that were administered by gavage and i.p. 25 mg/kg of the HAT agonist, MOM. Mice were subsequently subjected to fear conditioning treatment to see if the drug is active after induction of learning.

MOM has medium solubility (DMSO 10% in $H_2O$). MOM was administered 25 mg/kg to WT mice (i.p.). The mice liver and hippocampus were extracted 1 hr after treatment. The liver showed a very slight increase of AcH3, indicating that the drug has either very little efficacy OR very little membrane permeability (FIG. 6). The hippocampus had no increase in AcH3 levels, indicating the drug is either ineffective OR does not cross the blood brain barrier (BBB) (FIG. 6). Although MOM failed to increase AcH3 levels in the hippocampus and liver, the experiment was repeated with a new administration (gavage and i.p. 25 mg/kg). Fear conditioning treatment of the mice was subsequently carried out to see if the drug is active after induction of learning. In addition to the mouse liver and hippocampus, the mouse cortex was also extracted. Hippocampus, cortex, and liver samples again showed no increase of AcH3 levels, indicating the drug is either ineffective OR does not cross the BBB OR does not cross the cell membrane (FIG. 7).

Figure 8:
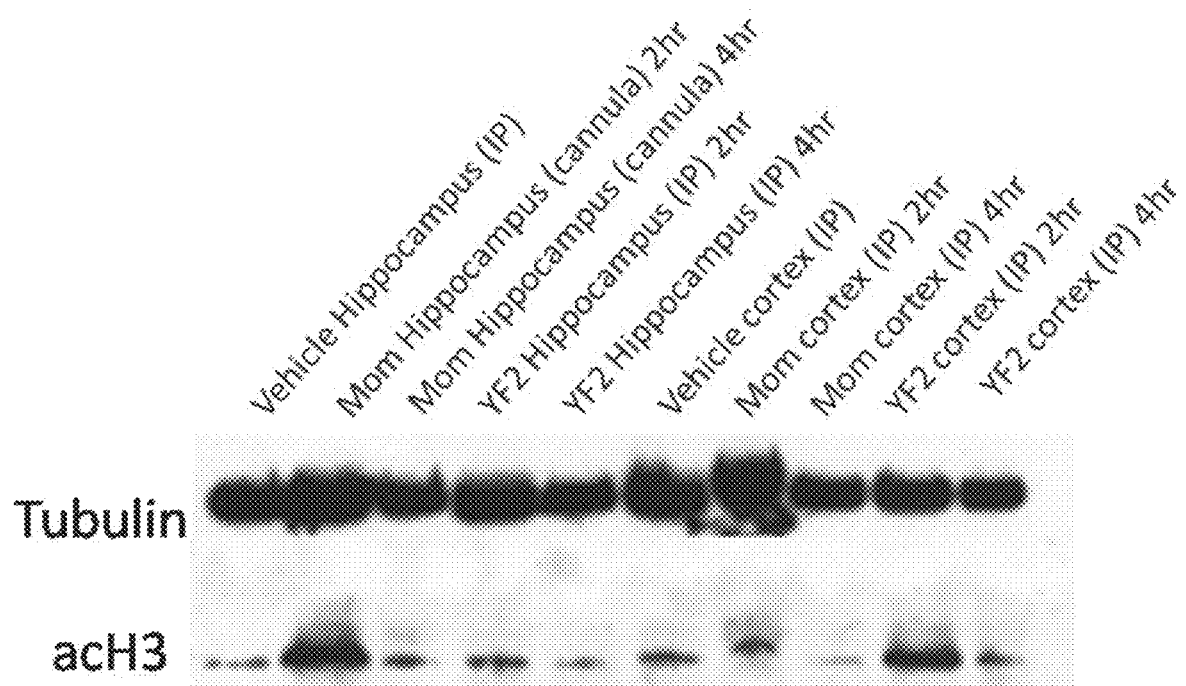
FIG. 8 is a photograph of a western blot showing acetylation levels of H3 in the cortex and hippocampus. Mice were administered with MOM via cannula (100 µg/µl per side) or mice were administered YF2 (50 mg/kg, i.p.).
Figure 9:
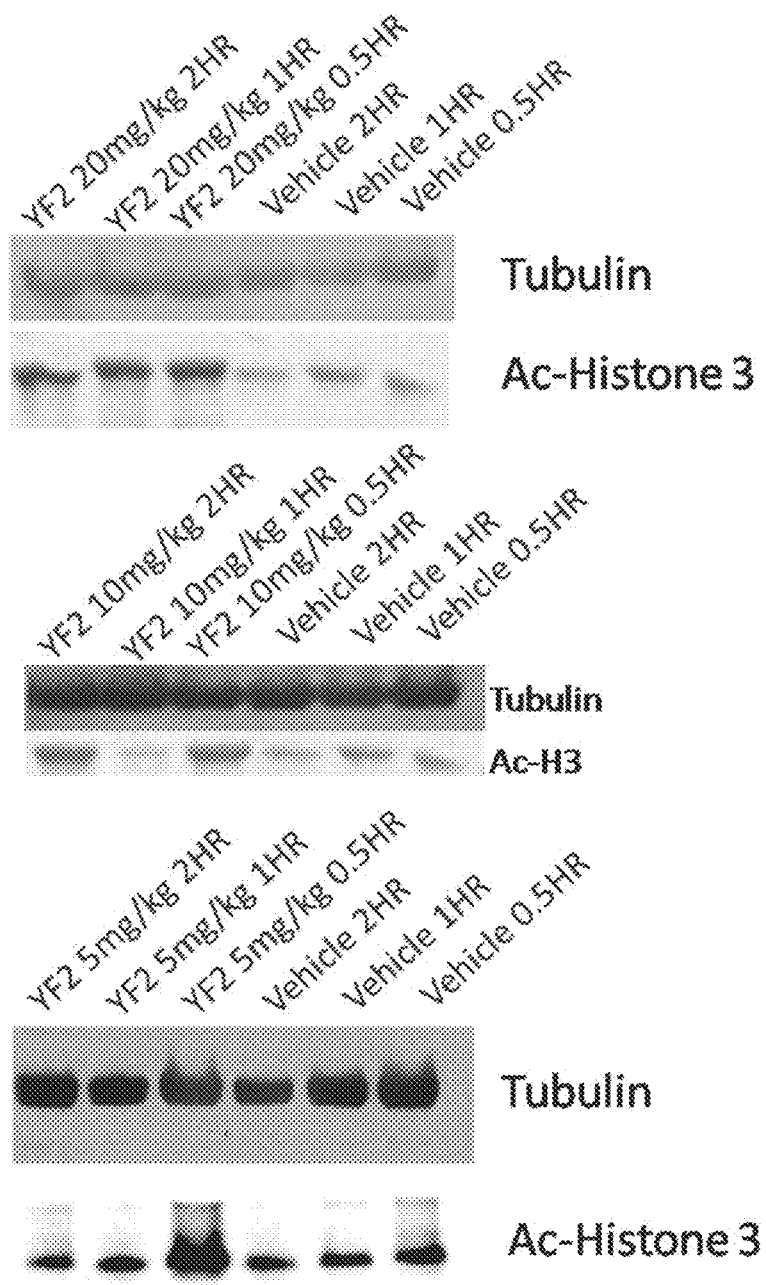
FIG. 9 is a photograph of a western blot showing acetylation levels of H3 in the hippocampus. Mice were administered with YF2 (i.p. dissolved in saline) at 5 mg/kg, 10 mg/kg, or 20 mg/kg.

Although MOM failed in increasing AcH3 levels, the experiment was repeated with a different chemical vehicle (10% DMSO and 10% Tween 80). The BBB was by-passed by giving it through cannulas implanted onto the dorsal hippocampus. Both the hippocampus and cortex were extracted at 2 hrs or 4 hrs after treatment. Compared to vehicle, mice that were administered with MOM via cannula (100 µg/µl per side) showed an increase of AcH4 (lane 1 vs. lanes 2, 3). Mice that were given the drug i.p. showed no increase of AcH3 (FIG. 8). This data indicates that the compound MOM does not cross the BBB.

Figure 10:
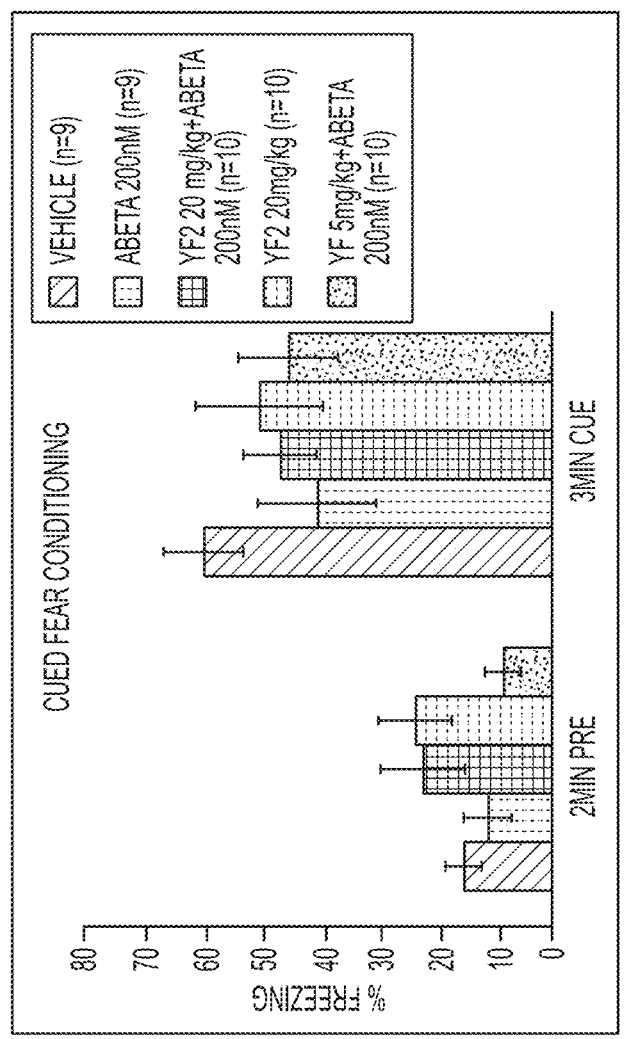
FIG. 10 is a bar graph demonstrating cued fear conditioning responses after administration of the HAT activator, YF2, to mice treated with amyloid-beta (Aβ or A-beta).

A new compound YF2 (FIG. 3), was synthesized. The preparation of YF2 was without a column and 2 phases were visible: clear and oily. YF2 (50 mg/kg, i.p.) was subsequently administered to mice. Two and four hrs after its administration, the mice were sacrificed and hippocampi were extracted. Interestingly, YF2 was able to cross the BBB, penetrate the cells and increase AcH3 (lane 1 vs. lanes 9, 10) (FIG. 8). Given that the compound was not 100% clean and needed to be further purified/verified, we synthesized more YF2 and purified it. Purity was verified through Nuclear Magnetic Resonance (NMR). Mice were administered with YF2 (i.p. dissolved in saline) at 5, 10, 20 mg/Kg. Hippocampus extraction was made at 3 different time points (0.5, 1 and 2 hrs post treatment). We then ran a western blotting for AcH3. Except for the 1 hr-10 mg/kg administration of YF2, YF2 dramatically increased AcH3 levels (FIG. 10), indicating that YF2 crosses the BBB and the cell membrane.

Example 3—Contextual and Cued Fear Conditioning Experiments

Contextual and cued fear conditioning was performed to assess whether the compound is capable of ameliorating amyloid-beta (Aβ) induced memory defect. Aβ is a peptide which is elevated in Alzheimer's disease. The hippocampus plays a key role in contextual memory and in Alzheimer's Disease. This type of cognitive test is much faster than other behavioral tasks that require multiple days of training and testing [Q1, Q2]; each herein incorporated by reference in its entirety. The conditioning chamber was in a sound-attenuating box. A clear Plexiglas window allowed the experimenter to film the mouse performance with a camera placed on a tripod and connected to the Freezeframe software (MED Ass. Inc.). To provide background white noise (72 dB), a single computer fan was installed in one of the sides of the sound-attenuating chamber. The conditioning chamber had a 36-bar insulated shock grid floor. The floor was removable, and after each experimental subject, we cleaned it with 75% ethanol and then with water. Only one animal at a time was present in the experimentation room.

For the cued and contextual conditioning experiments, mice were placed in the conditioning chamber for 2 min before the onset of a discrete tone (CS) (a sound that lasted 30 sec at 2800 Hz and 85 dB). In the last 2 sec of the CS, mice were given a foot shock (US) of 0.8 mA for 2 sec through the bars of the floor. After the CS/US pairing, the mice were left in the conditioning chamber for another 30 sec and were then placed back in their home cages. Freezing behavior, defined as the absence of all movement except for that necessitated by breathing, was scored using the Freezeview software.

To evaluate contextual fear learning, freezing was measured for 5 min (consecutively) in the chamber in which the mice was trained 24 hr after training. To evaluate cued fear learning, following contextual testing, the mice were placed in a novel context (triangular cage with smooth flat floor) for 2 min (pre-CS test), after which they were exposed to the CS for 3 min (CS test), and freezing was measured. Sensory perception of the shock was determined through threshold assessment. A sequence of single foot shocks was delivered to animals placed on the same electrified grid used for fear conditioning. Initially, a 0.1 mV shock was delivered for 1 sec, and the animal behavior was evaluated for flinching, jumping, and vocalization. At 30 sec intervals the shock intensity was increased by 0.1 mV to 0.7 mV and then returned to 0 mV in 0.1 mV increments at 30 sec intervals. Threshold to vocalization, flinching, and then jumping was quantified for each animal by averaging the shock intensity at which each animal manifests a behavioral response to the foot shock.

Figure 11:
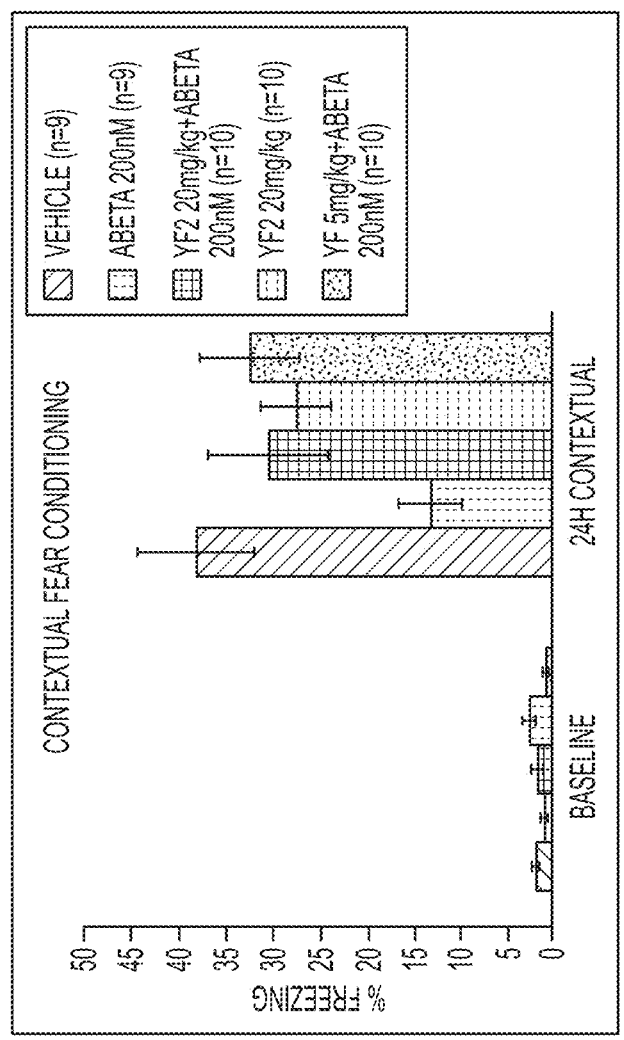
FIG. 11 is a bar graph demonstrating contextual fear conditioning responses after administration of the HAT activator, YF2, to mice treated with amyloid-beta (Aβ or A-beta).
Figure 12:
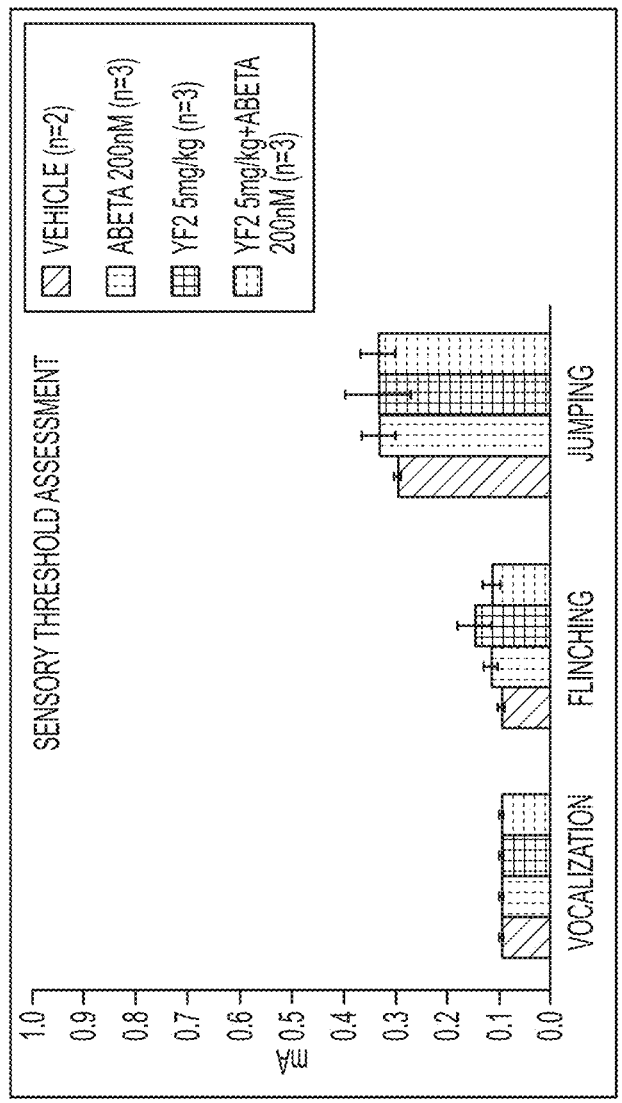
FIG. 12 is a bar graph demonstrating the assessment of sensory threshold in mice treated with vehicle, YF2 alone, Aβ alone, or YF2 plus Aβ.

YF2 was i.p. administered to mice (one group of mice was administered with 20 mg/kg, 2 hrs before the electric shock, whereas another group was administered with 5 mg/kg, 30 minutes before the electric shock). YF2 at both doses was capable of dramatically increasing the freezing time demonstrating that the compound rescues the defect in contextual memory. The compound alone at the highest concentration (20 mg/kg) did not affect contextual memory (FIG. 10) indicating that the compound per se is not toxic with respect to memory. Cued memory was not changed in the different groups indicating that YF2 does not affect amygdala function (FIG. 11). Finally, no difference was observed among different groups of mice in different sets of experiments in which we assessed sensory threshold in the presence of vehicle, YF2 alone, Aβ alone, or YF2 plus Aβ (FIG. 12).

Figure 13:
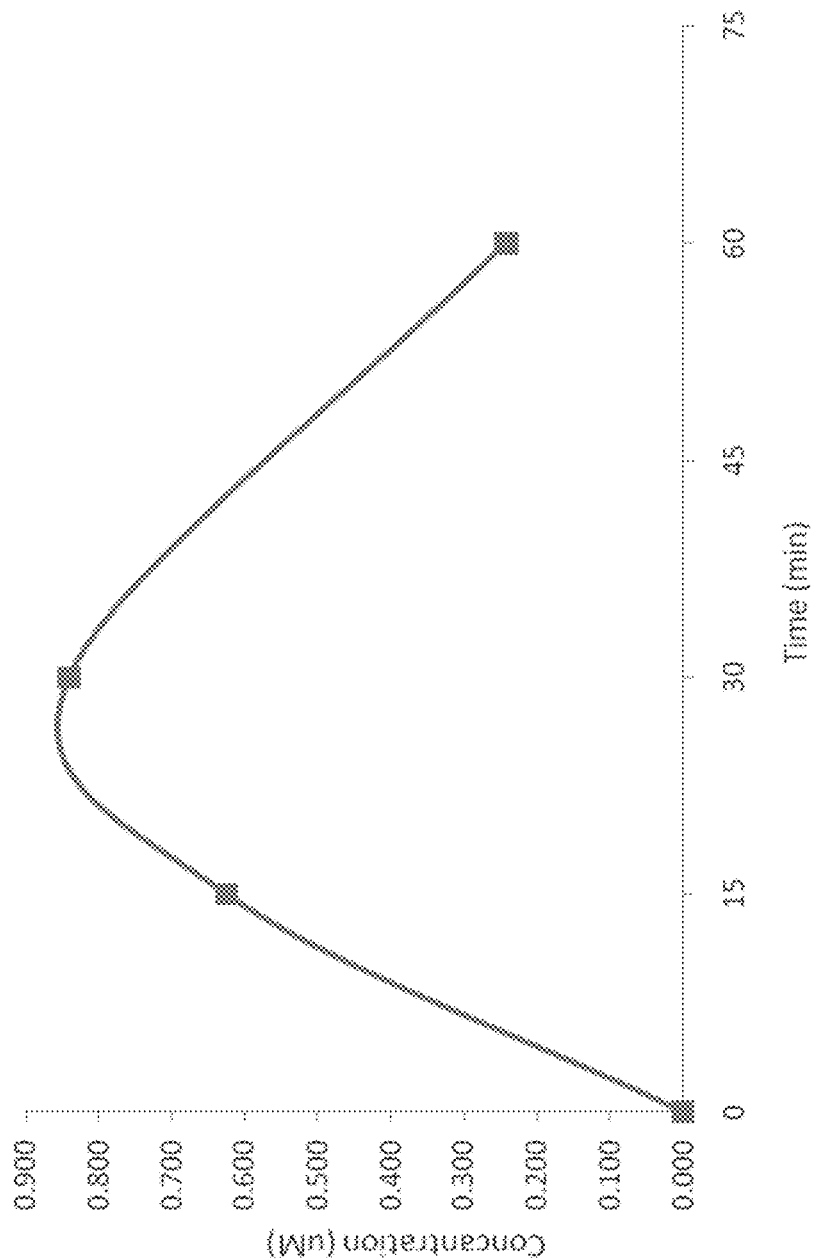
FIG. 13 is a graph showing the kinetics of the HAT agonist, YF2, in the blood. YF2 was administered (20 mg/kg. i.p.) to mice and then blood was sampled from tails at different time points.

Based on the results obtained during the fear conditioning tests, we decided to determine the kinetics of YF2 in blood to verify the best time point for treatment. To this purpose, we administered the compound (20 mg/kg. i.p.) and then sampled blood from tails at different time points. The kinetics of YF2 shows a peak around 30 minutes post-injection (FIG. 13).

REFERENCES

Q1. Gong, B., et al., Persistent improvement in synaptic and cognitive functions in an Alzheimer mouse model after rolipram treatment. J Clin Invest, 2004. 114(11): p. 1624-34.

Q2. Gong, B., et al., Persistent improvement in synaptic and cognitive functions in an Alzheimer mouse model following rolipram treatment. J. Clin. Invest., 2004. 114: p. 1624-1634.

Example 4—Two Day-Radial Arm Water Maze (RAWM)

The task is a hybrid of the Morris Water Maze (MWM) and the radial arm land maze. This task is altered in Aβ-infused mice. The motivation for the animals is the immersion in water. The mouse needed to swim in 6 alleys (arms) radiating from a central area until it found a hidden (submerged) platform at the end of one of the arms, based on visual cues placed in the room. The goal arm was kept constant for all trials, with a different start arm on successive trials, such that the learning criterion was reached in 2 days. The first day of the protocol was a training day. Mice were trained to identify the platform location by alternating between a visible and a hidden platform in a goal arm. The final 3 trials on day 1 and all 15 trials on day 2 used a hidden escape platform to force mice to use spatial cues to identify the location of the goal arm.

To avoid learning limitations imposed by exhausting practice and to avoid fatigue that may result from consecutive trials, spaced practice training were established by running the mice in cohorts of 4 and alternating different cohorts through the 15 training trials over 3 hours testing periods each day. On day 1, a visible platform was placed in a goal location. Mouse 1 of cohort 1 was gently placed in the pool near the perimeter of the wall of the first start arm (specified on a score sheet) and facing the center of the pool. The number of incorrect arm entries (entries in arms with no platform) was counted. If the animal entered the incorrect arm it was gently pulled back to the start arm. Each trial lasted up to 1 min. Failure to select an arm after 15 sec were counted as an error and the mouse was returned to the start arm. After 1 min, if the platform had not been located, the mouse was guided gently through the water by placing a hand behind it to direct it towards the platform. The mouse rested on the platform for 15 sec. After completing the trial, the mouse was removed from the pool, gently towel dried and placed back into its cage under a heat lamp. The goal platform location was different for each mouse.

After all the mice in the first cohort have had a trial to locate a visible platform, the platform was switched from visible to hidden. After each mouse from cohort 1 completed six alternating trials between visible and hidden platforms, the mice was left to rest under a heating source, and mice from the second cohort were tested in the same way. After completing the six alternating trials, mice from cohort 2 returned to their cages to rest.

Figure 14:
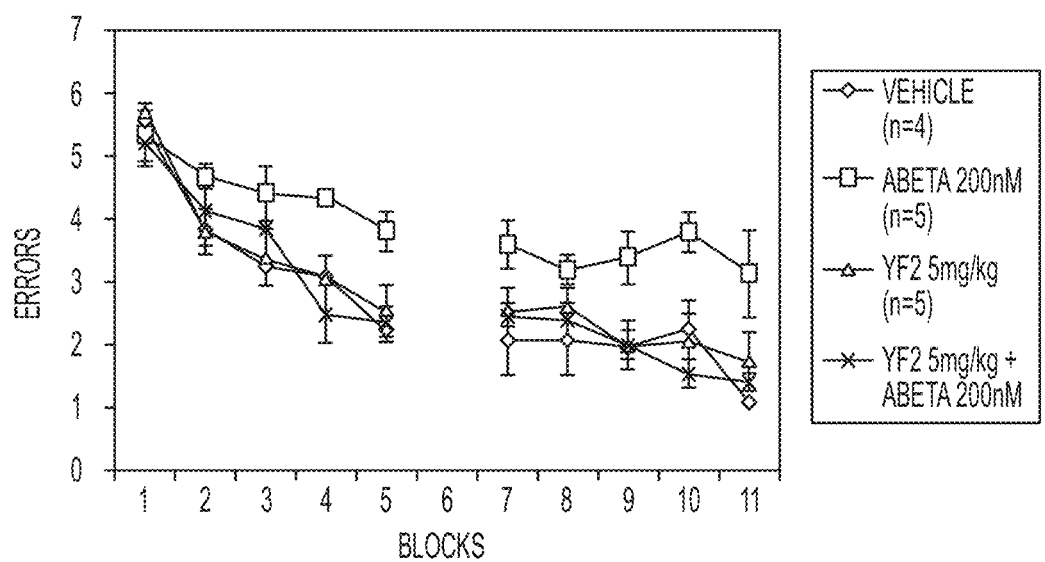
FIG. 14 is a graph showing the results from the radial arm water maze for mice that were administered the HAT agonist, YF2. The graph shows vehicle, Aβ (200 nM), YF2 (5 mg/kg) and YF2 (5 mg/kg)+Aβ (200 nM).

Next, mice from the first cohort completed trials 7-12 again using the alternating visible-hidden platform location. During resting time for mice from the first cohort, mice from the second cohort completed trials 7-12. At this point, all mice had performed 3 hidden platform trials. On day 2, the same procedure was repeated as on day 1 for all 15 trials using only the hidden platform. For data analysis, averages for each mouse were calculated using blocks of 3 trials. As shown in FIG. 14, vehicle-treated mice exhibit ~1 error over three trials near the end of the second day. The graph shows vehicle, Aβ(200 nM), YF2 (5 mg/kg) and YF2 (5 mg/kg)+Aβ(200 nM)

Figure 15:
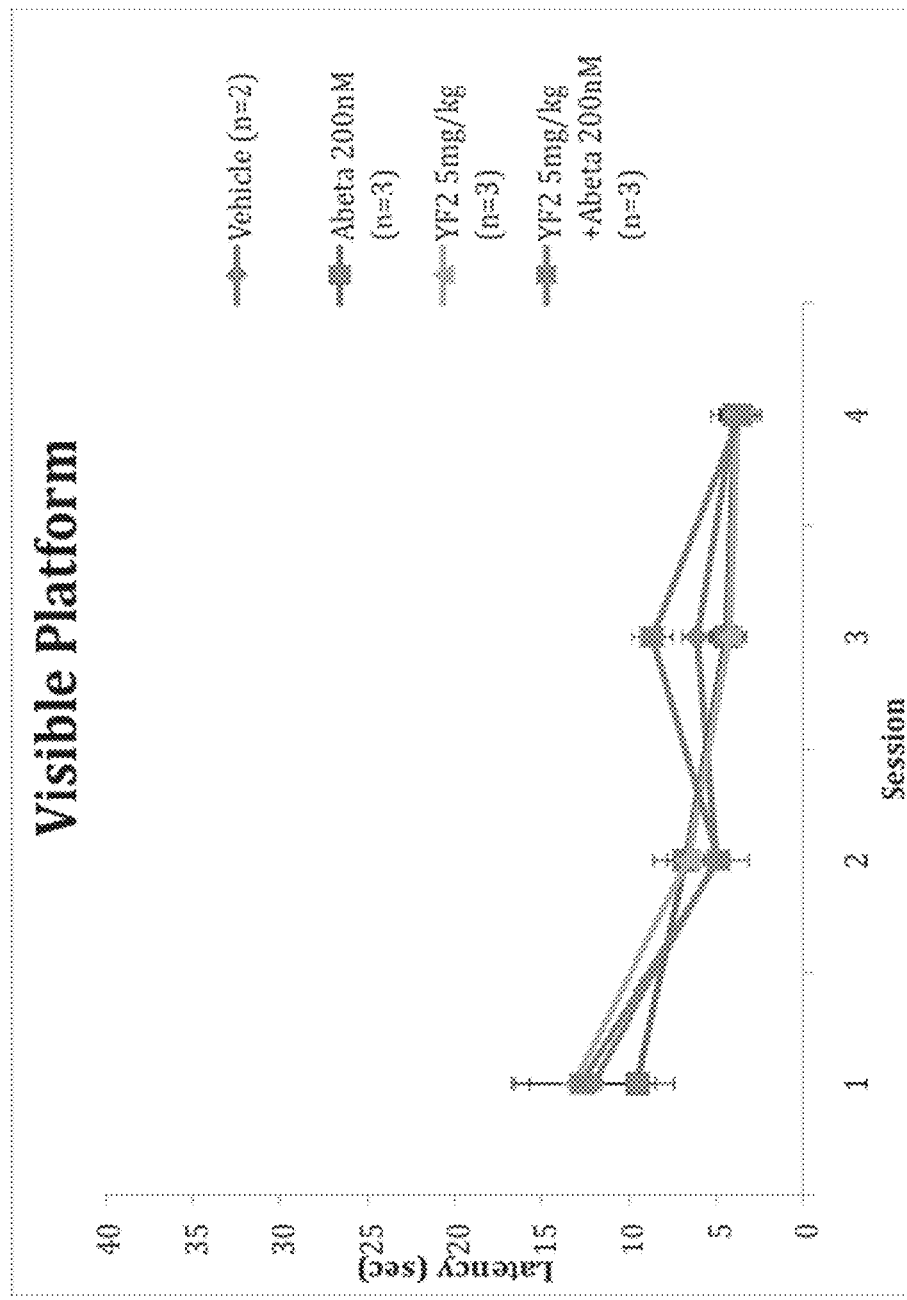
FIG. 15 is a graph showing the results from platform trials for mice that were administered the HAT activator, YF2.
Figure 16:
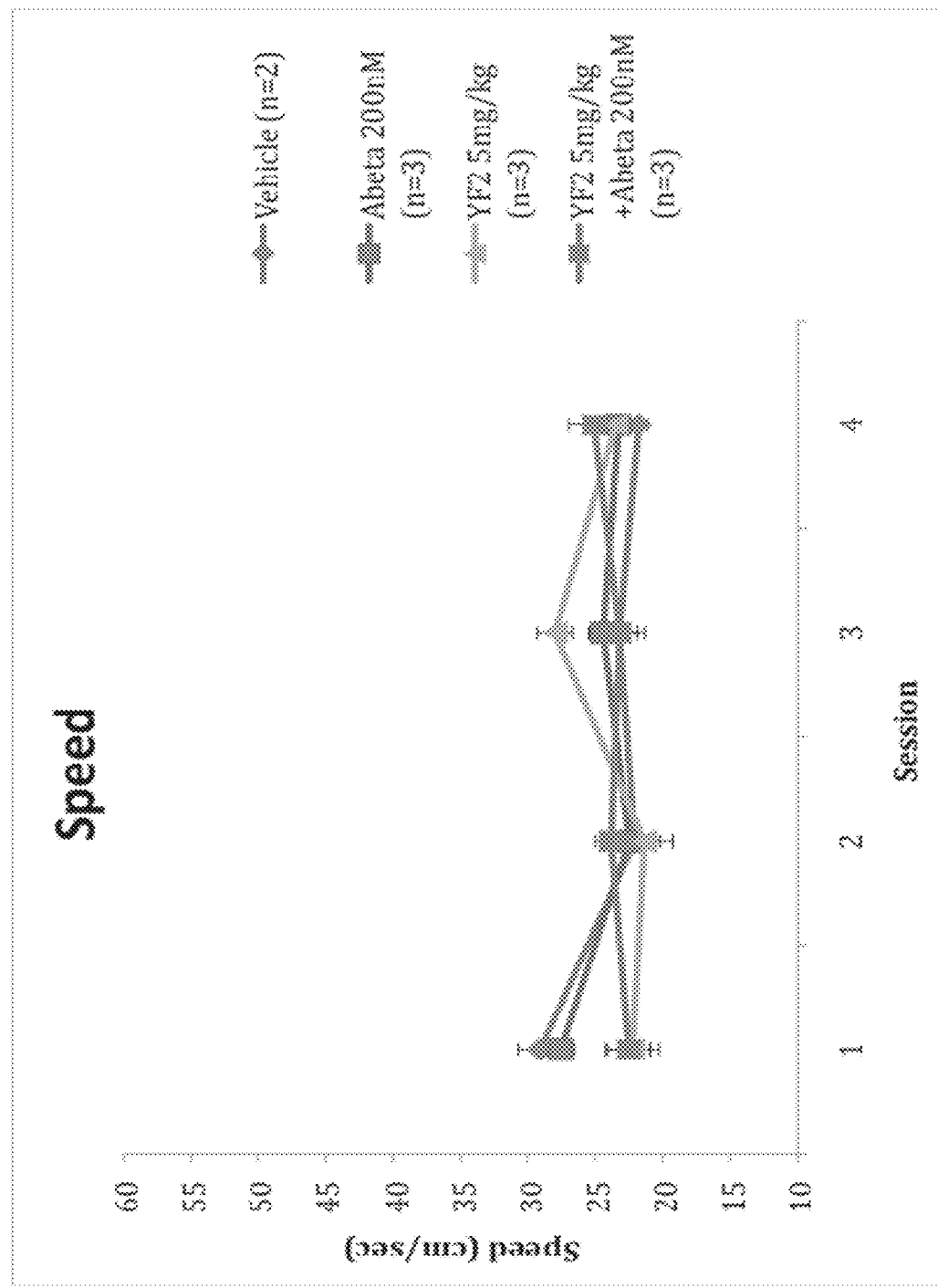
FIG. 16 is a graph showing the speed of mice during the radial arm water maze that were administered the HAT activator, YF2.

In contrast, Aβ-infused mice [bilateral injections of $A\beta_{42}$; 200 nM in a final volume of 1 μl over 1 min; twice on each testing day: 15 min prior to the $1^{st}$ trial (for the $1^{st}$ group of tests) and 15 min prior to the $7^{th}$ trial (for the $2^{nd}$ group of tests) into dorsal hippocampi], failed to learn, making 3-4 errors throughout the training session, with no improvement over trials. Treatment with YF2 [(i.p., 5 mg/kg, 30 min prior to the $1^{st}$ trial (for the $1^{st}$ group of tests) and 30 min prior to the $7^{th}$ trial (for the $2^{nd}$ group of tests)] rescued the Aβ-induced memory impairment. In addition, YF2 by itself did not affect the performance of the animals with this kind of test. Controls for sensory, motor and motivational skills of the mice that might have influenced the outcome of the test with the 2-day RAWM did not show any difference in the time needed to reach the visible platform and in the swimming speed among the four different groups of mice (FIG. 15 and FIG. 16).

Example 5—Dysregulation of Histone Acetylation in Alzheimer Disease

We have recently shown that the inhibition of histone de-acetylation through trichostatin A (TSA) ameliorates LTP and contextual fear conditioning (FC) in an amyloid-depositing animal model, the transgenic (Tg) mouse expressing the Swedish mutation in APP(K670M:N671L) together with the mutation in PS1(M146L, line 6.2), termed APP/PS1 mouse[A21, A22] (each herein incorporated by reference in its entirety). In addition, CBP HAT activity was essential for enhancing transcription in vitro following PS1 stimulation and CBP levels in APP/PS1 mice were significantly lower than in WT mice. Hippocampi from APP/PS1 mice exhibited, after FC training, approximately a 50% reduction in acetylated histone 4 levels, an acetylation that was shown to be important in memory formation[A23] (herein incorporated by reference in its entirety). Based on these findings and without being bound by theory, epigenetic changes, including histone acetylation, play an important role in the Aβ-induced damage of synaptic function and memory associated with AD.

In the brain, CREB phosphorylation is required for CREB ability to bind to CBP and to stimulate memory associated gene expression. CBP functions as a co-activator that facilitates interactions with the basal transcription machinery by working as an acetyltransferase (HAT) that catalyzes acetylation of the histones, causing a loss in chromosomal repression and increase in the transcription of memory associated genes. Unlike HATs, HDACs were found to remove an acetyl group from histones, thus restricting access of the transcriptional machinery to the DNA. Interestingly, HDAC inhibitors have been shown to enhance LTP and contextual fear memory, a form of associative memory in which animals must associate a neutral stimulus with an aversive one [A25] (herein incorporated by reference in its entirety).

Also, memory and LTP deficits of CBP+/− mice were reversed by the HDAC inhibitor, SAHA, supporting the potential use of this class of drugs as therapeutic agents against mental retardation in Rubinstein-Taybi syndrome (RTS)[A24] (herein incorporated by reference in its entirety). Nicotinamide, an HDAC III inhibitor, was found to restore cognition in the triple Tg mouse model of AD via a mechanism involving reduction of Thr231-phosphotau [A26] (herein incorporated by reference in its entirety). Moreover, HDAC inhibitors induced sprouting of dendrites, an increased number of synapses, and reinstated learning and access to long-term memories in the CK-p25 Tg mouse model of neuronal loss [A23] (herein incorporated by reference in its entirety). HDAC inhibitors could affect neuronal function through a variety of mechanisms including epigenetic and non-epigenetic changes [A27] (herein incorporated by reference in its entirety). Whether cognitive deficits following Aβ elevation may be induced by epigenetic modification on histone acetylation (via chromatin remodeling) has not been determined.

WT-PS1 stimulates the transcriptional activity ability of CBP whereas its AD M146L mutant did not produce such an effect [A20] (herein incorporated by reference in its entirety) indicating that CBP and its HAT activity in AD may be involved. In addition, a CBP mutant lacking HAT activity is not capable of responding to WT-PS1 in terms of increased transcription activating ability. Hence, CBP and its HAT region appear to be essential for enhancing transcription in vitro following PS1 stimulation. The inventors find that histone acetylation level of APP/PS1 mice is different than in WT mice, thus identifying AD as a disease of epigenetic etiology.

Significance.

Although AD was described almost a century ago, the molecular mechanisms that lead to the development of the neuronal pathology are still unknown. Without being bound by theory, epigenetics and histone acetylation might play a fundamental role in AD. Moreover, inhibition of HDAC or conversely, activation of a HAT, can effectively counteract the disease progression.

To determine if Aβ-induced synaptic and memory dysfunctions are ameliorated by inhibition of histone de-acetylation.

Based on data showing that TSA rescues the reduction of LTP and contextual learning in APP/PS1 mice, we will determine if the inhibitor also rescues these deficits after Aβ exposure in order to separate Aβ effects from other effects of APP and PS1 overexpression.

AD is thought to begin as a synaptic disorder that progressively leads to greater neuronal dysfunction, leading to memory loss [A28] (herein incorporated by reference in its entirety). To obtain evidence in favor of the involvement of epigenetics in Aβ-induced synaptic and memory dysfunction, we performed a series of experiments using the HDAC inhibitor TSA on 3-4 month-old APP/PS1 mice (for a detailed description of the experiments showing the characterization of these mice see our manuscripts [A17, A29] (each herein incorporated by reference in its entirety).

Figure 17:
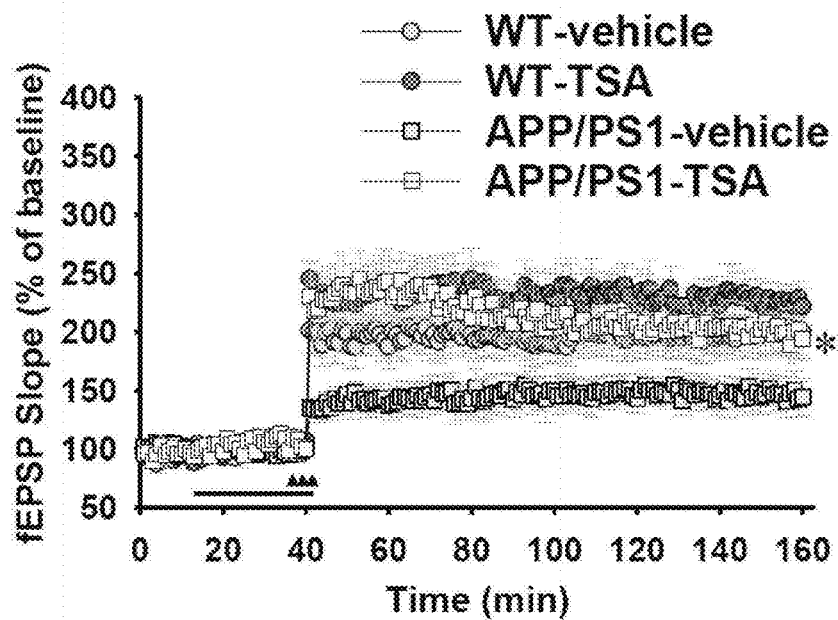
FIG. 17 is a graph that shows that TSA reverses CA1-LTP impairment in slices from 3-4 month old APP/PS1 mice. Summary graph showing that 30 min HDAC inhibition ameliorates LTP in APP/PS1 mice with no effect on WT littermates. *p<0.05 compared to vehicle-treated APP/PS1 slices (two-way ANOVA). The horizontal bar represents TSA application. The 3 arrows correspond to the 0-burst. TSA-treated APP/PS1 and WT mice (n=7 and n=8, respectively), vehicle-treated APP/PS1 and WT mice (n=6).

At this age the Tg mice just start showing the synaptic plasticity and memory impairments [A29] (herein incorporated by reference in its entirety). Basal synaptic transmission (BST) was similar between APP/PS1 and WT mice. We found no difference in BST among the 2 groups as previously shown in mice of this age [A29] (herein incorporated by reference in its entirety). Hippocampal slices were then perfused with TSA (1.65 μM) for 30 min before inducing LTP through tetanic stimulation of the Schaeffer collateral pathway. Potentiation in TSA treated APP/PS1 slices was far greater than in vehicle-treated APP/PS1 slices (FIG. 17). But, TSA did not change the amplitude of LTP in hippocampal slices of WT mice compared to WT slices treated with vehicle alone. Moreover, TSA perfusion did not affect baseline transmission in APP/PS1 and WT slices that received no tetanus.

Figure 18:
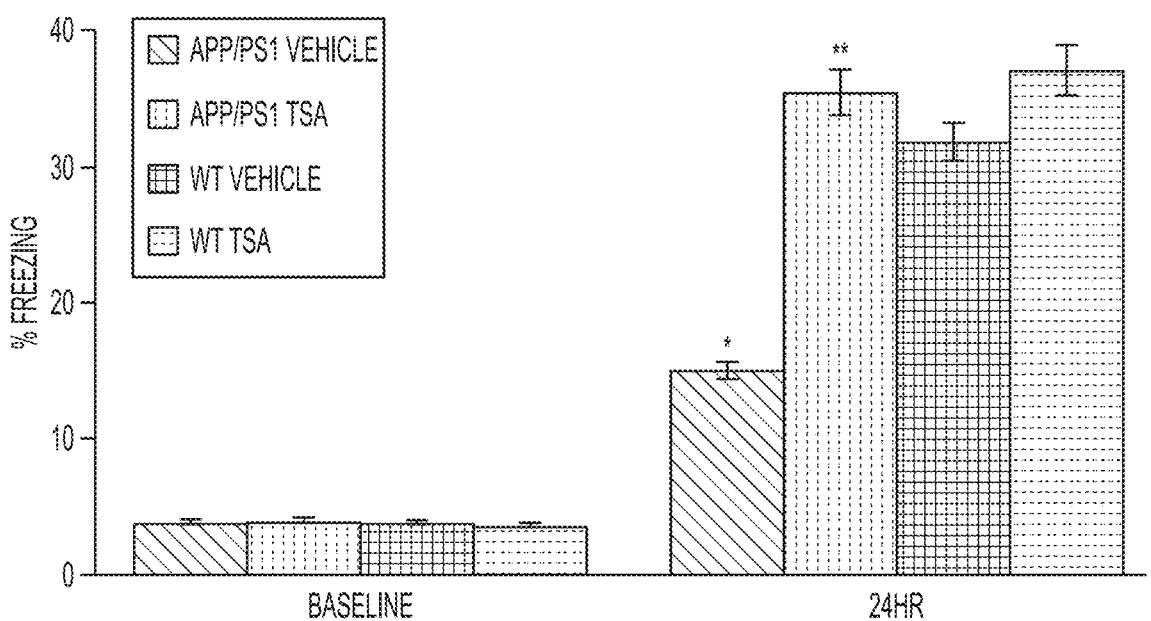
FIG. 18 is a graph that shows that HDAC inhibition improves contextual FC in 3-4 month-old APP/PS1 mice. (Baseline) APP/PS1 and WT littermates treated with TSA or vehicle show no difference in immediate freezing in the training chamber. (24 hrs) Contextual FC performed 24 hrs after training shows a reduction of freezing in APP/PS1 mice treated with vehicle compared to vehicle-treated WT littermates. Treatment with TSA ameliorates deficit in freezing responses in APP/PS1 mice, and has no effect in WT mice. * p<0.05 vs. APP/PS1-vehicle. (n=13 for all groups).

Following experiments on acute effect of TSA in synaptic dysfunction, we determined if TSA is beneficial against impairment of contextual FC in APP/PS1 mice[417]. 4 month-old mice were divided into 4 groups: APP/PS1 with TSA, APP/PS1 with vehicle, WT with TSA and WT with vehicle. TSA and vehicle control solution were administered i.p. at a concentration of 2 µg/g body weight. We found a similar shock threshold among the various groups of mice. Then, mice were trained to associate neutral stimuli with an aversive one. They were placed in a novel context (FC box), exposed to a white noise cue paired with a mild foot shock, and injected with TSA 2 hrs before training. Fear learning was assessed 24 hrs later by measuring freezing behavior—the absence of all movement except for that necessitated by breathing—in response to representation of the context. We found no difference in the freezing behavior among the 4 groups of mice during the training phase of the FC. 24 hrs later, freezing behavior was decreased in vehicle-treated APP/PS1 mice compared to vehicle-treated WT littermates in analyzing contextual learning (FIG. 18). TSA improved memory in Tg mice.

In future experiments, we will confirm electrophysiological and behavioral findings described in FIG. 17 and FIG. 18 using a structurally dissimilar inhibitor of histone-deacetylases, sodium butyrate (NaB). As for TSA experiments, slices from 3-4 month old APP/PS1 mice will be treated with NaB (300 µM) for 30 min prior to applying a theta-burst stimulation to induce LTP. Controls will be performed on slices from APP/PS1 mice treated with vehicle, and WT littermate mice treated with NaB or vehicle. Similarly to TSA, we will also check if NaB (1.2 g/Kg) re-establishes normal contextual fear memory in APP/PS1 mice.

The APP and PS1 transgenes could affect neuronal function through different mechanisms [A30, A31] (each herein incorporated by reference in its entirety), including direct effects by Aβ The trafficking and signaling properties of full-length APP and its cleavage products are likely different, which could impact aspects of synaptic function differently. To separate Aβ effects from other effects of APP and PS1 overexpression, we will determine whether Aβ per se is responsible for the deficits observed in our studies on Tg mice. Since it has already been described that natural oligomers of human Aβ, in the absence of monomers and fibrils, markedly inhibit LTP in vivo [A6] (herein incorporated by reference in its entirety), we will apply 200 nM oligomeric Aβ$_{42}$ concurrently with TSA (1.65 µM) for 30 minutes to WT slices prior to inducing LTP. In addition, we will impair contextual fear memory through bilateral infusion of 200 nM oligomeric Aβ$_{42}$ onto dorsal hippocampi 15 min prior to training for FC, concurrently with TSA (2 µgr/gr body weight, 2 hrs prior to training, i.p.). Without being bound by theory, oligomeric Aβ$_{42}$ should inhibit LTP and fear memory, and demonstrate that TSA reestablishes normal LTP and contextual fear memory following Aβ42 treatment. TSA alone should not have any effect. In additional experiments we will use NaB (300 µM) plus 200 nM Aβ42 for 30 min prior to applying a theta-burst stimulation to induce LTP. Controls will be performed on slices treated with vehicle. Similarly to TSA, we will also check if NaB (1.2 g/Kg) re-establishes normal contextual fear memory in Aβ42-infused mice. Collectively, these experiments will demonstrate that inhibition of histone deacetylase is beneficial against synaptic and memory dysfunction caused by elevation of oligomeric Aβ.

To Characterize CBP Involvement Following Aβ Elevation.

Based on the observations that i) WT-PS1 no longer promotes transcription on F11 cells transfected with a CBP construct lacking HAT activity, and that ii) CBP levels are reduced in APP/PS1 mice, we will determine if CBP HAT activity and levels are affected in APP/PS1 mice and after Aβ elevation.

Figure 19:
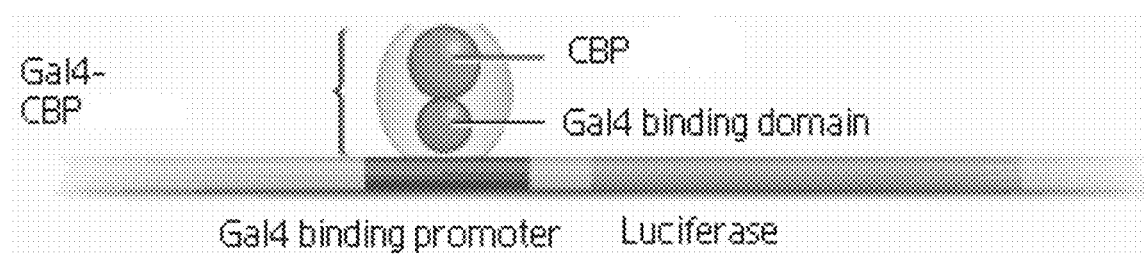
FIG. 19 is a schematic of a CBP/Gal4 hybrid and a reporter plasmid in which luciferase expression is driven by a Gal4 yeast promoter. CBP is CREB binding protein.
Figure 20:
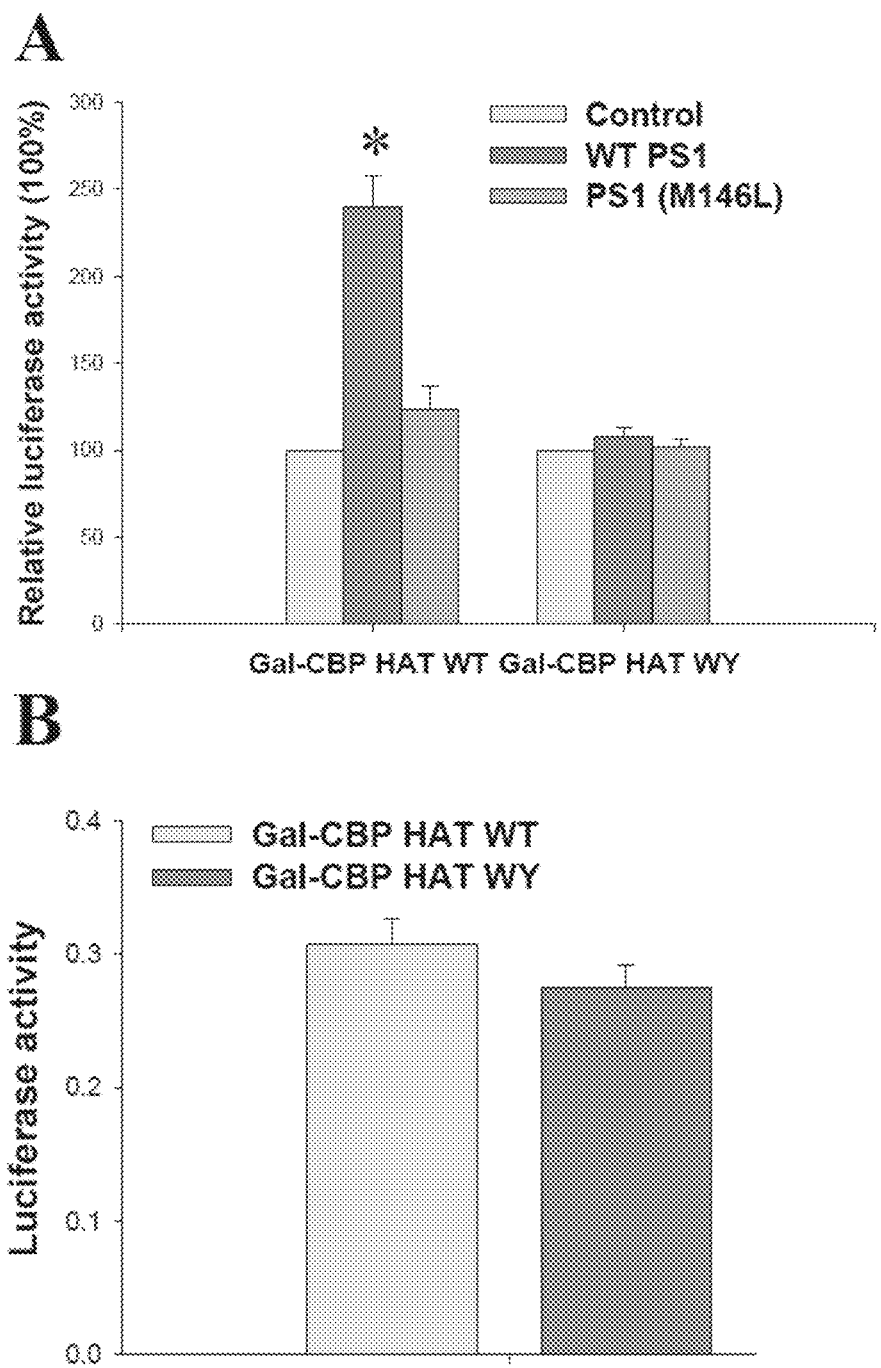
FIG. 20 are graphs that show the Role of CBP and its HAT region on transcription following PS1 stimulation.

We have recently examined if the HAT activity of CBP has any role in the stimulus effect of WT-PS1 by using a construct in which full-length CBP contains a mutation (WY—amino acids 1503-1504 replaced by alanine and serine). This mutation, which completely abolishes its HAT activity [A32] (herein incorporated by reference in its entirety), was linked to the DNA binding domain of Gal4 (FIG. 19). In contrast to the enhanced promoter activity of full-length WT-CBP, no activity was observed with WY-CBP (FIG. 20A). There was no difference in the basal activity between WT and WY Gal-CBP (FIG. 20B). Thus, a CBP mutant lacking HAT activity is not capable of responding to WT-PS1 in terms of increased transcription activating ability. Hence, CBP and its HAT region appear to be essential for enhancing transcription in vitro following PS1 stimulation. Additionally, we decided to measure endogenous CBP levels in APP/PS1 mice.

Figure 21:
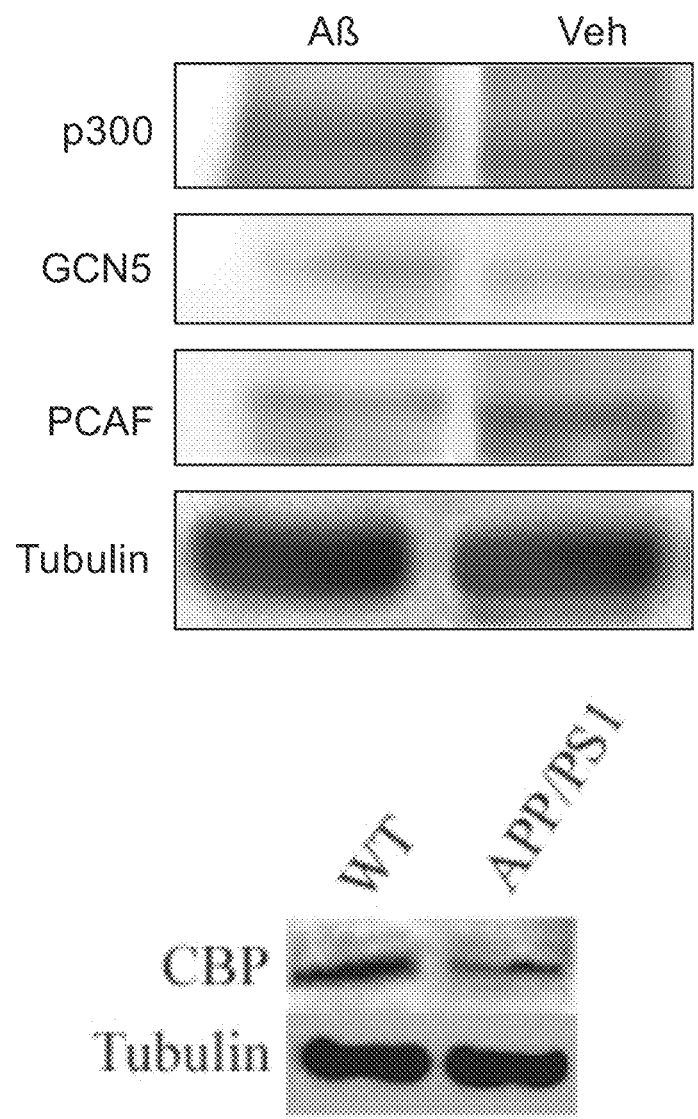
FIG. 21 shows photographs of western blots showing that endogenous expression of CBP and PCAF is reduced in APP/PS1 mice. A decrease in PCAF and CBP levels, but not p300 or GCN5, was observed in Aβ-infused mice. 4 month old APP/PS1 mice displayed reduced CBP levels compared to WT controls.

Western blot analysis from the hippocampus of 4 month old APP/PS1 mice revealed a significant decrease in CBP levels compared to WT controls (FIG. 21). In future experiments we will replicate these results. Alternative strategies will include measurement of CBP from the nuclear fraction given that changes in the CBP distribution (cytoplasm vs. nucleus) have been observed in F11 cells following overexpression of PS1(M146L) compared to WT-PS1 [A20] (herein incorporated by reference in its entirety). We will also directly measure CBP HAT activity in APP/PS1 mice both in basal condition and 1 hr after training for contextual learning compared to their WT littermates. Controls will be performed using a latent inhibition training paradigm to exclude that changes in CBP HAT activity are due to novel context alone or the electric shock instead of the association between them [A25] (herein incorporated by reference in its entirety). In the latent inhibition paradigm animals will be pre-exposed to a novel context prior to receiving the electric shock so that the animal will form a spatial memory that blocks the formation of an associative contextual fear memory. Finally, we will measure HDAC activity using a new fluorimetric assay on hippocampi using the experimental paradigm as in the HAT assay. Without being bound by theory, these experiments will establish if CBP and/or HDACs are altered following overexpression of the APP and PS1 transgenes.

Similar to the electrophysiological and behavioral experiments described herein, we will ask whether TSA administration will rescue changes in CBP levels and CBP HAT activity. We will repeat the same experiments as described herein after treatment with TSA (2 µg/g body weight; i.p), 2 hrs prior to harvesting hippocampi from APP/PS1 mice. Vehicle- and TSA-treated WT littermates will serve as controls. To separate APP and PS1 overexpression effects from Aβ per se effects, experiments described herein (including CBP levels, CBP-HAT activity and total HDAC activity with TSA or with vehicle only) will be repeated in the presence of 200 nM oligomeric Aβ42 infused onto dorsal hippocampi of WT mice compared to vehicle infused mice. Without being bound by theory, these experiments will establish if CBP and/or HDACs are altered following Aβ elevation.

Determine which Histones Acetylation Levels Change Following aβ-Elevation.

Data have shown ~50% reduction in acetylated histone 4 levels in hippocampi of APP/PS1 mice. In future experiments, we will extend our investigation to histones 2B and 3 which also play a key role in transcription and memory [A23-A25] (each herein incorporated by reference in its entirety). We will finally check if Aβ elevation affects histone acetylation.

Figure 22:
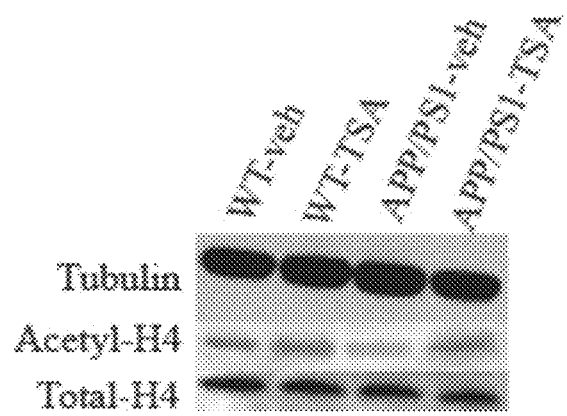
FIG. 22 is a photograph of a western blot showing acetylated H4 expression is reduced in APP/PS1 mice 1 hour after contextual FC. Treatment with TSA, 2 hours before training, rescued the histone 4 acetylation level defect of Tg mice. n=3 per each group.

We will also test if defects seen in APP/PS1 mice, compared to WT littermates, are due to epigenetic effects. Acetylation of histones 2B, 3 and 4 was shown to play a key role in transcription and memory [A23-A25] (each herein incorporated by reference in its entirety). Acetylation of H4 in hippocampus from WT and APP/PS1 animals was measured. Vehicle control solution was administered i.p. 2 hrs before FC training. 1 hr after contextual FC, the APP/PS1 and WT mice were euthanized and hippocampi were extracted. Western blot analysis demonstrated that, compared to WT mice, APP/PS1 animals had an overall reduction of more than 50% in acetylated histone 4 levels (FIG. 22). Whether HDAC inhibition might rescue the histone 4 acetylation levels defect observed in APP/PS1 mice was also tested. Injection of TSA (2 µg/g body weight; i.p) 2 hours prior to contextual fear conditioning enhanced H4 acetylation of APP/PS1 mice (FIG. 22). Without being bound by theory, AD is likely to be a disease with an epigenetic motif and HDAC inhibitors can elevate decreased levels of histone 4 in an AD mouse model.

In future experiments, we will measure basal acetylation levels of histone 4, as well as controls using the latent inhibition paradigm described herein. In addition, we will extend our studies to histones 2B and 3 by measuring their acetylation in the hippocampus of APP/PS1 and WT littermates of 4 months of age both in basal conditions and following training for FC, with and without TSA as for histone 4. Controls will be also performed using a latent inhibition training paradigm as described herein. Finally, we will confirm these findings using a structurally dissimilar inhibitor of histone-deacetylases, NaB. As for TSA experiments, we will check if NaB (1.2 g/Kg) re-establishes normal histone/s acetylation levels in APP/PS1 mice.

To separate APP and PS1 overexpression effects from Aβ per se effects, experiments described herein related to measurements of different histones acetylation levels will be repeated in the presence of 200 nM oligomeric Aβ42 infused onto dorsal hippocampi of WT mice compared to vehicle infused mice. Without being bound by theory, oligomeric Aβ42 will affect histone 4 acetylation levels. Remaining histones acetylation levels should be consistent with findings from Transgenic (Tg) mice. Additional experiments will be performed with NaB. As for TSA experiments, we will check if NaB (1.2 g/Kg) re-establishes normal histone/s acetylation levels in Aβ42-infused mice. Without being bound by theory, these experiments will demonstrate that epigenetic changes, such as reduced histone acetylation, play an important role in the Aβ-induced damage of synaptic function and memory associated with AD.

Methods

Animals:

Double Tg mice will be obtained by crossing APP and PS1 animals (genotyped by PCR)[429] (herein incorporated by reference in its entirety). For Aβ experiments we will use C57Bl6 mice.

Aβ preparation: Oligomeric Aβ$_{42}$ will be prepared from commercially available synthetic peptides (American Peptides Co), as described[433,434] (each herein incorporated by reference in its entirety).

For electrophysiology, 400 µm slices will be cut and maintained in an interface chamber at 29° C. for 90 min prior to recording, as reported (herein incorporated by reference in its entirety). Briefly, CA1 fEPSPs will be recorded by placing stimulating and the recording electrodes in CA1 Stratum radiatum. Following BST assessment, a 15 min baseline will be recorded every min at an intensity that evokes a response ~35% of the maximum evoked response. LTP will be induced using 0-burst stimulation (4 pulses at 100 Hz, with the bursts repeated at 5 Hz and each tetanus including 3 ten-burst trains separated by 15 sec).

For contextual and cued conditioning, mice will be placed in the conditioning chamber for 2 min before the onset of a discrete tone (CS) (a 30 s, 85 dB sound at 2800 Hz), as described[417] (herein incorporated by reference in its entirety). In the last 2 s of the CS, mice will be given a 2 s, 0.60 mA foot shock (US) through the bars of the floor. After the CS/US pairing, mice will be left in the conditioning chamber for 30 s and will then be placed back in their home cages. Freezing behavior will be scored using the Freezeview software (MED Ass). To evaluate contextual fear learning, freezing will be measured for 5 min in the chamber in which the mice will be trained 24 hr after training. To evaluate cued fear learning, 24 hr after contextual testing, mice will be placed in a novel context for 2 min (pre-CS test), after which they will be exposed to the CS for 3 min (CS test), and freezing will be measured.

Sensory perception of the shock will be determined through threshold assessment, as describee[417] (herein incorporated by reference in its entirety).

CBP levels will be measured with western blot using specific CBP antibodies. The nuclear fraction will be contained in the pellet obtained from homogenated tissue, centrifuged at 7,700×g for 1 min.

CBP HAT activity will be measured by immunoprecipitation from the lysis of hippocampal extracts using CBP antibodies. After isolation, HAT activity will be assessed using indirect enzyme-linked immunosorbent assay kit to detect acetyl residues according to the manufacturer's instruction (Upstate).

For HDAC activity assay, I will use a fluorimetric kit from Biovision (CA), according to the manufacturer instruction.

For histone acetylation assay, Western blot will be performed from snap-frozen in liquid nitrogen hippocampi. Nuclear proteins will be acid-extracted and separated onto a denaturing, 7%-12% acrylamide gel followed by electroblotting onto nitrocellulose. Acetylated histones (H3, H2A and H2B) will be detected using antibodies purchased from Upstate and the Amersham ECF Kit accordingly to the manufacturer protocol.

Statistical Analyses:

Experiments will be performed in blind. Results will be analyzed with ANOVA with post-hoc correction with drug or genotype as main effect.

REFERENCES

A1. Malm et al, *Proc Natl Acad Sci USA*, 2006. 103:8852-7.
A2. Cleary et al, *Nat Neurosci,* 2005. 8:79 84.
A3. Cullen et al, *Neuroreport,* 1997. 8:3213-7.
A4. Itoh et al, *Eur J Pharmacol,* 1999. 382:167-75.
A5. Vitolo, et al, *Proc Natl Acad Sci USA,* 2002. 99:13217-21.

A6. Walsh et al, *Nature,* 2002. 416:535-9.
A7. Chen et al, *J Neurosci Res,* 2000. 60:65-72.
A8. Lambert et al, *Proc Natl Acad Sci USA,* 1998. 95:6448-53.
A9. Kang et al, *Nature,* 1987. 325:733-6.
A10. Sherrington et al, *Nature,* 1995. 375:754-60.
A11. Levy-Lahad et al, *Science,* 1995. 269:970-3.
A12. Czech et al, *Prog Neurobiol,* 2000. 60:363-84.
A13. Takahashi et al, *Neurosci Lett,* 1999. 260:121-4.
A14. Rakyan et al, *Biochem J,* 2001. 356:1-10.
A15. Puzzo et al, *J Neurosci,* 2005. 25:6887-97.
A16. Puzzo et al, in *Soc Neurosci. Abstr.* 2006. Atlanta.
A17. Gong et al, *J. Clin. Invest.,* 2004. 114:1624-1634.
A18. Korzus et al, *Neuron,* 2004. 42:961-72.
A19. Saura et al, *Neuron,* 2004. 42:23-36.
A20. Francis et al, *Neuroreport,* 2006. 17:917-21.
A21. Holcomb et al, *Nat Med,* 1998. 4:97-100.
A22. Gong et al, *Cell,* 2006. 126:775-88.
A23. Fischer et al, *Nature,* 2007. 447:178-82.
A24. Alarcon et al, *Neuron,* 2004. 42:947-59.
A25. Levenson et al, *J Biol Chem,* 2004. 279:40545-59.
A26. Green et al, *J Neurosci,* 2008. 28:11500-10.
A27. Kazantsev et al, *Nat Rev Drug Discov.* 2008. 7:854-68.
A28. Masliah, E., *Histol Histopathol,* 1995. 10:509-19.
A29. Trinchese et al, *Ann Neurol,* 2004. 55:801-14.
A30. Kamal et al, *Nature,* 2001. 414:643-8.
A31. Cao et al, *Science,* 2001. 293:115-20.
A32. Bordoli et al, *Nucleic Acids Res,* 2001. 29:589-97.
A33. Stine et al, *J Biol Chem,* 2003. 278: 11612-22.
A34. Puzzo et al, *J Neurosci.,* 2008. 28:14537-14545.

Example 6—Impairment of Chromatin Remodeling Following Amyloid Elevation

In addition to CREB and CBP link to AD, epigenetic changes might also contribute to AD development. Hippocampal levels of acetylated histone 4, an acetylation important in memory formation [B19] (herein incorporated by reference in its entirety), were markedly reduced in an amyloid-depositing animal model after fear conditioning training. Without being bound by theory, changes in histone acetylation play an important role in AD.

Furthermore, after training for fear conditioning, levels of hippocampal acetylated H4 in APP/PS1 mice were dramatically lower than in wild-type littermates, indicating that changes in histone acetylation are involved in memory loss in AD. This observation is consistent with the finding that HDAC inhibition induced sprouting of dendrites, an increased number of synapses, and reinstated learning and access to LTM in the CK-p25 transgenic mouse with neuronal loss [B19] (herein incorporated by reference in its entirety). Although levels of histone acetylation were not investigated, the use of HDAC inhibitors in two additional studies is encouraging. Nicotinamide, an HDAC III inhibitor, was found to restore cognition in the triple transgenic mouse model of AD via a non-epigenetic mechanism involving reduction of cytosolic Thr231-phosphotau [B49] (herein incorporated by reference in its entirety). However, many questions remain to be answered: Does a treatment with HDAC inhibitors rescue the defects in histone acetylation, synaptic plasticity and memory both in transgenic mice with a mild plaque load and those with a more profound amyloid deposition? Can the beneficial effect of HDAC inhibitors be extended to other forms of explicit memory in addition to fear memory, such as reference memory? Are other histones, such as histones H2B and 3 which are also known to play a key role in transcription and memory [B19, B25, B26] (each herein incorporated by reference in its entirety), abnormally acetylated during memory processes in AD? Given that experiments were performed on mice overexpressing mutated APP and PS1 transgenes which might cause a variety of effects independent of Aβ elevation, is histone acetylation affected following Aβ elevation? Does the histone acetyl-transferase CBP play a role in the reduction of histone acetylation in APP/PS1 mice and following Aβ elevation?

The inventors will also discuss in this Example whether chromatin changes at the level of histone acetylation occur following elevation of Aβ during memory processes. Without being bound by theory, the results obtained will provide a new type of mechanism for Aβ-induced impairment of memory and synaptic function.

The therapies for AD that are currently in use include augmentation of the cholinergic system by usage of acetylcholinesterase inhibitors, or blockage of glutamate neurotoxicity through NMDA antagonists. These agents have a limited efficacy. Major efforts are underway to inhibit tangle formation, to combat inflammation and oxidative damage, and to decrease Aβ load in the brain either by the use of agents that inhibit β and γ secretases or increase a secretase, by the use of drugs that inhibit Aβ oligomerization, or by the use of treatments such as immunization with Aβ that appear to augment the removal of Aβ from the brain. However, the role of APP, Aβ40, and the secretases in normal physiological function might present a problem in providing effective and safe approaches to AD therapy. Drugs interfering with transcription machinery and histone acetylation might represent a new approach to AD treatment to make the cell with its synaptic contacts in which memories are thought to reside, more robust and resistant to the effects of Aβ.

HDAC Inhibition Ameliorates Deficits in Hippocampal Long-Term Potentiation in APP/PS1 Mice.

The observation that inspired these studies was the result of a series of experiments in which we tested whether a brief application of the HDAC inhibitor TSA was capable of rescuing the defect in LTP shown by slices from 3-4 month-old APP/PS1 mice (for a detailed description of the experiments showing the characterization of these mice [B50]; herein incorporated by reference in its entirety). At this age the transgenic mice just start showing the synaptic plasticity and memory impairments [B14, B50] (each herein incorporated by reference in its entirety)). As previously demonstrated [B50] (each herein incorporated by reference in its entirety), basal synaptic transmission (BST) was similar between APP/PS1 and WT mice. Hippocampal slices were then perfused with TSA (1.65 µM) for 30 min before inducing LTP through tetanic stimulation of the Schaeffer collateral pathway. Potentiation in TSA treated APP/PS1 slices was far greater than in vehicle-treated APP/PS1 slices (two-way ANOVA: $F_{1,12}$=13.166, p=0.004; FIG. 17). On the other hand, TSA did not change the amplitude of LTP in hippocampal slices from WT mice compared to WT slices treated with vehicle alone ($F_{1,12}$=0.512, p=0.488, FIG. 17). Moreover, TSA perfusion did not affect baseline transmission in APP/PS1 and WT slices that received no tetanus (n=3 per each group). Thus, HDAC inhibition is capable of rescuing the defect in LTP in the APP/PS1 animal model of Aβ deposition.

HDAC Inhibition Rescues the Defect in Associative Memory in APP/PS1 Mice.

Similar to humans affected by AD [B51] (herein incorporated by reference in its entirety), APP/PS1 mice exhibit a deficit in associative memory [B46] (herein incorporated by reference in its entirety). In rodents, associative learning can be assessed by contextual fear conditioning. This behavioral task, which is based on the association of a neutral stimulus with an aversive one, is dependent on hippocampal function [B52] (herein incorporated by reference in its entirety). Thus, following experiments on acute effect of TSA in synaptic dysfunction, we determined if TSA is beneficial against impairment of contextual fear conditioning in 3-4 month old APP/PS1 mice [B14] (herein incorporated by reference in its entirety). Animals were divided into 4 groups: APP/PS1 with TSA, APP/PS1 with vehicle, WT with TSA and WT with vehicle. TSA and vehicle control solution were administered i.p. at a concentration of 2 mg/Kg body weight. We found a similar shock threshold among the various groups of mice. Then, mice were trained to associate neutral stimuli with an aversive one. They were placed in a novel context (fear conditioning box), exposed to a white noise cue paired with a mild foot shock, and injected with TSA 2 hrs before training. Fear learning was assessed 24 hrs later by measuring freezing behavior—the absence of all movement except for that necessitated by breathing—in response to representation of the context. We found no difference in the freezing behavior among the 4 groups of mice during the training phase of the fear conditioning ($F_{3,47}$=0.02997, p=0.9929, n=12-13/group; FIG. 18). Twenty-four hours later, we found a decreased freezing behavior in vehicle-treated APP/PS1 mice compared to vehicle-treated WT littermates in the analysis of the contextual learning ($F_{3,47}$=0.0526, p=0.0280, n=12-13/group; FIG. 18).

Freezing in vehicle-treated APP/PS1 mice was about 46% that of vehicle-treated WT mice [vehicle-treated APP/PS1 mice: 14.88±2.97% vs. vehicle-treated WT littermates: 31.68±5.32%; n=13 (11 females plus 2 males) and n=13 (11 females plus 2 males), respectively; t=2.76, p=0.0109; FIG. 18]. However, the freezing time was increased in APP/PS1 mice after the injection of TSA to about 236.27% of vehicle-treated APP/PS1 mice [TSA-treated APP/PS1 mice: 35.15±6.99%, n=12 (10 females plus 2 males); t=2.744, p=0.0116; FIG. 18]. Statistical analysis revealed that freezing in APP/PS1 mice was not significantly different with respect to both TSA-treated (t=0.1902, p=0.8508) and vehicle-treated WT mice (t=0.3982, p=0.6941). TSA-treated WT mice showed a slight non-significant increase in freezing compared to vehicle-treated WT mice [TSA-treated WT mice: 36.95±6.43%; n=13 (11 females plus 2 males); t=0.6316, p=0.5336, FIG. 18]. We next tested cued fear conditioning, a hippocampus-independent task [B46] (herein incorporated by reference in its entirety), and did not find a difference in freezing behavior among the 4 groups (both in the pre-CS group, $F_{3,25}$=0.8763, p=0.4666, and in the CS group, $F_{3,24}$=0.6398, p=0.5968). This result indicates that the function of the amygdala, which is involved mainly in cued conditioning and is known to be normal in APP/PS1 mice, is not affected by the inhibition of HDACs by TSA, as previously demonstrated [B53] (herein incorporated by reference in its entirety). Taken together, these data show that the inhibition of histone deacetylation is able to re-establish normal associative memory in the APP/PS1 mouse while also restoring normal synaptic plasticity.

HDAC Inhibition Rescues the Defect in Associative Memory by Aβ Elevation.

Figure 24:
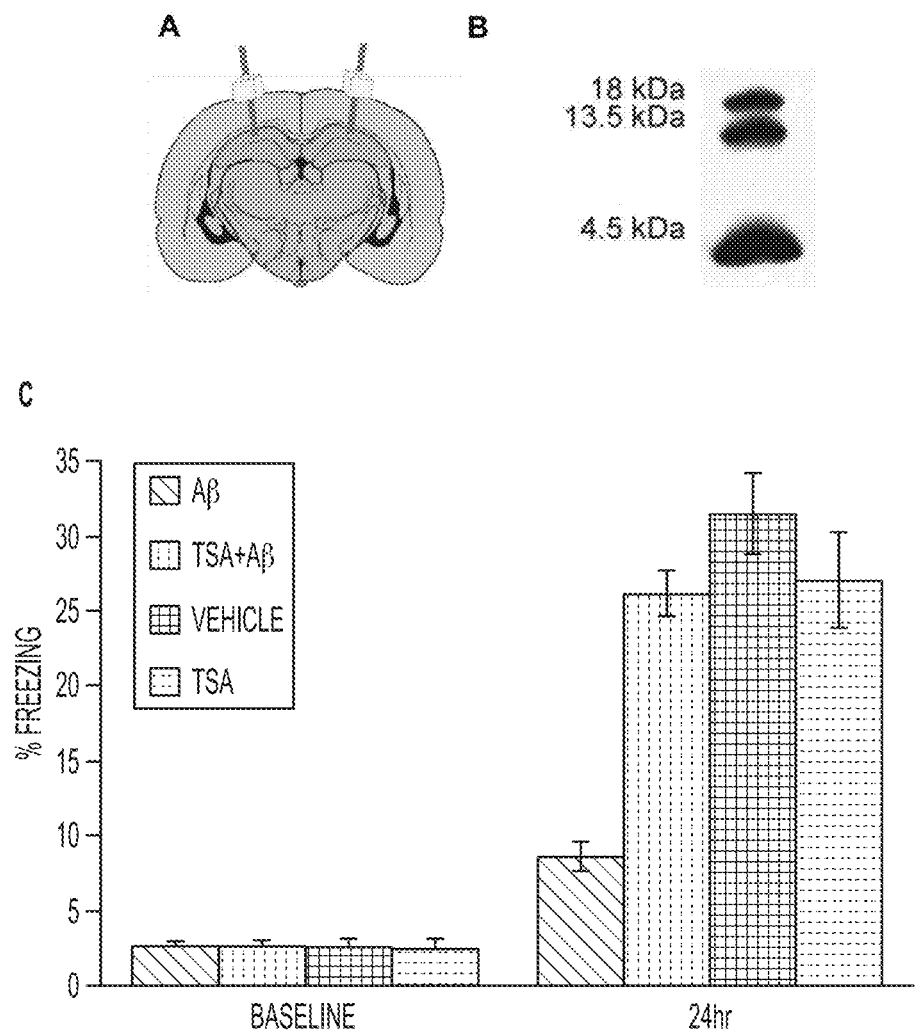
FIG. 24 depicts HDAC inhibition improves contextual fear conditioning in mice in which dorsal hippocampi were infused with a preparation containing oligomeric Aβ42.

The APP and PS1 transgenes could affect neuronal function through different mechanisms [B23, B24] (each herein incorporated by reference in its entirety), including direct effects by Aβ. Full-length APP and its cleavage products could differently impact H4 acetylation. To separate Aβ effects from other effects of APP and PS1 overexpression, we next determined whether Aβ per se is responsible for the deficit in H4 acetylation observed in our studies on transgenic mice. Since it has already been described that natural oligomers of human Aβ, markedly inhibit memory in vivo [B54, B55] (each herein incorporated by reference in its entirety), we applied a preparation containing oligomeric Aβ42 (200 nM in a volume of 1 μl, bilaterally, slowly over 1 min) into dorsal hippocampi (FIG. 24A-B), 15 min prior to training for fear conditioning, with injection of TSA or vehicle (2 mg/kg body weight, 2 hrs prior to training, i.p.). Infusion occurred 5-7 days after implanting cannulas onto dorsal hippocampi. We found no difference in the freezing behavior among the 4 groups of mice during the training phase of the fear conditioning ($F_{3,41}$=0.04188, p=0.9884, n=8-14/group; FIG. 24C). Twenty-four hours later, freezing behavior was decreased in Aβ-infused mice compared to vehicle-infused mice in the analysis of the contextual learning ($F_{3,41}$=3.619, p=0.0209, n=8-14/group; FIG. 24C). Freezing in Aβ-infused mice was about 25% that of vehicle-infused mice [Aβ-infused mice: 8.580±2.119% vs. vehicle-infused mice: 31.46±5.373% n=12 and 11 males, respectively; t=3.147, p=0.0049; FIG. 24C]. However, the freezing time was increased in Aβ-infused mice after the injection of TSA to about 300% of Aβ-infused mice (TSA+Aβ treated mice: 26.17±4.747% n=14 males; t=3.066, p=0.0053; FIG. 24). Statistical analysis revealed that freezing in Aβ-infused mice that were injected with TSA was not significantly different with respect to both TSA-injected (t=0.1902, p=0.8508) and vehicle-injected mice (t=0.3982, p=0.6941) that were infused with vehicle. TSA-treated mice showed similar amounts of freezing as vehicle-treated mice [TSA-treated mice: 27.01±7.246%; n=8 males; t=0.4335, p=0.6701, FIG. 24C]. We next tested cued fear conditioning, and did not find a difference in freezing behavior among the 4 groups (both in the pre-CS group, $F_{3,52}$=1.547, p=0.2135, and in the CS group, $F_{3,52}$=0.4838, p=0.6950). Taken together, these data show that the inhibition of histone deacetylation is able to re-establish normal associative memory following Aβ elevation.

APP/PS1 Mice Display a Reduced Endogenous Level of Histone 4 Acetylation in Response to a Learning Task.

Given that HDAC inhibitors are known to acetylate other molecules besides histones [B49] (herein incorporated by reference in its entirety), our next goal was to determine whether the effect of TSA on the defect in fear memory of APP/PS1 mice was linked, at least in part, to chromatin changes at the level of histone acetylation. Acetylation of H4 was shown to play a key role in transcription and memory [B19] (herein incorporated by reference in its entirety). Thus, we asked whether the memory deficit observed in APP/PS1 mice are associated with altered acetylation of H4. We measured acetylation of H4 in hippocampus from 3 to 4 month old wild-type (WT) and APP/PS1 animals, after training for fear conditioning. Vehicle control solution was administered i.p. 2 hrs before training and 1 hour after it mice were euthanized and hippocampi were extracted. Western blot analysis demonstrated that, compared to WT mice, APP/PS1 animals had an overall reduction of more than 50% in acetylated H4 levels (t=2.702, p=0.0355; FIG. 25A). Interestingly, in interleaved experiments, injection of the class I/II HDAC inhibitor, TSA (2 mg/kg body weight; i.p, 2 hours prior to training for fear conditioning) enhanced H4 acetylation of APP/PS1 mice (t=3.283, p=0.0168 compared to vehicle-treated APP/PS1 littermates; FIG. 25A). Furthermore, H4 acetylation levels in hippocampi from TSA-treated APP/PS1 mice were similar to levels in TSA-treated WT littermates (t=0.2116, p=0.8385; FIG. 5A). Finally, as previously demonstrated [B26] (herein incorporated by reference in its entirety), TSA increased H4 acetylation levels in WT mice (t=7.659, p=0.0001) compared to hippocampi from vehicle-treated WT littermates; FIG. 25A).

We next wanted to determine if there are any changes in the basal acetylation levels of H4 in APP/PS1 mice, compared to wild-type mice. We therefore measured acetylation of H4 in hippocampi from 3 to 4 month old WT and APP/PS1 animals which were exposed to the context without receiving an electrical shock. We found no difference between the two experimental groups in basal acetylated H4 (t=0.076, p=0.9427; FIG. 25B). This demonstrates that i) the overexpression of mutated APP and PS1 transgenes affects epigenetic changes at the level of H4 acetylation after contextual fear learning; and ii) TSA is able to elevate the decreased levels of histone 4 in an AD mouse model.

Role of CBP and its HAT Region on Transcription Following PS1 Stimulation.

Studies of the mechanisms underlying memory formation have defined central roles for CRE-dependent gene expression, which is mediated by the transcription factor CREB and the coactivator CBP. CBP creates a bridge between CREB and the basal transcriptional machinery and acetylates histones. Histone acetylation, in turn, induces chromosomal changes resulting in loss of chromosomal repression (see FIG. 23). This allows successful transcription of the underlying genes needed for synthesis of proteins underlying memory formation. We have recently examined if the HAT activity of CBP has any role in the stimulus effect of WT-PS1 by using a construct in which full-length CBP contains a mutation (WY—amino acids 1503-1504 replaced by alanine and serine). This mutation, which completely abolishes its HAT activity [B56] (herein incorporated by reference in its entirety), was linked to the DNA binding domain of Gal4 (FIG. 19). In contrast to the enhanced promoter activity of full-length WT-CBP, no activity was observed with WY-CBP (FIG. 20A). There was no difference in the basal activity between WT and WY Gal-CBP (FIG. 20B). Thus, these findings indicate that a CBP mutant lacking HAT activity is not capable of responding to WT-PS1 in terms of increased transcription activating ability. Hence, CBP and its HAT region appear to be essential for enhancing transcription in vitro following PS1 stimulation.

APP/PS1 Mice Display Reduced CBP Levels.

We next decided to measure endogenous CBP levels in APP/PS1 mice. Western blot analysis from the hippocampus of 4 month old APP/PS1 mice revealed a significant decrease in CBP levels compared to WT controls (FIG. 21) consistent with the observation that cerebral CBP levels are reduced in mice lacking functional PSs [B15] (herein incorporated by reference in its entirety). In future experiments, we will replicate these results to increase the number of experiments to firmly establish that overexpression of mutated APP and PS1 transgenes affects CBP levels.

Aims

1. To Determine if Inhibition of Histone De-Acetylation Rescues Synaptic and Memory Defects Following Aβ Elevation.

Inhibition of histone de-acetylation through trichostatin A (TSA) rescues the deficits in LTP and contextual fear memory in APP/PS1 mice [B20, B21] (each herein incorporated by reference in its entirety), a transgenic animal expressing the Swedish mutation in APP(K670M:N671L) together with the mutation in PS1(M146L, line 6.2) [B22]. We will now test whether the structurally dissimilar inhibitor of histone-deacetylases, sodium butyrate (NaB), rescues the synaptic and memory deficits. Given that these observations were obtained in 4 month old APP/PS1 mice when amyloid plaques are just starting to form, we will extend them to 7 month old transgenic animals which have a more profound Aβ deposition. In addition, given that APP and PS1 transgenes could affect neuronal function via different mechanisms [B23, B24] (each herein incorporated by reference in its entirety), including direct effects by Aβ, we will investigate whether inhibition of histone de-acetylation rescues defects of LTP and contextual fear memory induced by Aβ per se. We will also extend these findings to another form of explicit learning, the reference memory.

Research Design and Methods.

Rationale.

A widely accepted concept in the memory field is that memories are stored in the brains as long-lasting changes in synaptic strength. Consistent with this concept AD is thought to begin as a synaptic disorder that progressively leads to greater neuronal dysfunction, leading to memory loss [B57] (herein incorporated by reference in its entirety). Without being bound by theory, HDAC inhibition counteracts the impairment of synaptic plasticity and memory following amyloid elevation. We will test this with an additional and structurally dissimilar inhibitor, NaB, in addition to TSA. Next, given that APP and PS1 transgenes could affect neuronal function through different mechanisms [B23, B24] (each herein incorporated by reference in its entirety), we will determine whether Aβ per se is responsible for the deficit in histone acetylation observed in our studies on transgenic mice. Moreover, we will extend our findings to older APP/PS1 mice when they have a severe plaque load [B50] (herein incorporated by reference in its entirety). Finally, we will extend our findings to another form of explicit memory in addition to fear memory, the reference memory. Without being bound by theory, inhibition of histone deacetylase is beneficial against synaptic and memory dysfunction caused by elevation of oligomeric Aβ.

Experimental Design

We will confirm electrophysiological and behavioral findings described in FIG. 17 and FIG. 18 using the structurally dissimilar inhibitor NaB. As for TSA experiments, slices from 3-4 month old APP/PS1 mice will be treated with NaB (300 µM) for 30 min prior to applying a theta-burst stimulation to induce LTP. Controls will be performed on slices from APP/PS1 mice treated with vehicle, and WT littermate mice treated with NaB or vehicle. Similarly to TSA, we will also check if NaB (1.2 g/Kg) re-establishes normal contextual fear memory in APP/PS1 mice. In these behavioral experiments, animals were divided into 4 groups: APP/PS1 with NaB, APP/PS1 with vehicle, WT with NaB and WT with vehicle. Controls will be also performed using a latent inhibition training paradigm to exclude that HDAC inhibitors act through an effect on novel context alone or the electric shock instead of the association between them [B26] (herein incorporated by reference in its entirety). In the latent inhibition paradigm animals will be pre-exposed to a novel context prior to receiving the electric shock so that the animal will form a spatial memory that blocks the formation of an associative contextual fear memory [B26] (herein incorporated by reference in its entirety).

We will separate APP and PS1 overexpression effects from Aβ per se effects. We have already demonstrated that TSA rescues the defect of contextual fear memory induced by a preparation containing oligomeric Aβ42 (see FIG. 24). Thus, we will determine whether TSA rescues the defect in LTP induced by 200 nM oligomeric Aβ42. Since it has already been described that natural oligomers of human Aβ, in the absence of monomers and fibrils, markedly inhibit LTP in vivo [B29] (herein incorporated by reference in its entirety), we will apply 200 nM oligomeric Aβ42 concurrently with TSA (1.65 µM) for 30 minutes to WT slices prior to inducing LTP. In interleaved control experiments we will apply oligomeric Aβ42 alone, or TSA alone, or vehicle.

We will replicate findings described herein using NaB (300 µM) plus 200 nM Aβ42 for 30 min prior to applying a theta-burst stimulation to induce LTP. Controls will be performed on slices treated with vehicle. As for TSA, we will also check if NaB (1.2 g/Kg) rescues defect in contextual fear memory in Aβ42-infused mice. In these behavioral experiments controls will be also performed using a latent inhibition training paradigm to exclude that HDAC inhibitors act through an effect on novel context alone or the electric shock instead of the association between them [B26] (herein incorporated by reference in its entirety).

We will repeat all of the experiments described herein with older mice (7 months), when a more severe plaque load exists and synaptic dysfunction includes also BST [B50] (herein incorporated by reference in its entirety).

We will extend our findings on contextual fear memory to another form of explicit memory, the reference memory. We have recently implemented a method that has the advantage of taking very short time [B58] (herein incorporated by reference in its entirety). The method is a hybrid of the Morris water maze and the radial arm land maze. The motivation for the animals is the immersion in water. The mouse needs to swim in 6 alleys (arms) radiating from a central area until it finds a hidden (submerged) platform at the end of one of the arms. The goal arm is kept constant for all trials, with a different start arm on successive trials, such that the learning criterion will be reached in 2 days. The number of incorrect arm entries will be. At the end of the task, the mice will perform visible platform testing to exclude the possibility that visual, motor and motivational deficits affect the outcome of the experiments. In these experiments 3-4 and 7 month-old APP/PS1 and WT littermates will be injected with TSA or NaB, 2 hrs prior to performing the task. Vehicle will be used in control experiments. Similar experiments assessing reference memory will be also performed in Aβ42-infused mice (for these experiments mice will be divided into the following groups: Aβ42-infused animals+ TSA or NaB or vehicle, vehicle-infused animals+ TSA or NaB or vehicle).

Without being bound by theory, we will show that HDAC inhibition rescues the deficits of LTP and memory. If not, as an alternative strategy, we will try higher concentrations of the HDAC inhibitors, or a structurally dissimilar HDAC inhibitor such as MS-275 which has also been shown to cross the blood-brain-barrier [B59] (herein incorporated by reference in its entirety). Then, the rodent will undergo electrophysiological and behavioral testing as described herein. Without being bound by theory, oligomeric Aβ42 will inhibits LTP and fear memory, and demonstrate that TSA ameliorates LTP and contextual fear memory following Aβ42 treatment. TSA alone should not have any effect. Findings from young mice or Aβ-infused animals should be confirmed in 7 month old transgenics. If not, as an alternative strategy, we will try longer treatments with the HDAC inhibitors, starting 1 or 4 weeks before testing. Finally, without being bound by theory, findings with the reference memory task should be in agreement with those obtained with fear conditioning. If so, these results should demonstrate that inhibition of histone deacetylase is beneficial against cognitive loss in general in AD-like animal models. If not, this will be equally interesting as it will demonstrate a dissociation between different types of memory and usage of HDAC inhibitors.

Studies investigating mechanisms underlying LTP in acute hippocampal slices indicate that transcription is not necessary for potentiation occurring prior to 2 hours [B26] (herein incorporated by reference in its entirety). However, we observed an effect of TSA immediately after induction of LTP (FIG. 17). This finding is consistent with the result of Levenson et al. [B26] (herein incorporated by reference in its entirety). The LTP induction paradigm they applied induces a form of LTP that is dependent upon transcription for either induction or expression. This was proved by using 5,6-dichlorobenzimidazole riboside (DRB), a transcription inhibitor, in WT mice. DRB was able to block both the early and late phase of a TSA-induced LTP increase, indicating that both the early and late enhancements of LTP by TSA are dependent upon transcriptional modulation [B26] (herein incorporated by reference in its entirety).

TSA and other HDAC inhibitors represent a new approach to AD treatment that appears to make the synapse more robust and resistant to the effects of Aβ. With regards to the use of HDAC inhibitors, it has been criticized that inhibition of HDACs might alter gene expression globally and thus affect memory processes in a nonspecific manner. However, Vecsey et al [B53] (herein incorporated by reference in its entirety) showed that TSA does not globally alter gene expression but instead increases the expression of specific genes during memory consolidation. They were able to show that HDAC inhibitors, including TSA, enhance memory and synaptic plasticity mainly by the activation of key genes that are dependent on CREB transcriptional activation [B53] (herein incorporated by reference in its entirety). Thus, it is likely that TSA may be capable of stopping memory degradation in the presence of Aβ accumulation as well as improving brain functions that have already deteriorated, as in the case of the 3-month-old APP/PS1 mouse. Interestingly, 'rewiring' of the brain and recovery of memory using HDAC inhibitors was recently reported in CK-p25 transgenic mice [B19] (herein incorporated by reference in its entirety). Therefore, it is possible that HDAC inhibitors could be capable of re-establishing neural networks in the AD brain. This indicates that using small molecules to target HDACs in AD patients could facilitate access to long-term memories. HDAC inhibitors with minimized side-effects are currently being developed by the pharmaceutical industry. It remains to be seen if these newer inhibitors can readily enter the brain and if they are as effective as TSA.

HDAC inhibitors could affect neuronal function through a variety of mechanisms including epigenetic and non-epigenetic changes [B19, B60] (each herein incorporated by reference in its entirety). Thus, the block of HDACs class I/II may increase the acetylation of non-histone substrates that, in turn, can contribute to the amplification of cellular processes associated with memory. Green et al. [B49] (herein incorporated by reference in its entirety) showed that inhibition of class III NAD+-dependent HDACs using vitamin B3 restored cognitive deficits in the triple transgenic AD mice, via a mechanism involving the reduction of Thr231-phosphotau in the cytoplasm.

2. To Determine if Histones 2B, 3 and 4 are Abnormally Acetylated Following Aβ Elevation.

Hippocampi from 3-4 month old APP/PS1 mice exhibit, after fear conditioning training, approximately a 50% reduction in acetylated histone 4 (H4) levels, an acetylation that was shown to be important in memory formation [B19]

(herein incorporated by reference in its entirety). In future experiments, we will extend our investigation to histones 2B and 3 because they also play a key role in transcription and memory [B19, B25, B26] (each herein incorporated by reference in its entirety). Furthermore, we will examine older transgenic mice with a more severe plaque load (7 months). Finally, to separate Aβ effects from other effects of APP and PS1 overexpression, we will check if Aβ infusion into the hippocampi affects acetylation of histones 2B, 3 and 4.

Research Design and Methods.

Rationale.

Figure 25:
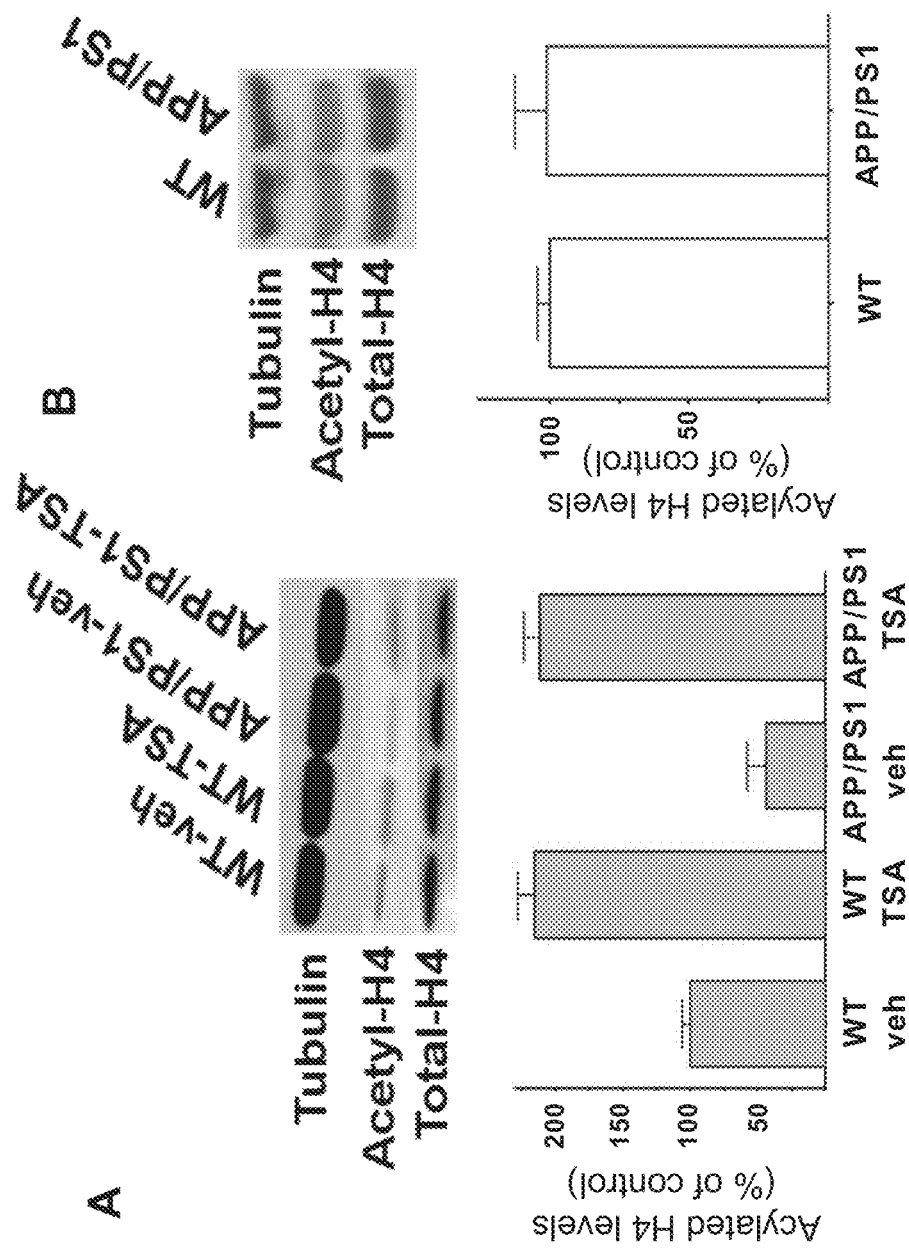
FIG. 25 depicts histone acetylation reduction in APP/PS1 mice.

Overexpression of mutated APP and PS1 transgenes affects changes in H4 acetylation occurring during contextual fear learning (see FIG. 25). In addition, HDAC inhibition through TSA is able to elevate the decreased levels of H4 in an AD mouse model. Without being bound by theory, epigenetic mechanisms at the level of histone acetylation may be impaired during learning and memory in AD. Additional histones undergoing changes in acetylation during learning and memory are H2B and H3 [B19, B25] (each herein incorporated by reference in its entirety). Therefore, in future experiments we will extend our studies to these histones. Moreover, we will test the structurally dissimilar inhibitor of histone-deacetylases, NaB. Next, given that APP and PS1 transgenes could affect neuronal function through different mechanisms [B23, B24] (each herein incorporated by reference in its entirety), we will determine whether Aβ per se is responsible for the deficit in histone acetylation observed in our studies on transgenic mice. Finally, we will extend our findings to older APP/PS1 mice when they have a severe plaque load [B50] (herein incorporated by reference in its entirety).

Experimental Design

We will measure acetylation of H2B and H3 in the hippocampus of APP/PS1 and WT littermates of 4 months of age, both in basal conditions and following training for fear conditioning, with TSA (2 mg/kg body weight; i.p, 2 hours prior to training for fear conditioning) or vehicle as for H4. Controls will be performed using a latent inhibition training paradigm to exclude that histone modifications are due to novel context alone or the electric shock instead of the association between them [B26] (herein incorporated by reference in its entirety). Immediately following sacrifice, brain tissue will be dissected and the two hippocampi from each mouse pooled and flash frozen for later homogenization and analysis. Additional controls will use cerebellum.

We will test whether NaB (1.2 g/Kg) is also capable of ameliorating acetylation of H2B, 3 and 4 in the same experimental paradigm and controls as in the TSA experiments described herein in Example 6.

We will repeat all of the experiments described herein Example 6 to measure acetylation of H4, 2A and 3 in the presence of 200 nM oligomeric Aβ42 infused into dorsal hippocampi of WT mice compared to vehicle-infused mice. Controls will be performed using a latent inhibition training paradigm and also using cerebellum.

Findings in Example 6 will be confirmed with the structurally dissimilar NaB. As for TSA experiments, we will check if NaB (1.2 g/Kg) re-establishes normal histones acetylation levels in Aβ42-infused mice. Also for these experiments, controls will be performed on vehicle-infused mice and using a latent inhibition training paradigm, as well as cerebellum.

We will also investigate whether we can ameliorate levels of histone acetylation when profound amyloid load occurs. To address this question which is directly related to the therapeutic possibility of using HDAC inhibitors in advanced stages of AD pathology, we will repeat the experiments as described herein on older APP/PS1 mice (7 months).

Without being bound by theory, oligomeric Aβ42 will affect H4 acetylation levels and oligomeric Aβ42 will produce the same effects on acetylation levels of histones 2B and 3 as in transgenic mice. If not, we will try more prolonged applications of 200 nM oligomeric Aβ42 through Alzet osmotic mini-pumps (1 day, 1 week, 1 month). Problems related to the use of a synthetic preparation containing Aβ42 are greatly alleviated by the use of transgenic animals which produce natural forms of Aβ. Studies on H2B and 3 will provide a more complete picture of the type of epigenetic changes occurring at the level of histone acetylation. Finally, research in older mice will help understanding whether HDAC inhibitors might be used at older disease stages. Taken all together, the studies described herein will help establishing epigenetic changes as events occurring following Aβ elevation.

In addition to histone acetylation, other histone posttranslational modifications (PTMs) such as phosphorylation, sumoylation, ubiquitination, and methylation were shown to regulate transcription [B7] (herein incorporated by reference in its entirety). For example, histone modifications associated with active gene transcription, such as H3 Lys4 methylation and H3 Lys56 acetylation, were found to lead to gene expression. But, histone modifications associated with the inactivation of gene transcription, such as H3 Lys27 methylation and H2A Lys119 ubiquitination were found to cause gene silencing. PTMs that are modified as a consequence of chronic neuronal exposure to oligomeric forms of Aβ42 in mice. As described (see FIG. 24), 200 nM oligomeric Aβ42 will be infused into dorsal hippocampi of WT mice. The hippocampi of Aβ42-infused mice will be removed and compared to those of vehicle-infused mice. We will carry mass spectrometry, using immunoprecipitated H2B, 3 and 4, on hippocampi and search for different histone PTMs between Aβ42-infused mice and vehicle-infused animals. To control for non-specific effects, we will have a $3^{rd}$ group of mice in which we infuse a well studied neurotoxin, gamma-acetylenic GABA, which is not directly related to AD. We will then test several of the most interesting histone PTMs in our APP/PS1 mouse model. These mice will be sacrificed at 1 month (prior to plaque formation), 2 months (as plaques start to form), 3-4 months (at early stages of plaque formation), and 7 months (at late stages of plaque formation) of age to test when this histone PTMs occur. Without being bound by theory, epigenetic changes, such as reduced histone acetylation, are likely to play an important role in the Aβ-induced damage of synaptic function and memory associated with AD.

3. To Determine if Levels and/or Activity of the Histone Acetyl-Transferase CBP are Modified Following Aβ Elevation.

CBP HAT activity is essential for enhancing transcription in vitro following PS1 stimulation. Furthermore, CBP levels in 3-4 month old APP/PS1 mice were found to be lower than in WT mice. In future experiments, we will extend this observation to older transgenic mice and following hippocampal Aβ infusion. In addition, we will determine if CBP HAT activity is affected both in young and older APP/PS1 mice as well as after Aβ infusion. Finally, we will determine whether stimulation of HAT activity through a recently synthesized HAT agonist, MOM, rescues the deficits in LTP, memory, and histone acetylation following Aβ elevation.

Research Design and Methods.

Rationale.

Endogenous CBP levels are reduced in APP/PS1 mice (see FIG. 21). These data are consistent with the observation that cerebral CBP levels are reduced in mice lacking functional PSs [B15] (herein incorporated by reference in its entirety). In addition, given that CBP and its HAT region appear to be essential for enhancing transcription in vitro following PS1 stimulation (see FIG. 20), we will directly measure CBP HAT activity in APP/PS1 mice both in basal condition and 1 hr after training for contextual learning compared to their WT littermates. If we find a reduction in both CBP levels and/or HAT activity, we will also check whether use of a HAT agonist [B61] (herein incorporated by reference in its entirety) rescues the defect in contextual fear memory and histones acetylation. Next, given that APP and PS1 transgenes could affect neuronal function through different mechanisms [B23, B24] (each herein incorporated by reference in its entirety), we will determine whether Aβ per se is responsible for the deficit in CBP levels and/or activity observed in transgenic mice. Finally, we will extend our findings to older APP/PS1 mice when they have a severe plaque load [B50] (herein incorporated by reference in its entirety). Taken together, whether CBP levels and/or activity are altered following overexpression of the APP and PS1 transgenes will be assessed, in addition to whether CBP levels and/or activity are altered following Aβ elevation. The investigators will examine whether HAT agonists rescue defects in synaptic and memory function, as well as histone acetylation.

Experimental Design

We will measure CBP levels in the hippocampus of APP/PS1 and WT littermates of 4 months of age. Immediately following sacrifice, brain tissue will be dissected and the two hippocampi from each mouse pooled and flash frozen for later homogenization and analysis. Additional controls will use cerebellum.

We will directly measure CBP HAT activity in APP/PS1 mice both in basal condition and 1 hr after training for contextual learning compared to their WT littermates. Controls will be performed using a latent inhibition training paradigm to exclude that changes in CBP HAT activity are due to novel context alone or the electric shock instead of the association between them [B26] (herein incorporated by reference in its entirety). Additional controls will use cerebellum.

A HAT agonist, such as N-(4-chloro-3-trifluoromethylphenyl)-2-ethoxy-benzamide (CTB or also referred to as compound 6J) [B61] (herein incorporated by reference in its entirety) was synthesized. Another benzamide HAT agonist, MOM, was synthesized to check if up-regulation of HAT activity rescues the defect in LTP, contextual fear memory and histone acetylation of APP/PS1 mice. We have synthesized the compound (FIG. 26A) and shown that it induces histone acetylation (FIG. 26B). We will test whether MOM rescues the LTP defect in hippocampal slices from APP/PS1 mice following the same experimental paradigm as described herein. MOM (10 μM) or vehicle will be applied for 30 min prior to inducing LTP with the 0-burst. WT littermate slices treated with MOM or vehicle will be used as controls. Next, we will check if the agonist rescues the defect in contextual fear memory in APP/PS1 animals following the same experimental paradigm as described herein. We will also check if MOM re-establishes normal reference memory.

Given that MOM does not cross the blood brain barrier, cannulas will be implanted into the dorsal hippocampi of APP/PS1 mice and WT littermates to deliver it directly into the hippocampi. We will infuse 100 μg in 1 slowly over 1 min. The infusion will occur 2 hrs prior to applying the foot shock for fear conditioning. As in the experiments described herein, we will measure the amount of freezing at 24 hrs to assess contextual fear memory followed by cued fear memory at 48 hrs. For the water maze experiments, in turn, we will measure the number of incorrect arm entries. Finally, in a separate set of experiments hippocampi and cerebella will be removed at 1 hr after training for fear conditioning and histone acetylation levels will be measured. If we find that MOM rescues the LTP and memory defects, as well as hippocampal histone acetylation of APP/PS1 mice, we will conclude that HAT agonists might ameliorate the defect in LTP, memory and histone acetylation following overexpression of APP and PS1 transgenes. The protocol will also be carried out for testing the effect of the HAT activator, CTB.

All of the experiments described herein, including CBP levels, HAT activity, and usage of MOM and CTB, will be repeated in the presence of 200 nM oligomeric Aβ42 infused into dorsal hippocampi of WT mice compared to vehicle infused mice.

We will also investigate whether we can ameliorate defect in CBP levels and/or HAT activity when profound amyloid load occurs. To address this question, we will repeat the experiments described herein Example 6 on older APP/PS1 mice (7 months).

Problems related to the use of a synthetic preparation containing Aβ42 are greatly alleviated by the use of transgenic animals which produce natural forms of Aβ. Experiments examining CBP levels will be performed. However, if CBP levels are not affected, we will employ an alternative strategy by measuring CBP from the nuclear fraction. Changes in the CBP distribution have been observed in F11 cells. CBP is mostly found in the nucleus of cells over-expressing WT-PS1, whereas cells over-expressing the mutant form of PS1 show CBP in both the cytoplasm and the nucleus [B18] (herein incorporated by reference in its entirety). Thus, we should be able to determine if changes in CBP localization might play a role in the development of AD.

It is difficult to predict whether CBP HAT activity is changed. Moreover, one cannot exclude the possibility that changes in CBP HAT activity occur at a defined time after training for fear conditioning. Therefore, we will also measure hippocampal HAT activity at different time points (1 min, 5 min, 20 min and 2 hrs) after the electric shock (with controls similar to experiments described herein). Thus, a picture of the changes occurring at the level of the transcription machinery following Aβ elevation should be able to be obtained.

We will measure HDAC activity through a new fluorimetric assay on hippocampi using the experimental paradigm as in the HAT assay (basal, 1 min, 5 min, 20 min and 1 hour after foot shock). An additional alternative possibility is that other HATs are involved in the reduction of histone acetylation. These include GNATs family, MYST family, p300, and ACTR/SRC-1. We will measure levels and activity of these HATs.

Finally, one cannot exclude the possibility that MOM or CTB does not rescue the defect in LTP, memory and histones acetylation in APP/PS1 mice as well as Aβ-infused mice. If so, as an alternative strategy, we will try longer treatments with the HAT agonist, starting a week before testing or at 6 weeks of age prior to plaque appearance for the experiments on double transgenic animals.

General Methods of the Example

Animals.

Double transgenic mice will be obtained by crossing APP and PS1 animals (genotyped by PCR) [B20, B21, B50] (each herein incorporated by reference in its entirety). For Aβ experiments we will use C57Bl6 mice which will be obtained from a breeding colony. All the mice will be maintained on a 12 h light/dark cycle (with lights on at 6:00 A.M.) in temperature- and humidity-controlled rooms. Food and water will be available ad libitum.

Electrophysiological Studies.

We will cut 400 μm hippocampal slices from C57Bl6 mice and maintain them in an interface chamber at 29° C. for 90 min prior to recording, as previously reported [B11] (herein incorporated by reference in its entirety). The bath solution will consist of 124.0 mM NaCl, 4.4 mM KCl, 1.0 mM $Na_2HPO_4$, 25.0 mM $NaHCO_3$, 2.0 mM $CaCl_2$, 2.0 mM $MgSO_4$, and 10.0 mM glucose, continuously bubbled with 95% $O_2$ and 5% $CO_2$. As a stimulating electrode we will use a bipolar tungsten electrode, placed at the level of the Schaeffer collateral fibers. As a recording electrode we will use a glass pipette filled with bath solution and placed at the level of CA1 stratum *radiatum*. We will first assess basal synaptic transmission (BST) to plot the stimulus voltages against slopes of fEPSP and determine the intensity of stimulation of our LTP experiments (it should evoke a response ~35% of the maximum evoked response). Baseline for LTP will be recorded for 15 min, every min. LTP will be elicited using 0-burst stimulation (4 pulses at 100 Hz, with the bursts repeated at 5 Hz and each tetanus including 3 ten-burst trains separated by 15 sec).

Fear Conditioning.

Contextual fear conditioning will be assessed as previously described [B14, B21] (each herein incorporated by reference in its entirety). Mice will be placed in a conditioning chamber for 2 min before the onset of a tone (CS) (a 30 s, 85 dB sound at 2800 Hz). In the last 2 s of the CS, mice will be given a 2 s, 0.45 mA foot shock (US) through the bars of the floor. Then, the mice will be left in the conditioning chamber for another 30 s. Freezing behavior, defined as the absence of movement except for that needed for breathing, will be scored using the Freezeview software. Contextual fear learning, a type of memory for which hippocampal function is indispensable, will be evaluated 24 hrs after training by measuring freezing for 5 min in the chamber in which the mice will be trained. Cued fear learning, a type of memory that depends upon amygdala function, will be evaluated 24 hrs after contextual testing by placing mice in a novel context for 2 min (pre-CS test), after which they will be exposed to the CS for 3 min (CS test), and freezing will be measured.

Sensory perception of the shock will be determined through threshold assessment. Briefly, the electric current (0.1 mA for 1 s) will be increased at 30 s intervals by 0.1 mA to 0.7 mA. Threshold to flinching (first visible response to shock), jumping (first extreme motor response), and screaming (first vocalized distress) will be quantified for each animal by averaging of the shock intensity at which each animal manifest a behavioral response of that type to the foot shock. No difference in the sensory threshold assessment should be observed among different groups of mice in experiments in which fear conditioning is tested if the experimental procedure does not affect the sensory threshold of the animals.

Moreover, different groups of mice will be checked with the open-field test. The open field will be an arena made of white acrylic with internal dimensions of 72×72×33 cm (An area measuring 36×36 cm in the centre of the open field will be defined as the 'central zone'). Mice will be placed in the center of a standard open field and their behavior monitored for 1 hr and scored for proportion of time in the center compartment vs. periphery, and number of entries into the center compartment. Mice will be returned for a second hour block after 24 hr. No difference in exploratory behavior as demonstrated by a similar percentage of time spent in the center compartment and the number of entries into the center compartment should be observed if the manipulation does not affect exploratory capabilities of the mice.

Reference Memory.

The first day of the protocol will be a training day. Mice will be trained to identify the platform location by alternating between a visible and a hidden platform in a goal arm. The final 3 trials on day 1 and all 15 trials on day 2 will use a hidden escape platform to force mice to use spatial cues to identify the location of the goal arm. To avoid learning limitations imposed by exhausting practice and to avoid fatigue that may result from consecutive trials, spaced practice training will be established by running the mice in cohorts of 4 and alternating different cohorts through the 15 training trials over 3 hours testing periods each day. On day 1, a visible platform will be placed in a goal location. Mouse 1 of cohort 1 will be gently placed in the pool near the perimeter of the wall of the first start arm (specified on a score sheet) and facing the center of the pool. The number of incorrect arm entries (entries in arms with no platform) will be counted. If the animal enters the incorrect arm it is gently pulled back to the start arm. Each trial will last up to 1 minute. Failure to select an arm after 15 seconds will be counted as an error and the mouse will be returned to the start arm. After 1 minute, if the platform has not been located, the mouse will be guided gently through the water by placing a hand behind it to direct it towards the platform. The mouse will rest on the platform for 15 seconds. After completing the trial, the mouse will be removed from the pool, gently towel dried and placed back into its cage under a heat lamp. The goal platform location will be different for each mouse. After all the mice in the first cohort have had a trial to locate a visible platform, the platform will be switched from visible to hidden. After each mouse from cohort 1 completes six alternating trials between visible and hidden platforms, the mice will be left to rest under a heating source, and mice from the second cohort will be tested in the same way. After completing the six alternating trials, mice from cohort 2 will return to their cages to rest. Next, mice from the first cohort will complete trials 7-12 again using the alternating visible-hidden platform location. During resting time for mice from the first cohort, mice from the second cohort will complete trials 7-12. At this point, all mice will have to perform 3 hidden platform trials. On day 2, the same procedure will be repeated as on day 1 for all 15 trials using only the hidden platform. For data analysis, the number of errors will be input into statistics software (Statview by SAS, Chicago, Ill.), and averages for each mouse will be calculated using blocks of 3 trials. As described [B58] (herein incorporated by reference in its entirety), we expect that the mice will exhibit 1 or less errors over three trials near the end of the second day. Mice that fail to learn will make 3-5 errors throughout the training session, with no improvement over trials.

At the end of the task visible platform training will be used to test visual, motor and motivation skills of the mice. Both time to reach the platform and swimming speed will be recorded and analyzed with a video-tracking system (HVS 2020, HVS Image, UK).

Infusion Technique.

Following anaesthesia with 20 mg/kg Avertin, mice will be implanted with a 26-gauge guide cannula into the dorsal part of the hippocampi (coordinates: P=2.46 mm, L=1.50 mm to a depth of 1.30 mm) [B62] (herein incorporated by reference in its entirety). The cannulas will be fixed to the skull with acrylic dental cement (Paladur). After 6-8 days we will bilaterally inject 200 pM Aβ42, or vehicle in a final volume of 1 µl over 1 min through infusion cannulas that will be connected to a microsyringe by a polyethylene tube. For Morris water maze, mice will be injected 20 min prior to performing each session and the probe trial, whereas for fear conditioning mice will receive a single injection 20 min before the training. Mice will be handled once a day for 3 days before behavioral experiments. During infusion animals will be handled gently to minimize stress. After infusion, the needle will be left in place for another minute to allow diffusion. After behavioural testing, a solution of 4% methylene blue will be infused into the cannulas. Animals will be sacrificed and their brains removed, frozen, and then cut at −20° with cryostat for histological localization of infusion cannulas.

Aβ Preparation.

Oligomeric Aβ42 will be prepared from commercially available synthetic peptides (American Peptides Co), as described [B63, B64] (each herein incorporated by reference in its entirety). Briefly, the lyophilized peptide will be resuspended in cold 1,1,1,3,3,3-hexafluoro-2-propanol (HFIP, Sigma) and aliquoted in polypropylene vials. After 24 hrs the HFIP solution will be allowed to evaporate in a fume hood until a thin film of peptide is formed on the bottom of the vials. Peptide films will be dried under gentle vacuum and stored in sealed vials at −20° C. Prior to use, anhydrous DMSO (Sigma) will be added to obtain a pure monomeric Aβ/DMSO solution that will be sonicated for 10 min [B63] (herein incorporated by reference in its entirety). Oligomeric Aβ42 will be obtained by incubating an aliquot of monomeric Aβ/DMSO solution in sterile PBS at 4° C. overnight. The quality of these Aβ preparations will be routinely controlled using Western blot analysis in which Aβ samples will be resolved by Tris-Tricine PAGE under non-denaturing/non-reducing conditions, and then transferred on nitrocellulose membrane. Subsequent Western blotting will be carried out after membrane incubation with the anti-human Aβ monoclonal antibody 6E10 (Signet Lab). The immunostaining will be revealed by horseradish peroxidase chemi-luminescence.

Histone Acetylation Assay.

Western blot will be performed from snap-frozen in liquid nitrogen hippocampi and cerebella. Tissue will be homogenized in lysis buffer (62.5 mM Tris-HCl pH 6.8, 3% SDS, 1 mM DTT) and incubated at 4° C. for 10 min, then sonicated before centrifugation at 2,000 rpm for 5 min. Whole cell extracts will be electrophoresed on 10-20% gradient PAGE gel (Invitrogen) and then immunoblotted. Antibodies will be used at a 1:1,000 concentration for immunoblotting. All anti-histone antibodies will be purchased from Millipore. β-III-Tubulin antibody will be purchased from Promega. Immunoblot data will be quantified by measuring the band intensity using imaging software (NIH ImageJ). For quantitative immunoblot analysis, equal amounts of proteins will be loaded into each lane. To confirm equal loading, blots will be reprobed with corresponding pan-antibodies or antibodies for house-keeping proteins such as β-III-Tubulin. For quantification, we always use a signal in the linear range.

Mass Spectrometry.

Characterization of modifications on immunoprecipitated histones will be carried out by mass spectrometry. Immunoprecipitated histones will be purified by reverse-phase HPLC in the PSR or by SDS-PAGE, then subjected to enzymatic digestion. Resulting peptides will be analyzed by LC-MS/MS on a Waters Qtof mass spectrometer equipped with a Dionex nanflow LC. The standard digestion protocol using trypsin is not feasible due to the number of Lys residues in the N-terminal portion of histones, resulting in peptides too small to be analyzed. Since this is also the region most rich in modifications, a digestion protocol must be used that results in peptides of optimum size (800-2000 Da) for analysis by LC-MS/MS. We will derivatize the Lys residues with propionic anhydride thus limiting tryptic digestion to Arg only. We have already successfully carried out this derivatization and digestion procedure on a commercial preparation of recombinant histone H3.1 and have obtained tryptic peptides from the N-terminal region that are easily analyzed by mass spectrometry. For relative quantitation of histone modifications, we will use a stable isotope-labeling procedure [B65] (herein incorporated by reference in its entirety) to modify carboxylic acid groups on the tryptic peptides followed by mass spectrometric analysis.

CBP levels will be measured with western blot using specific CBP antibodies. The nuclear fraction will be contained in the pellet obtained from homogenated tissue, centrifuged at 7,700×g for 1 min.

CBP HAT activity will be measured by immunoprecipitation from the lysis of hippocampal extracts using CBP antibodies. After isolation, HAT activity will be assessed using indirect enzyme-linked immunosorbent assay kit to detect acetyl residues according to the manufacturer's instruction (Upstate).

HDAC activity will be measured using a fluorimetric kit from Biovision (CA), according to the manufacturer instruction.

Statistical Analyses. Experiments will be performed in blind. Results will be expressed as Standard Error of the Mean (SEM). Level of significance will be set for $p<0.05$. Results will be analyzed by Student's t test (pairwise comparisons) or ANOVA for repeated measures (multiple comparisons) with treatment condition as main effect. Planned comparisons will be used for post-hoc analysis. For behavior, experiments will be designed in a balanced fashion, and mice will be trained and tested at each of the different conditions in three or four separate experiments. Experiments will be analyzed with ANOVA with treatment as main effect.

REFERENCES

B1. Lodish H., B. A., Zipursky L S., Matsudaira P., Baltimore D., Darnell J., *Molecular Cell Biology.* 4 ed. 2000, New York: W. H. Freeman and Company.

B2. Kandel, E. R., *The molecular biology of memory storage: a dialog between genes and synapses.* Biosci Rep, 2001. 21(5): p. 565-611.

B3. Dash, P. K., B. Hochner, and E. R. Kandel, *Injection of the cAMP-responsive element into the nucleus of Aplysia*

B4. Montarolo, P. G., P. Goelet, V. F. Castellucci, J. Morgan, E. R. Kandel, and S. Schacher, *A critical period for macromolecular synthesis in long-term heterosynaptic facilitation in Aplysia*. Science, 1986. 234(4781): p. 1249-54.

B5. Bailey, C. H. and M. Chen, *Morphological basis of long-term habituation and sensitization in Aplysia*. Science, 1983. 220(4592): p. 91-3.

B6. Levenson, J. M. and J. D. Sweatt, *Epigenetic mechanisms in memory formation*. Nat Rev Neurosci, 2005. 6(2): p. 108-18.

B7. Peterson, C. L. and M. A. Laniel, *Histones and histone modifications*. Curr Biol, 2004. 14(14): p. R546-51.

B8. Korzus, E., M. G. Rosenfeld, and M. Mayford, *CBP histone acetyltransferase activity is a critical component of memory consolidation*. Neuron, 2004. 42(6): p. 961-72.

B9. Bourtchuladze, R., B. Frenguelli, J. Blendy, D. Cioffi, G. Schutz, and A. J. Silva, *Deficient long-term memory in mice with a targeted mutation of the cAMP-responsive element-binding protein*. Cell, 1994. 79(1): p. 59-68.

B10. Yin, J. C., J. S. Wallach, M. Del Vecchio, E. L. Wilder, H. Zhou, W. G. Quinn, and T. Tully, *Induction of a dominant negative CREB transgene specifically blocks long-term memory in Drosophila*. Cell, 1994. 79(1): p. 49-58.

B11. Vitolo, O. V., A. Sant'Angelo, V. Costanzo, F. Battaglia, O. Arancio, and M. Shelanski, *Amyloid beta-peptide inhibition of the PKA/CREB pathway and long-term potentiation: reversibility by drugs that enhance cAMP signaling*. Proc Natl Acad Sci USA, 2002. 99(20): p. 13217-21.

B12. Puzzo, D., O. Vitolo, F. Trinchese, J. P. Jacob, A. Palmeri, and O. Arancio, *Amyloid-beta peptide inhibits activation of the nitric oxide/cGMP/cAMP-responsive element-binding protein pathway during hippocampal synaptic plasticity*. J Neurosci, 2005. 25(29): p. 6887-97.

B13. Puzzo, D., A. Staniszewski, S. Deng, S. Liu, A. Palmeri, D. W. Landry, and O. Arancio. *Sildenafil rescues synaptic and cognitive impairment in a mouse model of Alzheimer's disease*. in *Soc Neurosci. Abstr.* 2006. Atlanta.

B14. Gong, B., O. V. Vitolo, F. Trinchese, S. Liu, M. Shelanski, and O. Arancio, *Persistent improvement in synaptic and cognitive functions in an Alzheimer mouse model following rolipram treatment*. J. Clin. Invest., 2004. 114: p. 1624-1634.

B15. Saura, C. A., S. Y. Choi, V. Beglopoulos, S. Malkani, D. Zhang, B. S. Shankaranarayana Rao, S. Chattarji, R. J. Kelleher, 3rd, E. R. Kandel, K. Duff, A. Kirkwood, and J. Shen, *Loss of presenilin function causes impairments of memory and synaptic plasticity followed by age-dependent neurodegeneration*. Neuron, 2004. 42(1): p. 23-36.

B16. Sherrington, R., E. I. Rogaev, Y. Liang, E. A. Rogaeva, G. Levesque, M. Ikeda, H. Chi, C. Lin, G. Li, K. Holman, and et al., *Cloning of a gene bearing missense mutations in early-onset familial Alzheimer's disease*. Nature, 1995. 375(6534): p. 754-60.

B17. Levy-Lahad, E, E. M. Wijsman, E. Nemens, L. Anderson, K. A. Goddard, J. L. Weber, T. D. Bird, and G. D. Schellenberg, *A familial Alzheimer's disease locus on chromosome 1*. Science, 1995. 269(5226): p. 970-3.

B18. Francis, Y. I., A. Stephanou, and D. S. Latchman, *CREB-binding protein activation by presenilin 1 but not by its M146L mutant*. Neuroreport, 2006. 17(9): p. 917-21.

B19. Fischer, A., F. et al., *Recovery of learning and memory is associated with chromatin remodelling*. Nature, 2007. 447(7141): p. 178-82.

B20. Holcomb, L., et al., *Accelerated Alzheimer-type phenotype in transgenic mice carrying both mutant amyloid precursor protein and presenilin 1 transgenes*. Nat Med, 1998. 4(1): p. 97-100.

B21. Gong, B., et al., *Ubiquitin Hydrolase Uch-L1 Rescues beta-Amyloid-Induced Decreases in Synaptic Function and Contextual Memory*. Cell, 2006. 126(4): p. 775-88.

B22. Francis, I. Y., M. Fa', H. Ashraf, H. Zhang, A. Staniszewski, D. Latchman, and O. Arancio, *Dysregulation of histone acetylation in the APP/PS1 mouse model of Alzheimer's disease*. J Alzheimers Dis, 2009. In press.

B23. Kamal, A., A. Almenar-Queralt, J. F. LeBlanc, E. A. Roberts, and L. S. Goldstein, *Kinesin-mediated axonal transport of a membrane compartment containing beta-secretase and presenilin-1 requires APP*. Nature, 2001. 414(6864): p. 643-8.

B24. Cao, X. and T. C. Sudhof, *A transcriptionally [correction of franscriptively] active complex of APP with Fe65 and histone acetyltransferase Tip60*. Science, 2001. 293 (5527): p. 115-20.

B25. Alarcon, J. M., G. Malleret, K. Touzani, S. Vronskaya, S. Ishii, E. R. Kandel, and A. Barco, *Chromatin acetylation, memory, and LTP are impaired in CBP+/- mice: a model for the cognitive deficit in Rubinstein-Taybi syndrome and its amelioration*. Neuron, 2004. 42(6): p. 947-59.

B26. Levenson, J. M., et al., *Regulation of histone acetylation during memory formation in the hippocampus*. J Biol Chem, 2004. 279(39): p. 40545-59.

B27. Cullen, W. K., Y. H. Suh, R. Anwyl, and M. J. Rowan, *Block of LTP in rat hippocampus in vivo by beta-amyloid precursor protein fragments*. Neuroreport, 1997. 8(15): p. 3213-7.

B28. Itoh, A., T. Akaike, M. Sokabe, A. Nitta, R. Lida, A. Olariu, K. Yamada, and T. Nabeshima, *Impairments of long-term potentiation in hippocampal slices of beta-amyloid-infused rats*. Eur J Pharmacol, 1999. 382(3): p. 167-75.

B29. Walsh, D. M., I. Klyubin, J. V. Fadeeva, W. K. Cullen, R. Anwyl, M. S. Wolfe, M. J. Rowan, and D. J. Selkoe, *Naturally secreted oligomers of amyloid beta protein potently inhibit hippocampal long-term potentiation in vivo*. Nature, 2002. 416(6880): p. 535-9.

B30. Pittenger, C. and E. R. Kandel, *In search of general mechanisms for long-lasting plasticity: Aplysia and the hippocampus*. Philos Trans R Soc Lond B Biol Sci, 2003. 358(1432): p. 757-63.

B31. Lander, et al., *Initial sequencing and analysis of the human genome*. Nature, 2001. 409(6822): p. 860-921.

B32. Kornberg, R. D. and Y. Lorch, *Twenty-five years of the nucleosome, fundamental particle of the eukaryote chromosome*. Cell, 1999. 98(3): p. 285-94.

B33. Biel, M., V. Wascholowski, and A. Giannis, *Epigenetics—an epicenter of gene regulation: histones and histone-modifying enzymes*. Angew Chem Int Ed Engl, 2005. 44(21): p. 3186-216.

B34. de la Cruz, X., S. Lois, S. Sanchez-Molina, and M. A. Martinez-Balbas, *Do protein motifs' read the histone code?* Bioessays, 2005. 27(2): p. 164-75.

B35. Strahl, B. D. and C. D. Allis, *The language of covalent histone modifications*. Nature, 2000. 403(6765): p. 41-5.

B36. Ng, H. H. and A. Bird, *Histone deacetylases: silencers for hire*. Trends Biochem Sci, 2000. 25(3): p. 121-6.

B37. Kimura, A., K. Matsubara, and M. Horikoshi, *A decade of histone acetylation: marking eukaryotic chromosomes with specific codes*. J Biochem, 2005. 138(6): p. 647-62.

B38. de Ruijter, A. J., A. H. van Gennip, H. N. Caron, S. Kemp, and A. B. van Kuilenburg, *Histone deacetylases (HDACs): characterization of the classical HDAC family*. Biochem J, 2003. 370(Pt 3): p. 737-49.

B39. Yang, X. J. and E. Seto, *HATs and HDACs: from structure, function and regulation to novel strategies for therapy and prevention*. Oncogene, 2007. 26(37): p. 5310-8.

B40. Gregoretti, I. V., Y. M. Lee, and H. V. Goodson, *Molecular evolution of the histone deacetylase family: functional implications of phylogenetic analysis*. J Mol Biol, 2004. 338(1): p. 17-31.

B41. Langley, B., et al., *Remodeling chromatin and stress resistance in the central nervous system: histone deacetylase inhibitors as novel and broadly effective neuroprotective agents*. Curr Drug Targets CNS Neurol Disord, 2005. 4(1): p. 41-50.

B42. Hockly, E., V. M. Richon, B. Woodman, D L Smith, X. Zhou, E. Rosa, K. Sathasivam, S. Ghazi-Noori, A. Mahal, P A Lowden, J. S. Steffan, J. L. Marsh, L. M. Thompson, C. M. Lewis, P. A. Marks, and G. P. Bates, *Suberoylanilide hydroxamic acid, a histone deacetylase inhibitor, ameliorates motor deficits in a mouse model of Huntington's disease*. Proc Natl Acad Sci USA, 2003. 100(4): p. 2041-6.

B43. Guan, J. S., S. J. Haggarty, E. Giacometti, J. H. Dannenberg, N. Joseph, J. Gao, T. J. Nieland, Y. Zhou, X. Wang, R. Mazitschek, J. E. Bradner, R. A. DePinho, R. Jaenisch, and L. H. Tsai, *HDAC2 negatively regulates memory formation and synaptic plasticity*. Nature, 2009. 459(7243): p. 55-60.

B44. Dineley, K. T., M. Westerman, D. Bui, K. Bell, K. H. Ashe, and J. D. Sweatt, *Beta-amyloid activates the mitogen-activated protein kinase cascade via hippocampal alpha7 nicotinic acetylcholine receptors: In vitro and in vivo mechanisms related to Alzheimer's disease*. J Neurosci, 2001. 21(12): p. 4125-33.

B45. Dineley, K. T., X. Xia, D. Bui, J. D. Sweatt, and H. Zheng, *Accelerated plaque accumulation, associative learning deficits, and up-regulation of alpha 7 nicotinic receptor protein in transgenic mice co-expressing mutant human presenilin 1 and amyloid precursor proteins*. J Biol Chem, 2002. 277(25): p. 22768-80.

B46. Gong, B., O. V. Vitolo, F. Trinchese, S. Liu, M. Shelanski, and O. Arancio, *Persistent improvement in synaptic and cognitive functions in an Alzheimer mouse model after rolipram treatment*. J Clin Invest, 2004. 114(11): p. 1624-34.

B47. Francis, Y. I., J. K. Diss, M. Kariti, A. Stephanou, and D. S. Latchman, *p300 activation by Presenilin 1 but not by its M146L mutant*. Neurosci Lett, 2007. 413(2): p. 137-40.

B48. Rouaux, C., N. Jokic, C. Mbebi, S. Boutillier, J. P. Loeffler, and A. L. Boutillier, *Critical loss of CBP/p300 histone acetylase activity by caspase-6 during neurodegeneration*. Embo J, 2003. 22(24): p. 6537-49.

B49. Green, K. N., et al., *Nicotinamide restores cognition in Alzheimer's disease transgenic mice via a mechanism involving sirtuin inhibition and selective reduction of Thr231-phosphotau*. J Neurosci, 2008. 28(45): p. 11500-10.

B50. Trinchese, F., et al., *Progressive age-related development of Alzheimer-like pathology in APP/PS1 mice*. Ann Neurol, 2004. 55(6): p. 801-14.

B51. Sperling, R. A., et al., *fMRI studies of associative encoding in young and elderly controls and mild Alzheimer's disease*. J Neurol Neurosurg Psychiatry, 2003. 74(1): p. 44-50.

B52. Phillips, R. G. and J. E. LeDoux, *Differential contribution of amygdala and hippocampus to cued and contextual fear conditioning*. Behav Neurosci, 1992. 106(2): p. 274-85.

B53. Vecsey, C. G., et al., *Histone deacetylase inhibitors enhance memory and synaptic plasticity via CREB:CBP-dependent transcriptional activation*. J Neurosci, 2007. 27(23): p. 6128-40.

B54. Malm, T, et al., *beta Amyloid infusion results in delayed and age-dependent learning deficits without role of inflammation or beta-amyloid deposits*. Proc Natl Acad Sci USA, 2006. 103(23): p. 8852-7.

B55. Cleary, J. P., et al., *Natural oligomers of the amyloid-beta protein specifically disrupt cognitive function*. Nat Neurosci, 2005. 8(1): p. 79-84.

B56. Bordoli, L., et al., *Plant orthologs of p300/CBP: conservation of a core domain in metazoan p300/CBP acetyltransferase-related proteins*. Nucleic Acids Res, 2001. 29(3): p. 589-97.

B57. Masliah, E, *Mechanisms of synaptic dysfunction in Alzheimer's disease*. Histol Histopathol, 1995. 10(2): p. 509-19.

B58. Alamed, J., D. M. Wilcock, D. M. Diamond, M. N. Gordon, and D. Morgan, *Two-day radial-arm water maze learning and memory task; robust resolution of amyloid-related memory deficits in transgenic mice*. Nat Protoc, 2006. 1(4): p. 1671-9.

B59. Eyupoglu, I. Y., et al., *Experimental therapy of malignant gliomas using the inhibitor of histone deacetylase MS-275*. Mol Cancer Ther, 2006. 5(5): p. 1248-55.

B60. Kim, D., et al., *SIRT1 deacetylase protects against neurodegeneration in models for Alzheimer's disease and amyotrophic lateral sclerosis*. EMBO J, 2007. 26(13): p. 3169-79.

B61. Mantelingu, K., et al., *Activation of p300 histone acetyltransferase by small molecules altering enzyme structure: probed by surface-enhanced Raman spectroscopy*. J Phys Chem B, 2007. 111(17): p. 4527-34.

B62. Paxinos, G., *Mouse brain in stereotaxic coordinates*. 2nd ed. 1998, New York: Academic Press.

B63. Stine, W. B., et al., *In vitro characterization of conditions for amyloid-beta peptide oligomerization and fibrillogenesis*. J Biol Chem, 2003. 278(13): p. 11612-22.

B64. Puzzo, D., et al., *Picomolar Amyloid-{beta} Positively Modulates Synaptic Plasticity and Memory in Hippocampus*. J. Neurosci., 2008. 28(53): p. 14537-14545.

B65. Garcia, B. A., et al., *Chemical derivatization of histones for facilitated analysis by mass spectrometry*. Nat Protoc, 2007. 2(4): p. 933-8.

Example 7: Cell Viability Assays for ACHN, U251, NCI-ADR-RES, A549, Hs578T, CCRF-CEM Assay Parameters
Read-out: Cell Proliferation by Cell-TiterGlo, and Cyquant,
Number of Compounds: 1 (YF2)
Concentrations: 10 (0.03, 0.1, 0.25, 0.5, 1, 2.5, 5, 15, 40 and 80 µM)
Reference Compound: Vinblastine (VBL)
Concentrations: 10
(0.001, 0.003, 0.01, 0.03, 0.1, 0.3, 1, 3, and 10 µM)
Time of Drug Treatment: 72 hours Replicates: 3
Solvent: Aqueous medium
Materials and Methods
Cells and Culture Medium:

All cell lines were purchased from the ATCC and were expanded and archived under liquid nitrogen at CDAS as low passage aliquots. Cells were maintained and passaged in recommended and optimal culture medium (ACHN: EMEM, 2 mM L-Gln, 10% FBS; A549: Ham's F12, 10% FBS; U251: RPMI 1640.2 mM L-Gln, 10% FBS; Hs578T: DMEM, 4 mM L-Gln, 1 U/mL of Bovine Insulin, 10% FBS; CCRF-CEM: ATCC RPMI, 2 mM L-Gln, 10% FBS; NCI-ADR-RES: RPMI 1640, 2 mM L-Gln, 10% FBS). All experiments were carried out with cells which had undergone less than 20 passages. Optimal seed densities were determined for all cell lines. All cells were plated at 1500 cells per well except CCRF-CEM which was plated at 6000 cells per well.

Drugs:

YF2 was supplied as a 80 mM stock solution in 100% DMSO. Vinblastine was purchased from Sigma (Catalogue Number V-1377) and resuspended at $1\times10^{-2}$M in 100% DMSO. All dilutions for both drugs were carried out in culture medium containing 0.2% DMSO such that the final solvent concentration never exceeded 0.1%.

Drug Treatment:

YF2 tested at 10 concentrations (0.03, 0.1, 0.25, 0.5, 1, 2.5, 5, 15, 40 and 80 µM) in triplicate wells. Vinblastine was used as a reference control and tested at 10 concentrations in a half-log series (0, 0.001, 0.003, 0.01, 0.03, 0.1, 0.3, 1, 3, and 10 µM). Cells were resuspended in medium at the appropriate concentration and 180 µl (1500 or 6000 cells) was added to each well following which 20 µl of drug at 10× of the final concentration was added to attain the desired drug concentration in every well. The drug treatment plates were incubated at 37° C. for 72 hours, following which cell viability was assayed by the Cell Titer Glo or Cyquant method as described below.

Cell Titer Glo Assay:

Following the 72 hour drug treatment period, the assay plates were centrifuged, and 100 µL of the medium was aspirated and replaced with 100 J.1L of Cell Titer Glo reagent (Promega) according to the manufacturer's recommended protocol. The reagent was mixed with the cells and the luminescence measured using a Perkin Elmer Envision instrument. The average luminescence signal obtained from wells containing untreated cells which had been incubated for the entire length of the assay period was used to set the 100% viability value. The percent proliferation was calculated as (Test signal)/(Avg. plate background signal)×100. The % viability was graphed against drug concentration to calculate an $IC_{50}$ for each drug.

Cyquant Assay:

Following the 72 hour drug treatment period the assay plates were centrifuged, the medium discarded, and frozen overnight. The plates were assayed using the Cyquant™ reagent (Invitrogen) according to the manufacturer's recommended protocol. The average fluorescence signal obtained from wells containing untreated cells which had been incubated for the entire length of the assay period was used to set the 100% proliferation value. The percent proliferation was calculated as (Test signal)/(Avg. plate background signal)×100. The % proliferation was graphed against drug concentration to calculate an $IC_{50}$ for each drug.

Example 8: YF2 Increases Histone Acetylation by HAT Activation, Not HDAC Inhibition HDAC inhibition causes an increase in histone acetylation. The inventors examined whether histone acetylation occurred via HDAC inhibition.

The summary of the results is depicted in Table 1. The mean $IC_{50}$ values of the compounds are summarized in Table 1.

TABLE 1

Inhibitory Effects of the Compounds on HDAC Activities

| HDACs | $IC_{50}$ (nM) or % Inhibition | |
|---|---|---|
| | YF2 | SAHA |
| HDAC1 | >200 µM | 31 |
| HDAC3/NCOR2 | >200 µM | 38 |
| HDAC5FL | >200 µM | >10 µM |
| HDAC6 | >200 µM | 30 |
| HADC7 | >200 µM | >10 µM |
| HDAC8 | >200 µM | 2,236 |
| HDAC10 | >200 µM | 65 |
| HDAC11 | >200 µM | >10 µM |
| Sirtuin 1 | >200 µM | >10 µM |
| Sirtuin 2 | >200 µM | >10 µM |

The experiments were done blind, where the YF2 compound of the invention corresponds to OA2. The studies show that YF2 has no HDAC inhibition properties. YF2 does not inhibit HDACs.

Materials and Methods
Materials:
HDAC Assay Buffer (BPS catalog number 50031)
HDAC Assay Developer (BPS catalog number 50030)
HDAC Substrate 1 (BPS number 50032)
HDAC Substrate 3 (BPS number 50037)
HDAC Class 2a Substrate 1 (BPS number 50040)
SAHA (Cayman Chemical, Ann Arbor, Mich., Catalog number 10009929)

TABLE 2

Compounds used in the studies

| Compound I.D. | Compound Supplied | Stock Conc. | Dissolving Solvent | Test Range (nM) | Intermediate Dilution |
|---|---|---|---|---|---|
| OA2* | Solution | 10 mM | DMSO | 3-200,000 | 10% DMSO in HDAC Assay Buffer |
| SAHA | Powder | 10 mM | DMSO | 0.3-10,000 | 10% DMSO in HDAC Assay Buffer |

*Compound OA2 is cloudy at 2 mM in 10% DMSO (The highest test point).
**SAHA, and HDACi, is a positive control for HDACs.

Experimental Conditions

TABLE 3

| Enzymes and Substrates | | | |
|---|---|---|---|
| Assay | Catalog # | Enzyme Used (ng)/ Reaction | Substrate |
| HDAC1 | 50051 | 1.5 | 10 μM of 50037 |
| HADC3/NCOR2 | 50003 | 1.33 | 10 μM of 50037 |
| HDAC5FL | 50045 | 1.25 | 2 μM of 50040 |
| HDAC6 | 50006 | 10 | 10 μM of 50037 |
| HDAC7 | 50007 | 0.3 | 2 μM of 50040 |
| HDAC8 | 50008 | 20 | 2 μM of 50040 |
| HDAC10 | 50010 | 1,300 | 10 μM of 50037 |
| HADC11 | 50011 | 400 | 2 μM of 50040 |
| Sirtuin 1 | 50012 | 400 | 10 μM of 50032 |
| Sirtuin 2 | 50013 | 5,600 | 10 μM of 50032 |

Assay Conditions.

A series of dilution of the test compounds were prepared with 10% DMSO in assay buffer and 5 μl of the dilution was added to a 50 μl reaction so that the final concentration of DMSO is 1% in all of reactions. All of the enzymatic reactions were conducted in duplicate at 37° C. for 30 minutes except of HDAC11 at room temperature for 3 hours. The 50 μl reaction mixture contains HDAC assay buffer, 5 μg BSA, an HDAC substrate, an HDAC enzyme and a test compound. After enzymatic reactions, 50 μl of HDAC Developer was added to each well and the plate was incubated at room temperature for an additional 20 minutes. Fluorescence intensity was measured at an excitation of 360 nm and an emission of 460 nm using a Tecan Infinite M1000 microplate reader.

Data Analysis.

HDAC activity assays were performed in duplicates at each concentration. The fluorescent intensity data were analyzed using the computer software, Graphpad Prism. In the absence of the compound, the fluorescent intensity ($F_t$) in each data set was defined as 100% activity. In the absence of HDAC, the fluorescent intensity ($F_b$) in each data set was defined as 0% activity. Compound OA2 has fluorescence at assay condition; therefore the fluorescent intensity at different concentration of OA2 was defined as background (Fb). The percent activity in the presence of each compound was calculated according to the following equation: % activity= $(F-F_b)/(F_t-F_b)$, where F=the fluorescent intensity in the presence of the compound.

The values of % activity versus a series of compound concentrations were then plotted using non-linear regression analysis of Sigmoidal dose-response curve generated with the equation $Y=B+(T-B)/1+10^{(Log\ EC50-X) \times Hill\ Slope}$, where Y=percentactivity, B=minimum percent activity, T=maximum percent activity, X=logarithm of compound and Hill Slope=slope factor or Hill coefficient. The $IC_{50}$ value was determined by the concentration causing a half-maximal percent activity.

Results of Effect of OA2 (YF2 Compound) on HDAC Inhibition

TABLE 4

| HDAC1 Assay-Data for the Effect of OA2 on HDAC1 Activity | | | | | | |
|---|---|---|---|---|---|---|
| OA2 | HDAC Activity (Fluorescence count) | | Background (Fluorescence count) | | % Activity | |
| (Log [nN4]) | Repeat1 | Repeat2 | Repeat1 | Repeat2 | Repeat1 | Repeat2 |
| No CPD | 17721 | 17257 | 796 | 803 | 101.39 | 98.61 |
| 0.5 | 17287 | 17200 | 796 | 798 | 98.80 | 98.28 |
| 1.0 | 17083 | 17178 | 788 | 786 | 97.64 | 98.21 |
| 1.5 | 16949 | 17020 | 830 | 784 | 96.72 | 97.14 |
| 2.0 | 16879 | 16826 | 796 | 779 | 96.42 | 96.10 |
| 2.5 | 16792 | 17072 | 827 | 775 | 95.81 | 97.49 |
| 3.0 | 16943 | 16784 | 829 | 802 | 96.63 | 95.68 |
| 3.5 | 16387 | 17135 | 866 | 827 | 93.12 | 97.60 |
| 4.0 | 16140 | 16336 | 920 | 868 | 91.35 | 92.53 |
| 4.5 | 16432 | 16128 | 1117 | 1035 | 92.01 | 90.19 |
| 5.3 | 24780 | 24451 | 14884 | 13403 | 63.73 | 61.76 |

Figure 52:
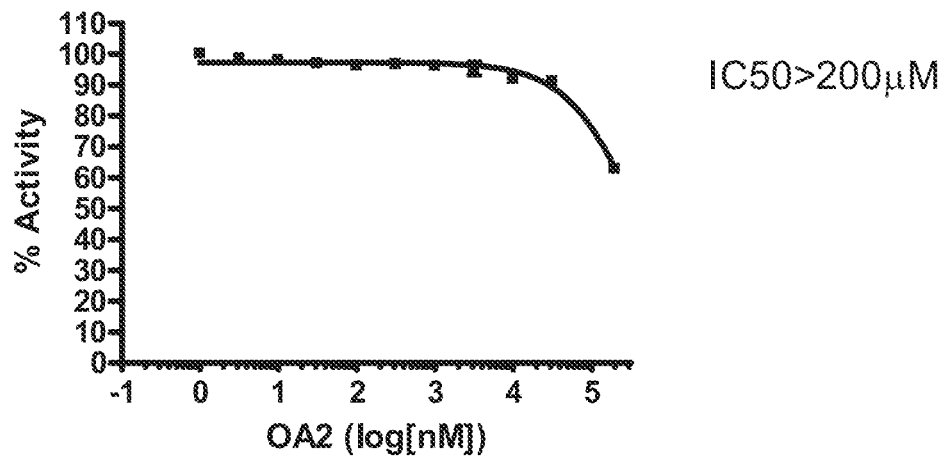
FIG. 52 is a graph showing the effect of OA2 (YF2 compound) on HDAC1 activity.

FIG. 52 corresponds to the results shown in Table 4.

TABLE 5

| HDAC3/NCOR2 Assay-Data for the Effect of OA2 on HDAC3/NCOR2 Activity | | | | | | |
|---|---|---|---|---|---|---|
| OA2 | HDAC Activity (Fluorescence count) | | Background (Fluorescence count) | | % Activity | |
| (Log [nM]) | Repeat1 | Repeat2 | Repeat1 | Repeat2 | Repeat1 | Repeat2 |
| No CPD | 10787 | 10452 | 805 | 828 | 101.71 | 98.29 |
| 0.5 | 10928 | 9694 | 813 | 976 | 102.35 | 89.76 |
| 1.0 | 10423 | 10379 | 812 | 818 | 98.01 | 97.56 |
| 1.5 | 10752 | 10231 | 813 | 803 | 101.44 | 96.12 |
| 2.0 | 10827 | 10078 | 809 | 798 | 102.25 | 94.61 |
| 2.5 | 10718 | 10173 | 818 | 803 | 101.07 | 95.51 |
| 3.0 | 10587 | 10073 | 831 | 811 | 99.62 | 94.38 |
| 3.5 | 10362 | 10080 | 854 | 824 | 97.14 | 94.27 |
| 4.0 | 11530 | 10216 | 927 | 898 | 108.31 | 94.90 |

TABLE 5-continued

HDAC3/NCOR2 Assay-Data for the Effect of OA2 on HDAC3/NCOR2 Activity

| OA2 | HDAC Activity (Fluorescence count) | | Background (Fluorescence count) | | % Activity | |
|---|---|---|---|---|---|---|
| (Log [nM]) | Repeat1 | Repeat2 | Repeat1 | Repeat2 | Repeat1 | Repeat2 |
| 4.5 | 9872 | 10001 | 1467 | 1091 | 87.66 | 88.97 |
| 5.3 | 20905 | 22163 | 13408 | 10875 | 89.40 | 102.23 |

Figure 53:
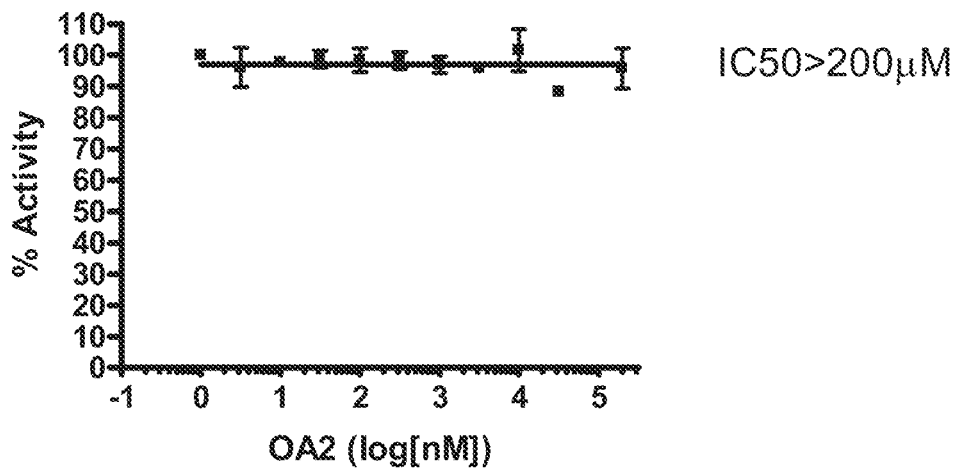
FIG. 53 is a graph showing the effect of OA2 (YF2 compound) on HDAC3/NCOR2 activity.

FIG. 53 corresponds to the results shown in Table 5.

TABLE 6

HDAC5FL Assay-Data for the Effect of OA2 on HDAC5FL Activity

| OA2 | HDAC Activity (Fluorescence count) | | Background (Fluorescence count) | | % Activity | |
|---|---|---|---|---|---|---|
| (Log [nM]) | Repeat1 | Repeat2 | Repeat1 | Repeat2 | Repeat1 | Repeat2 |
| No CPD | 4492 | 4892 | 345 | 348 | 95.40 | 104.60 |
| 0.5 | 4686 | 4386 | 355 | 343 | 99.80 | 92.90 |
| 1.0 | 4802 | 4581 | 341 | 347 | 102.59 | 97.50 |
| 1.5 | 4835 | 4874 | 359 | 342 | 103.20 | 104.10 |
| 2.0 | 5071 | 4991 | 344 | 356 | 108.64 | 106.80 |
| 2.5 | 5068 | 5006 | 344 | 354 | 108.60 | 107.17 |
| 3.0 | 4944 | 4685 | 342 | 354 | 105.76 | 99.80 |
| 3.5 | 4773 | 4686 | 353 | 389 | 101.30 | 99.30 |
| 4.0 | 4987 | 4983 | 449 | 407 | 104.91 | 104.82 |
| 4.5 | 4570 | 4514 | 451 | 398 | 95.40 | 94.11 |
| 5.3 | 9875 | 10983 | 7907 | 5878 | 68.63 | 94.13 |

Figure 54:
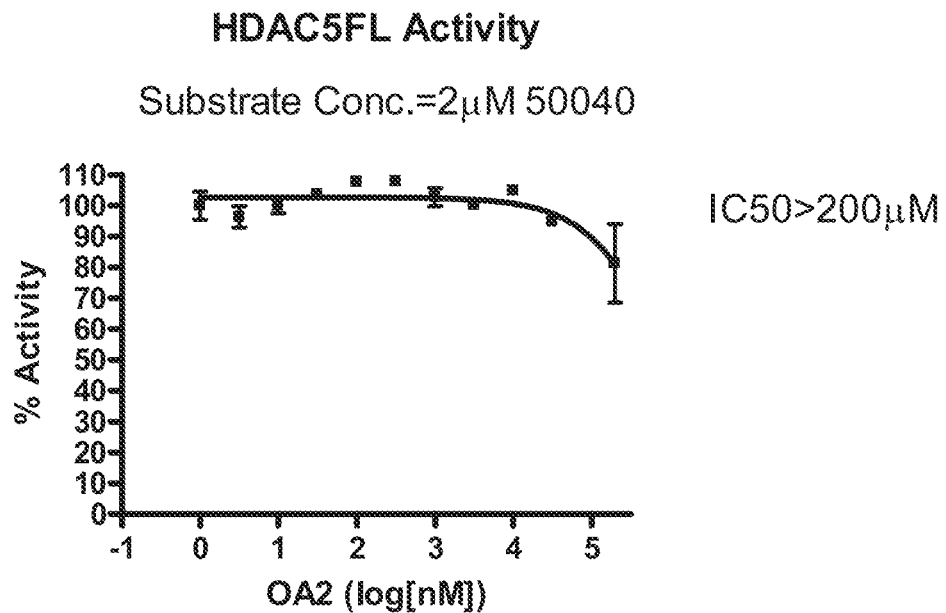
FIG. 54 is a graph showing the effect of OA2 (YF2 compound) on HDAC5FL activity.

FIG. 54 corresponds to the results shown in Table 6.

TABLE 7

HDAC7 Assay-Data for the Effect of OA2 on HDAC7 Activity

| OA2 | HDAC Activity (Fluorescence count) | | Background (Fluorescence count) | | % Activity | |
|---|---|---|---|---|---|---|
| (Log [nM]) | Repeat1 | Repeat2 | Repeat1 | Repeat2 | Repeat1 | Repeat2 |
| No CPD | 7528 | 7176 | 382 | 377 | 102.52 | 97.48 |
| 0.5 | 7578 | 7200 | 394 | 383 | 103.11 | 97.69 |
| 1.0 | 6756 | 6763 | 385 | 386 | 91.37 | 91.47 |
| 1.5 | 7471 | 7705 | 389 | 381 | 101.63 | 104.98 |
| 2.0 | 7679 | 7196 | 390 | 380 | 104.61 | 97.68 |
| 2.5 | 7071 | 7068 | 385 | 398 | 95.80 | 95.75 |
| 3.0 | 7083 | 7269 | 384 | 392 | 96.02 | 98.69 |
| 3.5 | 7453 | 6898 | 397 | 462 | 100.73 | 92.77 |
| 4.0 | 6801 | 7568 | 416 | 534 | 90.73 | 101.73 |
| 4.5 | 7238 | 7518 | 554 | 565 | 95.78 | 99.80 |
| 5.3 | 9692 | 9912 | 3002 | 2871 | 96.89 | 100.04 |

Figure 55:
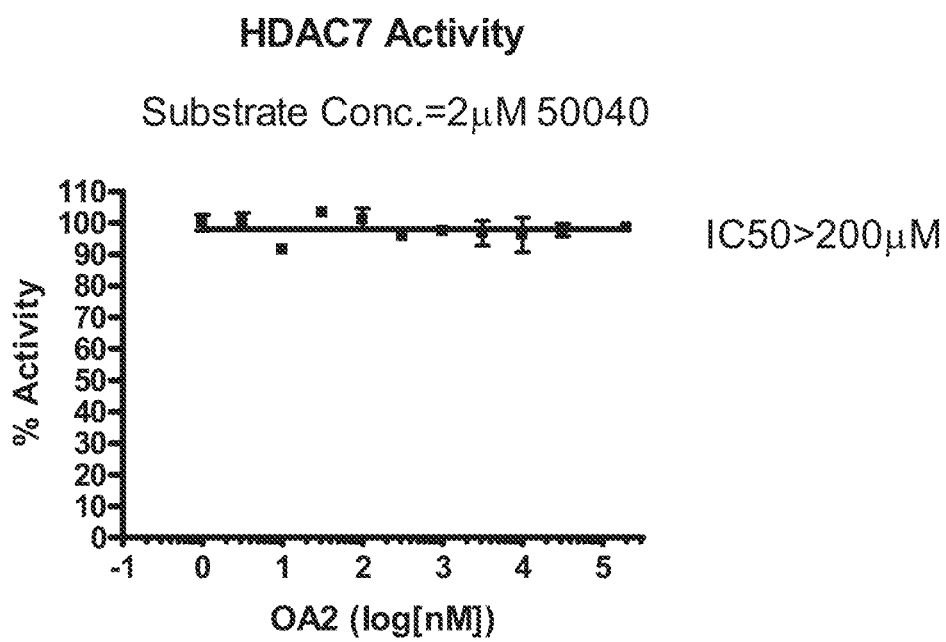
FIG. 55 is a graph showing the effect of OA2 (YF2 compound) on HDAC7 activity.

FIG. 55 corresponds to the results shown in Table 7.

TABLE 8

HDAC8 Assay-Data for the Effect of OA2 on HDAC8 Activity

| OA2 | HDAC Activity (Fluorescence count) | | Background (Fluorescence count) | | % Activity | |
|---|---|---|---|---|---|---|
| (Log [nM]) | Repeat1 | Repeat2 | Repeat1 | Repeat2 | Repeat1 | Repeat2 |
| No CPD | 3492 | 3483 | 346 | 346 | 100.14 | 99.86 |
| 0.5 | 3541 | 3581 | 339 | 342 | 101.88 | 103.15 |
| 1.0 | 3519 | 3391 | 349 | 342 | 101.02 | 96.94 |
| 1.5 | 3539 | 3456 | 336 | 331 | 102.04 | 99.40 |
| 2.0 | 3757 | 3425 | 338 | 340 | 108.80 | 98.23 |
| 2.5 | 3451 | 3428 | 335 | 341 | 99.09 | 98.36 |
| 3.0 | 3398 | 2995 | 337 | 347 | 97.28 | 84.45 |
| 3.5 | 3808 | 3407 | 346 | 366 | 109.88 | 97.12 |
| 4.0 | 3361 | 3365 | 433 | 374 | 94.14 | 94.27 |
| 4.5 | 3045 | 3090 | 375 | 364 | 85.17 | 86.60 |
| 5.3 | 6631 | 8117 | 4962 | 4635 | 58.33 | 105.63 |

Figure 56:
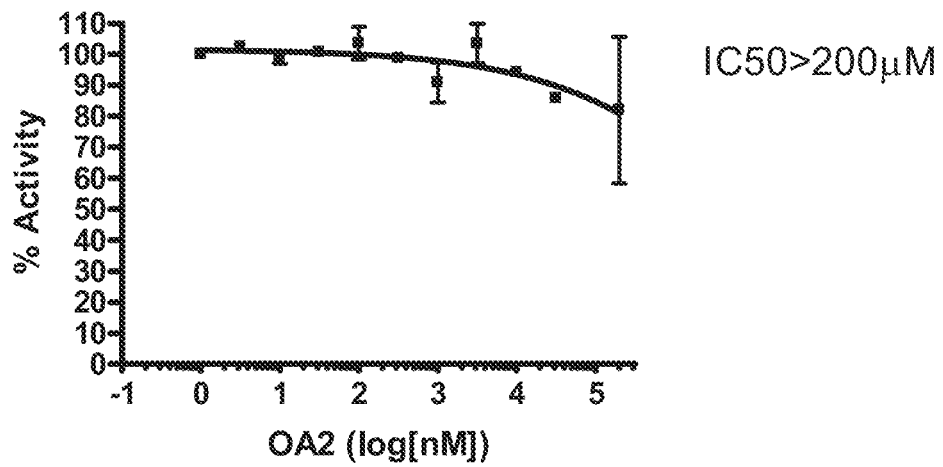
FIG. 56 is a graph showing the effect of OA2 (YF2 compound) on HDAC8 activity.

FIG. 56 corresponds to the results shown in Table 8.

TABLE 9

HDAC10 Assay-Data for the Effect of OA2 on HDAC10 Activity

| OA2 | HDAC Activity (Fluorescence count) | | Background (Fluorescence count) | | % Activity | |
|---|---|---|---|---|---|---|
| (Log [nM]) | Repeat1 | Repeat2 | Repeat1 | Repeat2 | Repeat1 | Repeat2 |
| No CPD | 11695 | 12141 | 497 | 507 | 98.05 | 101.95 |
| 0.5 | 10894 | 12032 | 492 | 501 | 91.08 | 101.05 |
| 1.0 | 12341 | 12402 | 497 | 492 | 103.77 | 104.31 |
| 1.5 | 12564 | 12368 | 525 | 500 | 105.57 | 103.85 |
| 2.0 | 12262 | 12573 | 500 | 497 | 103.04 | 105.77 |
| 2.5 | 12472 | 12556 | 500 | 493 | 104.90 | 105.64 |
| 3.0 | 11935 | 12471 | 530 | 521 | 99.94 | 104.64 |

TABLE 9-continued

HDAC10 Assay-Data for the Effect of OA2 on HDAC10 Activity

| OA2 (Log [nM]) | HDAC Activity (Fluorescence count) | | Background (Fluorescence count) | | % Activity | |
|---|---|---|---|---|---|---|
| | Repeat1 | Repeat2 | Repeat1 | Repeat2 | Repeat1 | Repeat2 |
| 3.5 | 11622 | 12684 | 501 | 607 | 96.95 | 106.25 |
| 4.0 | 11588 | 12318 | 597 | 547 | 96.50 | 102.89 |
| 4.5 | 11448 | 12305 | 623 | 495 | 95.38 | 102.89 |
| 5.3 | 25769 | 22285 | 12210 | 12714 | 116.56 | 86.05 |

Figure 57:
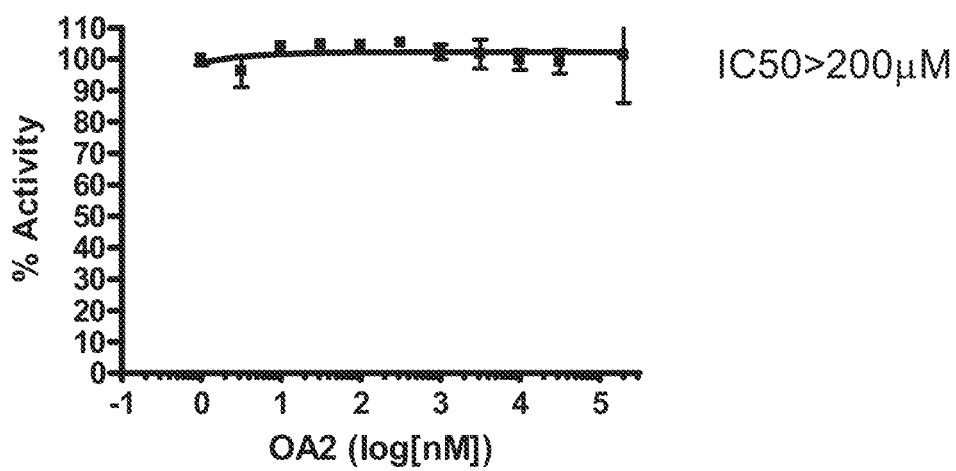
FIG. 57 is a graph showing the effect of OA2 (YF2 compound) on HDAC10 activity.

FIG. 57 corresponds to the results shown in Table 9.

TABLE 10

HDAC11 Assay-Data for the Effect of OA2 on HDAC11 Activity

| OA2 (Log [nM]) | HDAC Activity (Fluorescence count) | | Background (Fluorescence count) | | % Activity | |
|---|---|---|---|---|---|---|
| | Repeat1 | Repeat2 | Repeat1 | Repeat2 | Repeat1 | Repeat2 |
| No CPD | 2840 | 2860 | 426 | 406 | 99.59 | 100.41 |
| 0.5 | 2761 | 2530 | 411 | 423 | 96.30 | 86.81 |
| 1.0 | 2828 | 2898 | 425 | 415 | 98.93 | 101.81 |
| 1.5 | 2765 | 2851 | 411 | 406 | 96.82 | 100.35 |
| 2.0 | 2812 | 2864 | 408 | 409 | 98.75 | 100.88 |
| 2.5 | 2672 | 2655 | 412 | 408 | 92.93 | 92.24 |
| 3.0 | 2829 | 2806 | 417 | 424 | 98.95 | 98.01 |
| 3.5 | 2719 | 2712 | 427 | 463 | 93.43 | 93.14 |
| 4.0 | 2835 | 2860 | 467 | 524 | 96.12 | 97.14 |
| 4.5 | 3289 | 3064 | 699 | 617 | 108.09 | 98.85 |
| 5.3 | 6249 | 5842 | 2911 | 3158 | 132.07 | 115.35 |

Figure 58:
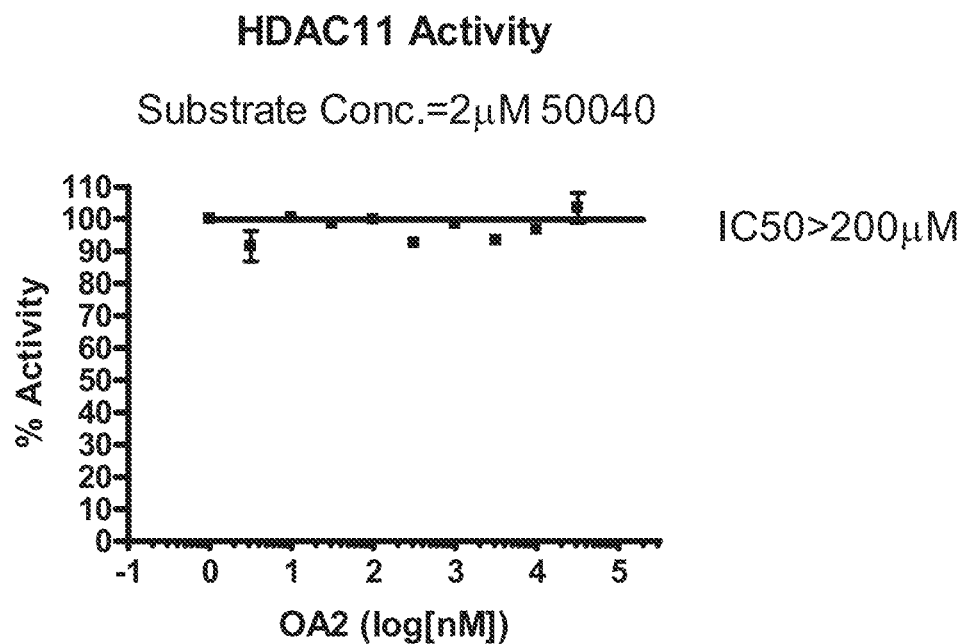
FIG. 58 is a graph showing the effect of OA2 (YF2 compound) on HDAC11 activity.

FIG. 58 corresponds to the results shown in Table 10.

TABLE 11

Sirtuin 1 Assay-Data for the Effect of OA2 on Sirtuin 1 Activity

| OA2 (Log [nM]) | HDAC Activity (Fluorescence count) | | Background (Fluorescence count) | | % Activity | |
|---|---|---|---|---|---|---|
| | Repeat1 | Repeat2 | Repeat1 | Repeat2 | Repeat1 | Repeat2 |
| No CPD | 5823 | 5974 | 412 | 410 | 97.91 | 100.64 |
| 0.5 | 5627 | 5940 | 414 | 420 | 94.26 | 99.92 |
| 1.0 | 5240 | 5913 | 422 | 413 | 87.25 | 99.42 |
| 1.5 | 5980 | 5273 | 418 | 457 | 100.27 | 87.48 |
| 2.0 | 5827 | 5527 | 411 | 411 | 97.98 | 92.56 |
| 2.5 | 6028 | 5987 | 413 | 416 | 101.56 | 100.81 |
| 3.0 | 6454 | 5681 | 422 | 452 | 108.86 | 94.87 |
| 3.5 | 5782 | 5964 | 422 | 426 | 96.93 | 100.23 |
| 4.0 | 5786 | 5408 | 442 | 441 | 96.69 | 89.85 |
| 4.5 | 5976 | 5697 | 502 | 524 | 98.83 | 93.79 |
| 5.3 | 7483 | 7591 | 2022 | 1997 | 99.02 | 100.98 |

Figure 59:
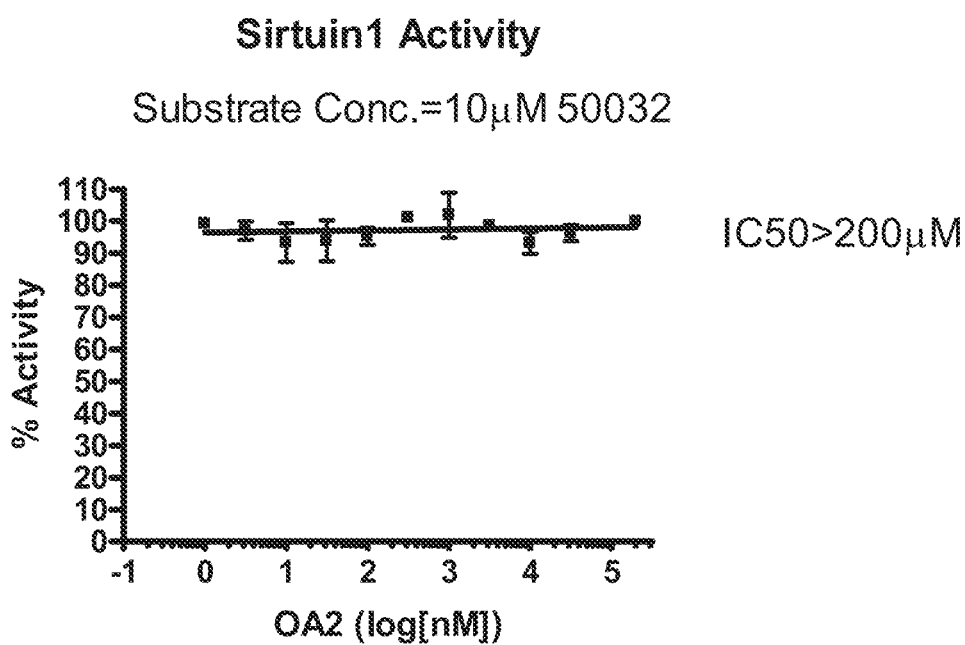
FIG. 59 is a graph showing the effect of OA2 (YF2 compound) on Sirtuin1 activity.

FIG. 59 corresponds to the results shown in Table 11.

TABLE 12

Sirtuin 2 Assay-Data for the Effect of OA2 on Sirtuin 2 Activity

| OA2 (Log [nM]) | HDAC Activity (Fluorescence count) | | Background (Fluorescence count) | | % Activity | |
|---|---|---|---|---|---|---|
| | Repeat1 | Repeat2 | Repeat1 | Repeat2 | Repeat1 | Repeat2 |
| No CPD | 3910 | 3919 | 413 | 419 | 99.87 | 100.13 |
| 0.5 | 3835 | 3981 | 420 | 413 | 97.71 | 101.89 |
| 1.0 | 3780 | 3821 | 406 | 422 | 96.21 | 97.38 |
| 1.5 | 3858 | 3954 | 408 | 410 | 98.59 | 101.33 |
| 2.0 | 3712 | 3912 | 420 | 413 | 94.20 | 99.91 |
| 2.5 | 3729 | 3788 | 409 | 420 | 94.74 | 96.43 |
| 3.0 | 3714 | 3861 | 405 | 409 | 94.53 | 98.73 |
| 3.5 | 3806 | 3856 | 422 | 417 | 96.80 | 98.23 |
| 4.0 | 3844 | 3883 | 425 | 426 | 97.71 | 98.83 |
| 4.5 | 3717 | 3811 | 485 | 480 | 92.45 | 95.14 |
| 5.3 | 5686 | 5717 | 2225 | 2245 | 98.64 | 99.53 |

Figure 60:
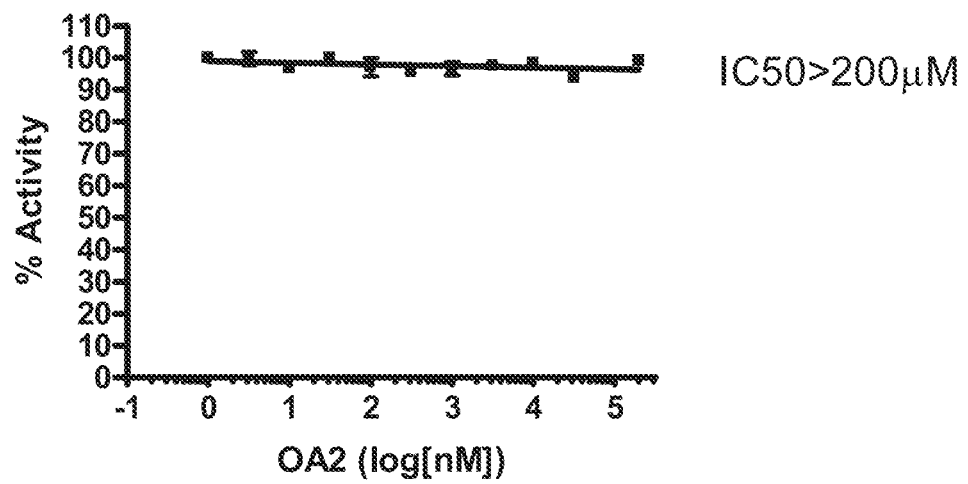
FIG. 60 is a graph showing the effect of OA2 (YF2 compound) on Sirtuin2 activity.

FIG. 60 corresponds to the results shown in Table 12.

TABLE 13

HDAC6 Assay-Data for the Effect of OA2 on HDAC6 Activity

| OA2 (Log [nM]) | HDAC Activity (Fluorescence count) | | Background (Fluorescence count) | | % Activity | |
|---|---|---|---|---|---|---|
| | Repeat1 | Repeat2 | Repeat1 | Repeat2 | Repeat1 | Repeat2 |
| No CPD | 5844 | 5616 | 773 | 733 | 102.29 | 97.71 |
| 0.5 | 5998 | 6074 | 832 | 737 | 104.75 | 106.28 |
| 1.0 | 6006 | 5728 | 747 | 704 | 106.10 | 100.51 |
| 1.5 | 5541 | 6126 | 746 | 706 | 96.75 | 108.50 |
| 2.0 | 5733 | 5981 | 748 | 731 | 100.33 | 105.31 |
| 2.5 | 5678 | 5677 | 763 | 709 | 99.30 | 99.28 |
| 3.0 | 5717 | 5446 | 758 | 716 | 100.06 | 94.62 |
| 3.5 | 5575 | 5616 | 781 | 735 | 96.79 | 97.61 |
| 4.0 | 5516 | 5789 | 828 | 786 | 94.62 | 100.10 |
| 4.5 | 4994 | 5418 | 1081 | 1030 | 79.13 | 87.65 |
| 5.3 | 8327 | 9938 | 4925 | 4721 | 70.40 | 102.77 |

Figure 74:
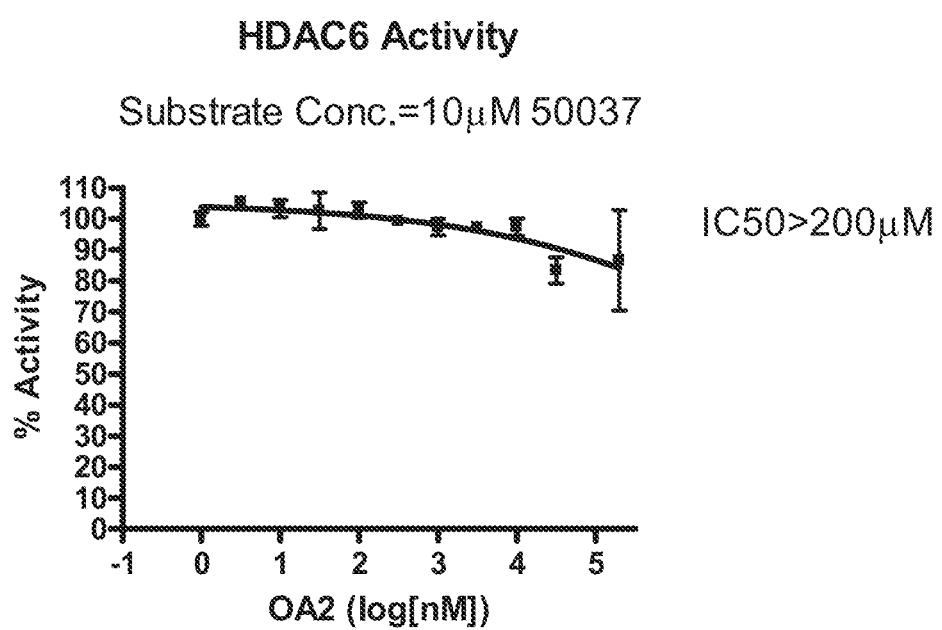
FIG. 74 is a graph showing the effect of OA2 (YF2 compound) on HDAC6 activity.
Figure 75A:
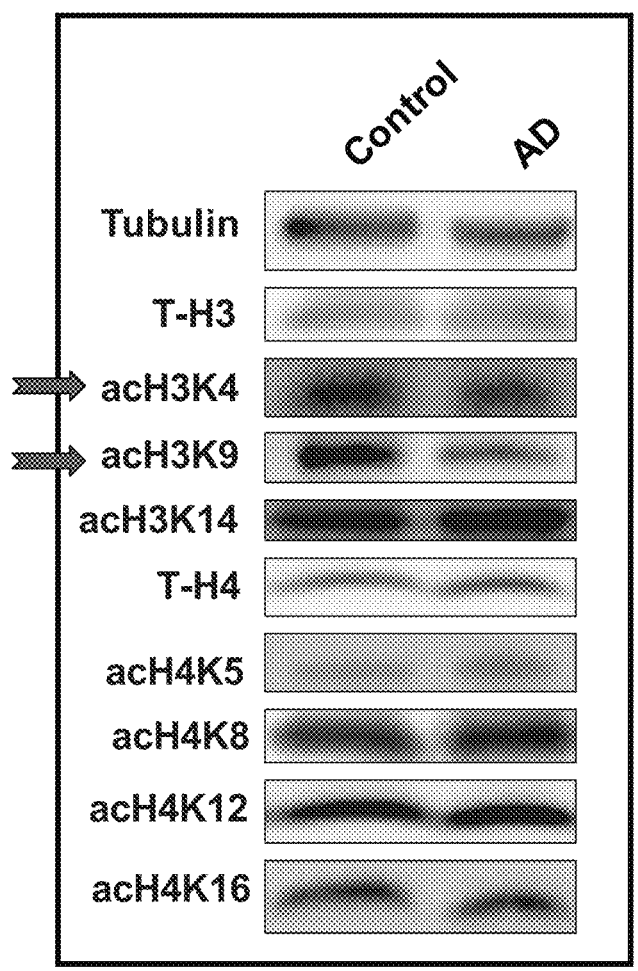
FIG. 75 is (A) a Western blot and (B) a graph showing histone acetylation levels important for memory are reduced in AD patients relative to control.
Figure 75B:
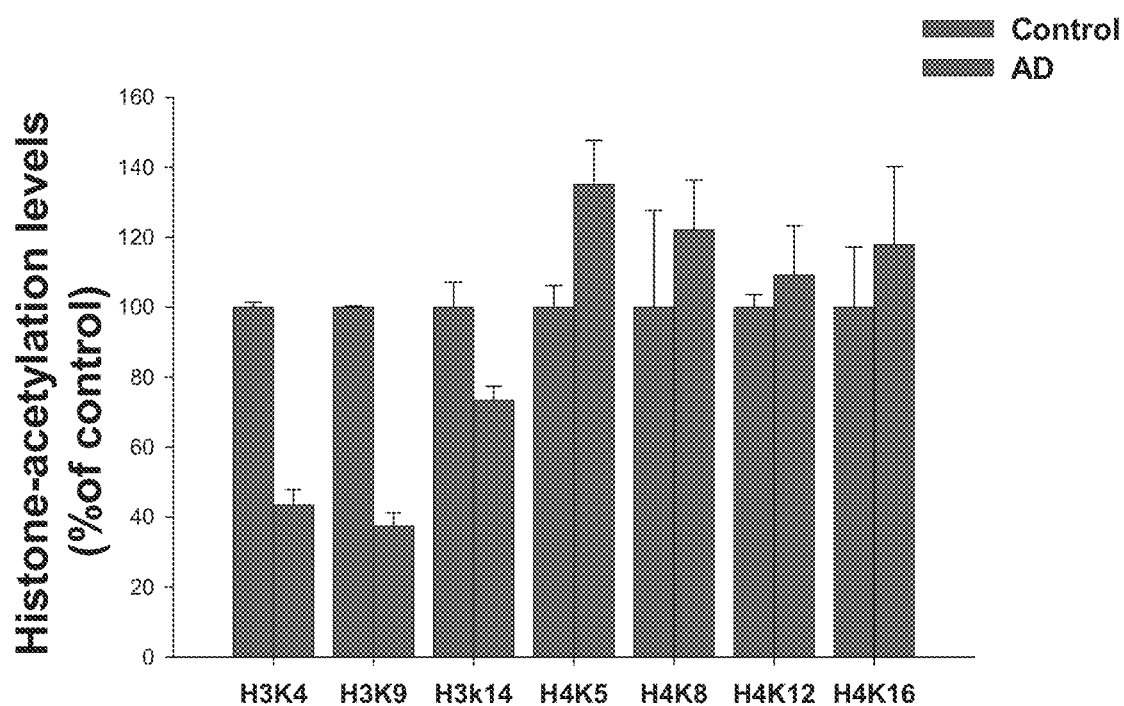
Figure 78:
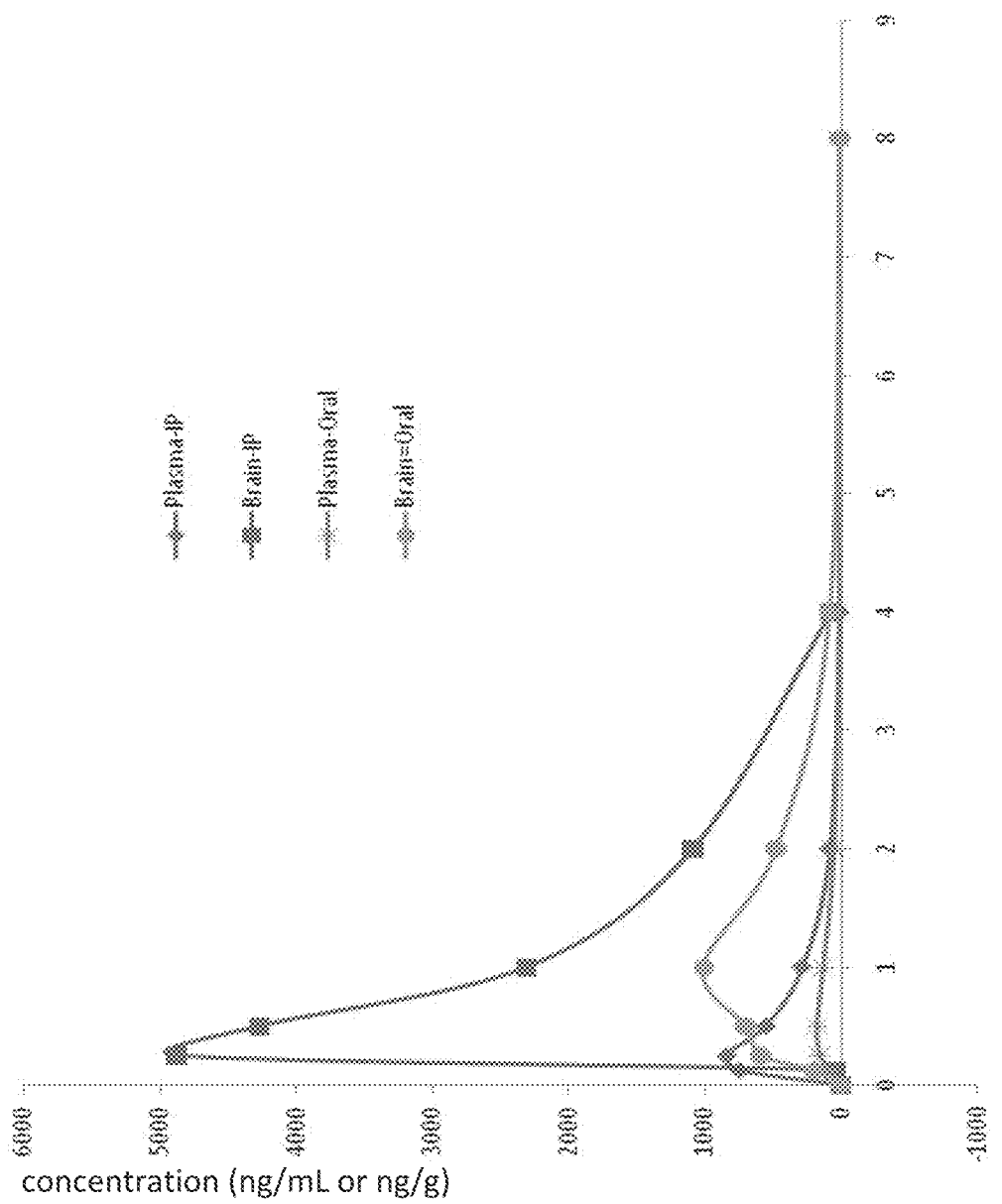
FIG. 78 is a graph showing i.p. and oral pharmacokinetic properties of YF2.
Figure 79:
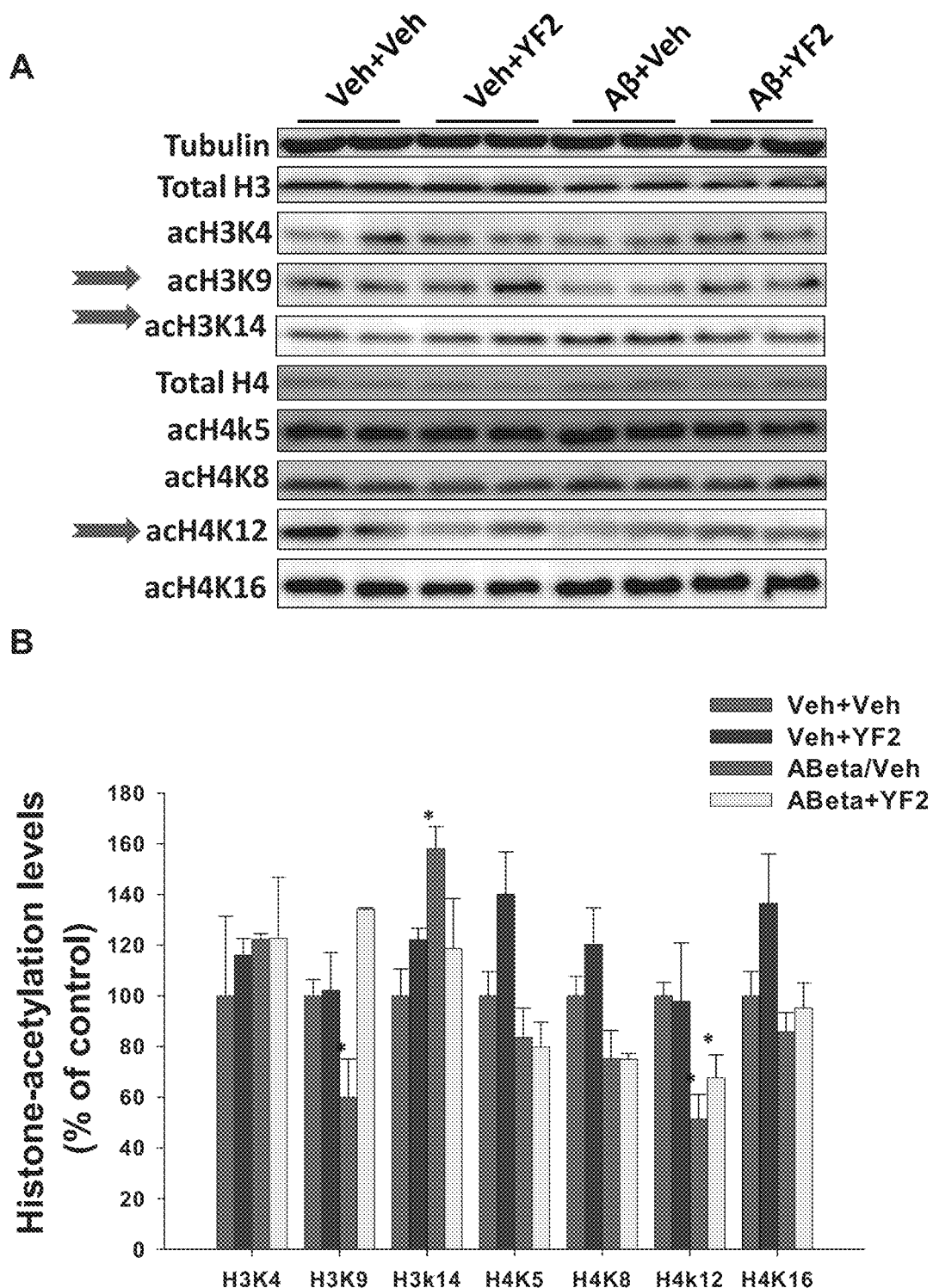
FIG. 79 is (A) a Western blot and (B) a graph showing that YF2 restores histone acetylation levels following Aβ elevation in basal conditions.
Figure 81:
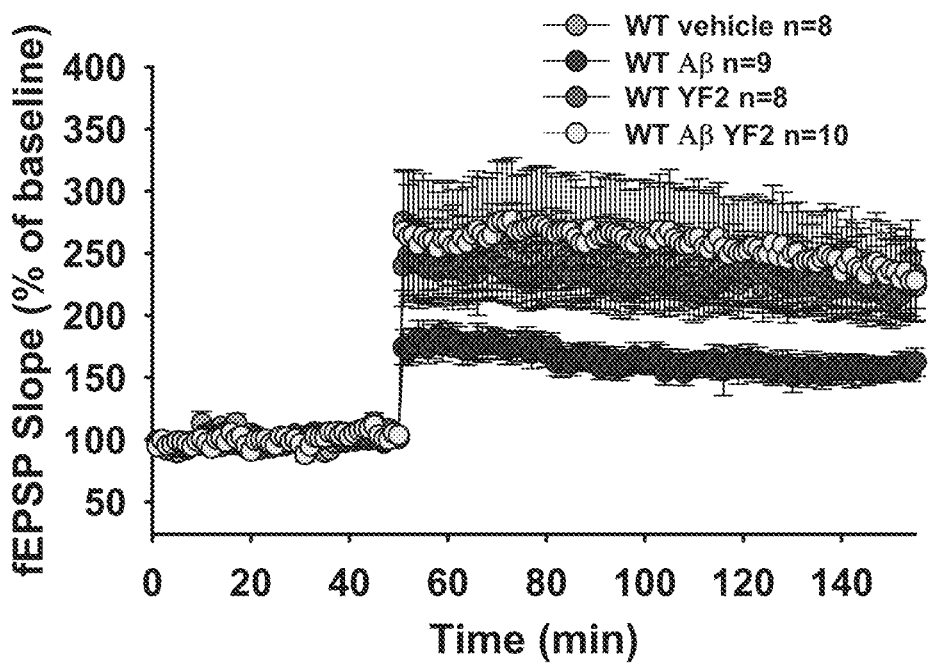
FIG. 81 shows that YF2 rescues the synaptic defect following Aβ elevation.
Figure 82:
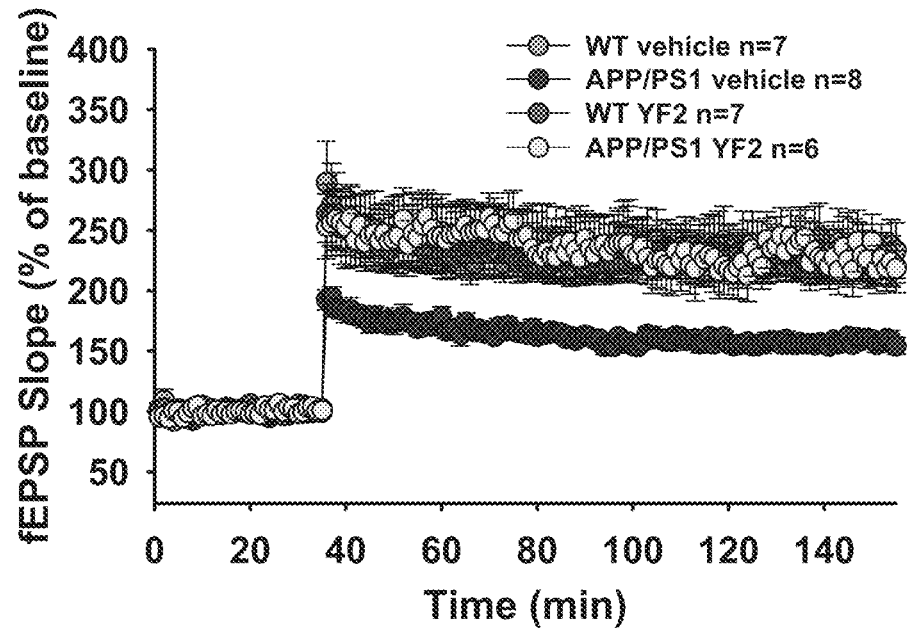
FIG. 82 shows that YF2 rescues the memory defect in APP/PS1 mice.

FIG. 74 corresponds to the results shown in Table 13.

Results of Effect of SAHA on HDAC Inhibition

Figure 61:
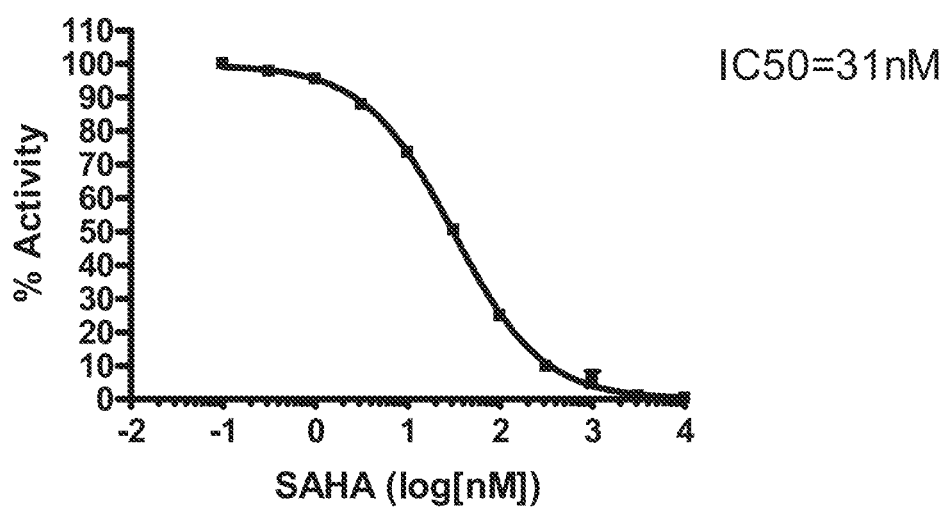
FIG. 61 is a graph showing the effect of the HDAC inhibitor, SAHA, on HDAC1 activity.
Figure 62:
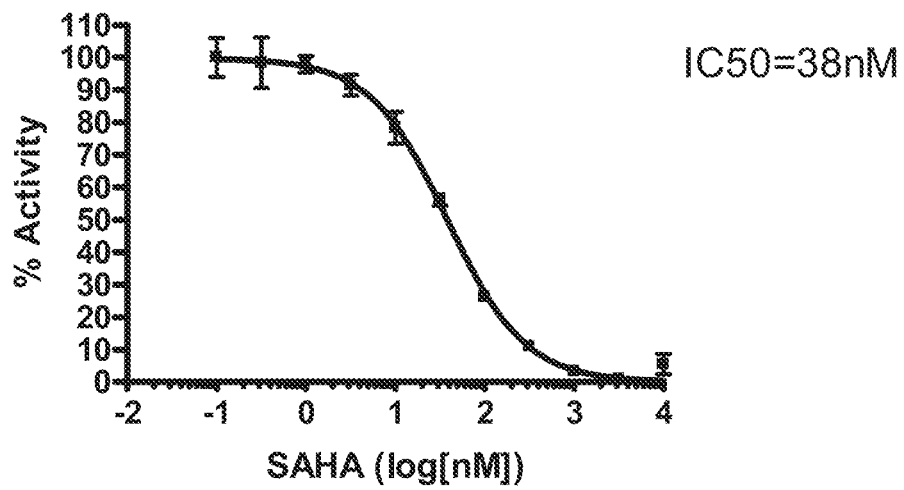
FIG. 62 is a graph showing the effect of the HDAC inhibitor, SAHA, on HDAC3/NCOR2 activity.
Figure 63:
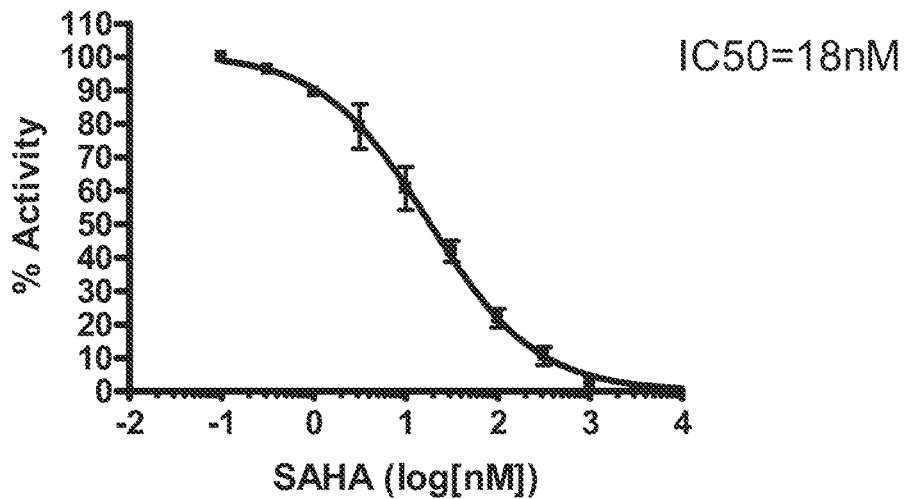
FIG. 63 is a graph showing the effect of the HDAC inhibitor, SAHA, on HDAC6 activity.

SAHA is an HDAC inhibitor (HDACi). It serves as a positive control for HDACs. FIGS. 61-63 show the inhibitory effect of SAHA on the HDACs HDAC1, HDAC3/NCOR2, and HDAC6. SAHA also inhibited HDAC5FL, HDAC7, HDAC8, HDAC10, Sirtuin 1, and Sirtuin 2 (see Table 1).

Example 9: Design of Selective HAT Activators

Early amnesic changes in Alzheimer's disease (AD) are thought to be linked to synaptic dysfunction. In this regard, β-amyloid (Aβ), a peptide that is produced in elevated amounts in the disease, has been found to inhibit memory[1,2] (each herein incorporated by reference in its entirety) and its electrophysiological model, long-term potentiation (LTP)[3-8] (each herein incorporated by reference in its entirety). Since memory is modulated by epigenetics through regulation of gene expression, deregulation of one of the epigenetic mechanisms such as histone (H) acetylation, might lead to memory disruption. Reduction of histone acetylation causes the chromatin structure to close, so that the information contained within the DNA might be less amenable to transcription factors and memory formation[9] (herein incorporated by reference in its entirety).

The main strategy that is currently used to up-regulate histone acetylation involves HDAC inhibitors. However, the pleiotropic effect of nonspecific HDAC inhibition may hamper their therapeutic potential[10-13] (each herein incorporated by reference in its entirety). We have demonstrated that hippocampal levels of two HATs, CBP and PCAF, are reduced following Aβ elevation. We have therefore focused towards another target which also up-regulates histone acetylation, the HATs. To this end we have synthesized a HAT activator, YF2. We propose a course of investigation involving the design of selective HAT activators that target specifically CBP and PCAF downstream of Aβ. The aims of our proposal are:

1) To design and synthesize new HAT activators which are optimized for AD;
2) To identify compounds with high affinity and good selectivity for selective HAT activators that target specifically CBP and PCAF;
3) To determine if new HAT activators have good pharmacokinetic (PK) profile and are safe;
4) To select HAT activators that rescue synaptic dysfunction in APP/PS1 mice;
5) Further screen HAT activators to determine if they are beneficial against cognitive abnormalities in APP/PS1 mice.

Background and Significance:

The post-translational acetylation status of chromatin is governed by the competing activities of two classes of enzymes, HATs and HDACs. HDAC inhibitors have been shown to enhance LTP and contextual fear memory, a form of associative memory in which animals must associate a neutral stimulus with an aversive one[P17] (herein incorporated by reference in its entirety). Also, memory and LTP deficits of CBP+/- mice were reversed by HDAC inhibition[P15] (herein incorporated by reference in its entirety). The potential of inhibiting HDACs to counteract neurodegenerative disorders has been widely explored[14] (herein incorporated by reference in its entirety). For instance, in a set of experiments, Tsai et al. have reported that HDAC inhibitors induced sprouting of dendrites, increased number of synapses, and reinstated learning and access to long-term memories in the CK-p25 Tg mouse model of neurodegeneration[15,16] (each herein incorporated by reference in its entirety). Moreover, in recent studies we have shown that the HDAC inhibitor TSA ameliorates LTP and contextual fear conditioning (FC) in the double Tg APP(K670M:N671L)/PS1(M146L, line 6.2) (APP/PS1) mouse model of amyloid deposition[17] (herein incorporated by reference in its entirety). Bolden et al., (2006, Nature Reviews Drug Discovery, 5:769-84; herein incorporated by reference in its entirety) describe the histone deacetylases family, the reference which is incorporated by reference in its entirety. HATs, however, have been investigated to a lesser extent.

HATs can be divided in two main groups, the nuclear HATs and cytoplasmic HATs[18] (herein incorporated by reference in its entirety). Nuclear A-type HATs can be grouped into at least 4 different families based on sequence conservation within the HAT domain: Gcn5 and p300/CBP associated factor (PCAF), MYST (MOZ, Ybf2/Sas3, Sas2 and Tip60), p300 and CBP (named for the two human paralogs p300 and CBP) and Rtt109. While the Gcn5/PCAF and MYST families have homologs from yeast to man, p300/CBP is metazoan-specific, and Rtt109 is fungal-specific. Cytoplasmic B-type HATs, such as HAT1, are involved in histone deposition[P22] (herein incorporated by reference in its entirety). Marmorstein and Roth (2001, *Curr Opin in Genet and Develop.*, 11:155-161; herein incorporated by reference in its entirety) list in Table 1 the HAT families and their transcriptional-related functions, the reference which is incorporated by reference in its entirety.

Although other nuclear HAT families have been described, such as the steroid receptor coactivators, TAF250, ATF-2, and CLOCK, their HAT activities have not been investigated as extensively as the major HAT classes[18] (herein incorporated by reference in its entirety). These 4 families show high sequence similarity within families but poor to no sequence similarity between families. Furthermore, the size of the HAT domain of the different families is different[P22] (herein incorporated by reference in its entirety). Interestingly, HATs are highly conserved in mammals[P22] (herein incorporated by reference in its entirety). Of all these HATs, three were shown to be involved in memory: CBP, p300[19,20] (each herein incorporated by reference in its entirety), and PCAF[21] (herein incorporated by reference in its entirety). Interestingly, both CBP and PCAF levels are reduced by Aβ elevation.

HAT activators are a viable approach to enhance histone acetylation. Two scaffolds for HAT activators have been identified. The first one includes CTPB and its derivative CTB[22,23] (each herein incorporated by reference in its entirety). The second one includes only one compound, nemorosone[24] (herein incorporated by reference in its entirety). CTPB/CTB were found to be insoluble and membrane-impermeable[22,23] (each herein incorporated by reference in its entirety). Moreover, CTPB has unfavorable characteristics to be used in CNS diseases (MW equal to 553,29, clogP equal to 12.70) and the clogP of CTB is 5.13. Nemorosone has a MW of 502 and a clogP of 8.42. In summary, ample evidence exists supporting a promising therapeutic role for HAT activators in the treatment of CNS disorders including AD. We will exploit this possibility by developing new chemical entities targeting specifically CBP and PCAF.

Research Design and Methods:

1) To Design and Synthesize New HAT Activators which are Optimized for AD.

We have designed a new compound based on SAR studies of the CTPB/CTB scaffold, named YF2. YF2 (MW 430.13, clogP 5.15, clogBB 0.17) has increased solubility, membrane permeability and blood-brain barrier permeability, is safe in acute toxicity tests. YF2 rescued the reduction in hippocampal levels of H3 acetylation following Aβ elevation, enhanced enzymatic activity of PCAF, CBP and Gcn5 as well as p300, had excellent selectivity for PCAF, CBP and Gcn5 over HDACs, and was capable of rescuing deficits in fear and reference memory induced by Aβ exposure. We are refining its druggability using a medicinal chemistry (medchem) approach, focusing on the synthesis of drug-like lead compounds with good PK and ADMET profile. We will design and synthesize HAT activators bearing different moieties at different positions of one of the two aromatic rings of YF2. In particular, we will substitute a dimethylamino group which is likely to be alkylated by microsomes and protect an aromatic ring from oxidative reactions. Additionally, we will explore the HAT binding site i) by evaluating the importance of the amide group between the two aromatic rings, ii) by constraining the molecular structure, iii) by modifying the distance between two aromatic rings that currently form YF2, iv) by replacing one of the two aromatic rings with an eterocyclic ring, and v) by increasing the hindrance of the substituents of one of the two aromatic rings. We will find HAT activators with a) HAT specificity and potency, b) great CNS penetration, and c) safety.

2) To Identify Compounds with High Affinity and Good Selectivity for Selective HAT Activators that Target Specifically CBP and PCAF.

Following assessment of HAT activator potency ($EC_{50}$), we will check selectivity with respect to CBP and PCAF. For HAT activators found to show good potency (<100 nM), selectivity (at least 50-fold vs p300, Gcn5, MYST families and HDACs) and solubility, we will use a functional assay to determine if they increase hippocampal H3 and H4 acetylation in adult mice.

3) To Determine Whether New HAT Activators have Good Pharmacokinetic (PK) Profile and are Safe.

Selected HAT activators will be screened against unfavorable PK properties including bioavailability, brain uptake, and BBB penetration. Compounds passing these tests will be evaluated for rudimentary ADMET characteristics including tests of acute and chronic toxicity.

4) To Select HAT Activators that Rescue LTP in APP/PS1 Mice.

We will determine if selected HAT activators ameliorate LTP defect in APP/PS1 slices using electrophysiological techniques[25] (herein incorporated by reference in its entirety).

5) Further Screen HAT Activators to Examine if they Ameliorate Cognitive Abnormalities in APP/PS1 Mice.

We will determine if HAT activators screened in slices can protect APP/PS1 mice against impairments of contextual and reference memory using behavioral assays[25] (herein incorporated by reference in its entirety). Next, we will characterize our compounds for their more global selectivity against targets other than HATs. We will also screen them with a battery of assays focusing on two areas that have resulted in the withdrawal of many drugs from the market: drug-drug interactions (liver metabolism), hERG channel blockage (cardiac dysfunction).

YF2, Alzheimer's Disease, and Drug Discovery Research:

Currently used AD therapies have limited efficacy. Major efforts are underway to inhibit tangle formation, to combat inflammation and oxidative damage, and to decrease Aβ load in the brain[26-28] (each herein incorporated by reference in its entirety). However, the role of APP, Aβ, and the secretases in normal physiological function[29-31] (each herein incorporated by reference in its entirety) might present a problem in providing effective and safe approaches to AD therapy. Developing agents that interact with Aβ targets that lead to neuronal dysfunction is another approach that is currently tested by many laboratories. Without being bound by theory, HAT activators represent a new class of compounds that might effectively counteract the disease progression.

REFERENCES

1. Malm, T., et al., *beta-Amyloid infusion results in delayed and age-dependent learning deficits without role of inflammation or beta-amyloid deposits*. Proc Natl Acad Sci USA, 2006. 103(23): p. 8852-7.
2. Cleary, J. P., et al., *Natural oligomers of the amyloid-beta protein specifically disrupt cognitive function*. Nat Neurosci, 2005. 8(1): p. 79-84.
3. Cullen, W. K., et al., *Block of LTP in rat hippocampus in vivo by beta-amyloid precursor protein fragments*. Neuroreport, 1997. 8(15): p. 3213-7.
4. Itoh, A., et al., *Impairments of long-term potentiation in hippocampal slices of beta-amyloid-infused rats*. Eur J Pharmacol, 1999. 382(3): p. 167-75.
5. Vitolo, O. V., et al., *Amyloid beta-peptide inhibition of the PKA/CREB pathway and long-term potentiation: reversibility by drugs that enhance cAMP signaling*. Proc Natl Acad Sci USA, 2002. 99(20): p. 13217-21.
6. Walsh, D. M., et al., *Naturally secreted oligomers of amyloid beta protein potently inhibit hippocampal long-term potentiation in vivo*. Nature, 2002. 416(6880): p. 535-9.
7. Chen, Q. S., et al., *Impairment of hippocampal long-term potentiation by Alzheimer amyloid beta-peptides*. J Neurosci Res, 2000. 60(1): p. 65-72.
8. Lambert, M. P., et al., *Diffusible, nonfibrillar ligands derived from Abeta*1-42 *are potent central nervous system neurotoxins*. Proc Natl Acad Sci USA, 1998. 95(11): p. 6448-53.
9. Rakyan, V. K., et al., *The marks, mechanisms and memory of epigenetic states in mammals*. Biochem J, 2001. 356(Pt 1): p. 1-10.
10. Gwack, Y., et al., *CREB-binding protein and histone deacetylase regulate the transcriptional activity of Kaposi's sarcoma-associated herpesvirus open reading frame* 50. J Virol, 2001. 75(4): p. 1909-17.
11. Lu, F., et al., *Chromatin remodeling of the Kaposi's sarcoma-associated herpesvirus ORF*50 *promoter correlates with reactivation from latency*. J Virol, 2003. 77(21): p. 11425-35.
12. Knutson, S. K., *In vivo characterization of the role of histone deacetylase* 3 *in metabolic and transcriptional regulation*, in *Biochemistry*. 2008, Vanderbilt: Nashville. p. 167.
13. Rajan, I., et al., *Loss of the putative catalytic domain of HDAC*4 *leads to reduced thermal nociception and seizures while allowing normal bone development*. PLoS One, 2009. 4(8): p. e6612.
14. Langley, B., et al., *Remodeling chromatin and stress resistance in the central nervous system: histone deacetylase inhibitors as novel and broadly effective neuroprotective agents*. Curr Drug Targets CNS Neurol Disord, 2005. 4(1): p. 41-50.
15. Fischer, A., et al., *Recovery of learning and memory is associated with chromatin remodelling*. Nature, 2007. 447(7141): p. 178-82.
16. Kim, D., et al., *SIRT*1 *deacetylase protects against neurodegeneration in models for Alzheimer's disease and amyotrophic lateral sclerosis*. EMBO J, 2007. 26(13): p. 3169-79.
17. Francis, Y. I., et al., *Dysregulation of histone acetylation in the APP/PS*1 *mouse model of Alzheimer's disease*. J Alzheimers Dis, 2009. 18(1): p. 131-9.
18. Marmorstein, R. and R. C. Trievel, *Histone modifying enzymes: structures, mechanisms, and specificities*. Biochim Biophys Acta, 2009. 1789(1): p. 58-68.
19. Roelfsema, J. H. and D. J. Peters, *Rubinstein-Taybi syndrome: clinical and molecular overview*. Expert Rev Mol Med, 2007. 9(23): p. 1-16.

20. Alarcon, J. M., et al., *Chromatin acetylation, memory, and LTP are impaired in CBP+/− mice: a model for the cognitive deficit in Rubinstein-Taybi syndrome and its amelioration.* Neuron, 2004. 42(6): p. 947-59.
21. Maurice, T., et al., *Altered memory capacities and response to stress in p300/CBP-associated factor (PCAF) histone acetylase knockout mice.* Neuropsychopharmacology, 2008. 33(7): p. 1584-602.
22. Mantelingu, K., et al., *Activation of p300 histone acetyltransferase by small molecules altering enzyme structure: probed by surface-enhanced Raman spectroscopy.* J Phys Chem B, 2007. 111(17): p. 4527-34.
23. Balasubramanyam, K., et al., *Small molecule modulators of histone acetyltransferase p300.* J Biol Chem, 2003. 278(21): p. 19134-40.
24. Dal Piaz, F., et al., *The identification of a novel natural activator of p300 histone acetyltranferase provides new insights into the modulation mechanism of this enzyme.* Chembiochem. 11(6): p. 818-27.
25. Trinchese, F., et al., *Progressive age-related development of Alzheimer-like pathology in APP/PS1 mice.* Ann Neurol, 2004. 55(6): p. 801-14.
26. Nakagami, Y., et al., *A novel beta-sheet breaker, RS-0406, reverses amyloid beta-induced cytotoxicity and impairment of long-term potentiation in vitro.* Br J Pharmacol, 2002. 137(5): p. 676-82.
27. Walsh, D. M., et al., *Certain inhibitors of synthetic amyloid beta peptide (Abeta) fibrillogenesis block oligomerization of natural Abeta and thereby rescue long-term potentiation.* J Neurosci, 2005. 25(10): p. 2455-62.
28. Schenk, D., et al., *Immunization with amyloid-beta attenuates Alzheimer-disease-like pathology in the PDAPP mouse.* Nature, 1999. 400(6740): p. 173-7.
29. Wu, J., R. Anwyl, and M. J. Rowan, *beta-Amyloid-(1-40) increases long-term potentiation in rat hippocampus in vitro.* Eur J Pharmacol, 1995. 284(3): p. R1-3.
30. Kowalska, M. A. and K. Badellino, *beta-Amyloid protein induces platelet aggregation and supports platelet adhesion.* Biochem Biophys Res Commun, 1994. 205(3): p. 1829-35.
31. Mattson, M. P., Z. H. Guo, and J. D. Geiger, *Secreted form of amyloid precursor protein enhances basal glucose and glutamate transport and protects against oxidative impairment of glucose and glutamate transport in synaptosomes by a cyclic GMP-mediated mechanism.* J Neurochem, 1999. 73(2): p. 532-7.

Example 10: HAT Agonists for the Treatment of AD

We have demonstrated that hippocampal levels of CREB binding protein (CBP) and p300/CBP associated factor (PCAF), two histone acetyltransferases (HATs) that catalyze histone acetylation and are relevant to memory formation[P14-P16] (each herein incorporated by reference in its entirety), are reduced following Aβ elevation.

We have designed and synthesized a HAT Activator compound, YF2 (FIG. 29). YF2 was prepared by Mitsunobu reaction between 2-(dimethylamino)ethanol and 3, which was obtained through the reaction of the acid 2 and 4-chloro-3-(trifluoromethyl)aniline, in the presence of EDC. The acid was synthesized by ester hydrolysis of 1. Finally, YF2 was treated with HCl/Et2O in order to obtain a water soluble compound.

Ethyl 2-ethoxy-6-hydroxybenzoate (1) (0.095 mol) was dissolved in 40 mL of EtOH and 100 mL of NaOH aq. 1N. The resulting solution was stirred to reflux for 2 h. EtOH was evaporated and the aqueous phase was acidified by adding HCl conc. at 0° C. and the resulting precipitate (2, 91% of yield) was collected by filtration and dried. $^1$H NMR (300 MHz, CDCl$_3$) δ 12.15 (s, 1H), 11.58 (s, 1H), 7.38 (t, 1H, J=8.4 Hz), 6.70 (d, 1H, J=8.4 Hz), 6.45 (d, 1H, J=8.4 Hz), 4.31 (t, 2H, J=6.9 Hz), 1.56 (q, 3H, J=6.9 Hz). N-(3-dimethylaminopropyl)-N-ethylcarbodiimide hydrochloride (0.071 mol) was added portionwise at 0° C. to a solution of 2 (0.055 mol) and 3-chloro-4-(trifluoromethyl)aniline hydrochloride (0.06 mol) in 70 mL of CH$_2$C$_{12}$. The mixture was stirred at rt overnight. The solvent was evaporated off; compound 3 (82% of yield) was obtained by crystallization from MeOH. $^1$H NMR (300 MHz, CDCl$_3$) δ 13.28 (s, 1H), 10.65 (br s, 1H), 7.91 (d, 1H, J=2.1 Hz), 7.76 (dd, 1H, J$_1$=2.1, J$_2$=8.7 Hz), 7.48 (d, 1H, J=8.7 Hz), 7.31 (t, 1H, J=8.4 Hz), 6.67 (d, 1H, J=8.4 Hz), 6.43 (d, 1H, J=8.4 Hz), 4.27 (q, 2H, J=6.9 Hz), 1.64 (t, 3H, J=6.9 Hz).

Diisopropyl azodicarboxylate (0.036 mol) was added dropwise at 0° C. to a solution of 3 (0.028 mol), 2-dimethylaminoethanol (0.036 mol) and triphenylphosphine (0.036 mol) in 50 mL of THF. The reaction was stirred at rt for 24 h. The solvent was evaporated and the residue was dissolved in AcOEt (50 mL) and washed with H$_2$O (3×50 mL), dried over Na$_2$SO$_4$, filtered and evaporated. Purification by flash chromatography (10% MeOH in CH$_2$Cl$_2$) gave a colorless oil (YF2) that was treated with Et$_2$O HCl 2M (70% of yield). $^1$H NMR (300 MHz, CDCl$_3$) δ 8.70 (br s, 1H), 7.98 (d, 1H, J=8.1 Hz), 7.79 (s, 1H), 7.45 (d, 1H, J=8.4 Hz), 7.28 (t, 1H, J=8.4 Hz), 6.59 (dd, 2H, J$_1$=3.2, J$_2$=8.4 Hz), 4.19 (t, 2H, J=5.4 Hz), 4.11 (q, 2H, J=7.2 Hz), 2.65 (t, 2H, J=5.4 Hz), 2.25 (s, 6H), 1.39 (t, 3H, J=7.2 Hz); MS ESI (m/z) 431 (M+1).

Figure 72:
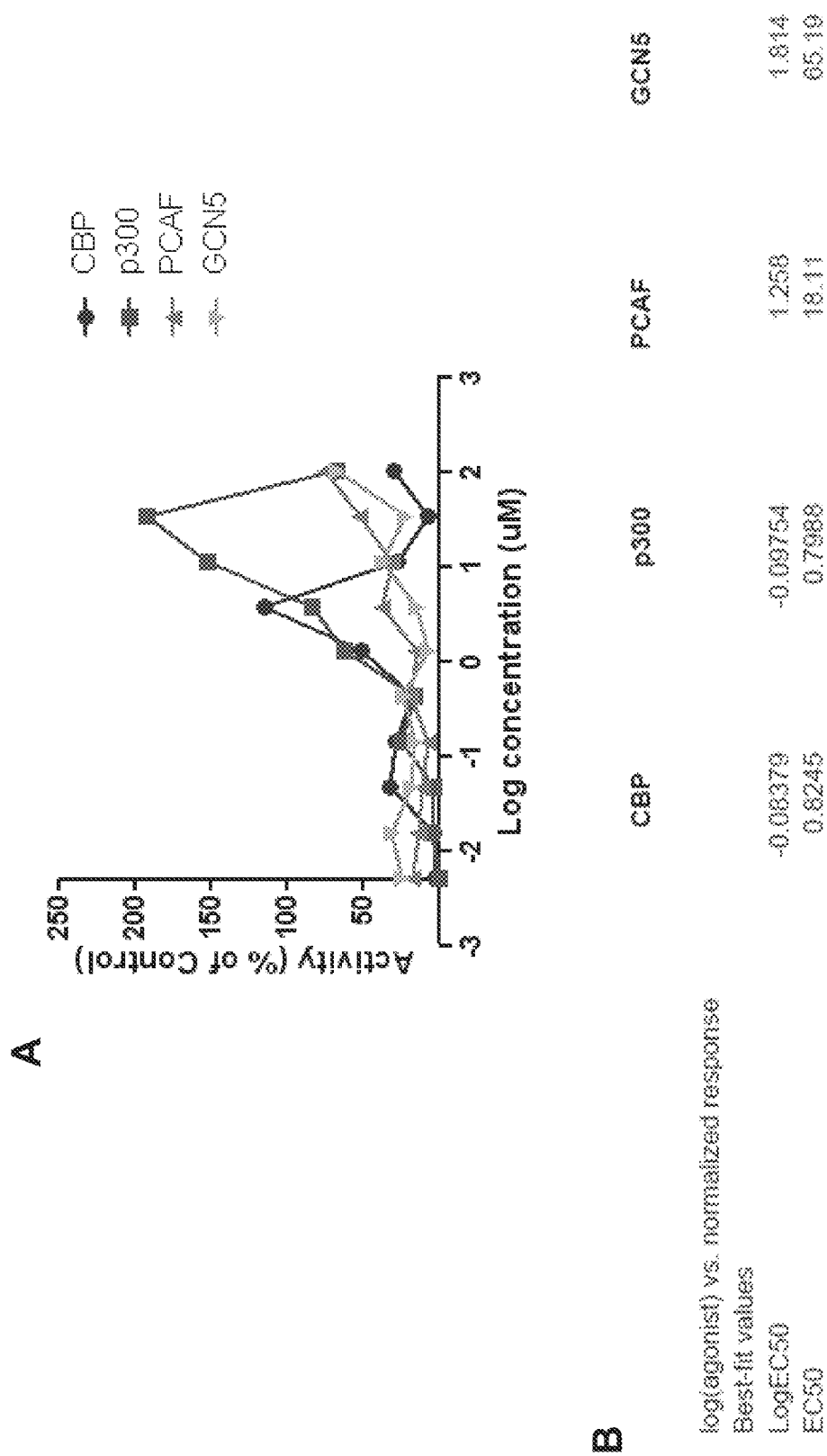
FIG. 72A are dose-response curves for human CBP, p300, PCAF and GCN5 activation by different YF2 concentrations.
FIG. 72B is a table that represents the calculated $EC_{50}$ values of CBP, p300, PCAF, and GCN5.
Figure 73:
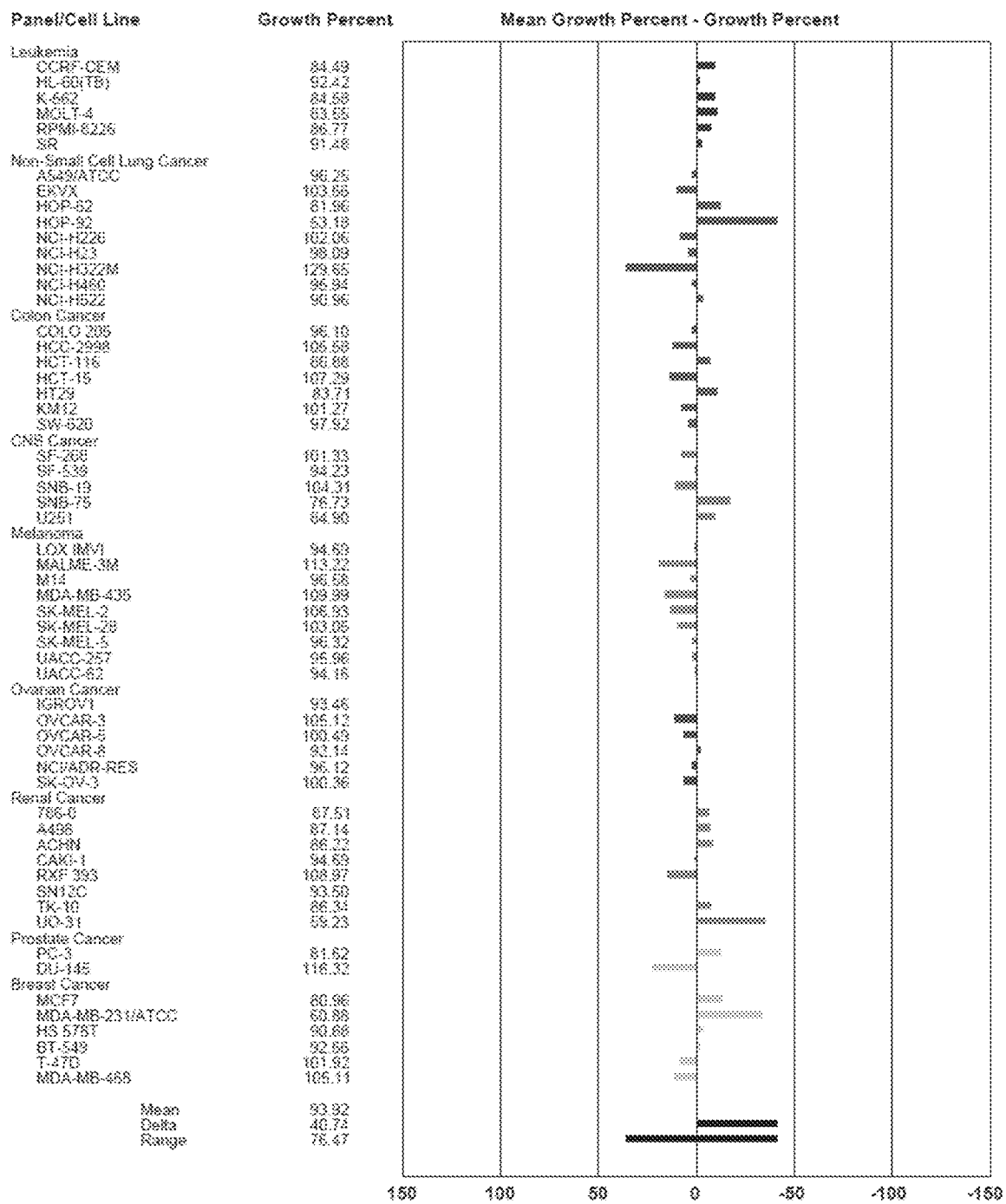
FIG. 73 is a graph showing NIH cell lines growth inhibition values for 10 μM YF2 treatment.

In In vitro assays, YF2 has activity versus CBP, PCAF, and GCN5. The EC$_{50}$'s of YF2 for CBP, PCAF, and GCN5 are 2.75 µM, 29.04 µM and 49.31 µM, respectively. Additionally, YF2 did not interfere with p300 and HDAC activity (HDAC 1, 3, 5, 6, 7, 8, 10, 11, and sirt1-2). YF2 also increases p300 activity as shown in FIG. 72.

Encouraged by these results, we then investigated YF2 pharmacokinetic (PK) and blood-brain barrier (BBB) penetration capability. After i.p. and i.v. administration at 20 mg/kg to BALB/c mice, plasma and brain concentrations were determined by LC-MS/MS. The data in Table 14 indicates that YF2 is rapidly absorbed in the brain (T$_{max}$ at 15 min).

TABLE 14

Pharmacokinetic parameters of YF2.

| Parameters | | IP Administration | | | IV Administration | | |
|---|---|---|---|---|---|---|---|
| | | Plasma | Brain | Ratio* | Plasma | Brain | Ratio* |
| T$_{max}$ | (h) | 0.25 | 0.25 | — | 0.125 | 0.125 | — |
| C$_{max}$ | (ng/mL or ng/g) | 843 | 4878 | 5.8 | 2132 | 27892 | 13.1 |
| AUC$_{0-t}$ | (ng · h/ mL or ng · h/g) | 806 | 6493 | 8.1 | 1967 | 22222 | 11.3 |
| AUC$_{0-\infty}$ | (ng · h/ mL or ng · h/g) | 813 | 6564 | 8.1 | 2020 | 22581 | 11.2 |

TABLE 14-continued

Pharmacokinetic parameters of YF2.

| Parameters | | IP Administration | | | IV Administration | | |
|---|---|---|---|---|---|---|---|
| | | Plasma | Brain | Ratio* | Plasma | Brain | Ratio* |
| t½ | (h) | 0.60 | 0.63 | — | 0.70 | 0.63 | — |
| MRT | (h) | 0.85 | 1.03 | — | 0.84 | 0.74 | — |
| F | (%) | 41.0 | 29.2 | — | — | — | — |

*Ratio = brain/plasma
YF2 $EC_{50}$'s for CBP, PCAF and GCN5 are: 2.75 µM, 29.04 µM and 49.31 µM, respectively The amount of YF2 in the brain was higher than that in the plasma with an $AUC_{0-t}$ ratio of 8.2 and 10.8 for i.p. and i.v. administration, respectively. The elimination half-lives of YF2 in the brain and plasma were ~40 min. The $T_{max}$ values in the brain and plasma were similar, indicating that the distribution of YF2 to the brain is also fast. Additionally, in acute toxicity experiments YF2 did not induce any adverse effects up to 300 mg/kg (i.p.).

Figure 64:
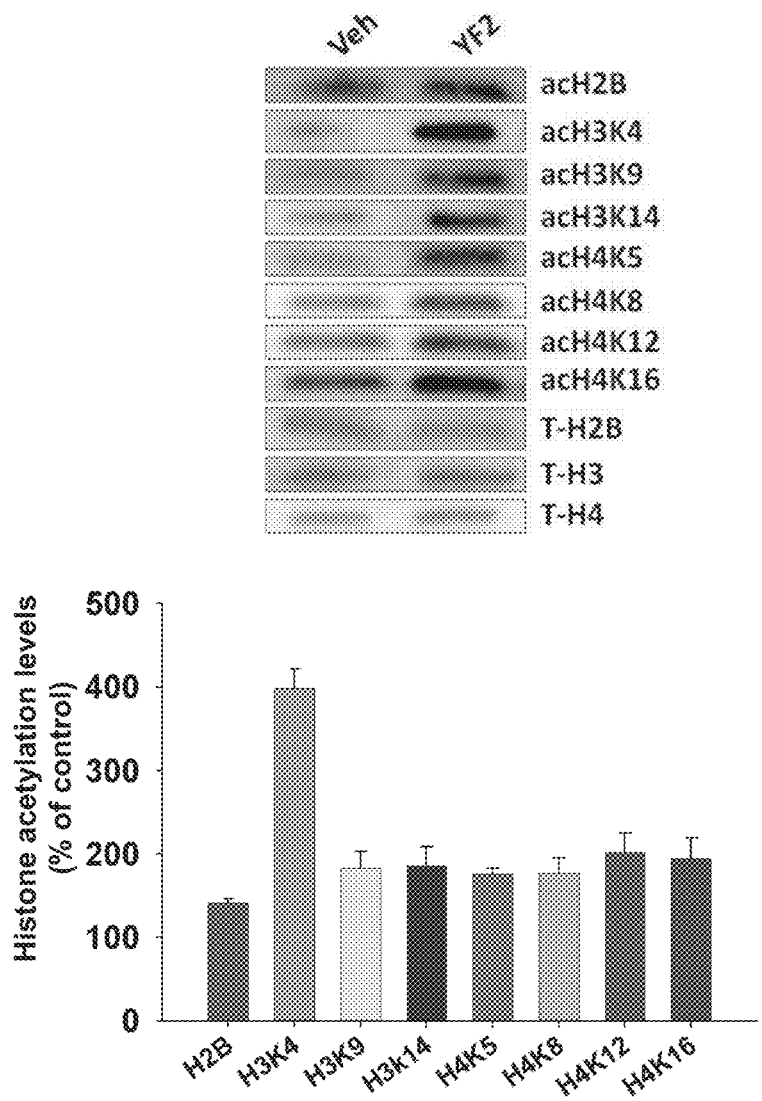
FIG. 64 shows that an acute administration of YF2 increased specific acetylation of H3, H4, and H2B in hippocampal lysates. n=3 and p<0.05 per group.

We then tested if YF2 increases histone acetylation in mouse hippocampus. The compound was i.p. administered at 20 mg/Kg, mice were sacrificed 30 min later, and hippocampi were removed and quickly frozen for WB analysis. As shown in FIG. 64, YF2 increased acetylation of histone lysines that were shown to be involved in memory formation (H3K4, H3K9, H3K14, H4K5, H4K8, H4K12, H4K16, and H2B)[P15, P33] (each herein incorporated by reference in its entirety).

Figure 65:
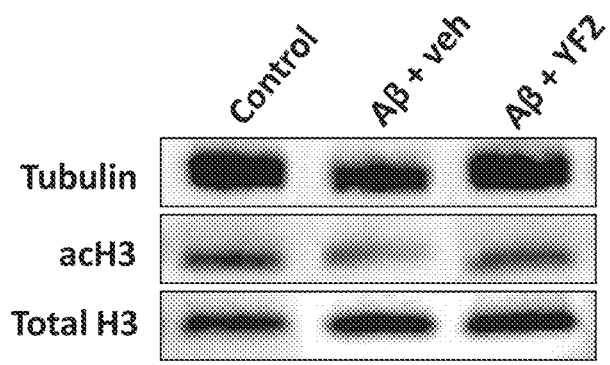
FIG. 65 is a photograph of a western blot showing that YF2 (i.p., 5 mg/kg) was able to rescue the Aβ-induced decrease in H3 acetylation levels (n=3 per each group, p<0.05). Aβ (200 nM in a final volume of 1 μl over 1 min, 75 min before mice were sacrificed) was infused through cannulas onto dorsal hippocampi.
Figure 66C:
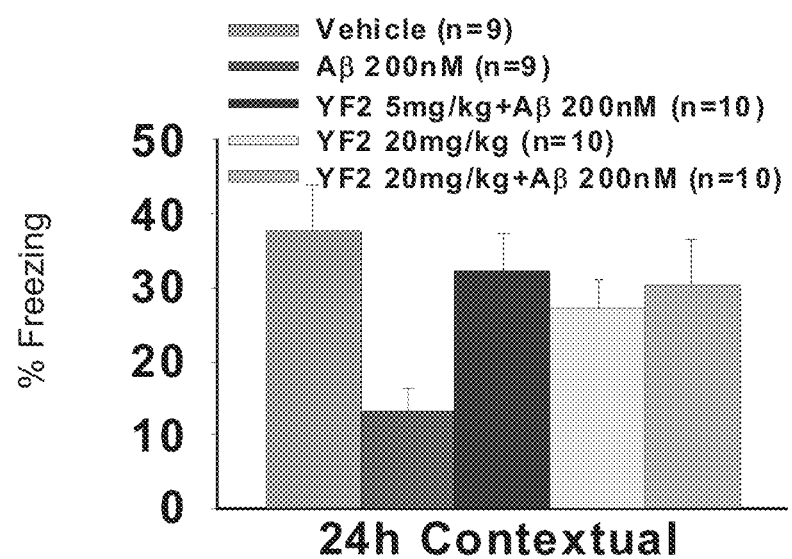
FIG. 66C is a graph that shows the beneficial effect of YF2 on Aβ42-induced cognitive dysfunction using a water maze/reference memory test. YF2 ameliorates the reference memory deficit in $A\beta_{42}$-infused mice, P<0.01.
Figure 68:
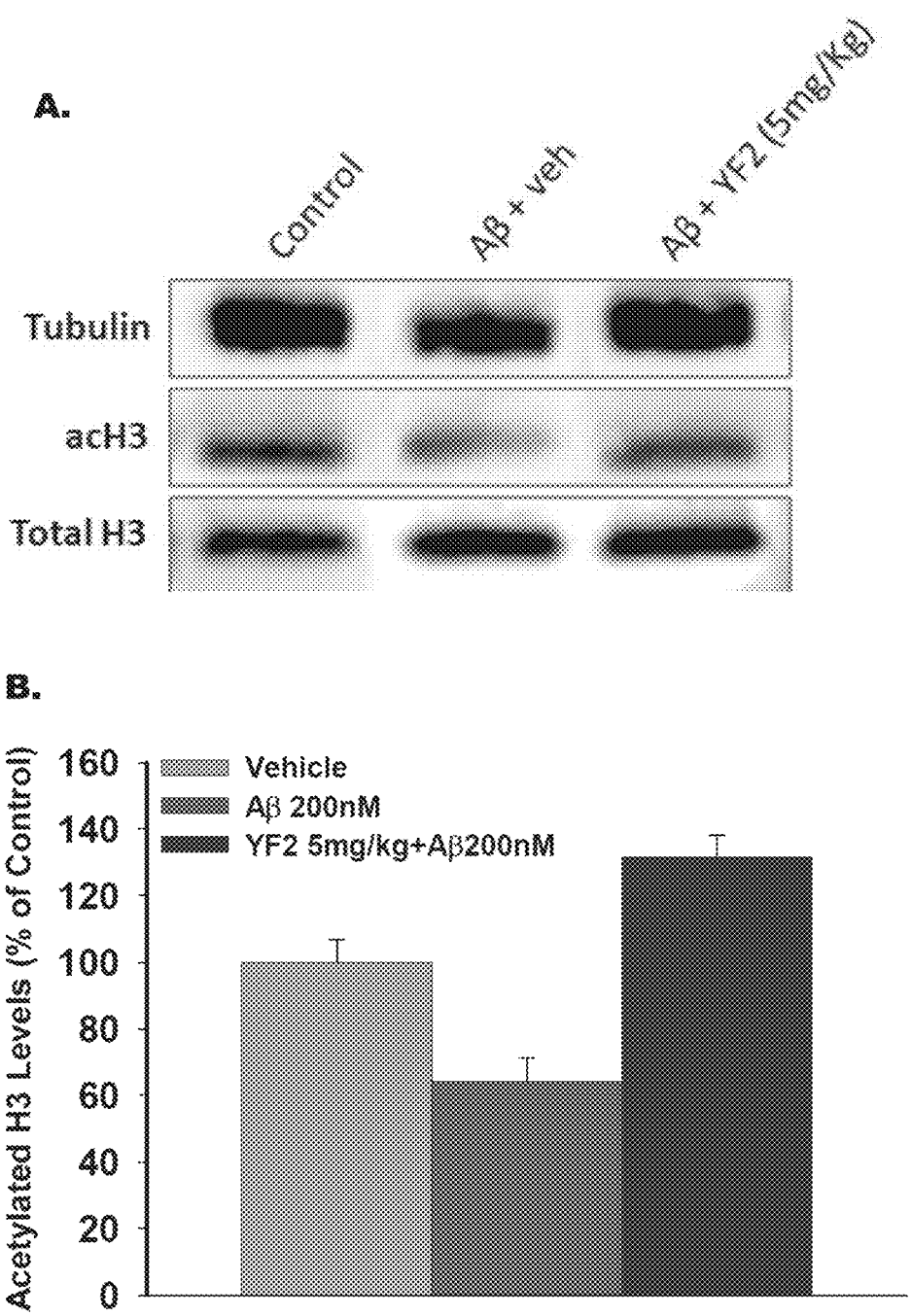
FIGS. 68A-B show that YF2 rescues the reduction in acetylated H3 levels after infusion of Aβ42.
Figure 69:
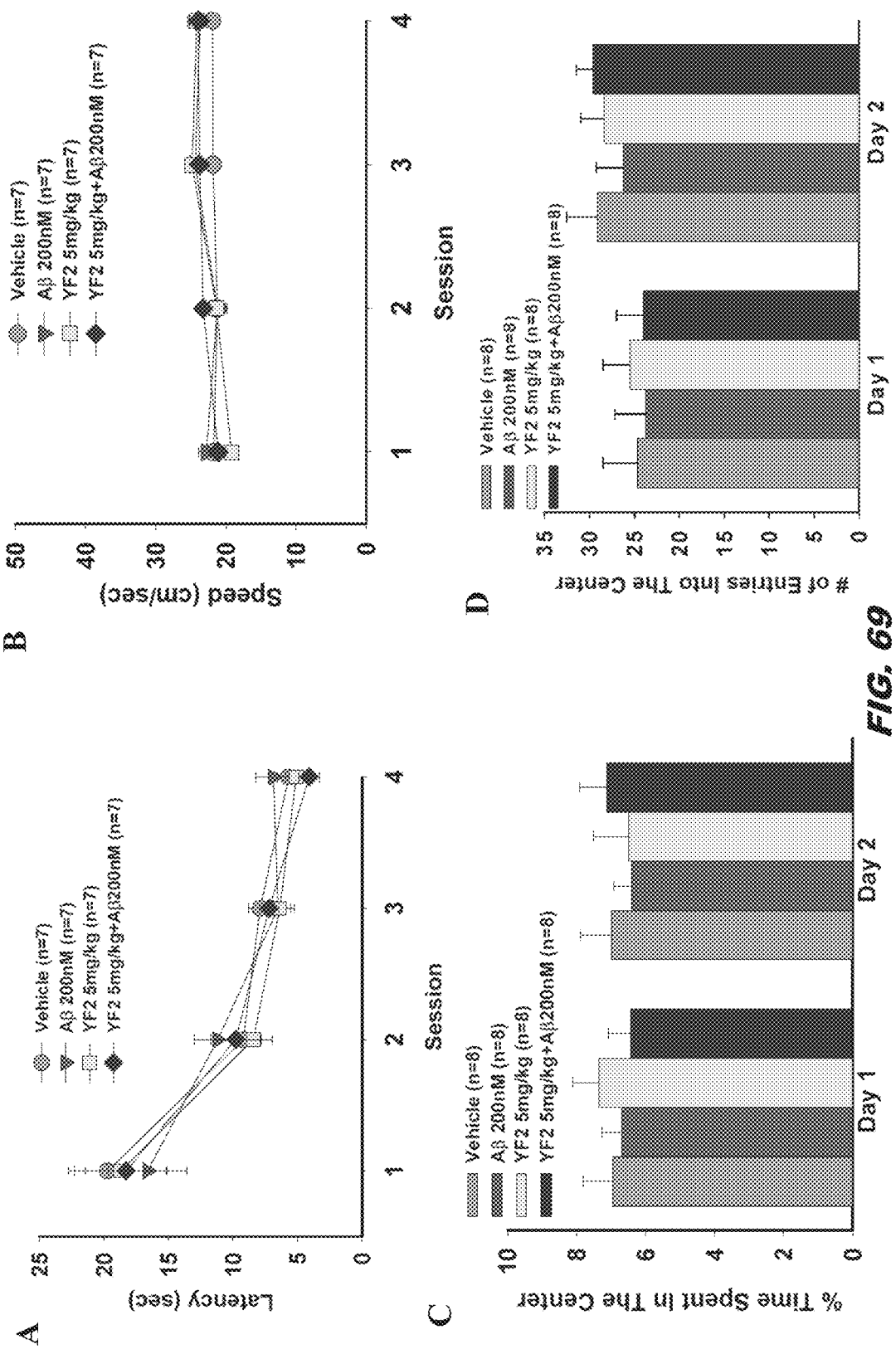
FIGS. 69A-D are graphs that show the Latency (FIG. 69A) and speed (FIG. 69B) to reach a visible platform and open field assessment of YF2 in mice infused with Aβ42. Percent of time spend in the center are shown in FIG. 69C and number of entries into the center are shown in FIG. 69D.
Figure 70:
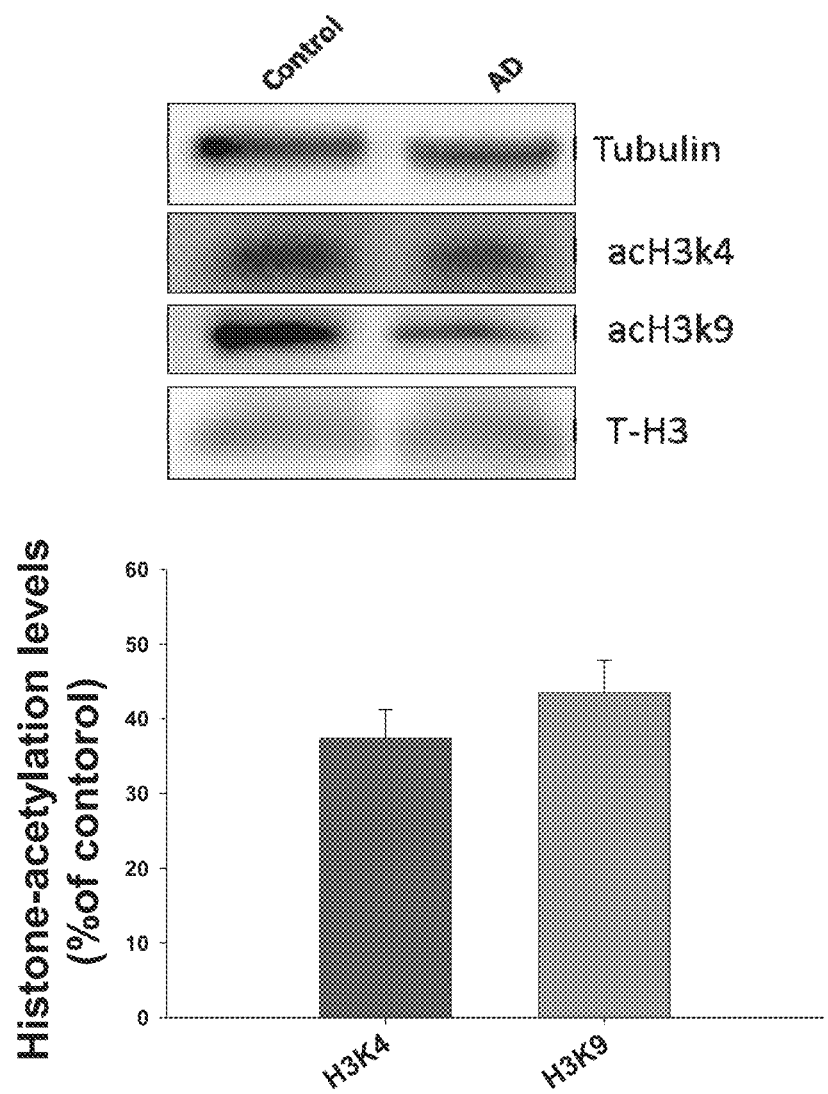
FIG. 70 shows that histone acetylation levels are reduced in AD patients. Compared to control, Alzheimer's disease patients showed a decrease in acetylation of histone residues important for memory.
Figure 71:
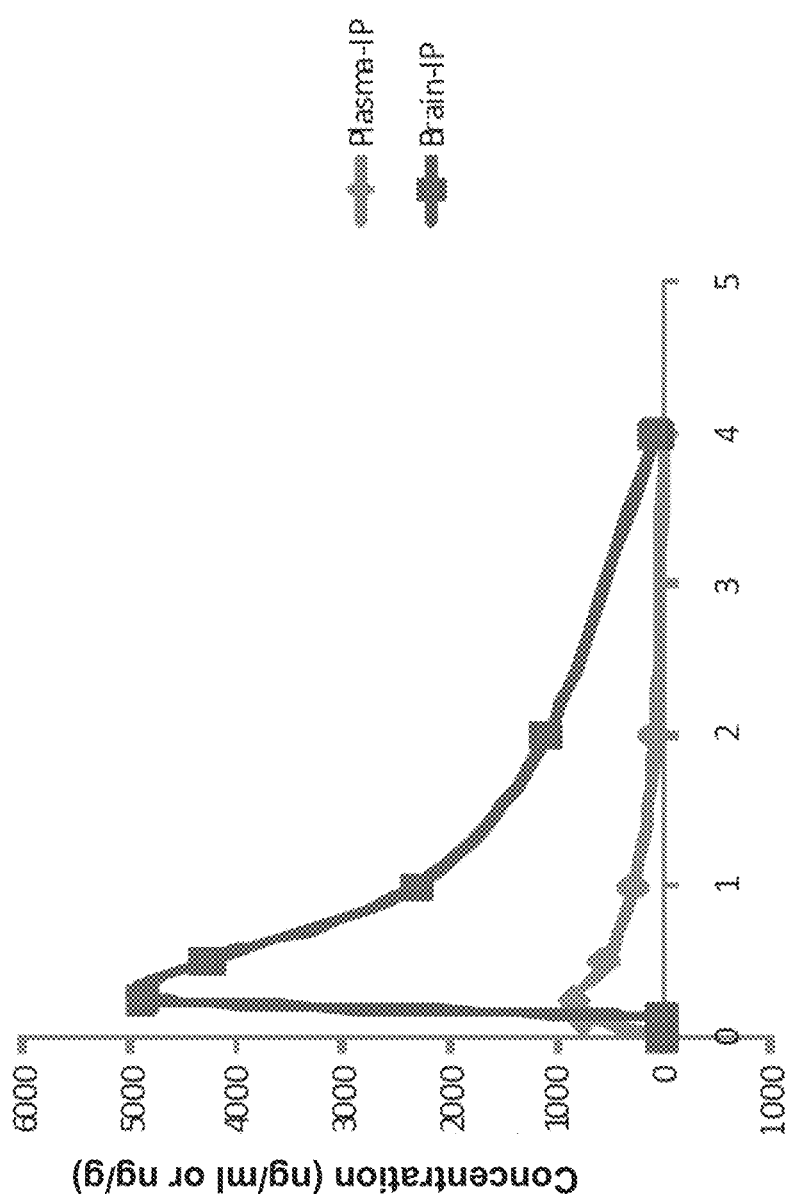
FIG. 71 is a graph showing pharmacokinetic properties of YF2. The amount of YF2 in the brain is higher than that in the plasma. YF2 is rapidly absorbed in the brain (see Table 14). The elimination half-lives of YF2 in the brain and plasma are ~40 min. The distribution of YF2 to the brain is fast. YF2 does not induce any adverse effects up to 300 mg/kg (i.p.) in acute toxicity experiments.

Next, we checked if YF2 could attenuate synaptic and cognitive dysfunction after Aβ elevation. YF2 rescued the defect in H3 acetylation levels following Aβ infusion onto hippocampus (FIG. 65). Next, we induced LTP or contextual fear memory as well as reference memory in the presence of oligomeric $Aβ_{42}$, or vehicle. In the LTP experiments 200 nM $Aβ_{42}$ or vehicle were perfused through the bath solution for 20 min prior to the application of the 0-burst. In the behavioral experiments 200 nM $Aβ_{42}$ (in a final volume of 1 µl over 1 min) or vehicle were bilaterally infused 15 min prior to the foot shock or 15 min prior to the $1^{st}$ trial (for the $1^{st}$ group of tests in a 2-day radial arm water maze (RAWM) test assessing reference memory[P34] (herein incorporated by reference in its entirety)) and 15 min prior to the $7^{th}$ trial (for the $2^{nd}$ group of tests of the RAWM) into dorsal hippocampus of the animal that had been pre-implanted with a cannula the week before. Aβ reduced LTP and both reference and contextual fear memory (FIG. 66). However, YF2 (1 µM, for 30 min prior to the 0-burst in the LTP experiments; 5 or 20 mg/Kg, i.p., 15 min before Aβ administration in the behavioral experiments) ameliorated the electrophysiological and behavioral deficits (FIG. 66).

Without being bound by theory, given that these experiments were obtained with a synthetic preparation of Aβ42, it is difficult to know if this is the same as Aβ that causes synaptic dysfunction in AD brains. Thus, we validated these experiments in an Aβ-depositing mouse model, the APP/PS1 mouse[P35] (herein incorporated by reference in its entirety). These mice have been well characterized with respect to AD pathology[P34-38] (each herein incorporated by reference in its entirety). They start to show synaptic and memory impairment as early as 3 months of age[P34] (herein incorporated by reference in its entirety). Transgenic mice with a double mutation APP (K670M:N671L)/PS1(M146L) (line 6.2) start to develop large plaques in cortex and hippocampus at the age of 8-10 weeks. They have a reduction in LTP by 3 months of age together with impairment of contextual fear memory and spatial working memory.

As shown in FIG. 67, WT mice exhibited <2 errors over two trials near the end of the second day with the RAWM task. APP/PS1 in turn failed to learn and made >3 errors throughout the training session. The treatment with YF2 (20 mg/Kg, i.p. 30 min before training for FC or before the $1^{st}$ and $2^{nd}$ group of tests for the RAWM), however, rescued the memory defect in double Tgs without affecting memory in WT mice. We obtained similar results when double Tgs mice performed FC to assess contextual fear memory (FIG. 67).

In summary, Histone 3 and 4 acetylation is decreased following Aβ42 elevation. HATs levels (CBP and PCAF) are reduced following Aβ42 elevation. HDAC inhibition is beneficial against damage of synaptic function and memory following Aβ42 elevation. HAT activation is beneficial against memory loss following Aβ42 elevation. We have designed and synthesized a HAT activator, YF2, that shifts the balance of histone 3 acetylation and reinstates normal memory following Aβ elevation.

Example 11: HAT Activators with High Affinity and Good Selectivity for CBP and/or PCAF and/or P300

Compounds will be tested for HAT activator activity first, using the HAT Assay kit from Active Motif (USA, CA). For this assay, we will use the catalytic domain of human CBP, PCAF, p300 and GCN5 (Enzo Life Sci., USA). The catalytic domains for the remaining HATs will be produced using New England Biolabs *K. lactis* Protein Expression Kit. In addition to being potent activators of CBP and/or PCAF ($EC_{50}$<100 nM), the candidate compounds must also be selective. When assayed against all other HATs, they must show at least a 50 fold greater potency towards CBP and/or PCAF. Finally, on the most potent/selective compounds that show efficacy in tests of synaptic and memory dysfunction outlined in Examples 13 and 14 we will check selectivity against HDACs. While performing these tests, we will also evaluate solubility (neutral aqueous buffer >10 µg/ml).

Our next goal will be to confirm in vitro data, using a neuronal preparation. In particular, we will test new HAT activators in primary cultures and adult mice. We will first determine whether the compounds can increase specific histone acetylation in 10 day old cultured hippocampal neurons (prepared as described[P47]; herein incorporated by reference in its entirety). Media will be aspirated and replaced with 0.5 mL of PBS containing the HAT activator. After 30 min at 37° C., cells will be removed and lysed for WB analysis. Compounds that pass the test in hippocampal cultures will next be tested in adult mice, following an assessment of acute toxicity to determine the dose of compound to be administered to the animal (see "toxicity tests" below). Testing in adult mice is essential as cell cultures do not recapitulate the whole body with complex cell-cell interactions and in vivo drug PK, BBB penetration, etc (see also Example 12 below). Animals will be treated with the HAT activator, hippocampi will be collected 30 min after the i.p. injection, and lysed for WB analysis. All experiments will be performed in triplicate. If we find an increase in specific histone acetylation, the candidate compound will be deemed active.

On selected compounds we will also examine interactions with channels, receptors, transporters using the NIMH PDSP program (see http://pdsp.cwru.edu for a list of CNS targets), in addition to ADMET/Tox studies discussed in Example 12.

Example 12: To Determine Whether New Hat Activators have Good Pharmacokinetic (Pk) Profile and are Safe We will generate data addressing the rudimentary PK properties and toxicity of the novel HAT activators. If necessary, information obtained through the PK and toxicity studies will be used to guide additional chemical modifications of the new molecules with the ultimate goal of improving bioavailability, brain uptake, and safety. Pharmacokinetic assays that need to be performed will include the measurement of a) bioavailability and b) brain uptake. Mice will be i.p. injected with the activator (for final drug candidates PK tests will be also performed using p.o. and i.v. routes of administration). 5-6 mice/sex will be used for each time-point. For the assessment of bioavailability (concentration of compound in the blood as a function of time after administration), blood samples will be obtained from test animals following a single acute administration (collected at 5 min, 15 min, 30 min, 1 hr, 2 hrs, 4 hrs, and 24 hrs). Blood will be harvested by retro-orbital puncture, collected in heparanized tubes, and plasma obtained by centrifugation. Samples will be analyzed by LC-MS to measure the amounts of the candidate compound and possible metabolites. An indication of brain uptake and BBB penetration will be obtained by tissue extraction of the candidate compound from brain. Briefly, brain homogenates will be centrifuged 11,000 rpm for 10 min. An aliquot of the sample will be added to acetonitrile, then injected onto LC-MS/MS for analysis. Similar patterns of brain and plasma concentrations will be indicative of the fact that brain uptake reflects concentration of the blood. A peak brain/blood concentration ratio >1 will indicate that brain uptake for our compound is comparable with that of known CNS drugs in clinical use. For example, the brain/blood ratio for minaprine, a 6-phenylaminopyridazine CNS drug, is >2[P48] (herein incorporated by reference in its entirety).

Next, we will evaluate acute toxicity. All clinical signs, time of onset, duration, reversibility of toxicity and mortalities will be recorded. Animals will be observed periodically during the first 24 hrs with continuous monitoring given to the first 4 hrs, then at least once a day for 14 days or until they die to check food and liquid intake, weight, as well as locomotion and exploratory behavior. We will also evaluate maximum tolerated dose (MTD) and chronic toxicity. MTD will be computed as the maximum administered dose that does not produce any toxicity effect in terms of malaise or death (body weight will be monitored over time). Chronic toxicity will assessed at the MTD. All clinical signs, time of onset, duration, reversibility of toxicity and mortalities will be recorded. The occurrence of possible chronic toxicity signs will be assessed for at least 1 month after the end of the treatment.

It has been estimated that over half of all drugs fail to reach the market because of ADMET problems[P49] (herein incorporated by reference in its entirety). Therefore, before embarking on a course of costly animal toxicological work and following efficacy assessment (see Examples 13 and 14), we will take advantage of recent advances in in vitro ADMET testing to screen our best three compounds with a quick, inexpensive battery of assays. We will focus on two areas that have resulted in the withdrawal of many drugs from the market: drug-drug interactions (liver metabolism), hERG channel blockage (cardiac dysfunction). To test for drug-drug interactions related to hepatotoxicity, we will use the Cytochrome P450 inhibition assay (performed by SRI international). hERG channel blockage assay will be performed using the NIMH PDSP program.

Example 13: Selecting HAT Activators that Rescue LTP in APP/PS1 Mice

Synaptic dysfunction is a major hallmark of AD[P50] (herein incorporated by reference in its entirety). A qualifying aspect of our drug screening protocol will include a measurement of the effect of the newly-synthesized compounds onto synaptic function. The APP/PS1 mouse presents an impairment of LTP by the age of 3 months[P34] (herein incorporated by reference in its entirety) and therefore permits a relatively fast assessment of synaptic function without waiting a long time for mice aging. We will examine LTP because it is a type of synaptic plasticity that is thought to underlie learning and memory. Based on the findings that YF2 rescues the Aβ-induced reduction of LTP, we will screen the compounds indicated by our MedChem studies to select those that can re-establish normal LTP. The compounds will be applied for 30 min using the same experimental protocol as in FIG. 66A. Controls will be performed on slices from APP/PS1 mice treated with vehicle, and WT mice treated with compound or vehicle. If the compounds re-establish normal LTP in APP/PS1 slices, we will conclude that the compounds can rescue impairment of synaptic plasticity in APP/PS1 mice. We will also investigate another important aspect of the disease, the cognitive impairment (see Example 14).

Animals: Tg mice will be obtained by crossing APP (K670M:N671L) with PS1(M146L) (line 6.2) animals. The genotype will be identified by PCR on tail samples[P51 P53] (each herein incorporated by reference in its entirety).

Electrophysiology will be performed on males (see description in Gong et al[1354]; herein incorporated by reference in its entirety).

Statistical Analyses: see Example 14.

Example 14: Further Screening of HAT Activators to Examine if they Ameliorate Cognitive Abnormalities in APP/PS1 Mice Without being bound by theory, treatment with a novel HAT activator indicated by Example 13 can rescue the cognitive deficits in 3 and 6 month old APP/PS1 mice. As behavioral tasks we will use the RAWM and contextual FC, two types of tests assessing different types of memory (reference ad associative) that are affected in AD patients. The treatment will be performed with the same timing (i.e. 30 min before training for fear conditioning or before the $1^{st}$ and $2^{nd}$ group of tests for the RAWM). Conditions to be tested include: APP/PS1 and WT treated with HAT activators, APP/PS1 and WT treated with vehicle. After behavioral testing mice will be sacrificed and their blood and brains used for Aβ level, Tau protein, TARDBP and TDB levels, and alpha-synuclein measurements. As a control for effectiveness of HAT activation, we will measure hippocampal acetyl-H4 levels after administration of the compounds 30 min prior to training for fear conditioning and removal of the hippocampi 1 hr after the electric shock (APP/PS1 mice have been shown to have a reduction of acetylated H4 after the electric shock[P21] (herein incorporated by reference in its entirety)). Finally, we will screen them with a battery of assays focusing on two areas that have resulted in the withdrawal of many drugs from the market: drug-drug interactions, hERG channel blockage (see Example 12).

Animals: see Example 13.

Behavioral Studies: Experiments will be performed in blind only on male animals to reduce variability. A) Spatial memory. This type of reference memory can be studied with the 2-day RAWM test, as described[P56] (herein incorporated by reference in its entirety); see also FIG. 66B). The task is a hybrid of the Morris Water Maze (MWM) and the radial arm land maze. For these experiments, visible platform testing will be conducted to exclude that visual, motor and motivation deficits affect the mouse performance, as described[P34] (herein incorporated by reference in its entirety). B) Fear Conditioning to examine both contextual and cued learning will be assessed as described[P57] (herein incorporated by reference in its entirety). For these experiments, threshold assessment test will performed to check sensory perception of electric foot in different groups of mice[P57] (herein incorporated by reference in its entirety). In addition, the open-field test will be conducted to evaluate exploratory as described[P58,P59] (each herein incorporated by reference in its entirety).

Histone acetylation assay: Western blot will be performed from snap-frozen in liquid nitrogen hippocampi. Tissue will be homogenized in RIPA buffer, then sonicated before centrifugation at 10,000 rpm for 5 min. Whole cell extracts will be electrophoresed on 10-20% gradient PAGE gel (Invitrogen) and then immunoblotted. Antibodies will be used at a 1:1,000 concentration for immunoblotting. All anti-histone antibodies will be purchased from Millipore. Immunoblot data will be quantified by measuring the band intensity using imaging software (NIH ImageJ).

Determination of Aβ levels will be performed on homogenates of frozen hemi-brains and plasma as previously described[P34] (herein incorporated by reference in its entirety).

Determination of alpha-synuclein levels will be performed on homogenates of frozen hemi-brains using an α-Synuclein ELISA Kit (Catalog #NS400; Millipore, Billerica, Mass.) according to manufacturer's instructions.

Determination of TARDBP/TDP-43 levels will be performed on homogenates of frozen hemi-brains using a Human TAR DNA binding protein 43, TARDBP/TDP-43 ELISA Kit (Catalog #E1951 h; Wuhan EIAab Science Co, Wuhan, China) according to manufacturer's instructions.

Determination of total Tau and phosphorylated Tau (Thr 231) levels will be performed on homogenates of frozen hemi-brains and plasma using assay and kits according to manufacturer's instructions available from MesoScale Discovery (Gaithersburg, Md.) (see http://www.mesoscale.com/catalogsystemweb/webroot/products/assays/alzheimers.aspx).

Statistics: Experiments mice will be performed in blind. Results will be expressed as Standard Error Mean (SEM). Level of significance will be set for $p<0.05$. Results will be analyzed with ANOVA with post-hoc correction with drug or genotype as main effect.

REFERENCES

P1. Malm, T., et al., *beta-Amyloid infusion results in delayed and age-dependent learning deficits without role of inflammation or beta-amyloid deposits*. Proc Natl Acad Sci USA, 2006. 103(23): p. 8852-7.

P2. Cleary, J. P., et al., *Natural oligomers of the amyloid-beta protein specifically disrupt cognitive function*. Nat Neurosci, 2005. 8(1): p. 79-84.

P3. Cullen, W. K., et al., *Block of LTP in rat hippocampus in vivo by beta-amyloid precursor protein fragments*. Neuroreport, 1997. 8(15): p. 3213-7.

P4. Itoh, A., et al., *Impairments of long-term potentiation in hippocampal slices of beta-amyloid-infused rats*. Eur J Pharmacol, 1999. 382(3): p. 167-75.

P5. Vitolo, O. V., et al., *Amyloid beta-peptide inhibition of the PKA/CREB pathway and long-term potentiation: reversibility by drugs that enhance cAMP signaling*. Proc Natl Acad Sci USA, 2002. 99(20): p. 13217-21.

P6. Walsh, D. M., et al., *Naturally secreted oligomers of amyloid beta protein potently inhibit hippocampal long-term potentiation in vivo*. Nature, 2002. 416(6880): p. 535-9.

P7. Chen, Q. S., et al., *Impairment of hippocampal long-term potentiation by Alzheimer amyloid beta-peptides*. J Neurosci Res, 2000. 60(1): p. 65-72.

P8. Lambert, M. P., et al., *Diffusible, nonfibrillar ligands derived from Abeta1-42 are potent central nervous system neurotoxins*. Proc Natl Acad Sci USA, 1998. 95(11): p. 6448-53.

P9. Rakyan, V. K., et al., *The marks, mechanisms and memory of epigenetic states in mammals*. Biochem J, 2001. 356(Pt 1): p. 1-10.

P10. Gwack, Y., et al., *CREB-binding protein and histone deacetylase regulate the transcriptional activity of Kaposi's sarcoma-associated herpesvirus open reading frame 50*. J Virol, 2001. 75(4): p. 1909-17.

P11. Lu, F., et al., *Chromatin remodeling of the Kaposi's sarcoma-associated herpesvirus ORF50 promoter correlates with reactivation from latency*. J Virol, 2003. 77(21): p. 11425-35.

P12. Knutson, S. K., *In vivo characterization of the role of histone deacetylase 3 in metabolic and transcriptional regulation*, in Biochemistry. 2008, Vanderbilt: Nashville. p. 167.

P13. Rajan, I., et al., *Loss of the putative catalytic domain of HDAC4 leads to reduced thermal nociception and seizures while allowing normal bone development*. PLoS One, 2009. 4(8): p. e6612.

P14. Roelfsema, J. H. and D. J. Peters, *Rubinstein-Taybi syndrome: clinical and molecular overview*. Expert Rev Mol Med, 2007. 9(23): p. 1-16.

P15. Alarcon, J. M., et al., *Chromatin acetylation, memory, and LTP are impaired in CBP+/- mice: a model for the cognitive deficit in Rubinstein-Taybi syndrome and its amelioration*. Neuron, 2004. 42(6): p. 947-59.

P16. Maurice, T., et al., *Altered memory capacities and response to stress in p300/CBP-associated factor (PCAF) histone acetylase knockout mice*. Neuropsychopharmacology, 2008. 33(7): p. 1584-602.

P17. Levenson, J. M., et al., *Regulation of histone acetylation during memory formation in the hippocampus*. J Biol Chem, 2004. 279(39): p. 40545-59.

P18. Langley, B., et al., *Remodeling chromatin and stress resistance in the central nervous system: histone deacetylase inhibitors as novel and broadly effective neuroprotective agents*. Curr Drug Targets CNS Neurol Disord, 2005. 4(1): p. 41-50.

P19. Fischer, A., et al., *Recovery of learning and memory is associated with chromatin remodelling*. Nature, 2007. 447(7141): p. 178-82.

P20. Kim, D., et al., *SIRT1 deacetylase protects against neurodegeneration in models for Alzheimer's disease and amyotrophic lateral sclerosis*. EMBO J, 2007. 26(13): p. 3169-79.

P21. Francis, Y. I., et al., *Dysregulation of histone acetylation in the APP/PS1 mouse model of Alzheimer's disease.* J Alzheimers Dis, 2009. 18(1): p. 131-9.

P22. Marmorstein, R. and R. C. Trievel, *Histone modifying enzymes: structures, mechanisms, and specificities.* Biochim Biophys Acta, 2009. 1789(1): p. 58-68.

P23. Mantelingu, K., et al., *Activation of p300 histone acetyltransferase by small molecules altering enzyme structure: probed by surface-enhanced Raman spectroscopy.* J Phys Chem B, 2007. 111(17): p. 4527-34.

P24. Balasubramanyam, K., et al., *Small molecule modulators of histone acetyltransferase p300.* J Biol Chem, 2003. 278(21): p. 19134-40.

P25. Sbardella, G., et al., *Identification of long chain alkylidenemalonates as novel small molecule modulators of histone acetyltransferases.* Bioorg Med Chem Lett, 2008. 18(9): p. 2788-92.

P26. Dal Piaz, F., et al., *The identification of a novel natural activator of p300 histone acetyltranferase provides new insights into the modulation mechanism of this enzyme.* Chembiochem. 11(6): p. 818-27.

P27. Nakagami, Y., et al., *A novel beta-sheet breaker, RS-0406, reverses amyloid beta-induced cytotoxicity and impairment of long-term potentiation in vitro.* Br J Pharmacol, 2002. 137(5): p. 676-82.

P28. Walsh, D. M., et al., *Certain inhibitors of synthetic amyloid beta peptide (Abeta) fibrillogenesis block oligomerization of natural Abeta and thereby rescue long-term potentiation.* J Neurosci, 2005. 25(10): p. 2455-62.

P29. Schenk, D., et al., *Immunization with amyloid-beta attenuates Alzheimer-disease-like pathology in the PDAPP mouse.* Nature, 1999. 400(6740): p. 173-7.

P30. Wu, J., R. Anwyl, and M. J. Rowan, *beta-Amyloid-(1-40) increases long-term potentiation in rat hippocampus in vitro.* Eur J Pharmacol, 1995. 284(3): p. $R_1$-3.

P31. Kowalska, M. A. and K. Badellino, *beta-Amyloid protein induces platelet aggregation and supports platelet adhesion.* Biochem Biophys Res Commun, 1994. 205(3): p. 1829-35.

P32. Mattson, M. P., Z. H. Guo, and J. D. Geiger, *Secreted form of amyloid precursor protein enhances basal glucose and glutamate transport and protects against oxidative impairment of glucose and glutamate transport in synaptosomes by a cyclic GMP-mediated mechanism.* J Neurochem, 1999. 73(2): p. 532-7.

P33. Peleg, S., et al., *Altered histone acetylation is associated with age-dependent memory impairment in mice.* Science. 328(5979): p. 753-6.

P34. Trinchese, F., et al., *Progressive age-related development of Alzheimer-like pathology in APP/PS1 mice.* Ann Neurol, 2004. 55(6): p. 801-14.

P35. Holcomb, L., et al., *Accelerated Alzheimer-type phenotype in transgenic mice carrying both mutant amyloid precursor protein and presenilin 1 transgenes.* Nat Med, 1998. 4(1): p. 97-100.

P36. Kurt, M. A., et al., *Neurodegenerative changes associated with beta-amyloid deposition in the brains of mice carrying mutant amyloid precursor protein and mutant presenilin-1 transgenes.* Exp Neurol, 2001. 171(1): p. 59-71.

P37. McGowan, E., et al., *Amyloid phenotype characterization of transgenic mice overexpressing both mutant amyloid precursor protein and mutant presenilin 1 transgenes.* Neurobiol Dis, 1999. 6(4): p. 231-44.

P38. Sant'Angelo, A., F. Trinchese, and O. Arancio, *Usefulness of behavioral and electrophysiological studies in transgenic models of Alzheimer's disease.* Neurochem Res, 2003. 28(7): p. 1009-15.

P39. Coutts, R. T., P. Su, and G. B. Baker, *Involvement of CYP2D6, CYP3A4, and other cytochrome P-450 isozymes in N-dealkylation reactions.* J Pharmacol Toxicol Methods, 1994. 31(4): p. 177-86.

P40. Thompson, T. N., *Optimization of metabolic stability as a goal of modern drug design.* Med Res Rev, 2001. 21(5): p. 412-49.

P41. Chee, C. F., et al., *An efficient synthesis of (±)-panduratin A and (±)-isopanduratin A, inhibitors of dengue-2 viral activity.* Tetrahedron Letters, 2010. 51: p. 495-498.

P42. Kuehne, M. E. and P J Shannon, *Reduction of Amides and Lactams to Amines by Reactions with Phosphorus Oxychloride and Sodium Borohydride.* J. Org. Chem., 1977. 42: p. 2082-2087.

P43. Mondal, M., V. G. Puranik, and N. P. Argade, *Facile Synthesis of 1,3,7-Trihydroxyxanthone and Its Regioselective Coupling Reactions with Prenal: Simple and Efficient Access to Osajaxanthone and Nigrolineaxanthone F.* J. Org. Chem., 2006. 71: p. 4992-4995.

P44. Melgar-Fernandez, R., et al., *Synthesis of Novel Derivatives of (1S,4S)-2,5-Diazabicyclo[2.2.1]heptane and Their Evaluation as Potential Ligands in Asymmetric Catalysis.* Eur. J. Org. Chem., 2008: p. 655-672.

P45. Mahmoud, M. R., et al., *Synthesis of novel indeno[1,2-c]isoquinolines derivatives.* Synthetic Communications, 2010. 40: p. 666-676.

P46. Tsuritani, T., et al., *Efficient synthesis of 1,4-Diaryl-5-methyl-1,2,3-triazole, a potential mGluR1 antagonist, and the risk assessment study of arylazides.* Organic Process Research & Development, 2009. 13: p. 1407-1412.

P47. Ninan, I and O. Arancio, *Presynaptic CaMKII Is Necessary for Synaptic Plasticity in Cultured Hippocampal Neurons.* Neuron, 2004. 42(1): p. 129-41.

P48. Caccia, S., T. Fossati, and A. Mancinelli, *Disposition and metabolism of minaprine in the rat.* Xenobiotica, 1985. 15(12): p. 1111-9.

P49. Hodgson, J., *ADMET—turning chemicals into drugs.* Nat Biotechnol, 2001. 19(8): p. 722-6.

P50. Masliah, E., *Mechanisms of synaptic dysfunction in Alzheimer's disease.* Histol Histopathol, 1995. 10(2): p. 509-19.

P51. Duff, K., et al., *Increased amyloid-beta42(43) in brains of mice expressing mutant presenilin I.* Nature, 1996. 383(6602): p. 710-3.

P52. Hsiao, K., et al., *Correlative memory deficits, Abeta elevation, and amyloid plaques in transgenic mice.* Science, 1996. 274(5284): p. 99-102.

P53. Di Rosa, G., et al., *Calpain inhibitors: a treatment for Alzheimer's disease.* J Mol Neurosci, 2002. 19(1-2): p. 135-41.

P54. Gong, B., et al., *Ubiquitin Hydrolase Uch-L1 Rescues beta-Amyloid-Induced Decreases in Synaptic Function and Contextual Memory.* Cell, 2006. 126(4): p. 775-88.

P55. Bowers, E. M., et al., *Virtual ligand screening of the p300/CBP histone acetyltransferase: identification of a selective small molecule inhibitor.* Chem Biol. 17(5): p. 471-82.

P56. Alamed, J., et al., *Two-day radial-arm water maze learning and memory task; robust resolution of amyloid-related memory deficits in transgenic mice.* Nat Protoc, 2006. 1(4): p. 1671-9.

P57. Gong, B., et al., *Persistent improvement in synaptic and cognitive functions in an Alzheimer mouse model following rolipram treatment.* J. Clin. Invest., 2004. 114: p. 1624-1634.

P58. Sipos, E., et al., Beta-amyloid pathology in the entorhinal cortex of rats induces memory deficits: implications for Alzheimer's disease. Neuroscience, 2007. 147(1): p. 28-36.

P59. Puzzo, D., et al., Picomolar amyloid-beta positively modulates synaptic plasticity and memory in hippocampus. J Neurosci, 2008. 28(53): p. 14537-45.

Example 15: Further Screening of HAT Activators to Examine if they Ameliorate Cognitive Abnormalities in Mouse Models for Huntington's Disease We will examine whether treatment with a HAT activator compound indicated by Example 13 can rescue the cognitive deficits in a mouse model of Huntington's Disease (e.g., FVB-Tg(YAC128)$_{53}$Hay/J and FVB/NJ-Tg(YAC72) 2511Hay/J mice, available from the Jackson Laboratory, Bar Harbor Me.). As behavioral tasks, we will use the RAWM and contextual FC, two types of tests assessing different types of memory (reference ad associative). The treatment will be performed with the same timing (i.e. 30 min before training for fear conditioning or before the 1$^{st}$ and 2$^{nd}$ group of tests for the RAWM). Conditions to be tested include: Huntington's Disease mice and WT treated with HAT activators, Huntington's Disease mice and WT treated with vehicle. After behavioral testing mice will be sacrificed and their blood and brains used for Huntingtin protein level measurement. As a control for effectiveness of HAT activation, we will measure hippocampal acetyl-H4 levels after administration of the compounds 30 min prior to training for fear conditioning and removal of the hippocampi 1 hr after the electric shock. Finally, we will screen them with a battery of assays focusing on two areas that have resulted in the withdrawal of many drugs from the market: drug-drug interactions, hERG channel blockage (see Example 12).

Animals: Mouse models of Huntington's Disease (e.g., FVB-Tg(YAC128)$_{53}$Hay/J [Stock no. 004938] and FVB/NJ-Tg(YAC72)$_{2511}$Hay/J mice [Stock no. 003640]) will be obtained from the Jackson Laboratory (Bar Harbor Me.). See also, Hodgson et al., (May 1999) Neuron, Vol. 23, 181-192; herein incorporated by reference in its entirety.

Behavioral Studies: Experiments will be performed in blind only on male animals to reduce variability. A) Spatial memory. This type of reference memory can be studied with the 2-day RAWM test, as described[P56] (herein incorporated by reference in its entirety). The task is a hybrid of the Morris Water Maze (MWM) and the radial arm land maze. For these experiments, visible platform testing will be conducted to exclude that visual, motor and motivation deficits affect the mouse performance, as described[P34] (herein incorporated by reference in its entirety). B) Fear Conditioning to examine both contextual and cued learning will be assessed as described[P57] (herein incorporated by reference in its entirety). For these experiments, threshold assessment test will performed to check sensory perception of electric foot in different groups of mice[P57] (herein incorporated by reference in its entirety). In addition, the open-field test will be conducted to evaluate exploratory as described[P58,P59] (each herein incorporated by reference in its entirety).

Histone acetylation assay: Western blot will be performed from snap-frozen in liquid nitrogen hippocampi. Tissue will be homogenized in RIPA buffer, then sonicated before centrifugation at 10,000 rpm for 5 min. Whole cell extracts will be electrophoresed on 10-20% gradient PAGE gel (Invitrogen) and then immunoblotted. Antibodies will be used at a 1:1,000 concentration for immunoblotting. All anti-histone antibodies will be purchased from Millipore. Immunoblot data will be quantified by measuring the band intensity using imaging software (NIH ImageJ).

Determination of huntingtin levels will be performed on homogenates of frozen hemi-brains and plasma using a Huntingtin (Htt) ELISA Kit (Catalog #ABIN423526; Antibodies-online, Atlanta, Ga.) according to manufacturer's instructions.

Statistics: Experiments mice will be performed in blind. Results will be expressed as Standard Error Mean (SEM). Level of significance will be set for $p<0.05$. Results will be analyzed with ANOVA with post-hoc correction with drug or genotype as main effect.

Example 16: Further Screening of HAT Activators to Examine if they Ameliorate Motor Activity Abnormalities in Mouse Models for Parkinson's Disease PD is a degenerative disease with a neuronal death up to 75-95% of the dopamine neurons in the substantia nigra nucleus. We will examine whether treatment with a HAT activator compound indicated by Example 13 can rescue abnormal motor movements in a mouse model of Parkinson's Disease (PD) (e.g., see Parkinson's Disease mice models available from the Jackson Laboratory, Bar Harbor Me. at http://jaxmice.jax.org/list/ra1594.html; see also Emborg, Journal of Neuroscience Methods 139 (2004) 121-143; Lane Psychopharmacology (2008) 199:303-312; and Meredith et al., Acta Neuropathol (2008) 115:385-398; each herein incorporated by reference in its entirety). As behavioral tasks, we will examine, for example, dyskinesia, bradykinesia, tremor, and/or grip force for the evaluation of the compound's efficacy at various stages of PD. Conditions to be tested include: PD mice and WT treated with HAT activators, PD mice and WT treated with vehicle. After behavioral evaluation, mice will be sacrificed and their brains used for aggregated alpha-synuclein protein measurement. As a control for effectiveness of HAT activation, we will measure hippocampal acetyl-H4 levels.

Animals: Mouse models of Parkinson's Disease will be obtained from the Jackson Laboratory (Bar Harbor Me.). See also, Meredith et al., Acta Neuropathol (2008) 115:385-398; herein incorporated by reference in its entirety.

Behavioral Studies: Experiments will be performed in blind only on male animals to reduce variability, according to methods described by Fleming et al., ((2004) The Journal of Neuroscience, 24(42):9434-9440) and Hwang et al., ((2005) The Journal of Neuroscience, 25(8):2132-2137; each herein incorporated by reference in its entirety).

Histone acetylation assay: Western blot will be performed from snap-frozen in liquid nitrogen hippocampi. Tissue will be homogenized in RIPA buffer, then sonicated before centrifugation at 10,000 rpm for 5 min. Whole cell extracts will be electrophoresed on 10-20% gradient PAGE gel (Invitrogen) and then immunoblotted. Antibodies will be used at a 1:1,000 concentration for immunoblotting. All anti-histone antibodies will be purchased from Millipore. Immunoblot data will be quantified by measuring the band intensity using imaging software (NIH ImageJ).

Determination of alpha-synuclein levels will be performed on homogenates of frozen hemi-brains using an α-Synuclein ELISA Kit (Catalog #NS400; Millipore, Billerica, Mass.) according to manufacturer's instructions or via standard neuropathological methods (brain tissue histology).

Statistics: Experiments mice will be performed in blind. Results will be expressed as Standard Error Mean (SEM). Level of significance will be set for p<0.05. Results will be analyzed with ANOVA with post-hoc correction with drug or genotype as main effect.

Example 17: Further Screening of HAT Activators to Examine if they Ameliorate Cognitive Abnormalities in Mouse Models for Huntington's Disease Assays: Accelerating Rotarod (4 and 6 months) and Open Field (6 and 8 months.

Accelerating Rotarod Assay:

Animals: Mouse models of Huntington's Disease (YAC128) versus wildtype (WT) littermates.

Treatment: Mice were treated to either vehicle or YF2 (5 mg/kg) beginning at age 2 months. Number of subjects tested at 4 and 6 months is shown in Table 16.

TABLE 16

Subjects tested in accelerating Rotarod test at 4 months and 6 months of age.

|  | 4 Months | 6 Months |  |
| --- | --- | --- | --- |
|  | Count |  | Count |
| Total | 51 | Total | 32 |
| Male, WT, Veh | 9 | Male, WT, Veh | 4 |
| Male, WT, YF2 | 8 | Male, WT, YF2 | 6 |
| Male, YAC128, Veh | 4 | Male, YAC128, Veh | 1 |
| Male, YAC128, YF2 | 5 | Male, YAC128, YF2 | 3 |
| Female, WT, Veh | 9 | Female, WT, Veh | 6 |
| Female, WT, YF2 | 4 | Female, WT, YF2 | 4 |
| Female, YAC128, Veh | 9 | Female, YAC128, Veh | 6 |
| Female, YAC128, YF2 | 4 | Female, YAC128, YF2 | 4 |

Accelerating Rotarod: This assay is a common assay used to monitor motor coordination in mouse models of Huntington's disease (HD). After a training period to acclimatize the mice to the apparatus, mice are placed on a rod rotating at 5 rpm. Over the test period of 300 sec, the rod increases its rotational speed from 5 rpm to 40 rpm. The time at which the mouse falls off of the rod is recorded. Each mouse is subject to 3 runs per day (shown as a per day average) across 3 days (d1, d2, d3). Typically 8 to 12 mice per group are used in this assay. Both male and female data are shown for age 4 months (FIG. 83A) and 6 months (FIG. 83B).

Rotarod Summary:

Consistent with previously published findings, 4 month old male YAC128 mice fall off of the accelerating rotarod significantly sooner (and hence stay on the rod for a shorter period of time) than control littermates (ANOVA, $F(1,22)=8.768$; $p=0.0072$) (FIG. 83A). There are too few mice in the study to determine whether there is a significant effect as the mice age. Female YAC128 mice do not demonstrate a significant difference across genotype at age 4 mo (ANOVA, $F(1,22)=1.066$; $p=0.3130$), but is significantly affected at 6 months of age (ANOVA, $F(1,16)=13.671$; $p=0.0020$) (FIG. 83A).

Figure 83:
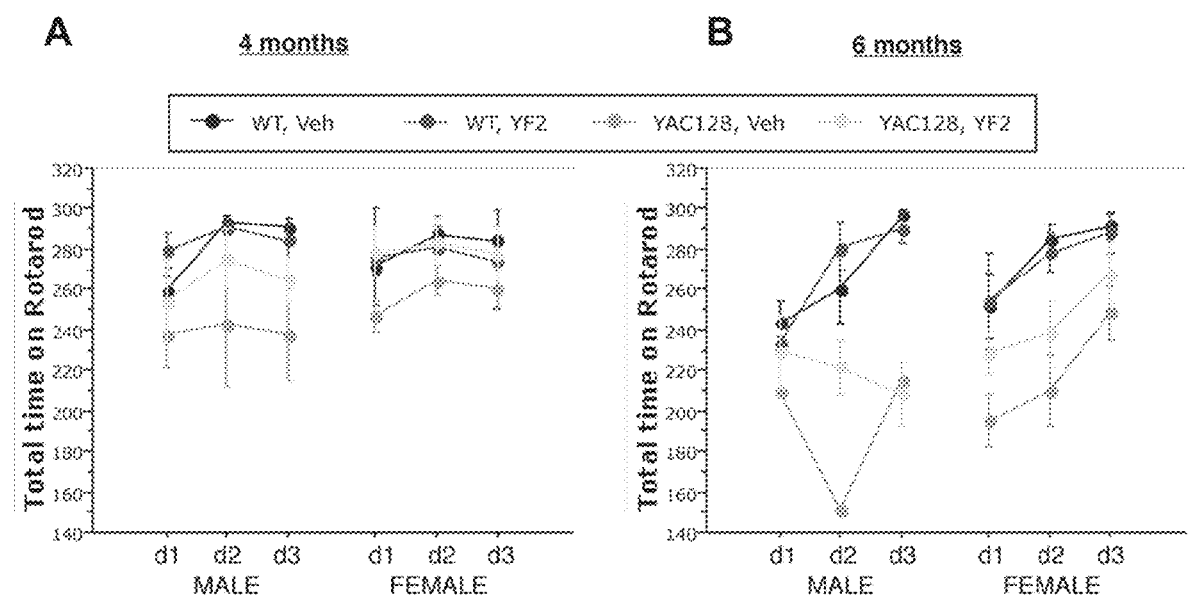
FIG. 83 shows accelerating rotarod data in wild-type and Huntington's Disease mice models treated with YF2 at (A) 4 months and (B) 6 months of age.

At 4 months of age, posthoc analysis (Fisher PLSD) in male mice reveals that although YAC128 mice treated with Vehicle perform significantly worse than WT mice treated with vehicle ($p=0.0021$), this significance is lost once YAC128 mice are treated with YF2 (WT mice treated with YF2 ($p=0.1946$) or WT mice treated with vehicle ($p=0.0792$)) (FIG. 83A).

At 6 months of age, posthoc analysis in female mice reveals a similar effect: although YAC128 mice treated with Vehicle perform significantly worse than WT mice treated with vehicle ($p=0.0100$), this significance is lost once YAC128 mice are treated with YF2 (WT mice treated with YF2 ($p=0.12734$) or WT mice treated with vehicle ($p=0.1690$)) (FIG. 83B).

Accelerating Rotarod Assay:

Animals: Mouse models of Huntington's Disease (YAC128) versus wildtype (WT) littermates.

Treatment: Mice were treated to either vehicle or YF2 (5 mg/kg) beginning at age 2 months. Number of subjects tested at 6 and 8 months is shown in Table 17.

TABLE 17

Subjects tested in accelerating Rotarod test at 6 months and 8 months of age.

|  | 6 Months | 8 Months |  |
| --- | --- | --- | --- |
|  | Count |  | Count |
| Total | 51 | Total | 32 |
| Male, WT, Veh | 9 | Male, WT, Veh | 4 |
| Male, WT, YF2 | 7 | Male, WT, YF2 | 5 |
| Male, YAC128, Veh | 4 | Male, YAC128, Veh | 1 |
| Male, YAC128, YF2 | 5 | Male, YAC128, YF2 | 2 |
| Female, WT, Veh | 9 | Female, WT, Veh | 6 |
| Female, WT, YF2 | 4 | Female, WT, YF2 | 4 |
| Female, YAC128, Veh | 8 | Female, YAC128, Veh | 6 |
| Female, YAC128, YF2 | 4 | Female, YAC128, YF2 | 4 |

Open Field: This assay is a common assay used to monitor total spontaneous locomotor activity and exploratory behavior in mouse models of Huntington's disease (HD). The spontaneous locomotor activity of the animals was measured using an automated photo-beam open-field system (Med-Associates, St Albans, Vt.). Mice were placed individually in the center of a clear open-field chamber (27.9 cm×27.9 cm×20 cm), and their horizontal and vertical activities were measured immediately for 30 min with three 16-beam FR arrays. Locomotor activity was assessed as the distance traveled in 5-min intervals. The number of mice typically used for open field range from 12 to 15 mice.

Open Field Summary:

Total locomotion measure of total activity in 30 min.

Figure 84:
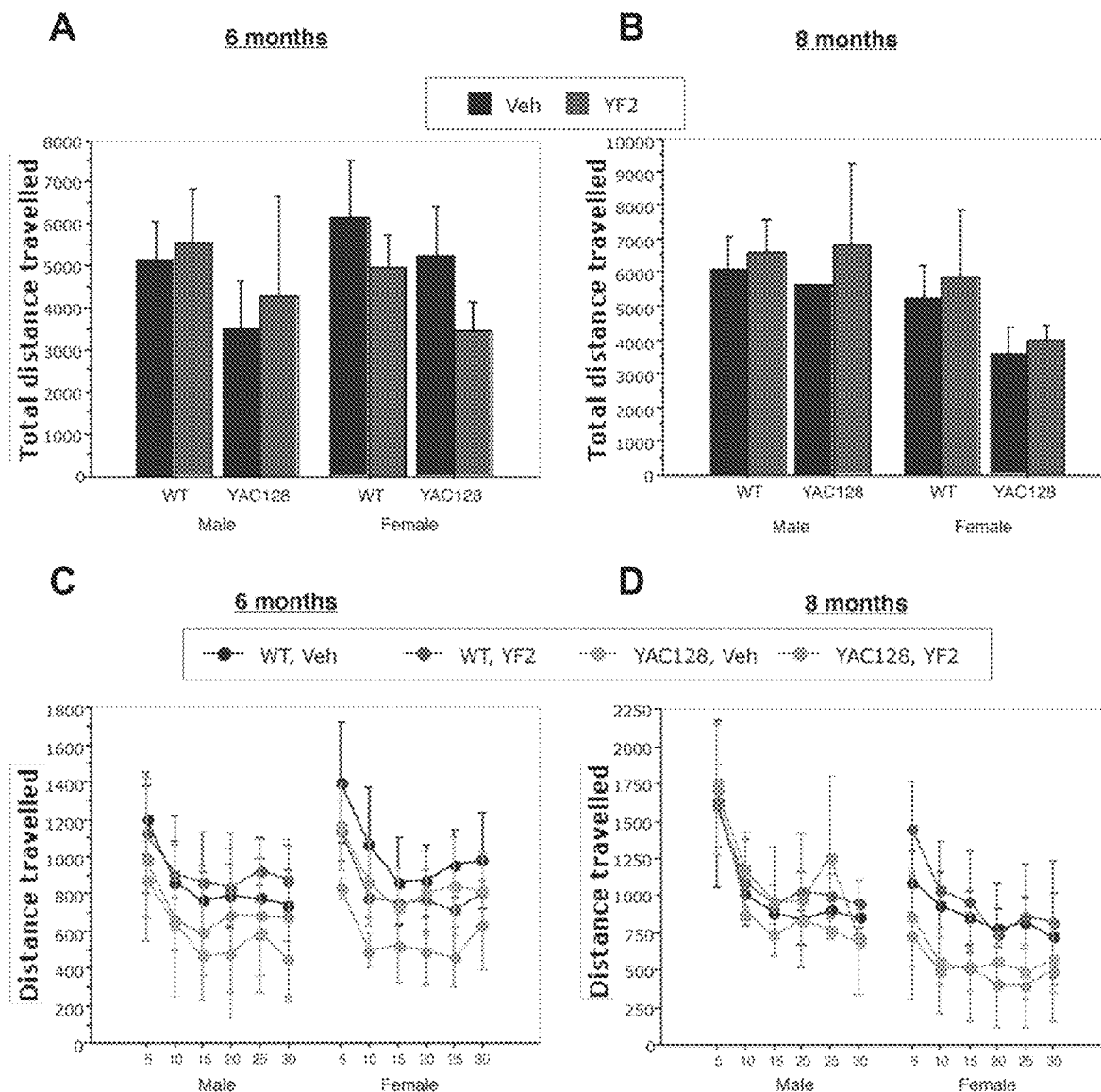
FIG. 84 shows total locomotion in an open field assay in wild-type and Huntington's Disease mice models treated with YF2. Total distance travelled is shown at (A) 6 months and (B) 8 months of age. Total locomotor activity is shown at (C) 6 months and (D) 8 months of age.

In light of the low n values for age 8 mo., statistical values have only been calculated for data collected at age 6 mo. (ANOVA followed by Fisher PLSD posthoc analysis). FIGS. 84 A and B show the total distance travelled in 30 min of male and female mice aged 6 months and 8 months. In FIGS. 84C and D the total locomotor data is shown across each 5 min bins, again segregated for male and female data.

Consistent with previously published findings, there is a significant decrease of total locomotor activity by male YAC128 mice when compared to control (ANOVA, $F(1,21)=5.651$; $p=0.0270$) and by female YAC128 mice when compared to control (ANOVA, $F(1,21)=6.149$; $p=0.0217$).

In male mice, no significant effect of treatment (Rx) was observed (ANOVA, $F(1,21)=0.942$; $p=0.3429$). In female mice, a significant effect of Rx was observed (ANOVA, $F(1,21)=8.838$; $p=0.0073$); however that effect was to diminish significantly (i.e. worsen) the distance traveled by the mice.

Total Locomotion in the Center of Maze Versus Periphery: Measures of Diminished Exploratory Behavior Possibly Due to Anxiety and Fear.

The total distance travelled data from above to the distance travelled in the center of the maze (FIGS. 85 A and B) and periphery (FIGS. 85 C and D) are shown.

Center Locomotion:

Previously published findings indicated that the YAC128 mice demonstrate diminished exploration in the center of the open field maze. The data indicates that while there is no significant decrease of locomotor activity in the center by male YAC128 mice when compared to control (ANOVA, F(1,21)=2.851; p=0.1061) there is a significant decrease by female YAC128 mice when compared to control (ANOVA, F(1,21)=9.995; p=0.0047) (FIGS. 85 A and B).

Locomotion in the Periphery:

For males, in contrast to center movement, there is a significant decrease of locomotor activity in the periphery by male YAC128 mice when compared to control (ANOVA, F(1,21)=6.766; p=0.0167), suggesting that the significant decrease of total locomotor activity is likely due to diminished activity rather than an avoidance of the center of the maze (FIGS. 85 C and D). For females, there is no significant decrease of locomotor activity in the periphery by female YAC128 mice when compared to control (ANOVA, F(1,21)=2.040; p=0.1680), suggesting that the significant decrease of total locomotor activity comes from an avoidance of moving in the center.

Total Rearing or Vertical Movements: Measure of Vertical Exploratory Movements, 30 Min.

Figure 86:
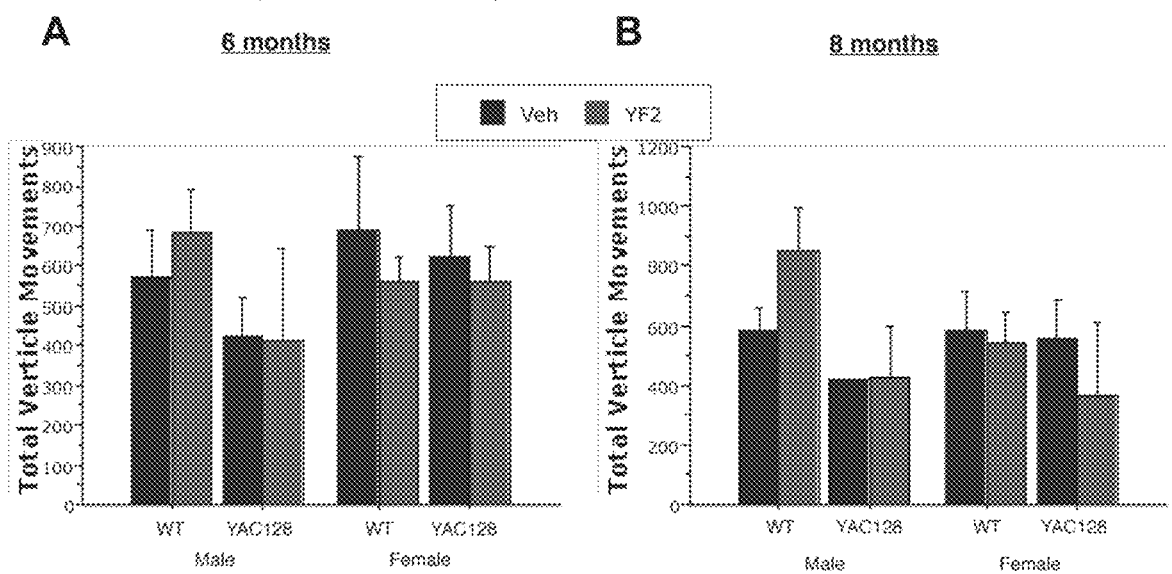
FIG. 86 shows total rearing or vertical movements in wild-type and Huntington's Disease mice models treated with YF2 at (A) 6 months and (B) 8 months of age.

Another measure of exploration are the vertical or rearing events. Consistent with previously published data, male YAC128 mice rear significantly less than control mice (ANOVA, F(1,21)=12.213; p=0.0022); however no significant effect of genotype was observed across the females (ANOVA, F(1,21)=0.290; p=0.5961) (FIG. 86). There was no significant effect of treatment on either male YAC128 mice (ANOVA, F(1,21)=0.704; p=0.4108) or female YAC128 mice (ANOVA, F(1,21)=2.622; p=0.1203).

EQUIVALENTS

Those skilled in the art will recognize, or be able to ascertain, using no more than routine experimentation, numerous equivalents to the specific substances and procedures described herein. Such equivalents are considered to be within the scope of this invention, and are covered by the following claims.

The invention claimed is:

1. A method for treating cancer in a subject, the method comprising administering to a subject a therapeutic amount of a pharmaceutical composition comprising a compound having the following structure:

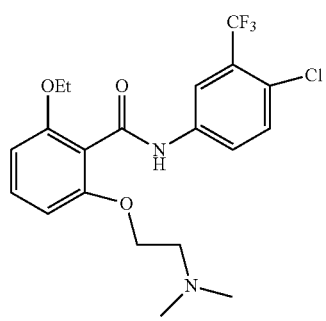 [SMILES: CCOc1cccc(OCCN(C)C)c1C(=O)Nc1ccc(Cl)c(C(F)(F)F)c1]

or a pharmaceutically acceptable salt or hydrate thereof.

2. The method of claim 1, wherein the therapeutic amount is at least about 1 mg/kg body weight, at least about 2 mg/kg body weight, at least about 3 mg/kg body weight, at least about 4 mg/kg body weight, at least about 5 mg/kg body weight, at least about 6 mg/kg body weight, at least about 7 mg/kg body weight, at least about 8 mg/kg body weight, at least about 9 mg/kg body weight, at least about 10 mg/kg body weight, at least about 15 mg/kg body weight, at least about 20 mg/kg body weight, at least about 25 mg/kg body weight, at least about 30 mg/kg body weight, at least about 40 mg/kg body weight, at least about 50 mg/kg body weight, at least about 75 mg/kg body weight, or at least about 100 mg/kg body weight.

3. The method of claim 1, wherein the cancer comprises B cell lymphoma, colon cancer, lung cancer, renal cancer, bladder cancer, T cell lymphoma, myeloma, leukemia, chronic myeloid leukemia, acute myeloid leukemia, chronic lymphocytic leukemia, acute lymphocytic leukemia, hematopoietic neoplasias, thymoma, lymphoma, sarcoma, liver cancer, non-Hodgkins lymphoma, Hodgkins lymphoma, uterine cancer, renal cell carcinoma, hepatoma, adenocarcinoma, breast cancer, pancreatic cancer, prostate cancer, head and neck carcinoma, thyroid carcinoma, soft tissue sarcoma, ovarian cancer, primary or metastatic melanoma, squamous cell carcinoma, basal cell carcinoma, brain cancer, angiosarcoma, hemangiosarcoma, bone sarcoma, fibrosarcoma, myxosarcoma, liposarcoma, chondrosarcoma, osteogenic sarcoma, chordoma, endotheliosarcoma, lymphangiosarcoma, lymphangioendotheliosarcoma, synovioma, testicular cancer, cervical cancer, gastrointestinal cancer, mesothelioma, Ewing's tumor, leiomyosarcoma, rhabdomyosarcoma, colon carcinoma, sweat gland carcinoma, sebaceous gland carcinoma, papillary carcinoma, Waldenstroom's macroglobulinemia, papillary adenocarcinomas, cystadenocarcinoma, bronchogenic carcinoma, bile duct carcinoma, choriocarcinoma, seminoma, embryonal carcinoma, Wilms' tumor, lung carcinoma, epithelial carcinoma, glioma, astrocytoma, medulloblastoma, craniopharyngioma, ependymoma, pinealoma, hemangioblastoma, acoustic neuroma, oligodendroglioma, meningioma, retinoblastoma, melanoma, neuroblastoma, small cell lung carcinoma, bladder carcinoma, multiple myeloma, or medullary carcinoma.

4. The method of claim 1, wherein the compound increases histone acetylation.

5. The method of claim 4, wherein histone acetylation comprises acetylation of histones H2B, H3, H4, or a combination thereof.

6. The method of claim 4, wherein histone acetylation comprises acetylation of histone lysine residues H3K4, H3K9, H3K14, H4K5, H4K8, H4K12, H4K16, or a combination thereof.

7. The method of claim 3, wherein the cancer is colon cancer, lung cancer, renal cancer, leukemia, CNS cancer, melanoma, ovarian cancer, breast cancer, or prostate cancer.

8. The method of claim 3, wherein the cancer is colon cancer, renal cancer, T cell leukemia, myeloma, leukemia, acute myeloid leukemia, acute lymphocytic leukemia, renal cell carcinoma, adenocarcinoma, glioblastoma, breast carcinoma, prostate carcinoma, or lung carcinoma.

9. The method of claim 1, wherein the compound is a pharmaceutically acceptable salt thereof.

10. The method of claim 1, wherein the compound is an acid addition salt thereof.

11. The method of claim 1, wherein the compound is a hydrochloride salt thereof.

* * * * *

UNITED STATES PATENT AND TRADEMARK OFFICE
CERTIFICATE OF CORRECTION

PATENT NO. : 11,034,647 B2
APPLICATION NO. : 16/708190
DATED : June 15, 2021
INVENTOR(S) : Yan Feng et al.

Page 1 of 1

It is certified that error appears in the above-identified patent and that said Letters Patent is hereby corrected as shown below:

In the Specification

Please correct Column 1, Lines 4-15, to read as follows:
This application is a divisional of U.S. Patent Application No. 13/493,490, filed June 11, 2012, which is a continuation-in-part of International Patent Application No. PCT/US2010/059925, filed December 10, 2010, which claims priority to U.S. Provisional Patent Application Nos. 61/285,287, filed December 10, 2009, 61/317,765, filed March 26, 2010, 61/354,964, filed June 15, 2010, 61/355,110, filed June 15, 2010, 61/363,009, filed July 9, 2010. U.S. Patent Application No. 13/493,490 also claims priority to U.S. Provisional Patent Application No. 61/539,697, filed September 27, 2011, the contents of each of which are hereby incorporated by reference in their entireties.

Signed and Sealed this
Eighteenth Day of January, 2022

Drew Hirshfeld
*Performing the Functions and Duties of the*
*Under Secretary of Commerce for Intellectual Property and*
*Director of the United States Patent and Trademark Office*